(12) United States Patent
Sherer et al.

(10) Patent No.: US 10,947,214 B2
(45) Date of Patent: Mar. 16, 2021

(54) TLR7/8 ANTAGONISTS AND USES THEREOF

(71) Applicant: Merck Patent GmbH, Darmstadt (DE)

(72) Inventors: Brian A. Sherer, Nashua, NH (US); Xiaoling Chen, Chestnut Hill, MA (US); Esther Cleary, Somerville, MA (US); Nadia Brugger, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/670,068

(22) Filed: Aug. 7, 2017

(65) Prior Publication Data

US 2018/0037570 A1 Feb. 8, 2018

Related U.S. Application Data

(60) Provisional application No. 62/371,917, filed on Aug. 8, 2016.

(51) Int. Cl.

| | |
|---|---|
| C07D 401/04 | (2006.01) |
| C07D 401/14 | (2006.01) |
| C07D 413/14 | (2006.01) |
| C07D 215/18 | (2006.01) |
| C07D 413/04 | (2006.01) |
| C07D 401/12 | (2006.01) |
| A61K 31/4709 | (2006.01) |
| C07D 215/12 | (2006.01) |
| C07D 215/14 | (2006.01) |
| C07D 241/42 | (2006.01) |
| C07D 451/02 | (2006.01) |
| C07D 471/04 | (2006.01) |
| C07D 471/08 | (2006.01) |
| C07D 471/10 | (2006.01) |
| C07D 487/04 | (2006.01) |

(52) U.S. Cl.
CPC ........ *C07D 401/14* (2013.01); *A61K 31/4709* (2013.01); *C07D 215/12* (2013.01); *C07D 215/14* (2013.01); *C07D 215/18* (2013.01); *C07D 241/42* (2013.01); *C07D 401/04* (2013.01); *C07D 401/12* (2013.01); *C07D 413/04* (2013.01); *C07D 413/14* (2013.01); *C07D 451/02* (2013.01); *C07D 471/04* (2013.01); *C07D 471/08* (2013.01); *C07D 471/10* (2013.01); *C07D 487/04* (2013.01)

(58) Field of Classification Search
CPC ... C07D 401/04; C07D 401/14; C07D 413/14
See application file for complete search history.

(56) References Cited

U.S. PATENT DOCUMENTS

| | | | |
|---|---|---|---|
| 9,938,282 B2 | 4/2018 | Wu et al. | |
| 2017/0174703 A1 | 6/2017 | Wu et al. | |

FOREIGN PATENT DOCUMENTS

| | | |
|---|---|---|
| CH | 578535 A5 | 8/1976 |
| CN | 104945377 | 9/2015 |
| CN | 104945377 A | 9/2015 |
| DE | 812911 C | 9/1951 |
| EP | 1726584 A1 | 11/2006 |
| WO | 03076427 A1 | 9/2003 |
| WO | 03105850 A1 | 12/2003 |
| WO | 04043929 A1 | 5/2004 |
| WO | 08148468 A1 | 12/2008 |
| WO | 09140200 A1 | 11/2009 |
| WO | 15027222 A2 | 2/2015 |
| WO | 15057655 A1 | 4/2015 |
| WO | 16073770 A1 | 5/2016 |
| WO | 16087593 A1 | 6/2016 |
| WO | WO2017/147328 | * 8/2017 |
| WO | WO2018/118781 | * 6/2018 |

OTHER PUBLICATIONS

Bromidge et al. (Bioorg. Med. Chem. Lett. 20, 2010, 7092-7096).*
Nayyar et al. (Bioorg. Med. Chem. Lett. 2006, 14, 847-856—STN CAPLUS, Registry No. 872452-14-7).abstract included only.*
Antonchick et al., Angewandte Chemie International Edition, 2013, 52(11): 3267-3271.
Kuwano et al., Chemical Communications—CHEMCOM, 2015, 51(35): 7558-7561.
Monga et al., Bioorganic & Medicinal Chemi, Pergamon, GB, 2004, 14(24): 6465-6472.
Nayyar et al., Bioorganic & Medicinal Chemi, Pergamon, GB, 2006, 14(3): 847-856.
Rahul et al., International Research Journal of Pharmacy, 2013, 4(1):284-292.
Berge et al., J. Pharmaceutical Sciences, 1977, 66: 1-19.
Barrat and Coffman, Immunol Rev, 223:271-283, 2008.
Foster, Adv. Drug Res., 1985, 14: 1-40.
Gillette et al. Biochemistry, 1994, 33: 2927-2937.
Hanzlik et al., J. Org. Chem., 1990, 55: 3992-3997.
Jarman et al. Carcinogenesis, 1995, 16(4): 683-688.

(Continued)

*Primary Examiner* — Brian E McDowell
(74) *Attorney, Agent, or Firm* — Grüneberg and Myers PLLC

(57) ABSTRACT

The present invention relates to compounds of Formula I

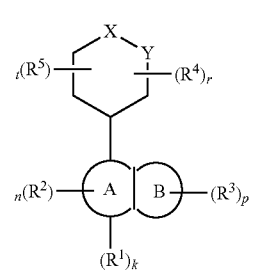

and pharmaceutically acceptable compositions thereof, useful as TLR7/8 antagonists.

8 Claims, No Drawings

(56) References Cited

OTHER PUBLICATIONS

Reider et al., J. Org. Chem., 1987, 52(15): 3326-3334.
Enevold et al., J Rheumatol, 37:905-10, 2010.
Smith, M.B. and March, J., Ed: , March's Advanced Organic Chemistry, 5th Ed, John Wiley & Sons, New York: 2001.
Sorrell, Thomas, "Organic Chemistry", University Science Books, Sausalito: 1999.
Philip J. Kocienski, in "Protecting Groups", Georg Thieme Verlag Stuttgart, New York, 1994.
Theodora W. Greene and Peter G. M. Wuts in "Protective Groups in Organic Synthesis", Wiley Interscience, 3rd Edition 1999.
Shcheblyakov, et al., "Toll-Like Receptors (TLRs): The Role in Tumor Progression", ACTA Naturae, vol. 2, No. 3 (6), 2010, pp. 21-29.
V.G. Belikov, "*Relationship between a chemical structure, properties of substances and their effect on an organism,*" Pharmacevtičeskaâ himiâ [Pharmaceutical Chemistry], Chapter 2.6. Moscow: MEDpress-inform, 2007, pp. 27-29, with English translation, 8 pages.
Vaitilingam et al., "*Synthesis and antimycobacterial activities of ring-substituted quinolinecarboxylic acid/ester analogues. Part 1*", Bioorganic & Medicinal Chemistry; 2004, 12(15): 4179-4188.

\* cited by examiner

TLR7/8 ANTAGONISTS AND USES THEREOF

RELATED APPLICATIONS

The present application claims the benefit of U.S. provisional application No. 62/371,917, filed on Aug. 8, 2016, the content of which is incorporated in its entirety by reference.

TECHNICAL FIELD OF THE INVENTION

The present invention provides for compounds of Formula (I) as toll-like receptor 7/8 (TLR7/8) antagonists and their use in the treatment of immune disorders, and other diseases related to TLR7/8 overexpression.

BACKGROUND OF THE INVENTION

Toll-like receptors (TLR) currently comprising a gene family of 10 receptors with different specificities are part of the cellular pathogen pattern recognition system, which has evolved for defense against a variety of infections (bacteria, virus, fungi). Activation of TLRs leads to cytokine responses, e.g. with release of interferons and activation of specified immune cells. The functional expression of selected TLRs in tissues is highly different. Part of the receptors are located at the cell surface such as TLR4 (stimulated by $E.\ coli$ lipopolysaccharide LPS), e.g. on epithelial cells, or TLR3, 7, 8 and 9 located at endosomal membranes in specified immune cells. The latter are all activated by nucleic acids, but recognize various types of them. For instance, TLR9 is activated by single stranded DNA containing CpG subsequences, TLR7 and 8 are activated by single stranded RNA, and TLR3 is activated by double-stranded RNA.

TLRs have been implicated in various autoimmune and inflammatory diseases, with the clearest example being the role played by TLR7 in the pathogenesis of systemic lupus erythematosus (Barrat and Coffman, Immunol Rev, 223: 271-283, 2008). Additionally, a TLR8 polymorphism has been associated with rheumatoid arthritis (Enevold et al., J Rheumatol, 37:905-10, 2010). Although various TLR7, TLR8 and TLR9 inhibitors have been described, additional TLR inhibitors are desirable. In particular, polynucleotides having inhibitory motifs for one or more of TLR7, TLR8 and TLR9 are needed to precisely inhibit an immune response in a subject (e.g., patient having an autoimmune disease or an inflammatory disorder).

For several years strong efforts are ongoing worldwide trying to exploit the strong immune activation induced by TLR7, 8 or 9 agonists for the treatment of cancer. Cancer immunotherapy, however, experienced a long history of failures. In recent years, though, the knowledge on cancer immune surveillance and the function of subsets of immune cells thereby was improved drastically. TLR7 or TLR9 agonists are in clinical development for cancer mono- or combination therapies, or as vaccine adjuvant. The TLR agonist approach for cancer immunotherapy is different from earlier efforts using, e.g. cytokines, interferons or monovalent vaccinations. TLR agonist mediated immune activation is pleiotropic via specified immune cells (primarily dendritic cells and B-cells, subsequently other cells), which generates an innate and adaptive immune response. Moreover, not only one interferon is induced, but rather the many different isoform's altogether, and not only type I (alpha, beta), but also (indirectly) type II (gamma, NK cells).

SUMMARY OF THE INVENTION

In one aspect, the invention provides compounds of Formula (I):

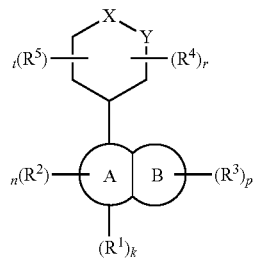

and pharmaceutically acceptable derivatives, solvates, salts, hydrates and stereoisomers thereof.

In another aspect, the invention provides compounds of Formula (I) which are dual antagonists of TLR7 and TLR8. In another aspect, the invention provides compounds of Formula (I) which are suitable for the treatment and/or prevention of disorders related to TLR7/8. In another aspect, the invention provides compounds which are able to modulate, especially inhibit the activity or function of TLR7/8 in disease states in mammals, especially in humans.

According to another aspect of the invention are provided methods for the treatment and/or prevention of auto-immune disorders.

According to another aspect, the present invention provides compounds of Formula (I) which are selective for TLR7 or TLR8.

According to another aspect, the present invention provides compounds of Formula (I) which are selective for TLR7 and TLR8.

DETAILED DESCRIPTION OF CERTAIN EMBODIMENTS

1. General Description of Compounds of the Invention

In certain aspects, the present invention provides for antagonists of TLR7/8. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Fused rings, as described herein, are described by embodiments for each ring; Ring A and Ring B. Together, Ring A and Ring B form a fused heteroaryl ring as allowed by valence (e.g., when Ring A is

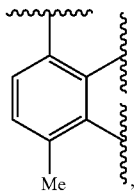 [SMILES: *c1ccc(C)c(*)c1*]

and Ring B is

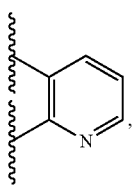 [SMILES: *c1cccnc1*]

then together Ring A and Ring B is

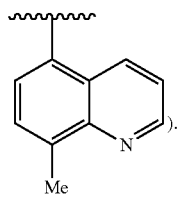 [SMILES: *c1ccc(C)c2ncccc12]

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure

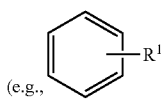

refers to at least

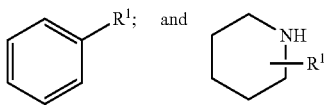

refers to at least

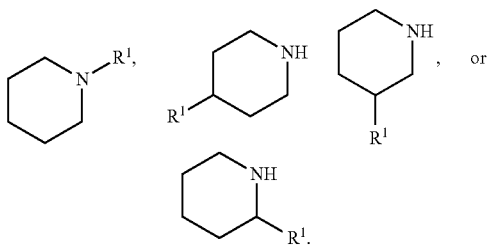

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which are optionally substituted with $R°$; —$(CH_2)_{0-4}O(CH_2)_{0-1}$-Ph which is optionally substituted with $R°$; —CH=CHPh, which is optionally substituted with $R°$; —$(CH_2)_{0-4}O(CH_2)_{0-1}$-pyridyl which is optionally substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each $R°$ is optionally substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^●$, -(haloR$^●$), —(CH$_2$)$_{0-2}$OH, —(CH$_2$)$_{0-2}$OR, —(CH$_2$)$_2$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●$$_2$, —NO$_2$, —SiR$^●$$_3$, —OSiR$^●$$_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^●$ include =O and =S.

Suitable divalent substituents on a saturated carbon atom of an "optionally substituted" group include the following: =OO, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●$$_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●$$_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH— aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O) NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH— -alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)— heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl, —CH$_2$NH$_2$, —CH$_2$SO$_2$CH$_3$,
-mono-, di-, or tri-alkyl silyl,
-alkyl, -alkenyl, -alkynyl, -aryl, -arylalkyl, -heteroaryl, -heteroarylalkyl, heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2$-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in TLR7/8 activity between a sample comprising a compound of the present invention, or composition thereof, and TLR7/8, and an equivalent sample comprising TLR7/8, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

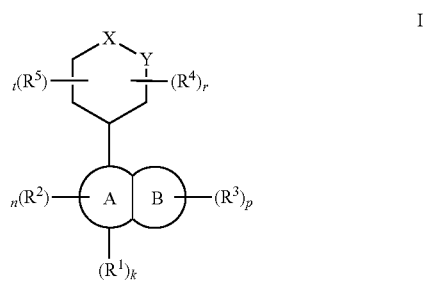

or a pharmaceutically acceptable salt thereof, wherein:

Ring A is aryl or heteroaryl having 1-4 heteroatoms independently selected from nitrogen, oxygen, or sulfur; each of which is optionally substituted;

Ring B is heteroaryl having 1-4 heteroatoms independently selected from nitrogen, oxygen, or sulfur; each of which is optionally substituted;

$R^1$ is —H, —$CH_3$, —$CF_3$, —CN, —F, —Cl, —$OCH_3$, or —$OCF_3$;

each $R^2$ is independently —H, —R, halogen, -haloalkyl, —OR, —SR, —CN, ~$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

each $R^3$ is independently —H, —R, halogen, -haloalkyl, —OR, —SR, —CN, ~$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

X is C($R^4$)$_2$, O, N$R^4$, S, S($R^4$), or S($R^4$)$_2$;
Y is C($R^4$)$_2$, O, N$R^4$, S, S($R^4$), or S($R^4$)$_2$;

each $R^4$ is independently —H, —R, halogen, -haloalkyl, —OR, —SR, —CN, ~$NO_2$, —$SO_2R$, —SOR, —C(O)R, —$CO_2R$, —C(O)N(R)$_2$, —C(NH)R, —C(NH)NR$_2$, —NRC(O)R, —NRC(O)N(R)$_2$, —$NRSO_2R$, or —N(R)$_2$;

each $R^5$ is independently —H, —R, halogen, -haloalkyl, —OR, —SR, —CN, ~$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

k is 1 or 2;
n is 0, 1, or 2;

p is 0, 1, or 2;
r is 0, 1, or 2; and
t is 0, 1, or 2.

In certain embodiments, $R^1$ is —H.
In certain embodiments, $R^1$ is —CH$_3$.
In certain embodiments, $R^1$ is —CF$_3$.
In certain embodiments, $R^1$ is —CN.
In certain embodiments, $R^1$ is —F.
In certain embodiments, $R^1$ is —Cl.
In certain embodiments, $R^1$ is —OCH$_3$.
In certain embodiments, $R^1$ is —OCF$_3$.

In certain embodiments, Ring A is phenyl or a 5-6 membered monocyclic heteroaryl having 1-4 heteroatoms independently selected from nitrogen, oxygen, or sulfur.

In certain embodiments, Ring A is phenyl or a 6 membered monocyclic heteroaryl having 1-4 heteroatoms independently selected from nitrogen, oxygen, or sulfur.

In certain embodiments, Ring A is phenyl, pyridyl, pyrimidinyl, pyrazinyl, pyridazinyl, or triazinyl.

In certain embodiments, Ring A is phenyl or pyridyl.

In certain embodiments, Ring A is

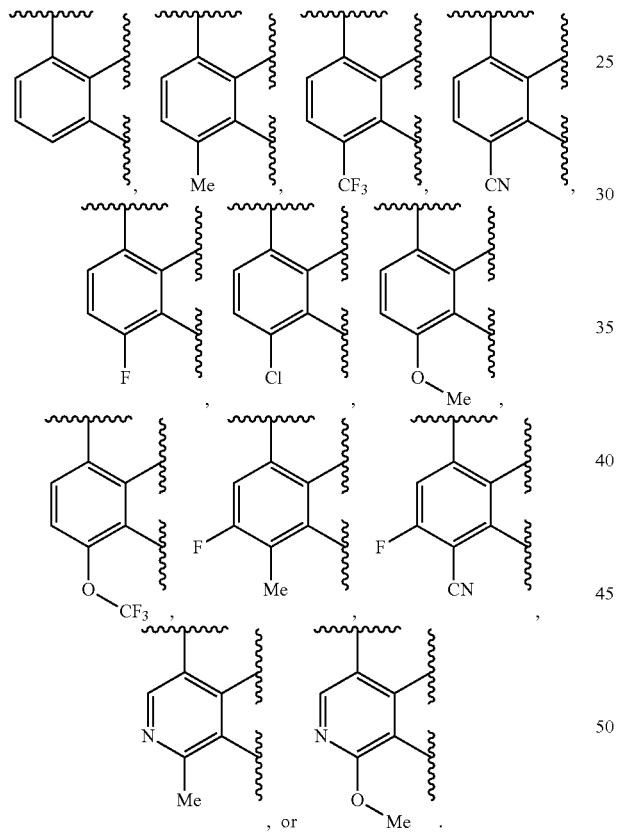

In certain embodiments, Ring A is

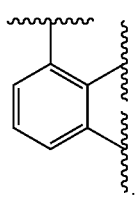 [SMILES: *c1cccc(*)c1*]

In certain embodiments, Ring A is

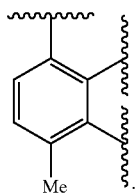

In certain embodiments, Ring A is

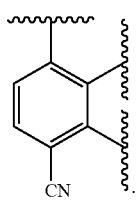

In certain embodiments, Ring A is

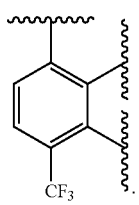

In certain embodiments, Ring A is

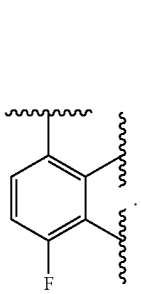 [SMILES: *c1ccc(F)c(*)c1*]

In certain embodiments, Ring A is

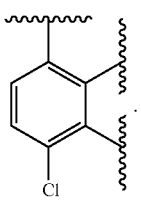 [SMILES: *c1ccc(Cl)c(*)c1*]

In certain embodiments, Ring A is

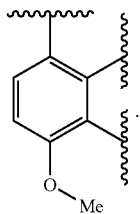 [SMILES: *c1ccc(OC)c(*)c1*]

In certain embodiments, Ring A is

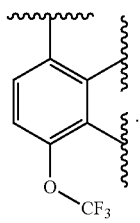

In certain embodiments, Ring A is

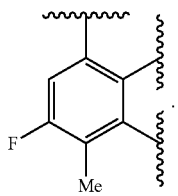

In certain embodiments, Ring A is

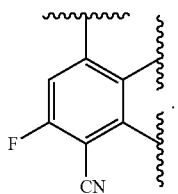

In certain embodiments, Ring A is

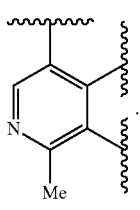 [SMILES: *c1cnc(C)c(*)c1*]

In certain embodiments, Ring A is

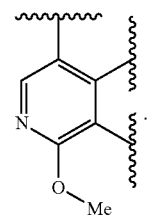 [SMILES: *c1cnc(OC)c(*)c1*]

In certain embodiments, Ring B is a 5-6 membered monocyclic heteroaryl having 1-4 heteroatoms independently selected from nitrogen, oxygen, or sulfur.

In certain embodiments, Ring B is pyridyl, pyrimidinyl, pyrazinyl, pyridazinyl, triazinyl, pyrrole, imidazole, isoxazole, oxazole, or thiazole; each of which is optionally substituted.

In certain embodiments, Ring B is

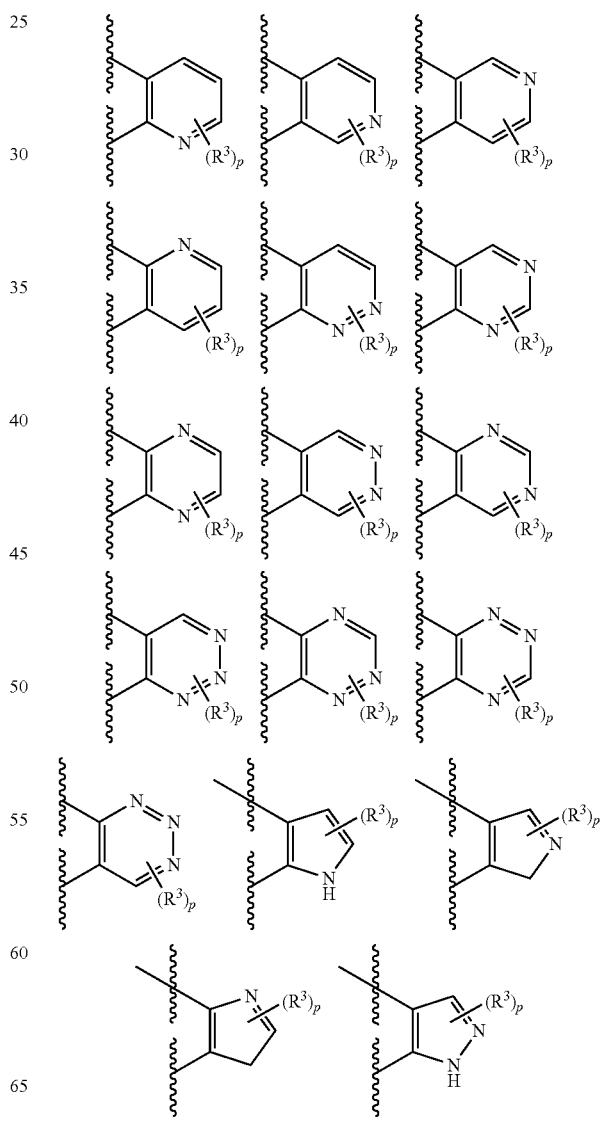

-continued

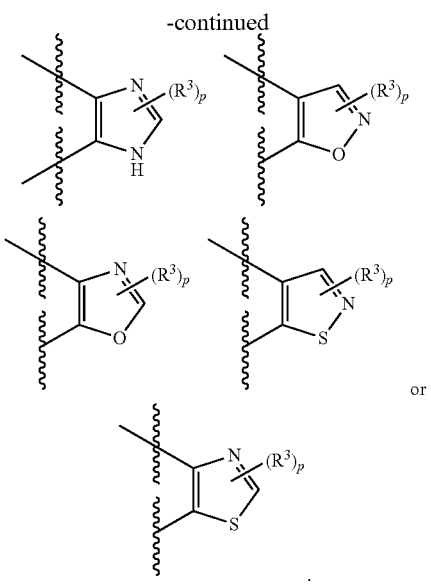

In certain embodiments, Ring B is

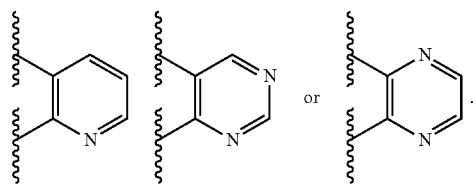

In certain embodiments, Ring B is

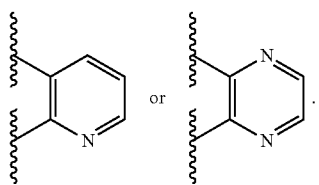 [SMILES: *c1cccnc1* ; *c1nccnc1*]

In certain embodiments, each $R^2$ is independently —H.

In certain embodiments, each $R^2$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^2$ is independently methyl, ethyl, ethyl, propyl, i-propyl, butyl, s-butyl, t-butyl, straight or branched pentyl, or straight or branched hexyl; each of which is optionally substituted.

In certain embodiments, each $R^2$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^2$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently F.

In certain embodiments, each $R^3$ is independently —H.

In certain embodiments, each $R^3$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^3$ is independently methyl, ethyl, ethyl, propyl, i-propyl, butyl, s-butyl, t-butyl, straight or branched pentyl, or straight or branched hexyl; each of which is optionally substituted.

In certain embodiments, each $R^3$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^3$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, X is C(R$^4$)$_2$. In certain embodiments, X is CH$_2$.

In certain embodiments, Y is C(R$^4$)$_2$ or NR$^4$. In certain embodiments, Y is CH$_2$. In certain embodiments, Y is NR$^4$.

In certain embodiments, each $R^4$ is independently —H.

In certain embodiments, each $R^4$ is independently C$_{1-6}$ aliphatic, halogen, -haloalkyl, —OR, —SR, —CN, —NO$_2$, —SO$_2$R, —SOR, —C(O)R, —CO$_2$R, —C(O)N(R)$_2$, —C(NH)R, —C(NH)NR$_2$, —NRC(O)R, —NRC(O)N(R)$_2$, —NRSO$_2$R, —N(R)$_2$; or 5-6 membered monocyclic heteroaryl ring having 1-4 heteroatoms independently selected from nitrogen, oxygen, or sulfur.

In certain embodiments, each $R^4$ is independently —H, C$_{1-6}$ aliphatic, —OR, —C(O)R, —CO$_2$R, —C(O)N(R)$_2$, —C(NH)R, —C(NH)NR$_2$, —NRC(O)R, —NRC(O)N(R)$_2$, —NRSO$_2$R, —N(R)$_2$; or 5-6 membered monocyclic heteroaryl ring having 1-4 heteroatoms independently selected from nitrogen, oxygen, or sulfur; each of which is optionally substituted.

In certain embodiments, each $R^4$ is independently C$_{1-6}$ aliphatic, —C(O)R, —C(NH)NR$_2$, —NRC(O)R, —N(R)$_2$; or 5-6 membered monocyclic heteroaryl ring having 1-4 heteroatoms independently selected from nitrogen, oxygen, or sulfur; each of which is optionally substituted.

In certain embodiments, each $R^4$ is independently

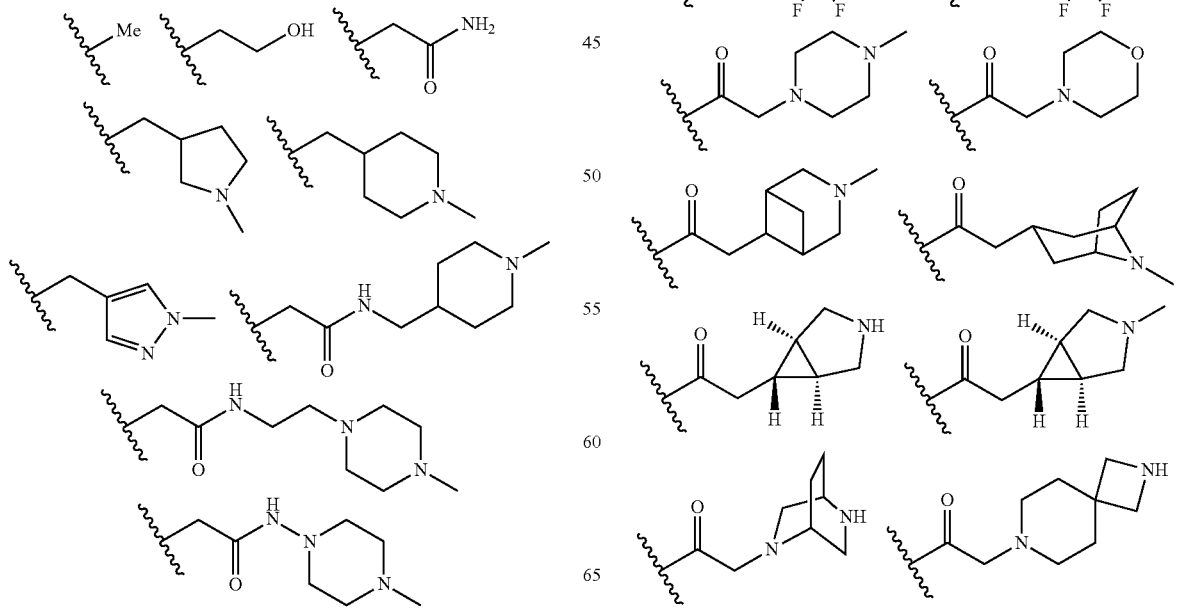

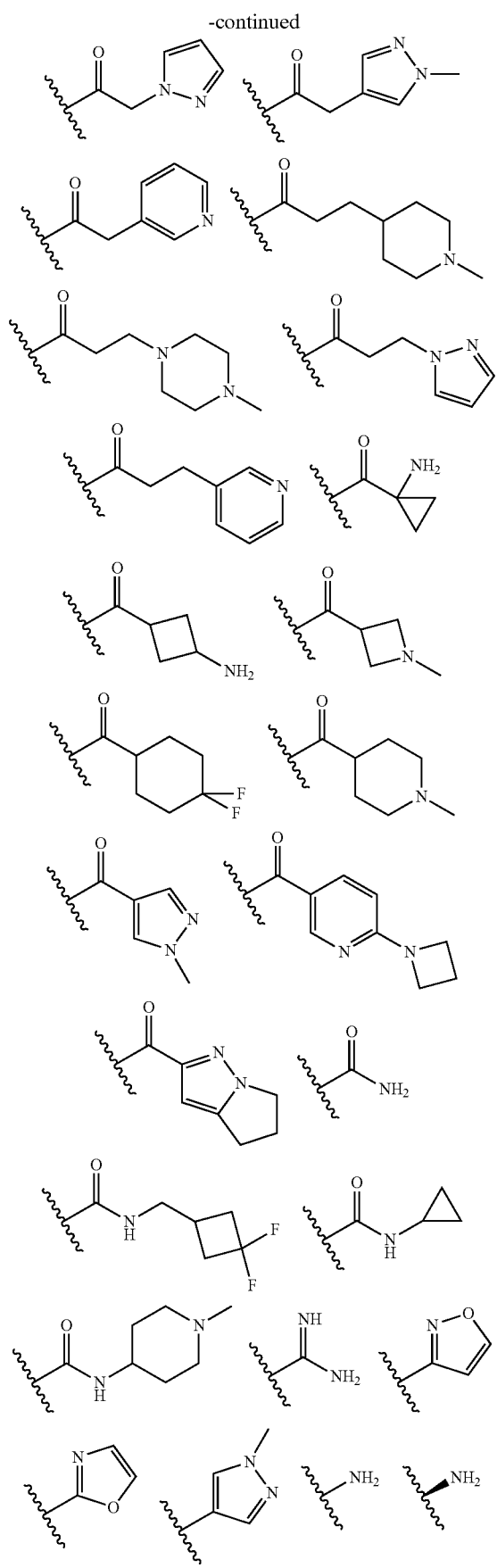
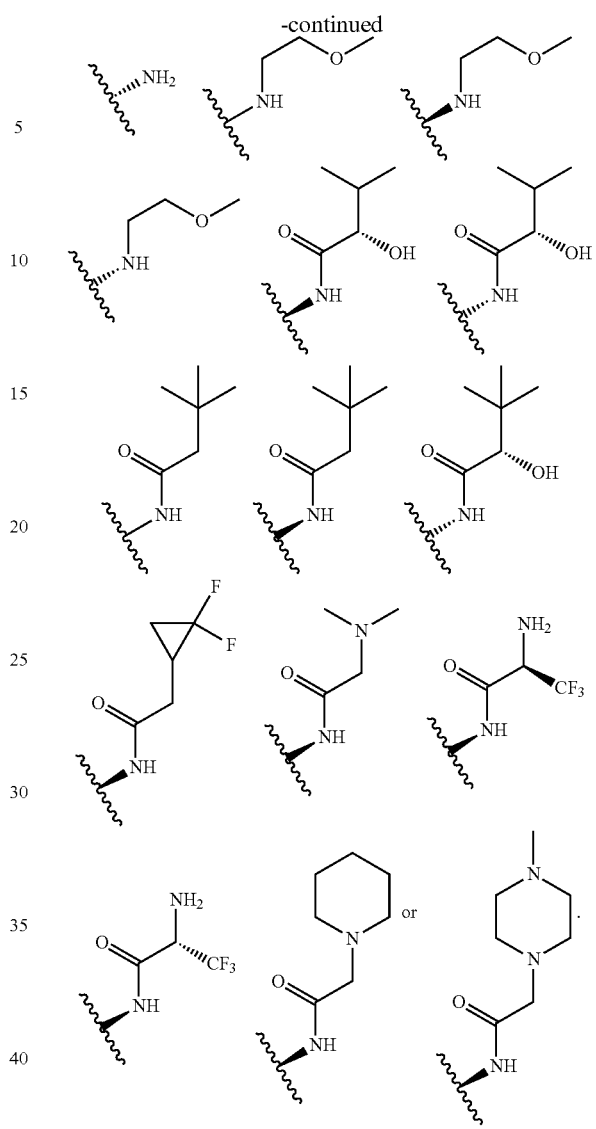

In certain embodiments, each $R^5$ is independently —H.

In certain embodiments, each $R^5$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^5$ is independently methyl, ethyl, ethyl, propyl, i-propyl, butyl, s-butyl, t-butyl, straight or branched pentyl, or straight or branched hexyl; each of which is optionally substituted.

In certain embodiments, each $R^5$ is independently

In certain embodiments, each of X, Y, Ring A, Ring B, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-a,

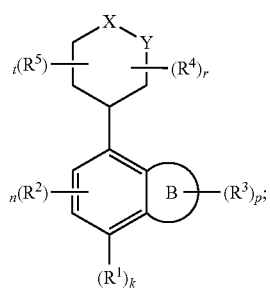

I-a or a pharmaceutically acceptable salt thereof, wherein each of X, Y, Ring B, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-b,

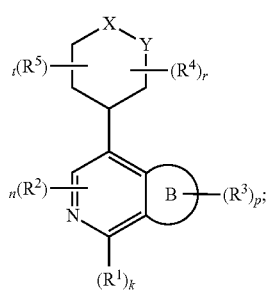

I-b or a pharmaceutically acceptable salt thereof, wherein each of X, Y, Ring B, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-c,

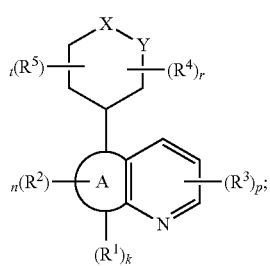

I-c or a pharmaceutically acceptable salt thereof, wherein each of X, Y, Ring B, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-d,

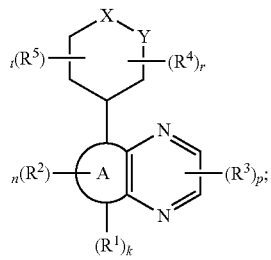

I-d or a pharmaceutically acceptable salt thereof, wherein each of X, Y, Ring B, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-e,

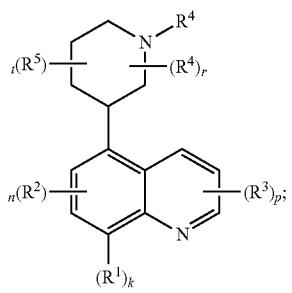

I-e or a pharmaceutically acceptable salt thereof, wherein each of $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-f,

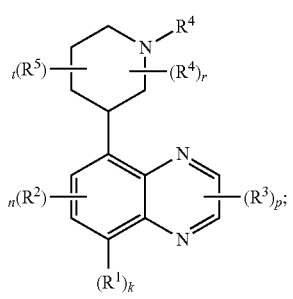

I-f or a pharmaceutically acceptable salt thereof, wherein each of $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-g, I-g

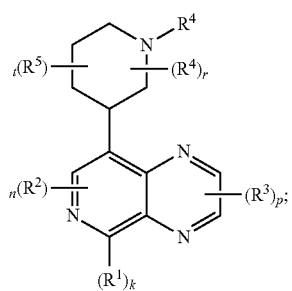

or a pharmaceutically acceptable salt thereof, wherein each of $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-h, I-h

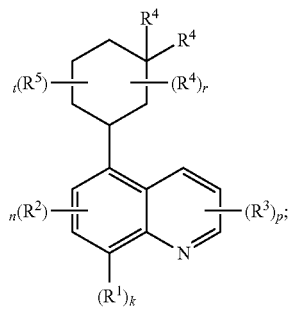

or a pharmaceutically acceptable salt thereof, wherein each of $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-j, I-j

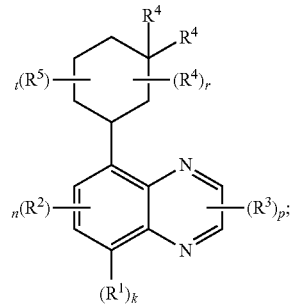

or a pharmaceutically acceptable salt thereof, wherein each of $R^1$, $R^2$, $R^3$, $R^4$, $R^5$, k, n, p, r, and t, is as defined above and described in embodiments, classes and subclasses above and herein, singly or in combination.

In certain embodiments, the invention provides a compound selected from Table 1:

TABLE 1

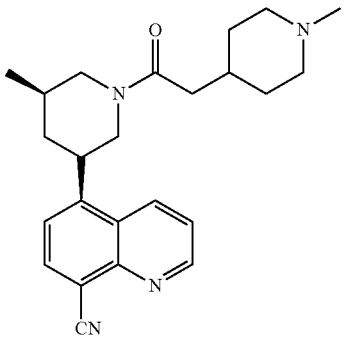
Compound 1

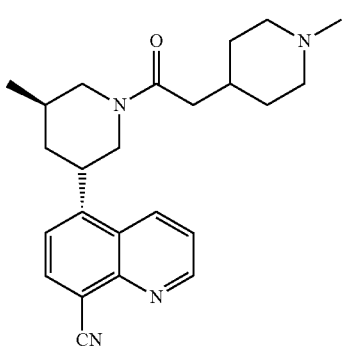
Compound 2

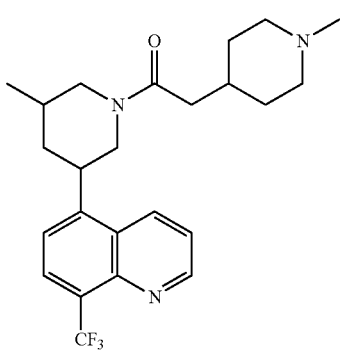
Compound 3

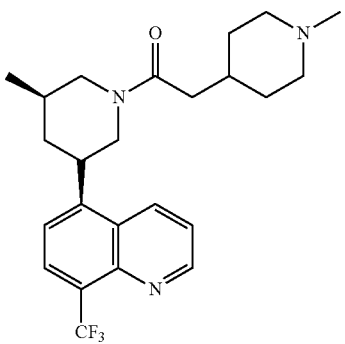
Compound 4

TABLE 1-continued
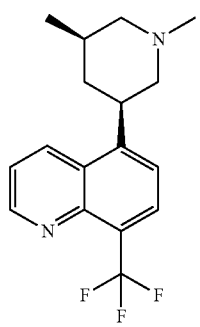 [SMILES: C[C@@H]1C[C@H](c2ccc(C(F)(F)F)c3ncccc23)CN(C)C1] Compound 5
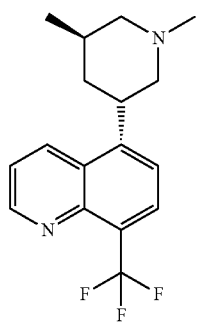 Compound 6
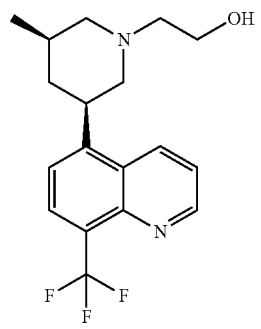 [SMILES: C[C@@H]1C[C@H](c2ccc(C(F)(F)F)c3ncccc23)CN(CCO)C1] Compound 7
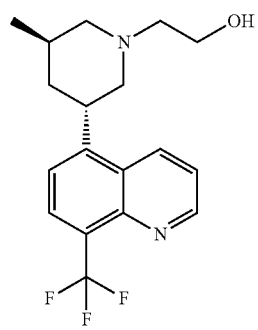 [SMILES: C[C@@H]1C[C@@H](c2ccc(C(F)(F)F)c3ncccc23)CN(CCO)C1] Compound 8
TABLE 1-continued
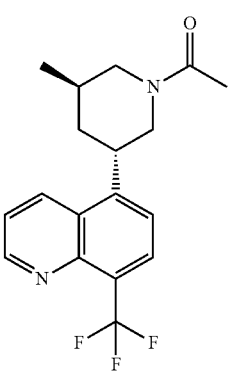 Compound 9
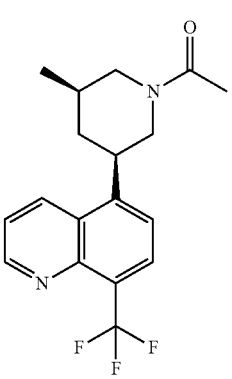 [SMILES: CC(=O)N1C[C@H](C)C[C@H](c2ccc(C(F)(F)F)c3ncccc23)C1] Compound 10
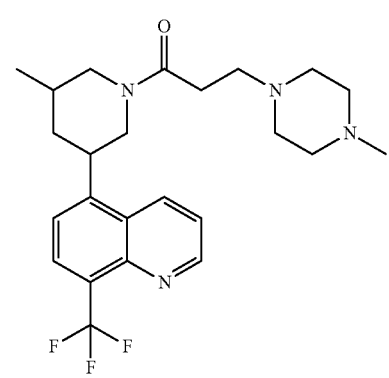 Compound 11
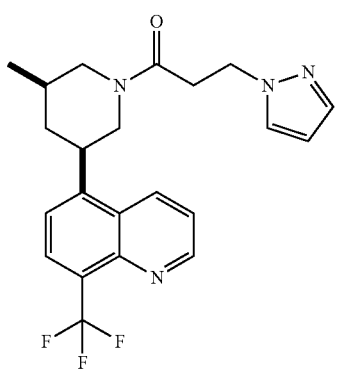 Compound 12

TABLE 1-continued
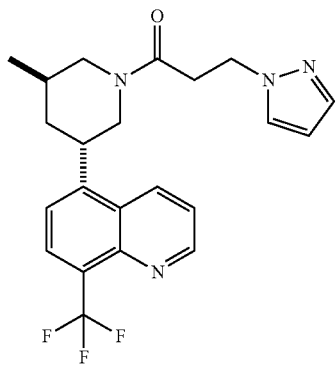
Compound 13
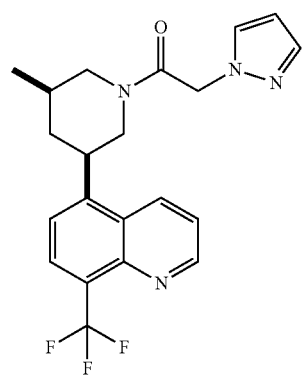
Compound 14
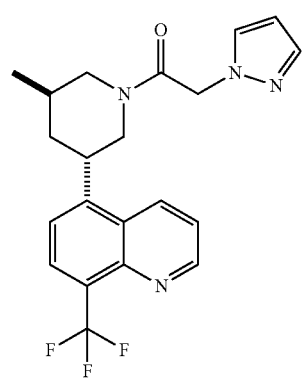
Compound 15
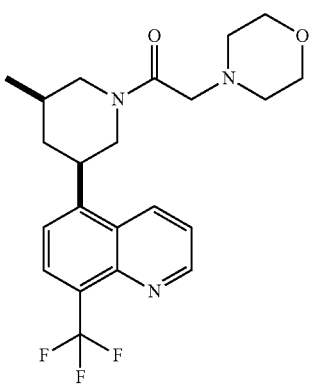
Compound 16
TABLE 1-continued
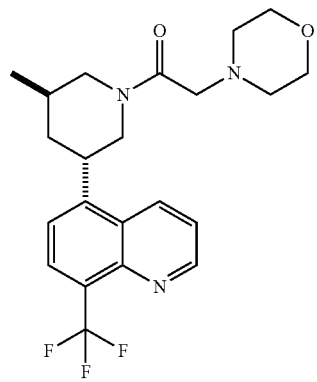
Compound 17
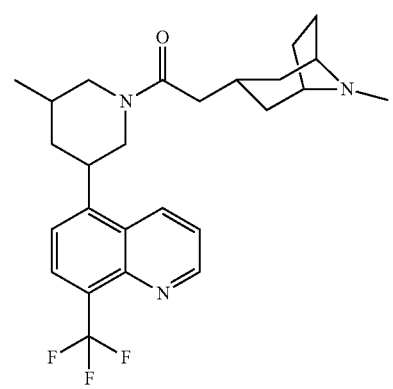
Compound 18
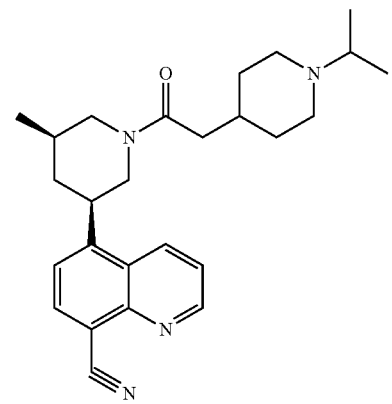 [SMILES: CC(C)N1CCC(CC(=O)N2C[C@H](C)C[C@H](c3ccc(C#N)c4ncccc34)C2)CC1]
Compound 19
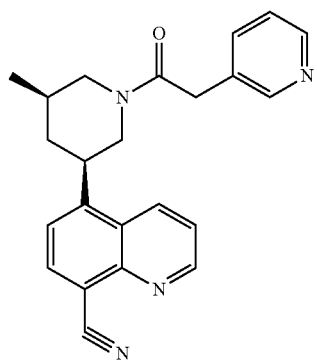 [SMILES: C[C@@H]1C[C@H](c2ccc(C#N)c3ncccc23)CN(C(=O)Cc2cccnc2)C1]
Compound 20

TABLE 1-continued
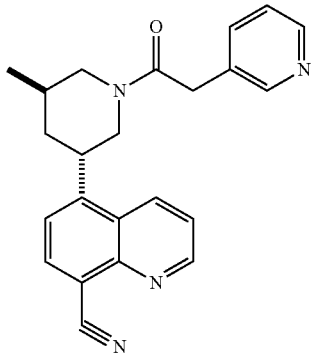
Compound 21
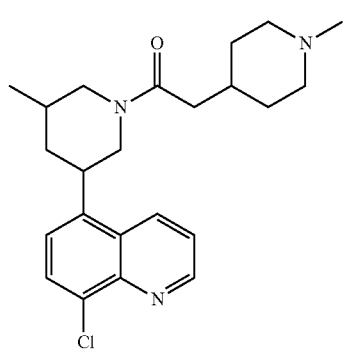
Compound 22
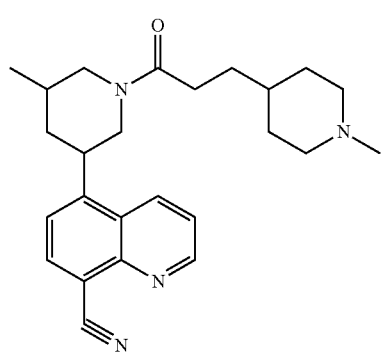
Compound 23
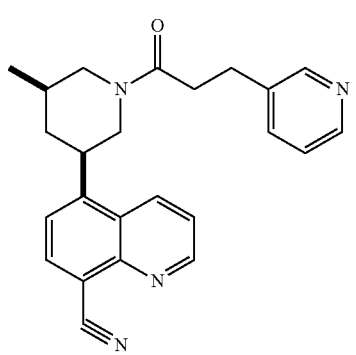
Compound 24
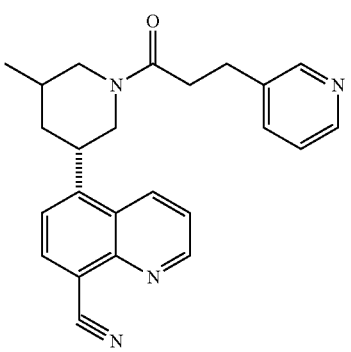
Compound 25
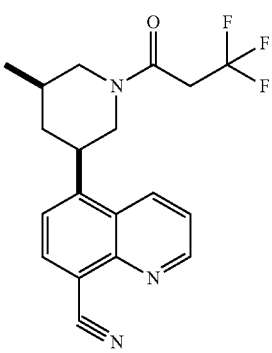
Compound 26
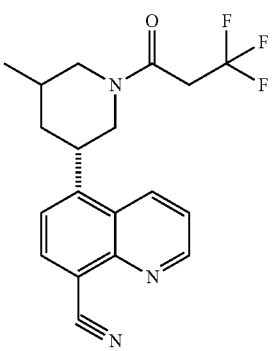
Compound 27
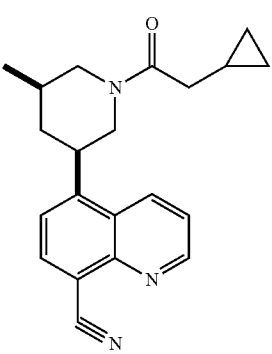
Compound 28

TABLE 1-continued
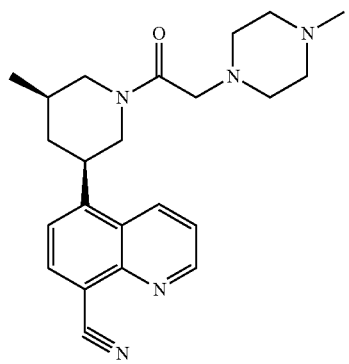
Compound 29
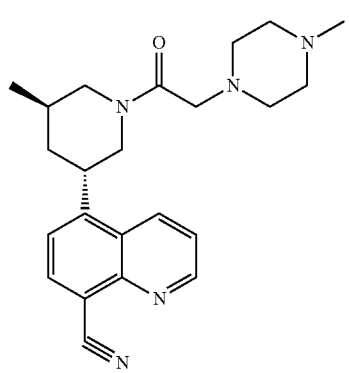
Compound 30
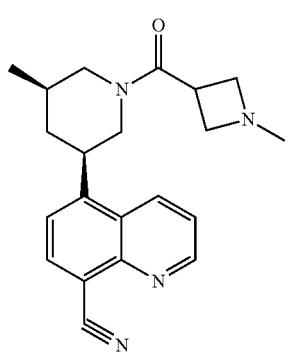
Compound 31
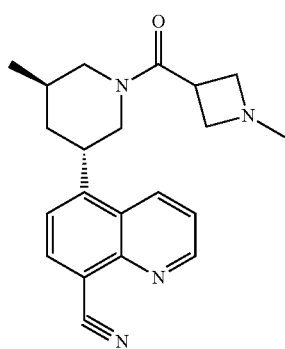
Compound 32
TABLE 1-continued
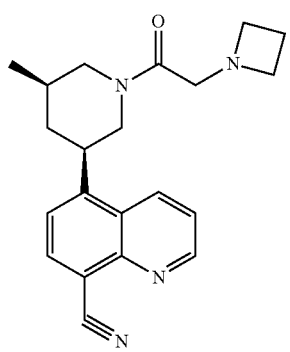 [SMILES: C[C@@H]1C[C@H](c2ccc(C#N)c3ncccc23)CN(C(=O)CN2CCC2)C1]
Compound 33
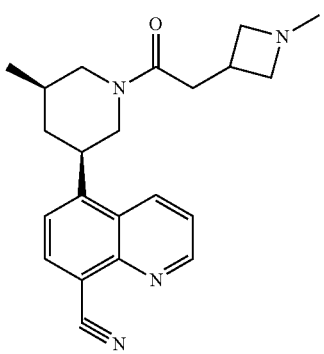
Compound 34
Compound 35
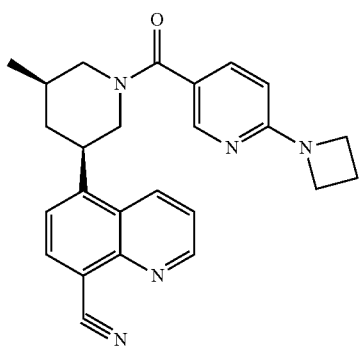 [SMILES: C[C@@H]1C[C@H](c2ccc(C#N)c3ncccc23)CN(C(=O)c2ccc(N3CCC3)nc2)C1]
Compound 36

TABLE 1-continued
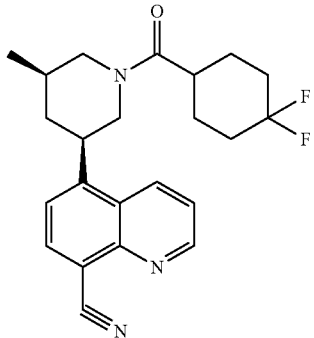 [SMILES: C[C@@H]1C[C@H](c2ccc(C#N)c3ncccc23)CN(C(=O)C2CCC(F)(F)CC2)C1]
Compound 37
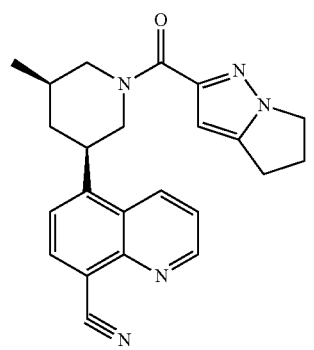 [SMILES: C[C@@H]1C[C@H](c2ccc(C#N)c3ncccc23)CN(C(=O)c2cc3n(n2)CCC3)C1]
Compound 38
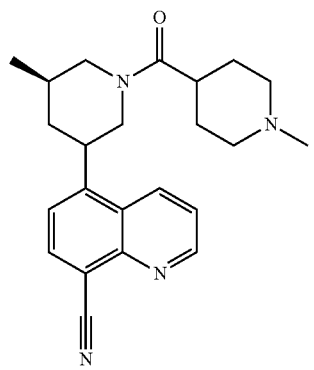
Compound 39
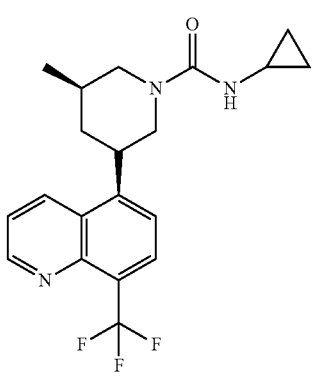
Compound 40
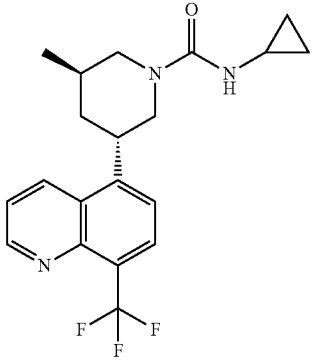 [SMILES: C[C@@H]1C[C@@H](c2ccc(C(F)(F)F)c3ncccc23)CN(C(=O)NC2CC2)C1]
Compound 41
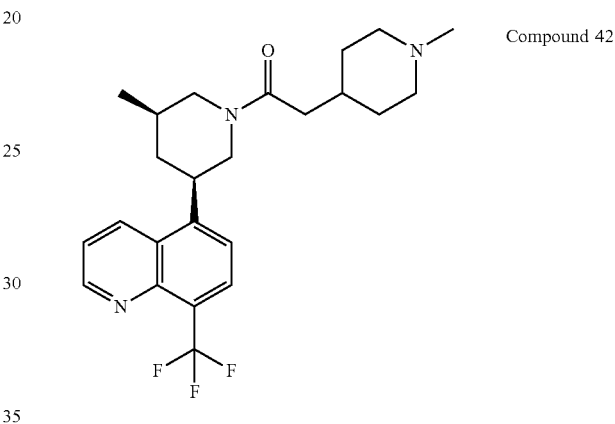
Compound 42
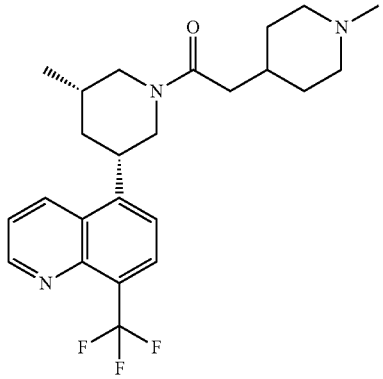 [SMILES: C[C@H]1C[C@@H](c2ccc(C(F)(F)F)c3ncccc23)CN(C(=O)CC2CCN(C)CC2)C1]
Compound 43
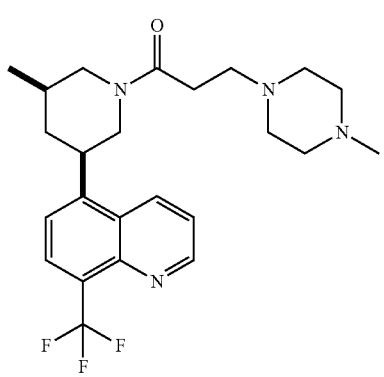
Compound 44

TABLE 1-continued
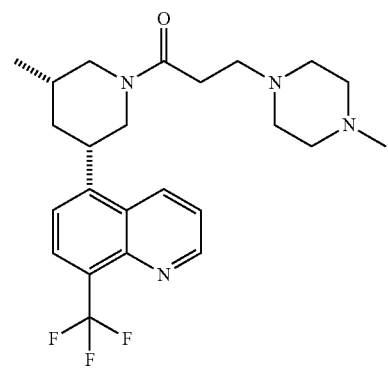
Compound 45
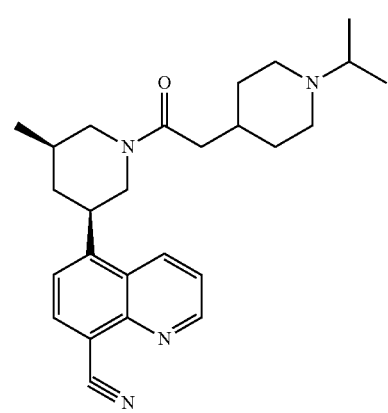 [SMILES: CC(C)N1CCC(CC(=O)N2C[C@H](C)C[C@H](c3ccc(C#N)c4ncccc34)C2)CC1]
Compound 46
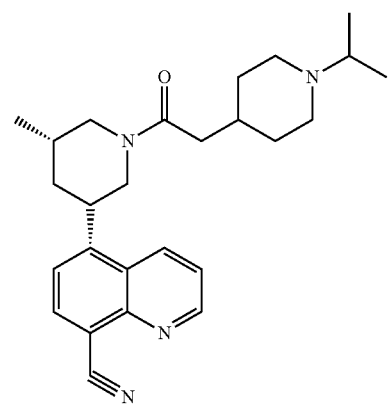
Compound 47
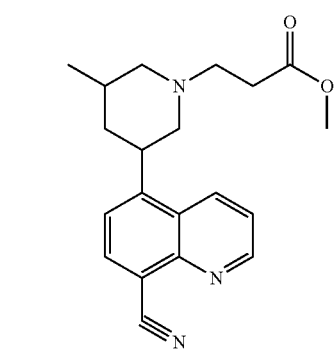
Compound 48
TABLE 1-continued
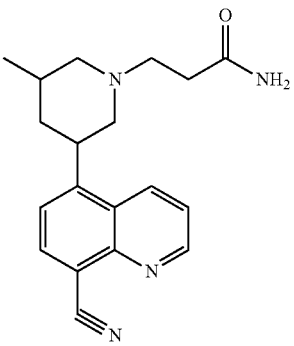 [SMILES: CC1CC(c2ccc(C#N)c3ncccc23)CN(CCC(N)=O)C1]
Compound 49
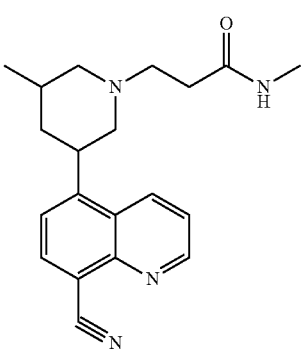
Compound 50
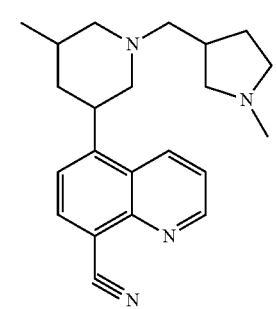 [SMILES: CC1CC(c2ccc(C#N)c3ncccc23)CN(CC2CCN(C)C2)C1]
Compound 51
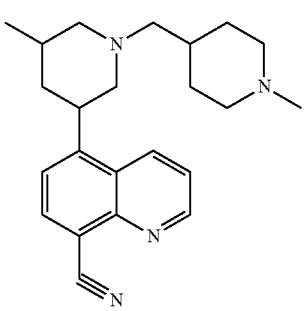
Compound 52
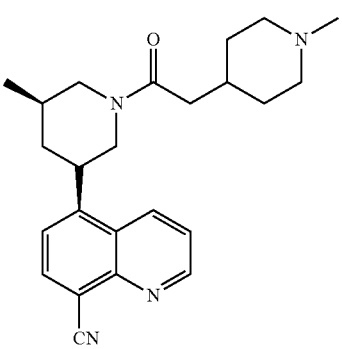
Compound 53

TABLE 1-continued
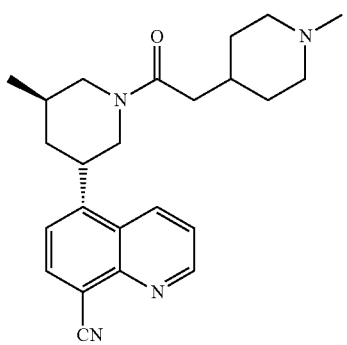
Compound 54
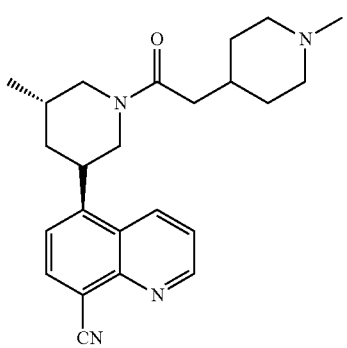
Compound 55
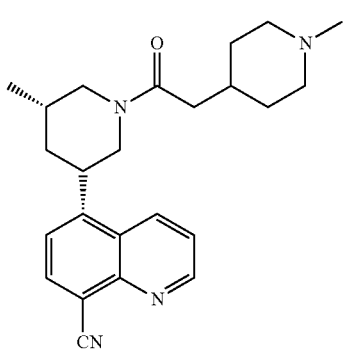
Compound 56
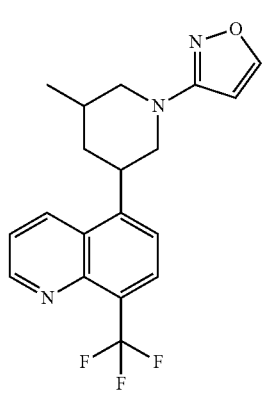 [SMILES: CC1CC(c2ccc(C(F)(F)F)c3ncccc23)CN(c2ccon2)C1]
Compound 57
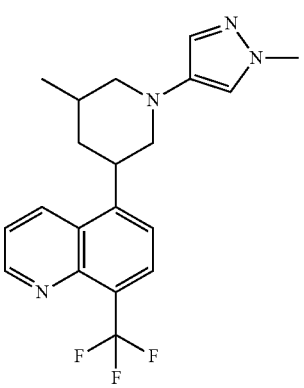 [SMILES: CC1CC(c2ccc(C(F)(F)F)c3ncccc23)CN(c2cnn(C)c2)C1]
Compound 58
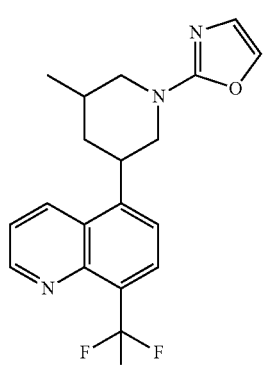
Compound 59
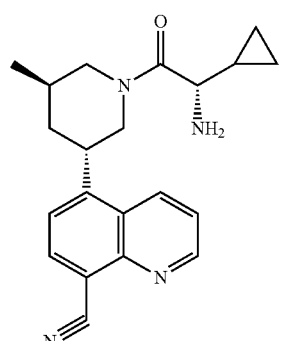
Compound 60
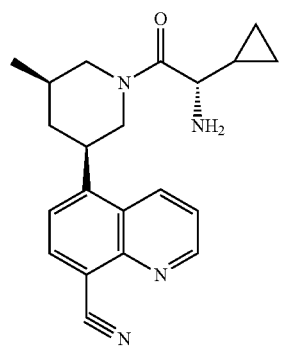 [SMILES: C[C@@H]1C[C@H](c2ccc(C#N)c3ncccc23)CN(C(=O)[C@@H](N)C2CC2)C1]
Compound 61

TABLE 1-continued
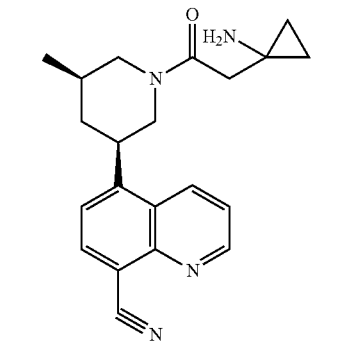 [SMILES: C[C@@H]1C[C@H](c2ccc(C#N)c3ncccc23)CN(C(=O)CC2(N)CC2)C1]
Compound 62
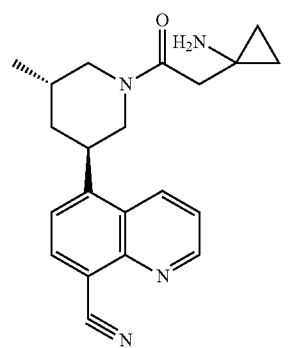 [SMILES: C[C@H]1C[C@H](c2ccc(C#N)c3ncccc23)CN(C(=O)CC2(N)CC2)C1]
Compound 63
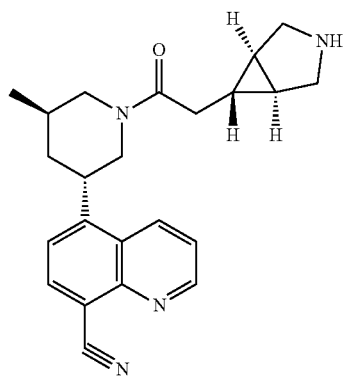 [SMILES: C[C@@H]1C[C@@H](c2ccc(C#N)c3ncccc23)CN(C(=O)C[C@H]2[C@@H]3CNC[C@@H]32)C1]
Compound 64
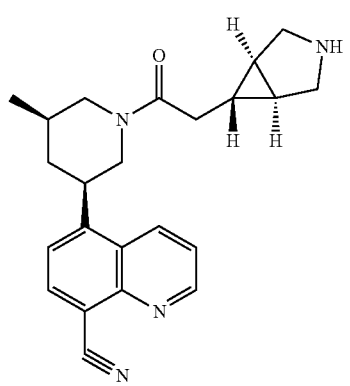 [SMILES: C[C@@H]1C[C@H](c2ccc(C#N)c3ncccc23)CN(C(=O)C[C@H]2[C@@H]3CNC[C@@H]32)C1]
Compound 65
TABLE 1-continued
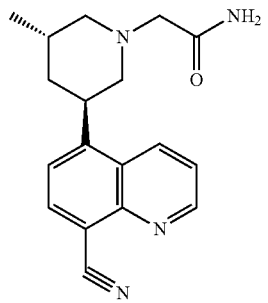 [SMILES: C[C@H]1C[C@H](c2ccc(C#N)c3ncccc23)CN(CC(N)=O)C1]
Compound 66
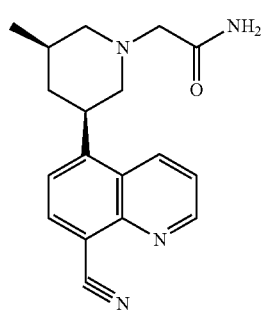 [SMILES: C[C@@H]1C[C@H](c2ccc(C#N)c3ncccc23)CN(CC(N)=O)C1]
Compound 67
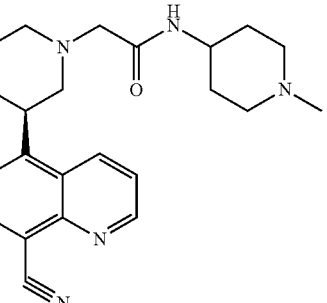
Compound 68
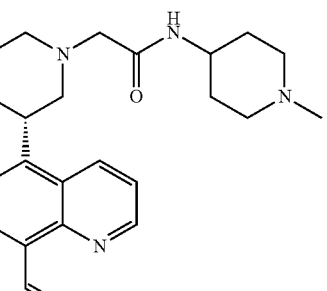
Compound 69
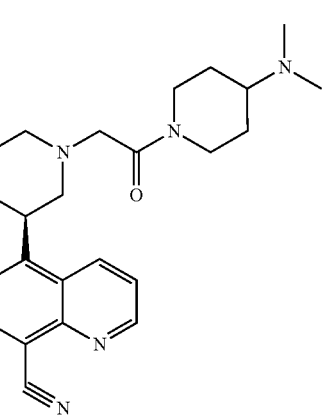
Compound 70

TABLE 1-continued
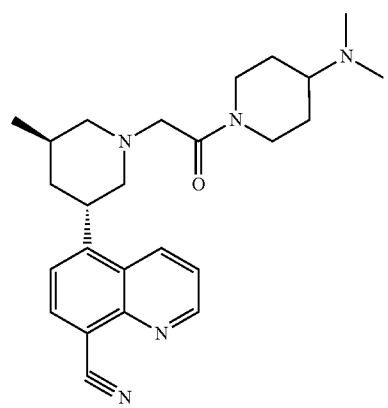
Compound 71
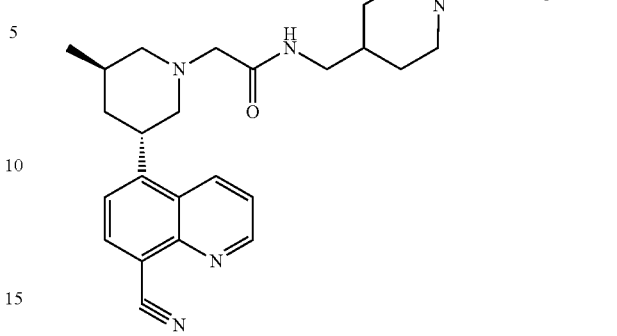
Compound 75
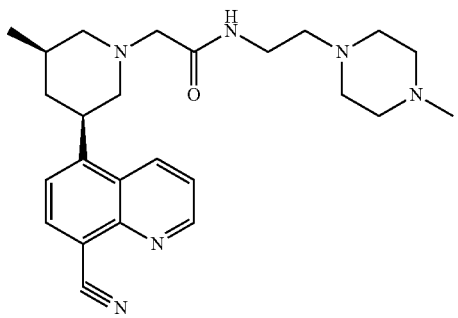
Compound 72
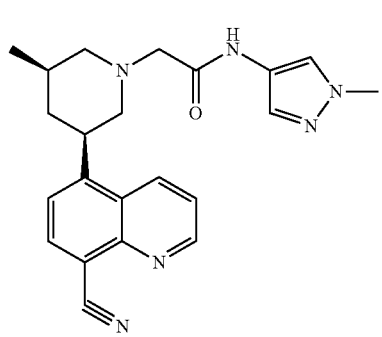
Compound 76
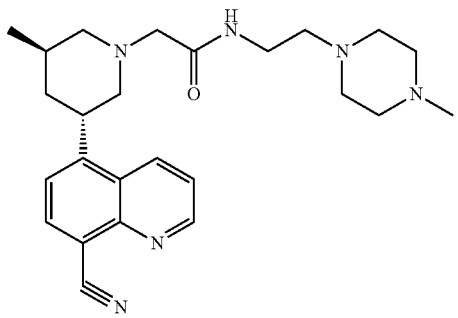
Compound 73
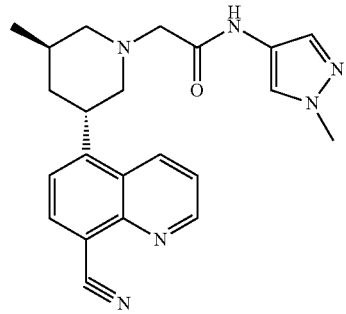 [SMILES: C[C@@H]1C[C@@H](c2ccc(C#N)c3ncccc23)CN(CC(=O)Nc2cnn(C)c2)C1]
Compound 77
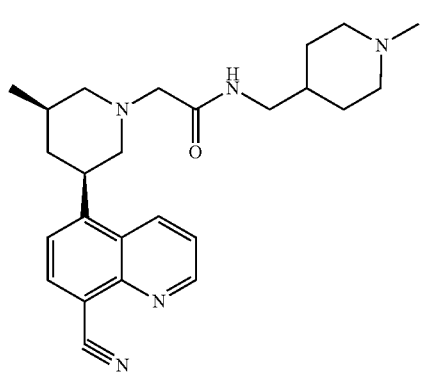
Compound 74
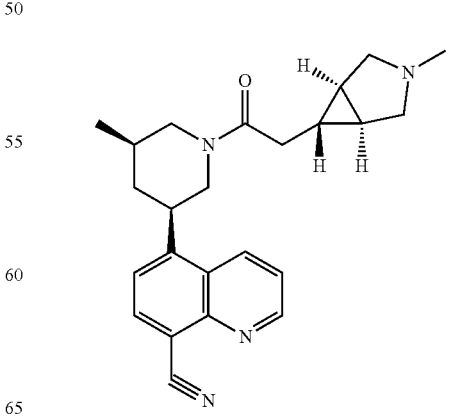
Compound 78

TABLE 1-continued
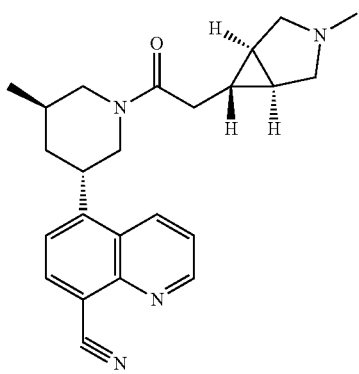
Compound 79
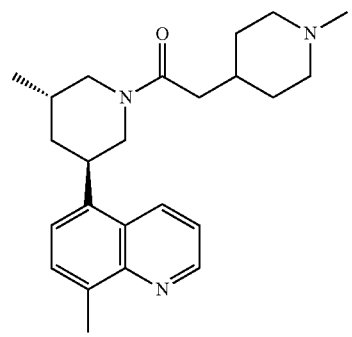
Compound 83
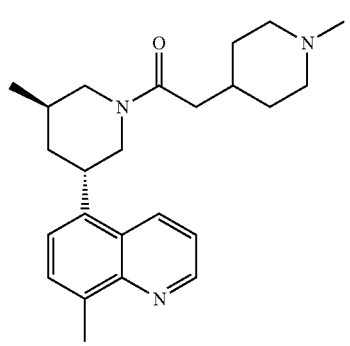
Compound 80
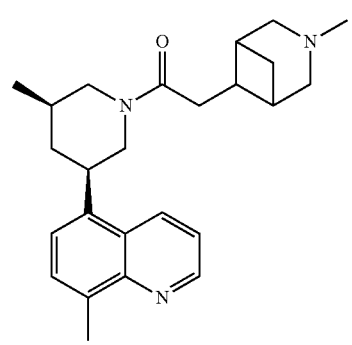
Compound 84
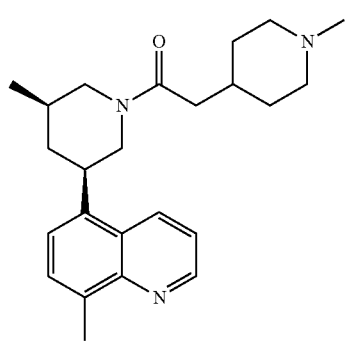
Compound 81
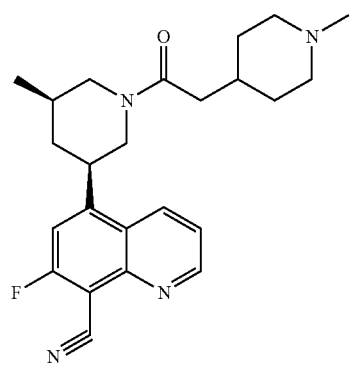
Compound 85
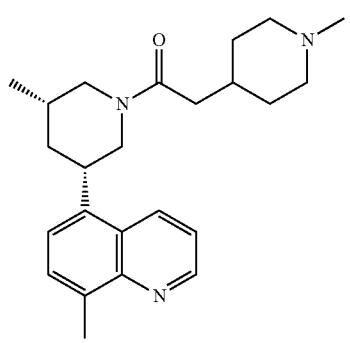
Compound 82
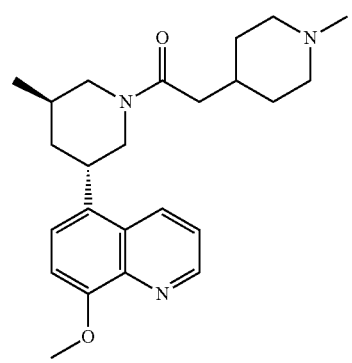
Compound 86

TABLE 1-continued
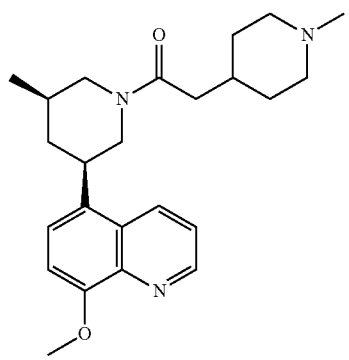 Compound 87
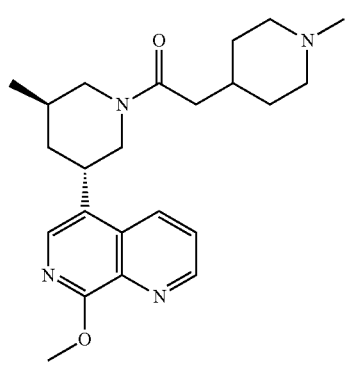 Compound 88
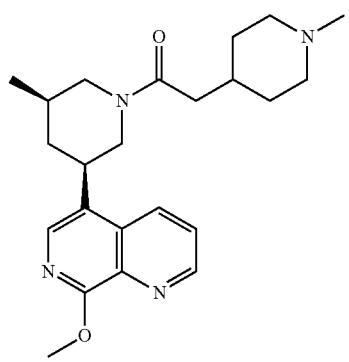 Compound 89
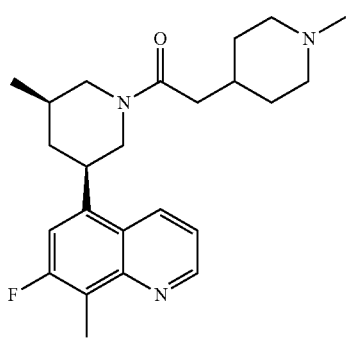 Compound 90
TABLE 1-continued
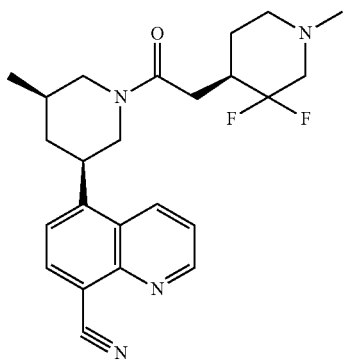 Compound 91
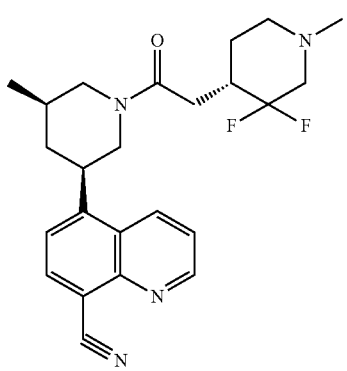 Compound 92
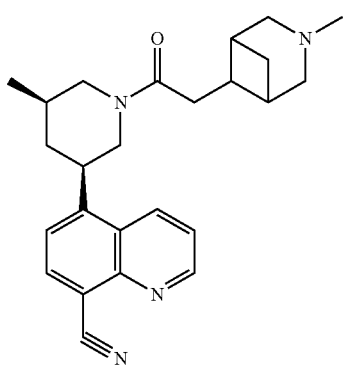 Compound 93
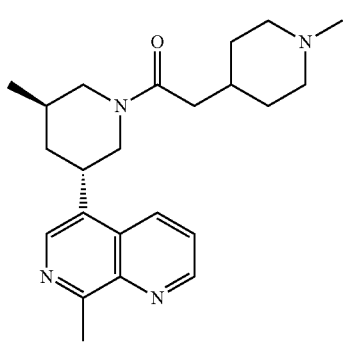 Compound 94

TABLE 1-continued
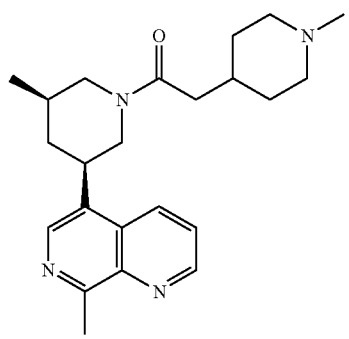
Compound 95
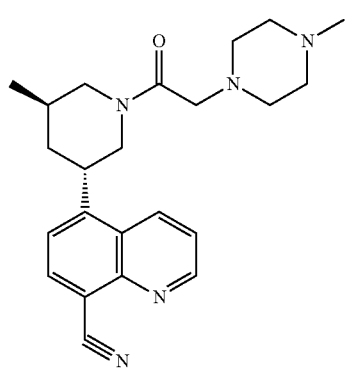
Compound 96
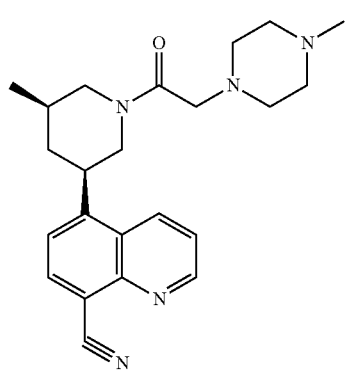
Compound 97
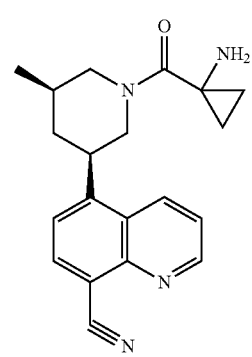 [SMILES: C[C@@H]1C[C@H](c2ccc(C#N)c3ncccc23)CN(C(=O)C2(N)CC2)C1]
Compound 98
TABLE 1-continued
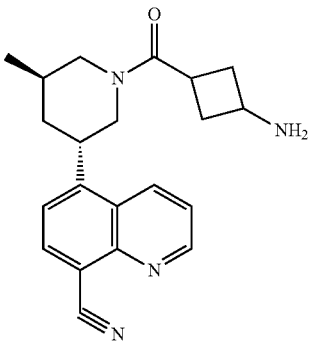 [SMILES: C[C@@H]1C[C@@H](c2ccc(C#N)c3ncccc23)CN(C(=O)C2CC(N)C2)C1]
Compound 99
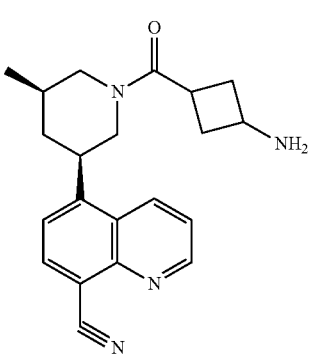 [SMILES: C[C@@H]1C[C@H](c2ccc(C#N)c3ncccc23)CN(C(=O)C2CC(N)C2)C1]
Compound 100
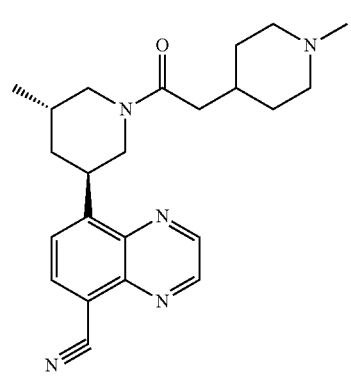
Compound 101
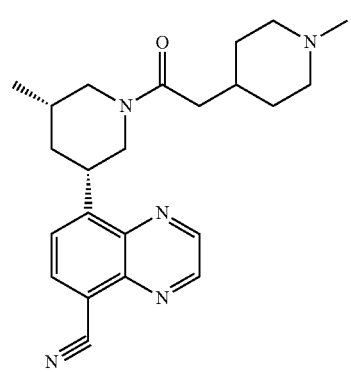
Compound 102

TABLE 1-continued
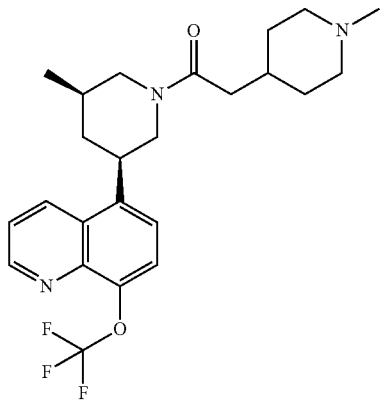 [SMILES: C[C@@H]1C[C@H](c2ccc(OC(F)(F)F)c3ncccc23)CN(C(=O)CC2CCN(C)CC2)C1]
Compound 103
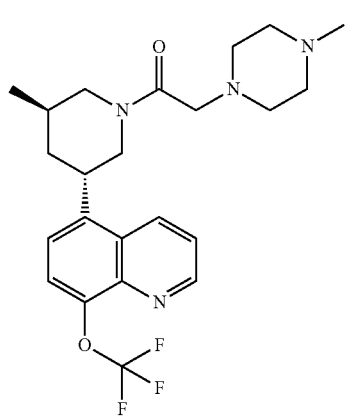
Compound 104
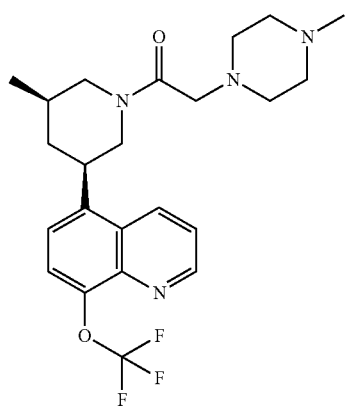
Compound 105
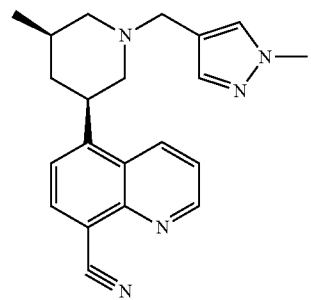
Compound 106
TABLE 1-continued
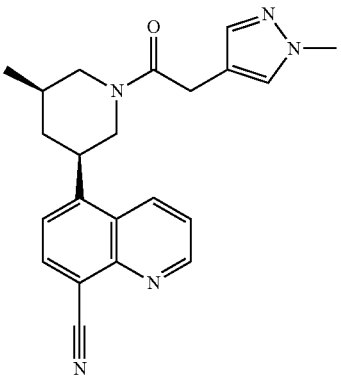
Compound 107
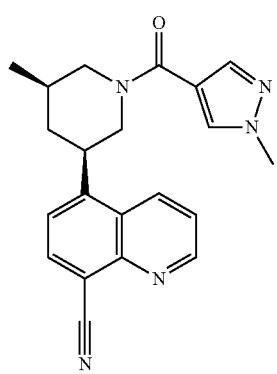
Compound 108
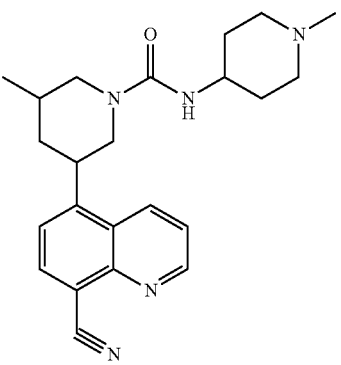
Compound 109
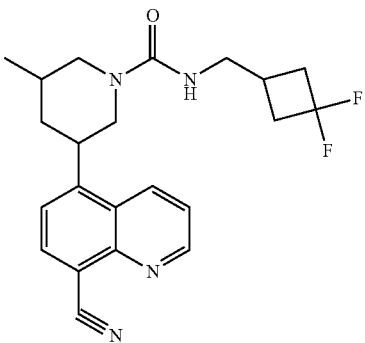 [SMILES: CC1CC(c2ccc(C#N)c3ncccc23)CN(C(=O)NCC2CC(F)(F)C2)C1]
Compound 110

TABLE 1-continued
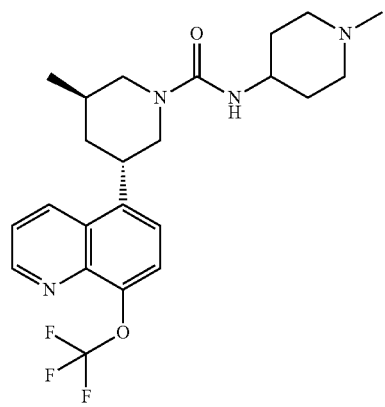 [SMILES: C[C@@H]1C[C@@H](c2ccc(OC(F)(F)F)c3ncccc23)CN(C(=O)NC2CCN(C)CC2)C1]
Compound 111
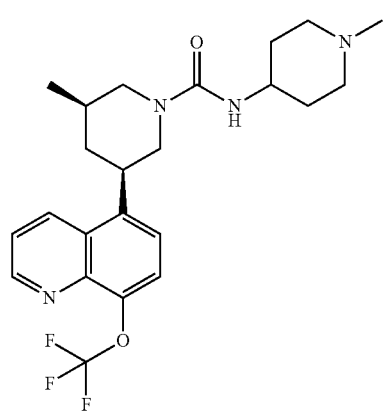 [SMILES: C[C@@H]1C[C@H](c2ccc(OC(F)(F)F)c3ncccc23)CN(C(=O)NC2CCN(C)CC2)C1]
Compound 112
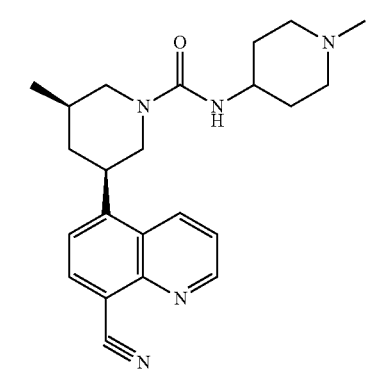
Compound 113
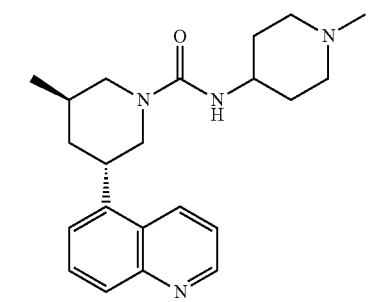
Compound 114
TABLE 1-continued
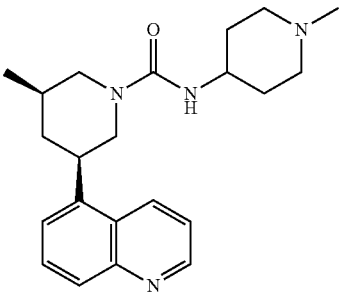
Compound 115
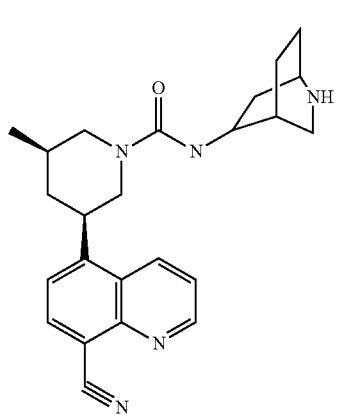 [SMILES: C[C@@H]1C[C@H](c2ccc(C#N)c3ncccc23)CN(C(=O)NC2CC3CCC2CN3)C1]
Compound 116
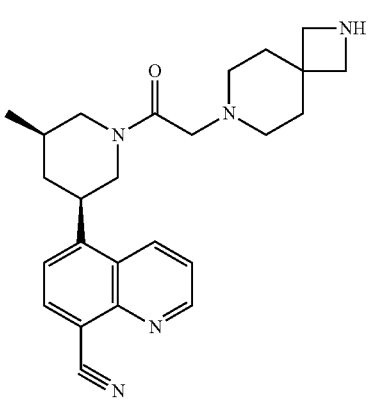 [SMILES: C[C@@H]1C[C@H](c2ccc(C#N)c3ncccc23)CN(C(=O)CN2CCC3(CC2)CNC3)C1]
Compound 117
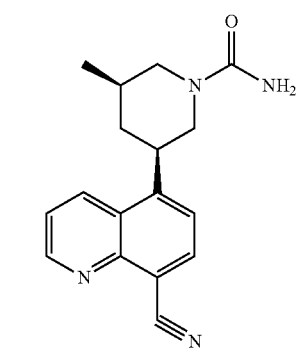 [SMILES: C[C@@H]1C[C@H](c2ccc(C#N)c3ncccc23)CN(C(N)=O)C1]
Compound 118

TABLE 1-continued
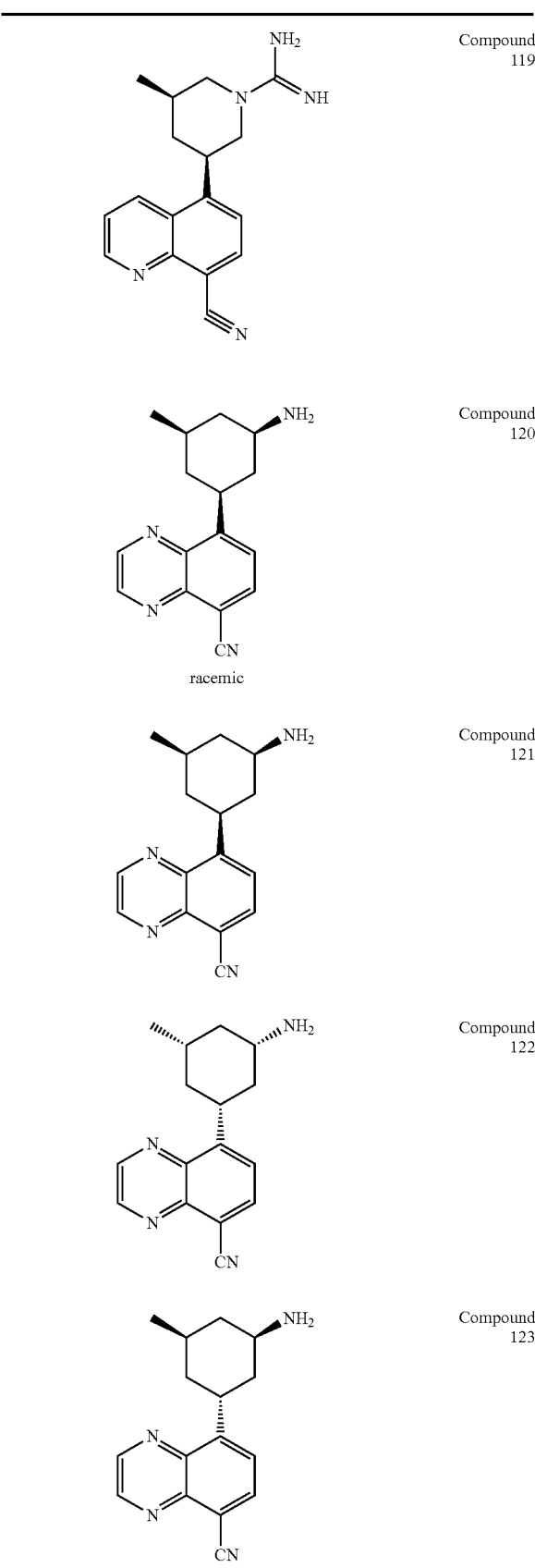
Compound 119
Compound 120 racemic
Compound 121
Compound 122
Compound 123
TABLE 1-continued
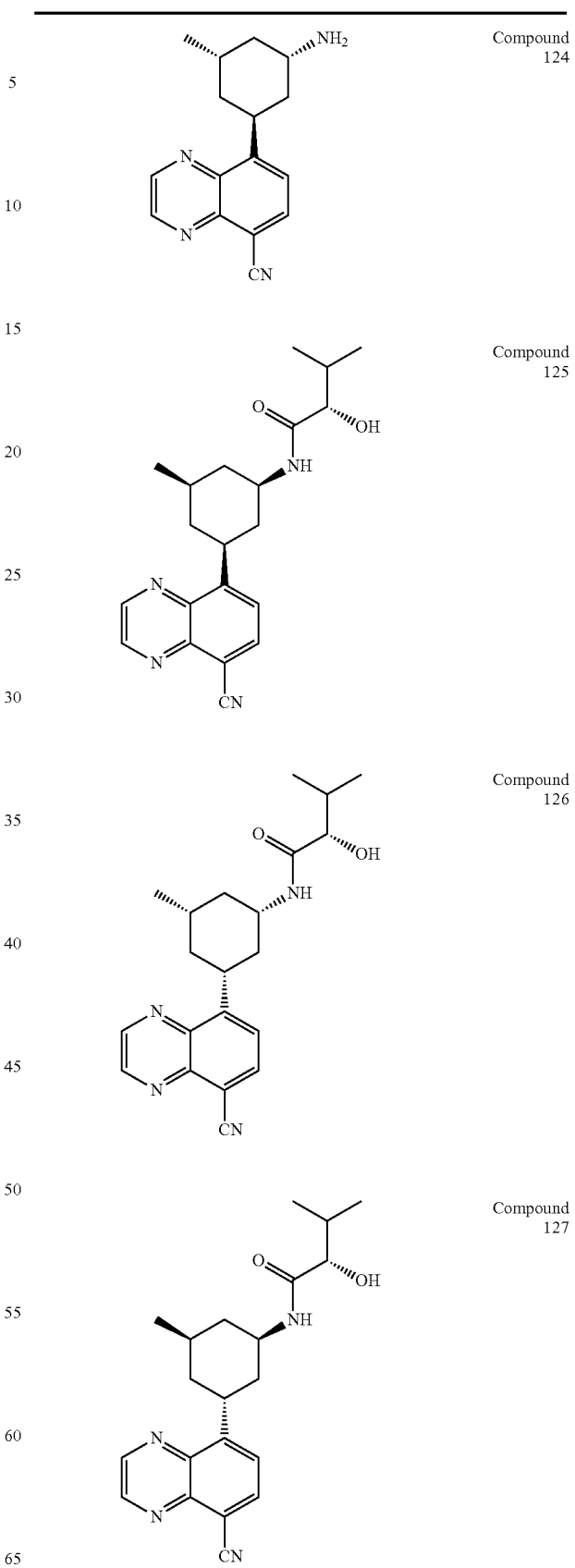
Compound 124
Compound 125
Compound 126
Compound 127

TABLE 1-continued
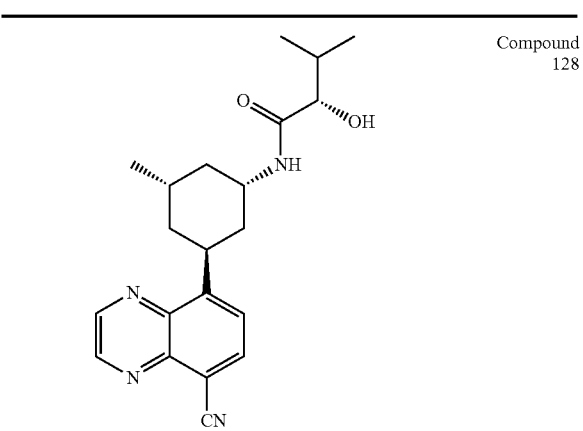
Compound 128
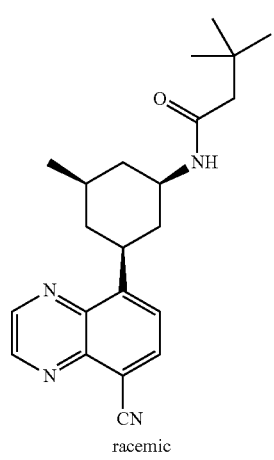
Compound 129
racemic
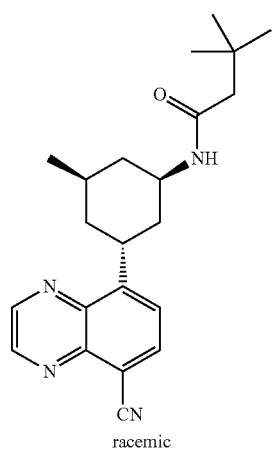
Compound 130
racemic
TABLE 1-continued
Compound 131
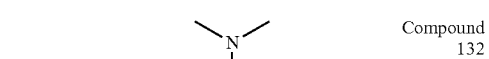
Compound 132
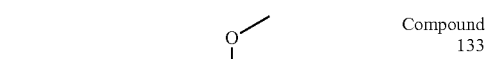
Compound 133
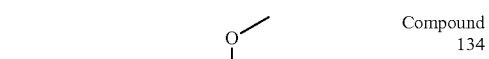
Compound 134

TABLE 1-continued
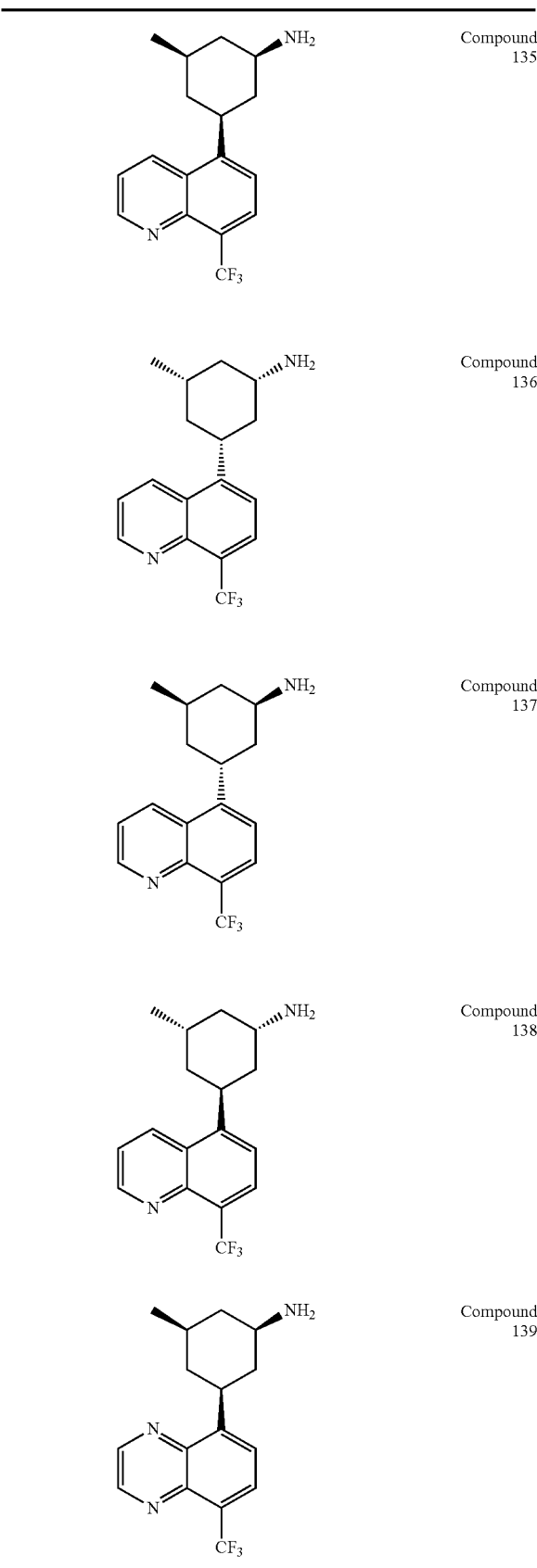
Compound 135
Compound 136
Compound 137
Compound 138
Compound 139
TABLE 1-continued
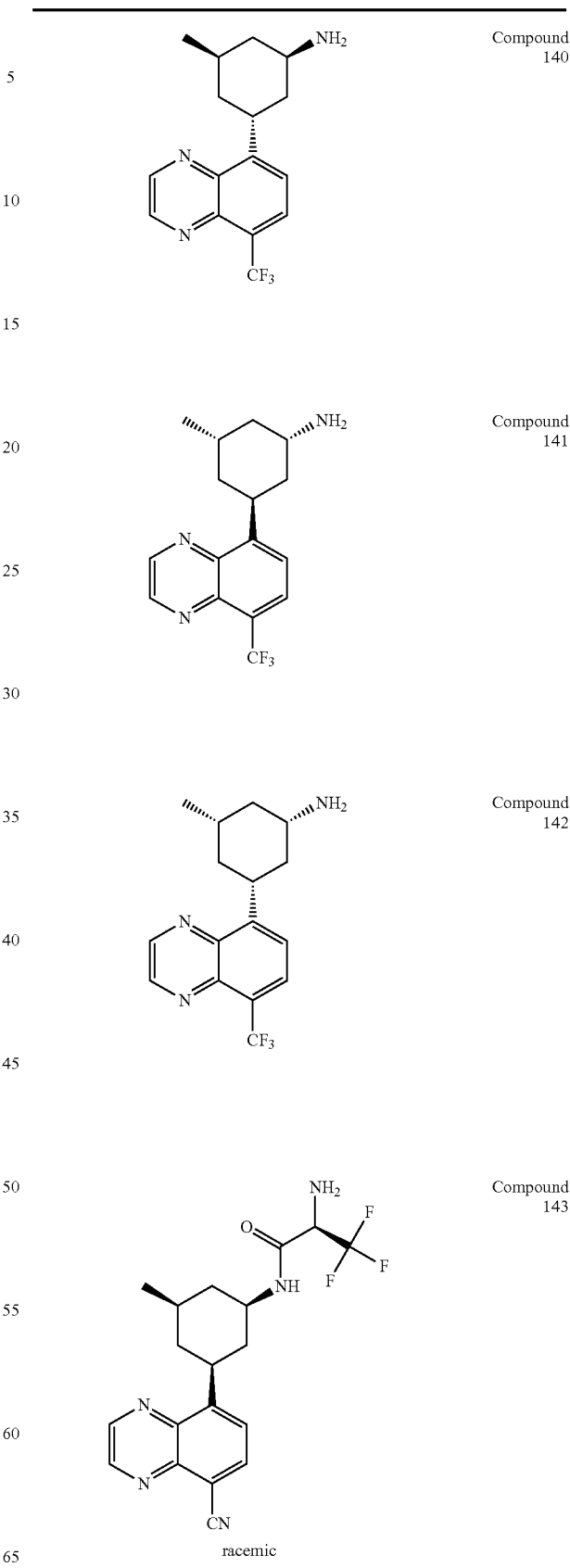
Compound 140
Compound 141
Compound 142
Compound 143
racemic TABLE 1-continued
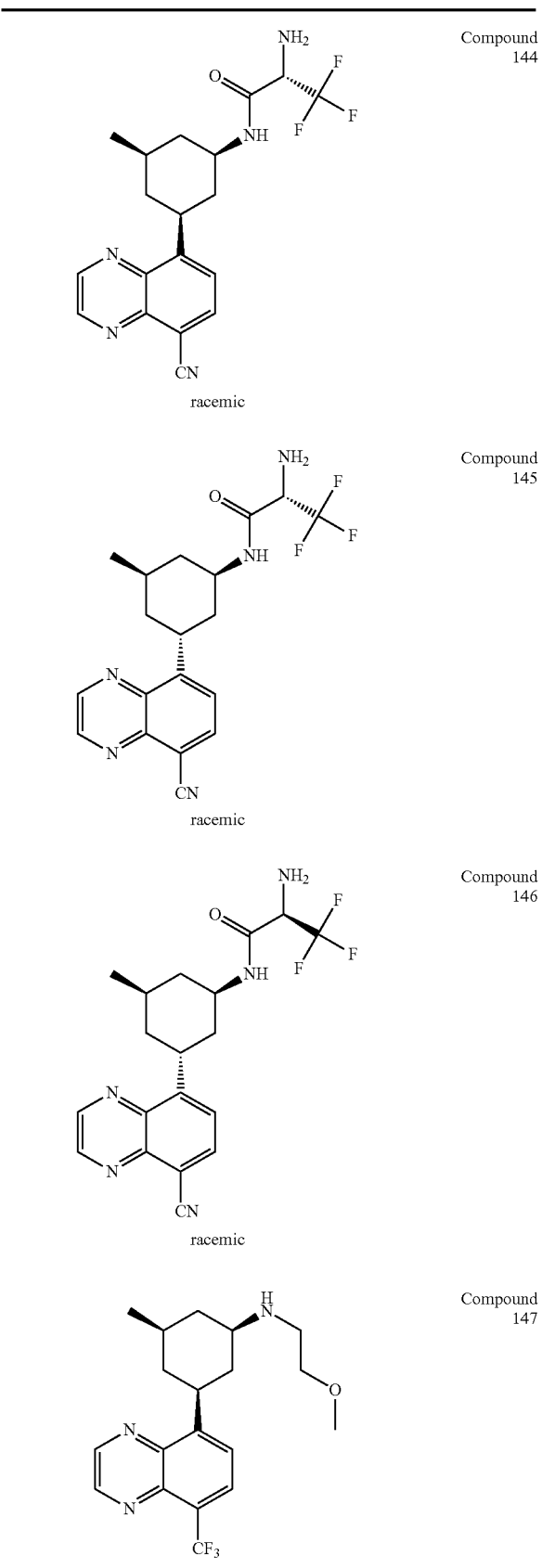
Compound 144
racemic
Compound 145
racemic
Compound 146
racemic
Compound 147
TABLE 1-continued
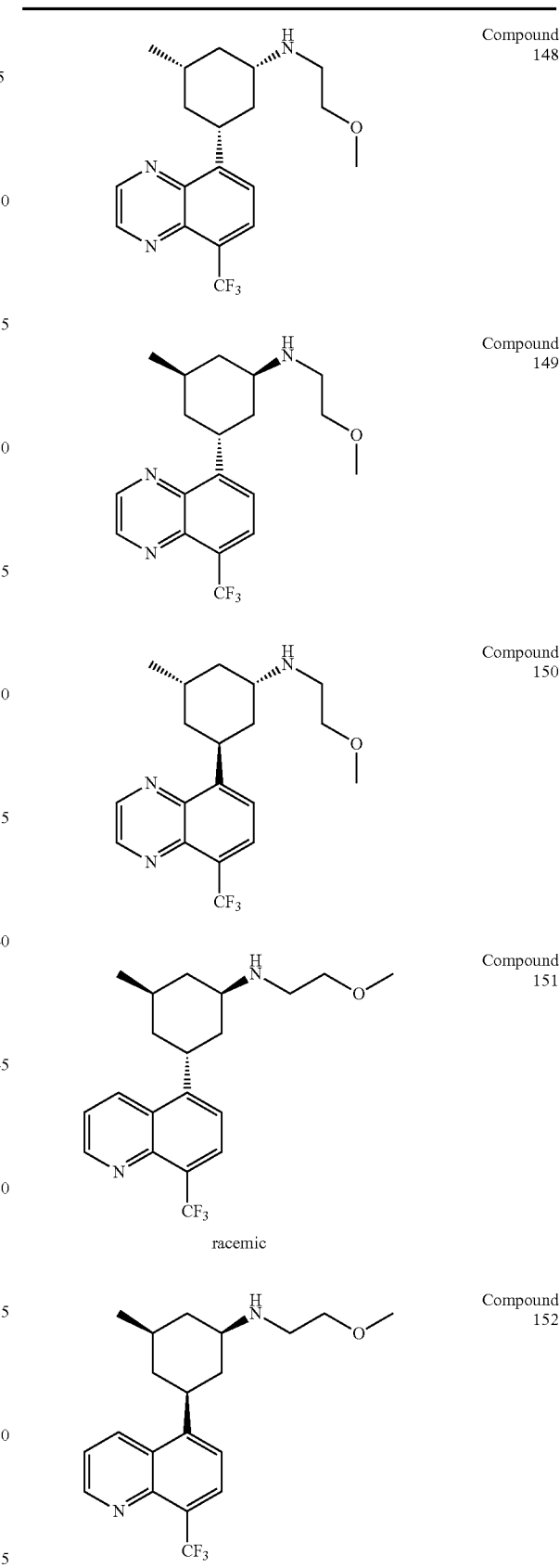
Compound 148
Compound 149
Compound 150
Compound 151
racemic
Compound 152

TABLE 1-continued

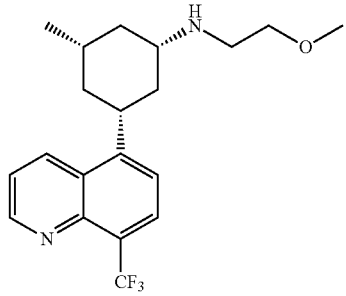 [SMILES: COCCN[C@H]1C[C@@H](C)C[C@@H](c2ccc(C(F)(F)F)c3ncccc23)C1]
Compound 153

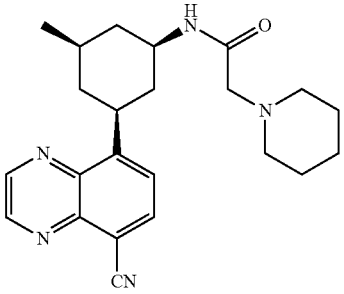
Compound 157
cis (+/−)

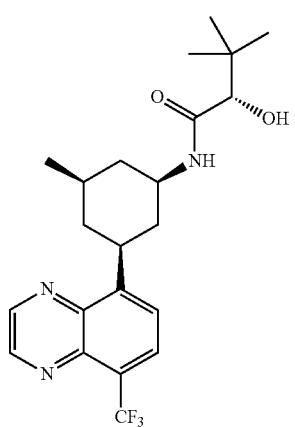 [SMILES: C[C@H]1C[C@@H](NC(=O)[C@@H](O)C(C)(C)C)C[C@@H](c2ccc(C(F)(F)F)c3nccnc23)C1]
Compound 154

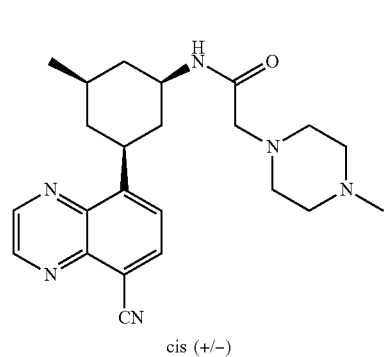
Compound 158
cis (+/−)

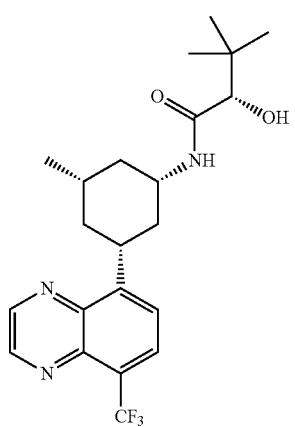 [SMILES: C[C@@H]1C[C@H](NC(=O)[C@@H](O)C(C)(C)C)C[C@H](c2ccc(C(F)(F)F)c3nccnc23)C1]
Compound 155

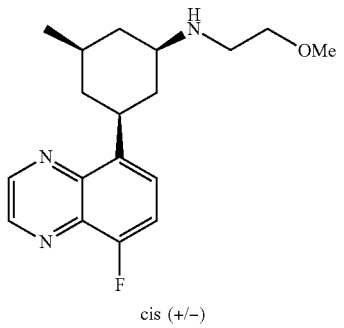
Compound 159
cis (+/−)

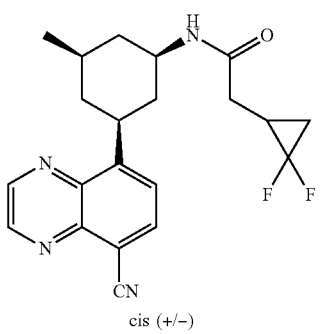
Compound 156
cis (+/−)

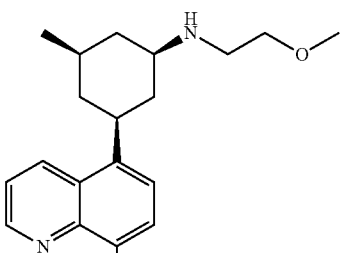
Compound 160
cis (+/−)

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g., 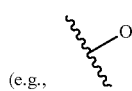

is understood to be

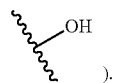).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit TLR7/8, or a mutant thereof, in a biological sample or in a patient. In certain embodiments, the amount of compound in compositions of this invention is such that is effective to measurably inhibit TLR7/8, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from a TLR7/8 related disorder, comprising administering to said subject an effective amount of a compound of formula I and related formulae.

The compounds of the present invention are useful as anticancer agents for cancers that are responsive to TLR7 activation. In certain embodiments, the cancers include, but are not limited to cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva; inherited cancers, retinomblastoma and Wilms tumor; leukemia, lymphoma, non-Hodgkins disease, chronic and acute myeloid leukaemia, acute lymphoblastic leukemia, Hodgkins disease, multiple myeloma and T-cell lymphoma; myelodysplastic syndrome, plasma cell neoplasia, paraneoplastic syndromes, cancers of unknown primary site and AIDS related malignancies.

In certain embodiments, the compounds of the invention are used to treat cancers of the skin or kidney. Sensitivity of a given cancer to activation of TLR7 can be assessed by, but not limited to measurement of a decrease in primary or metastatic tumor load (minor, partial or complete regression), alterations in the hemogram, altered hormone or cytokine concentrations in the blood, inhibition of further increase of tumor load, stabilization of the disease in the patient, assessment of biomarkers or surrogate markers relevant for the disease, prolonged overall survival of a patient, prolonged time to disease progression of a patient, prolonged progression-free survival of a patient, prolonged disease-free survival of a patient, improved quality of life of a patient, or modulation of the co-morbidity of the disease (for example, but not limited to pain, cachexia, mobilization, hopitalization, altered hemogram, weight loss, wound healing, fever).

The compounds according to the present invention may further be useful as immune response modifiers that can modulate the immune response in a number of different ways, rendering them useful in the treatment of a variety of disorders.

Provided herein are methods of inhibiting an immune response in an individual comprising administering to the individual an effective amount of an inhibitor of TLR7 and/or TLR8 (e.g., TLR inhibitor), using the compounds as described herein. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some variations, the TLR inhibitor inhibits a TLR7-dependent, a TLR8-dependent, and another TLR-dependent immune response. Unless otherwise noted, the term TLR inhibitor refers to any one of the TLR inhibitors disclosed herein. In some preferred embodiments, the individual is a human patient.

Methods of immunoregulation are provided by the present disclosure and include those that suppress and/or inhibit an immune response, including, but not limited to, an immune response. The present disclosure also provides methods for ameliorating symptoms associated with unwanted immune activation, including, but not limited to, symptoms associated with autoimmunity. Immune suppression and/or inhibition according to the methods described herein may be practiced on individuals including those suffering from a disorder associated with an unwanted activation of an immune response. The present disclosure also provides methods for inhibiting a TLR7 and/or TLR8 induced response (e.g., in vitro or in vivo). In some variations, the cell is contacted with the TLR inhibitor in an amount effective to inhibit a response from the cell that contributes to an immune response.

Inhibition of TLR7 and/or TLR8 are useful for treating and/or preventing a variety of diseases or disorders that are responsive to cytokines. Conditions for which TLR7 and/or TLR8 inhibitors may be used as treatments include, but are not limited to autoimmune diseases and inflammatory disorders. Provided herein are methods of treating or preventing a disease or disorder in an individual comprising administering to the individual an effective amount of an inhibitor of TLR7 and/or TLR8. Further, provided are methods for ameliorating symptoms associated with a disease or disorder comprising administering an effective amount of an inhibitor of TLR7 and/or TLR8 to an individual having the disease or disorder. Methods are also provided herein for preventing or delaying development of a disease or a disorder, comprising administering an effective amount of an inhibitor of one or more of TLR7 and/or TLR8 to an individual having the disease or the disorder. In certain embodiments, the inhibitor is a compound as described herein.

Provided herein are methods of inhibiting an immune response in an individual, the method comprising administering to the individual at least one TLR inhibitor as disclosed herein in an amount effective to inhibit the immune response in the individual. In some variations, the immune response is associated with an autoimmune disease. In further aspects, wherein inhibiting the immune response ameliorates one or more symptoms of the autoimmune disease. In still further aspects, wherein inhibiting the immune response treats the autoimmune disease. In yet further aspects, wherein inhibiting the immune response prevents or delays development of the autoimmune disease. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some aspects, at least one TLR inhibitor is administered in an amount effective to inhibit an immune response in the individual.

Provided herein are also methods of treating or preventing an autoimmune disease in an individual, comprising administering to the individual an effective amount of a TLR7 and/or TLR8 inhibitor. In some aspects, the autoimmune disease is characterized by joint pain, antinuclear antibody positivity, malar rash, or discoid rash. In some aspects, the autoimmune disease is associated with the skin, muscle tissue, and/or connective tissue. In some embodiments, the autoimmune disease is not evidenced in the individual by skin, muscle tissue, and/or connective tissue symptoms. In some embodiments, the autoimmune disease is systemic. Autoimmune diseases include, without limitation, rheumatoid arthritis (RA), autoimmune pancreatitis (AIP), systemic lupus erythematosus (SLE), type I diabetes mellitus, multiple sclerosis (MS), antiphospholipid syndrome (APS), sclerosing cholangitis, systemic onset arthritis, irritable bowel disease (IBD), scleroderma, Sjogren's disease, vitiligo, polymyositis, pemphigus vulgaris, pemphigus foliaceus, inflammatory bowel disease including Crohn's disease and ulcerative colitis, autoimmune hepatitis, hypopituitarism, graft-versus-host disease (GvHD), autoimmune skin diseases, uveitis, pernicious anemia, and hypoparathyroidism. Autoimmune diseases may also include, without limitation, polyangiitis overlap syndrome, Kawasaki's disease, sarcoidosis, glomerulonephritis, and cryopathies.

In some aspects, the autoimmune disease is selected from the group consisting of arthritis, pancreatitis, mixed connective tissue disease (MCTD), lupus, antiphospholipid syndrome (APS), systemic onset arthritis, and irritable bowel syndrome.

In other aspects, the autoimmune disease is selected from the group consisting of systemic lupus erythematosus (SLE), rheumatoid arthritis, autoimmune skin disease, and multiple sclerosis.

In other aspects, the autoimmune disease is selected from the group consisting of pancreatitis, glomerulonephritis, pyelitis, sclerosing cholangitis, and type I diabetes. In some aspects, the autoimmune disease is rheumatoid arthritis. In some aspects, the autoimmune disease is autoimmune pancreatitis (AIP). In some aspects, the autoimmune disease is glomerulonephritis. In some aspects, the autoimmune disease is pyelitis. In some aspects, the autoimmune disease is sclerosing cholangitis. In some aspects the autoimmune disorder is psoriasis. In some aspects, the autoimmune disease is a rheumatoid disease or disorder. In some aspects, the rheumatoid disease or disorder is rheumatoid arthritis. In some aspects, the disease is diabetes and/or diabetic-related disease or disorder. In some aspects, wherein the autoimmune disease is associated with RNA-containing immune complexes. In some aspects, the autoimmune disease is Sjogren's disease.

Provided herein are methods of inhibiting an immune response in an individual, the method comprising administering to the individual at least one TLR inhibitor as disclosed herein in an amount effective to inhibit the immune response in the individual. In some variations, the immune response is associated with an inflammatory disorder. As used herein, the term "inflammatory disorder" encompasses autoimmune diseases, as well as inflammatory conditions without a known autoimmune component (e.g., artherosclerosis, asthma, etc.). In further aspects, inhibiting the immune response ameliorates one or more symptoms of the inflammatory disorder. In still further aspects, inhibiting the immune response treats the inflammatory disorder. In yet further aspects, inhibiting the immune response prevents or delays development of the inflammatory disorder. In some aspects, the inflammatory disorder is selected from the group consisting of non-rheumatoid arthritis, kidney fibrosis, and liver fibrosis. In some aspects, the inflammatory disorder is an interface dermatitis. In some further aspects, the interface dermatitis is selected from the group consisting of lichen planus, lichenoid eruption, lichen planus-like keratosis, lichen striatus, keratosis lichenoides chronica, erythema multiforme, fixed drug eruption, pityriasis lichenoides, phototoxic dermatitis, radiation dermatitis, viral exanthems, dermatomyositis, secondary syphilis, lichen sclerosus et atrophicus, mycosis fungoides, bullous pemphigoid, lichen aureus, porokeratosis, acrodermatitis chronicus atrophicans, and regressing melanoma. In some aspects, the inflammatory condition is a skin disorder such as atopic dermatitis (eczema). In some aspects, the inflammatory disorder is a sterile inflammatory condition such as drug-induced liver and/or pancreas inflammation. In some further aspects, the inflammatory disease is an inflammatory liver disorder. In some other further aspects, the inflammatory disease is an inflammatory pancreatic disorder.

Provided herein are methods of inhibiting an immune response in an individual, the method comprising administering to the individual at least one TLR inhibitor as disclosed herein in an amount effective to inhibit the immune response in the individual. In some variations, the immune response is associated with chronic pathogen stimulation. In some variations, the immune response is associated with infection by HIV. In further aspects, wherein inhibiting the immune response ameliorates one or more symptoms of the viral disease or disorder resulting from infection by HIV. In still further aspects, wherein inhibiting the immune response treats the viral disease or disorder resulting from infection by HIV. In yet further aspects, wherein inhibiting the immune response prevents or delays development of the viral disease or disorder resulting from infection by HIV. Other variations provided herein relate to immunoinhibitory therapy of individuals having been exposed to or infected with HIV. Administration of a TLR inhibitor to an individual having been exposed to or infected with HIV results in suppression of HIV induced cytokine production. In some aspects, at least one TLR inhibitor is administered in an amount effective to suppress HIV induced cytokine production in an individual exposed to or infected with a HIV.

Provided herein are methods for inhibiting a TLR7 and/or TLR8-dependent immune response in an individual, the method comprising administering to the individual a TLR inhibitor in an amount effective to inhibit the immune response in the individual. In some variations, the immune response is associated with an autoimmune disease. In some aspects, the autoimmune disease is rheumatoid arthritis. In some aspects, the TLR inhibitor is effective in suppressing one or more symptoms of rheumatoid arthritis. In some aspects, the autoimmune disease is multiple sclerosis. In some aspects, the TLR inhibitor is effective in suppressing one or more symptoms of multiple sclerosis. In some aspects, the autoimmune disease is lupus. In some aspects, the TLR inhibitor is effective in suppressing one or more symptoms of lupus. In some aspects, the autoimmune disease is pancreatitis. In some aspects, the TLR inhibitor is effective in suppressing one or more symptoms of pancreatitis. In some aspects, the autoimmune disease is diabetes. In some aspects, the TLR inhibitor is effective in suppressing one or more symptoms of diabetes. In some aspects, the disease is Sjogren's disease. In some aspects, the TLR inhibitor is effective in suppressing one or more symptoms of Sjogren's disease. In some variations, the immune response is associated with an inflammatory disorder. In some aspects, the TLR inhibitor is effective in suppressing one or more symptoms of an inflammatory disorder. In some variations, the immune response is associated with chronic pathogen stimulation. In some aspects, the TLR inhibitor is effective in suppressing one or more symptoms of chronic pathogen stimulation. In some variations, the immune response is associated with viral disease resulting from infection with HIV. In some aspects, the TLR inhibitor is effective in suppressing one or more symptoms of viral disease resulting from infection with HIV. In any variation, the TLR inhibitor is a polynucleotide comprising an inhibitory motif for one or more of TLR7, TLR8, and TLR9.

In some embodiments of any of the methods involving administration of a TLR inhibitor to an individual (e.g., methods of inhibiting an immune response, treating or preventing an autoimmune disease or inflammatory disorder, etc.) the TLR inhibitor has a therapeutically acceptable safety profile. The TLR inhibitor may for example, have a therapeutically acceptable histological profile including an acceptably low, if any, toxicity of the liver, kidney, pancreas, or other organs. On occasion, polynucleotides have been associated with toxicity to certain organs such as the liver, kidney and pancreas. In some embodiments, the TLR inhibitor has a safety profile that is unexpected and advantageous. In some embodiments, a safety profile includes evaluation of toxicity, histological profile, and/or necrosis (e.g., liver, kidneys and/or heart). In some embodiments, the TLR inhibitor has a therapeutically acceptable level of toxicity. In some embodiments, the TLR inhibitor has a reduced level of toxicity as compared to another TLR inhibitor. In some embodiments, the TLR inhibitor induces a therapeutically acceptable reduction in body weight as compared to the initial body weight of a treated individual. In some embodiments, the TLR inhibitor induces less than 5%, 7.5%, 10%, 12.5, or 15% reduction in total body weight. In some embodiments, the TLR inhibitor has a therapeutically acceptable histology profile. In some embodiments, the TLR inhibitor has a better (e.g., lower severity score) histology profile, for example, as compared to a reference TLR inhibitor. In some embodiments, the TLR inhibitor has a better (e.g., lower severity score) histology profile upon evaluation of the liver, kidneys and/or heart, for example. In some embodiments, the TLR inhibitor has a therapeutically acceptable necrosis score. In some embodiments, the TLR inhibitor has reduced necrosis and/or better (e.g., lower) necrosis score, for example, as compared to a reference TLR inhibitor. In some embodiments, the TLR inhibitor has reduced renal and/or hepatocellular necrosis and/or a better renal and/or hepatocellular necrosis score, for example, as compared to a reference TLR inhibitor.

Accordingly, the invention provides a method of activating TLR7 in an animal, especially a mammal, preferably a human comprising administering an effective amount of a compound of Formula I to the animal. As with all compositions for inhibition of an immune response, the effective amounts and method of administration of the particular TLR inhibitor formulation can vary based on the individual, what condition is to be treated and other factors evident to one skilled in the art. An effective amount of a compound will vary according to factors known in the art but is expected to be a dose of about 0.1 to 10 mg/kg, 0.5 to 10 mg/kg, 1 to 10 mg/kg, 0.1 to 20 mg/kg, 0.1 to 20 mg/kg, or 1 to 20 mg/kg.

The invention also provides a method of treating a viral infection in an animal comprising administering an effective amount of a compound of Formula I to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose as indicated above with respect to the activation of TLR7, or a dose of about 100 ng/kg to about 50 mg/kg, preferably about 10 µg/kg to about 5 mg/kg.

In various embodiments, compounds of formula (I), and related formulae exhibit a IC50 for the binding to TLR7/8 of less than about 5 µM, preferably less than about 1 µM and even more preferably less than about 0.100 µM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit TLR7/8 activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing TLR7/8-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of TLR7/8 activity if expedient.

The invention also relates to the use of compounds according to formula (I) and/or physiologically acceptable salts thereof for the prophylactic or therapeutic treatment and/or monitoring of diseases that are caused, mediated and/or propagated by TLR7/8 activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by TLR7/8 activity. In certain embodiments, the invention provides the use of a compound according to formula I or physiologically acceptable salts thereof, for the production of a medicament for the prophylactic or therapeutic treatment of a TLR7/8-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with TLR7/8 activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with TLR7/8 activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

The TLR inhibitors of the present disclosure can be administered in combination with one or more additional therapeutic agents. As described herein, the TLR inhibitors can be combined with a physiologically acceptable carrier. The methods described herein may be practiced in combination with other therapies that make up the standard of care for the disorder, such as administration of anti-inflammatory agents.

In some embodiments, a TLR inhibitor as described herein is administered in combination with a corticosteroid. In some embodiments, the corticosteroid is a glucocorticosteroid. In some embodiments, the corticosteroid is a mineralocorticoid. Corticosteroids include, but are not limited to, corticosterone and derivatives, prodrugs, isomers and analogs thereof, cortisone and derivatives, prodrugs, isomers and analogs thereof (i.e., Cortone), aldosterone and derivatives, prodrugs, isomers and analogs thereof, dexamethasone and derivatives, prodrugs, isomers and analogs thereof (i.e., Decadron), prednisone and derivatives, prodrugs, isomers and analogs thereof (i.e., Prelone), fludrocortisones and derivatives, prodrugs, isomers and analogs thereof, hydrocortisone and derivatives, prodrugs, isomers and analogs thereof (i.e., cortisol or Cortef), hydroxycortisone and derivatives, prodrugs, isomers and analogs thereof, betamethasone and derivatives, prodrugs, isomers and analogs thereof (i.e., Celestone), budesonide and derivatives, prodrugs, isomers and analogs thereof (i.e., Entocort EC), methylprednisolone and derivatives, prodrugs, isomers and analogs thereof (i.e., Medrol), prednisolone and derivatives, prodrugs, isomers and analogs thereof (i.e., Deltasone, Crtan, Meticorten, Orasone, or Sterapred), triamcinolone and derivatives, prodrugs, isomers and analogs thereof (i.e., Kenacort or Kenalog), and the like. In some embodiments, the corticosteroid is fludrocortisone or a derivative, prodrug, isomer or analog thereof. In some embodiments, the corticosteroid is fludrocortisone. In some embodiments, the corticosteroid is hydroxycortisone or a derivative, prodrug, isomer or analog thereof. In some embodiments, the corticosteroid is hydroxycortisone.

In some embodiments, the corticosteroid is administered between about any of 0.001 mg to 1 mg, 0.5 mg to 1 mg, 1 mg to 2 mg, 2 mg to 20 mg, 20 mg to 40 mg, 40 to 80 mg, 80 to 120 mg, 120 mg to 200 mg, 200 mg to 500 mg, or 500 mg to 1000 mg per day. In some embodiments, the corticosteroid is administered between about any of 0.1 mg/kg to 0.5 mg/kg, 0.5 mg/kg to 1 mg/kg, 1 mg/kg to 2 mg/kg, 2 mg/kg to 5 mg/kg, 5 mg/kg to 10 mg/kg, 10 mg/kg to 15 mg/kg, 15 mg/kg to 20 mg/kg, 20 mg/kg to 25 mg/kg, 25 mg/kg to 35 mg/kg, or 35 mg/kg to 50 mg/kg per day.

In some embodiments, the TLR inhibitor used in combination therapy, given in amounts of the TLR inhibitor delivered, may be, for example, from about any of 0.1 to 10 mg/kg, 0.5 to 10 mg/kg, 1 to 10 mg/kg, 0.1 to 20 mg/kg, 0.1 to 20 mg/kg, or 1 to 20 mg/kg.

In some embodiments, the TLR inhibitor is administered simultaneously with one or more additional therapeutic agents including, but not limited to, a corticosteroid (simultaneous administration). In some embodiments, the TLR inhibitor is administered sequentially with an additional therapeutic agent including, but not limited to, a corticosteroid (sequential administration). In some embodiments, sequential administration includes administering the TLR inhibitor or additional therapeutic agent followed within about any of one minutes, five minutes, 30 minutes, one hour, five hours, 24 hours, 48 hours, or a week. In some embodiments, the TLR inhibitor is administered by the same route of administration as the additional therapeutic agent. In some embodiments, the TLR inhibitor is administered by a different route of administration than the additional therapeutic agent. In some embodiments, the additional therapeutic agent is administered parentally (e.g., central venous line, intra-arterial, intravenous, intramuscular, intraperitoneal, intradermal, or subcutaneous injection), orally, gastro-intestinally, topically, naso-pharyngeal and pulmonary (e.g. inhalation or intranasally). In some embodiments, the additional therapeutic agent is a corticosteroid.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamidel[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[2,3], onartuzumab[1,3], racotumomab, tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane 1123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolidel[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[23], virulizin[4], carfilzomib[1,3], endostatin[4], immucothel[4], belinostat[3], MGN-1703[4].

([1]Prop. INN (Proposed International Nonproprietary Name); [2]Rec. INN (Recommended International Nonproprietary Names); [3]USAN (United States Adopted Name); [4] no INN).

In some embodiments, the combination of a TLR inhibitor with one or more additional therapeutic agents reduces the effective amount (including, but not limited to, dosage volume, dosage concentration, and/or total drug dose administered) of the TLR inhibitor and/or the one or more additional therapeutic agents administered to achieve the same result as compared to the effective amount administered when the TLR inhibitor or the additional therapeutic agent is administered alone. In some embodiments, the combination of a TLR inhibitor with a corticosteroid reduces the effective amount of corticosteroid administered as compared to the corticosteroid administered alone. In some embodiments, the combination of a TLR inhibitor with the additional therapeutic agents reduces the frequency of administrations of the therapeutic agent compared to administration of the additional therapeutic agent alone. In some embodiments, the combination of a TLR inhibitor with the additional therapeutic agent reduces the total duration of treatment compared to administration of the additional therapeutic agent alone. In some embodiments, the combination of a TLR inhibitor with the additional therapeutic agent reduces the side effects associated with administration of the additional therapeutic agent alone. In some embodiments, the additional therapeutic agent is a corticosteroid. In some embodiments, the corticosteroid is fludrocortisone or a derivative, prodrug, isomer or analog thereof. In some embodiments, the corticosteroid is fludrocortisone. In some embodiments, the combination of an effective amount of the TLR inhibitor with the additional therapeutic agent is more efficacious compared to an effective amount of the TLR inhibitor or the additional therapeutic agent alone.

TLR inhibitors also may be useful as a vaccine adjuvant for use in conjunction with any material that modulates either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like. In some aspects, the combination therapy including but not limited to the combination of a TLR inhibitor and a vaccine is used in the treatment of an autoimmune disease or an inflammatory disorder. In some aspects, the combination therapy including but not limited to the combination of a TLR inhibitor and a vaccine is used in the treatment of an infectious disease.

In some embodiments, the combination therapy including but not limited to the combination of a TLR inhibitor and a corticosteroid is used in the treatment of an autoimmune disease or an inflammatory disorder. In some embodiments, the autoimmune disease is selected from but not limited to rheumatoid arthritis, systemic lupus erythematosus, autoimmune skin disease, multiple sclerosis, pancreatitis, glomerulonephritis, pyelitis, Sclerosing cholangitis, and type I diabetes. In some embodiments, the autoimmune disease is Sjogren's disease.

Also provided herein are kits comprising a TLR inhibitor as provided herein, and instructions for use in the methods of inhibiting a TLR7- and/or TLR8-dependent immune response.

The kits may comprise one or more containers comprising a TLR inhibitor (or a formulation comprising a TLR inhibitor) as described herein, and a set of instructions, generally written instructions although electronic storage media (e.g., magnetic diskette or optical disk) containing instructions are also acceptable, relating to the use and dosage of the TLR inhibitor or formulation for the intended treatment (e.g., suppression of a response to a TLR7 and/or TLR8 agonists, suppression of a TLR7 and/or TLR8-dependent immune response, ameliorating one or more symptoms of an autoimmune disease, ameliorating a symptom of chronic inflammatory disease, decreasing cytokine production in response to a virus, and/or treating and/or preventing one or more symptoms of a disease or disorder mediated by TLR7 and/or TLR8). The instructions included with the kit generally include information as to dosage, dosing schedule, and route of administration for the intended treatment. The containers for the TLR inhibitor (or formulations comprising a TLR inhibitor) may be unit doses, bulk packages (e.g., multi-dose packages) or sub-unit doses. The kits may further comprise a container comprising an adjuvant.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting TLR7/8 activity in a biological sample comprising the step of contacting said biological sample with a compound of this invention, or a composition comprising said compound.

According to another embodiment, the invention relates to a method of inhibiting TLR7/8, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of TLR7/8, including the evaluation of the many factors thought to influence, and be influenced by, the production of TLR7/8 and the interaction of TLR7/8. The present compounds are also useful in the development of other compounds that interact with TLR7/8 since the present compounds provide important structure-activity relationship (SAR) information that facilitate that development. Compounds of the present invention that bind to TLR7/8 can be used as reagents for detecting TLR7/8 in living cells, fixed cells, in biological fluids, in tissue homogenates, in purified, natural biological materials, etc. For example, by labeling such compounds, one can identify cells expressing TLR7/8. In addition, based on their ability to bind TLR7/8, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing TLR7/8 inside permeabilized cells. The compounds of the invention can also be utilized as commercial research reagents for various medical research and diagnostic uses. Such uses can include but are not limited to: use as a calibration standard for quantifying the activities of candidate TLR7/8 inhibitors in a variety of functional assays; use as blocking reagents in random compound screening, i.e. in looking for new families of TLR7/8 ligands, the compounds can be used to block recovery of the presently claimed TLR7/8 compounds; use in the co-crystallization with TLR7/8, i.e. the compounds of the present invention will allow formation of crystals of the compound bound to TLR7/8, enabling the determination of enzyme/compound structure by x-ray crystallography; other research and diagnostic applications, wherein TLR7/8 is preferably activated or such activation is conveniently calibrated against a known quantity of an TLR7/8 inhibitor, etc.; use in assays as probes for determining the expression of TLR7/8 in cells; and developing assays for detecting compounds which bind to the same site as the TLR7/8 binding ligands.

The compounds of the invention can be applied either themselves and/or in combination with physical measurements for diagnostics of treatment effectiveness. Pharmaceutical compositions containing said compounds and the use of said compounds to treat TLR7/8-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of TLR7/8, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All solvents used were commercially available and were used without further purification. Reactions were typically run using anhydrous solvents under an inert atmosphere of nitrogen. Flash column chromatography was generally carried out using Silica gel 60 (0.035-0.070 mm particle size).

All NMR experiments were recorded either on Bruker Mercury Plus 400 NMR Spectrometer equipped with a Bruker 400 BBFO probe at 400 MHz for proton NMR or on Bruker Mercury Plus 300 NMR Spectrometer equipped with a Bruker 300 BBFO probe at 300 MHz for proton NMR. All deuterated solvents contained typically 0.03% to 0.05% v/v tetramethylsilane, which was used as the reference signal (set at δ 0.00 for both $^1$H and $^{13}$C).

LC-MS analyses were performed on a SHIMADZU LC-MS machine consisting of an UFLC 20-AD system and LCMS 2020 MS detector. The column used was a Shim-pack XR-ODS, 2.2 am, 3.0×50 mm. A linear gradient was applied, starting at 95% A (A: 0.05% TFA in water) and ending at 100% B (B: 0.05% TFA in acetonitrile) over 2.2 min with a total run time of 3.6 min. The column temperature was at 40° C. with the flow rate at 1.0 mL/min. The Diode Array detector was scanned from 200-400 nm. The mass spectrometer was equipped with an electro spray ion source (ES) operated in a positive or negative mode. The mass spectrometer was scanned between m/z 90-900 with a scan time of 0.6 s.

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Intermediate 1: 8-bromoquinoxaline-5-carbonitrile

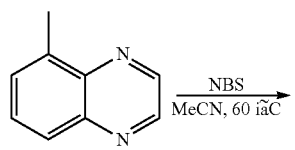

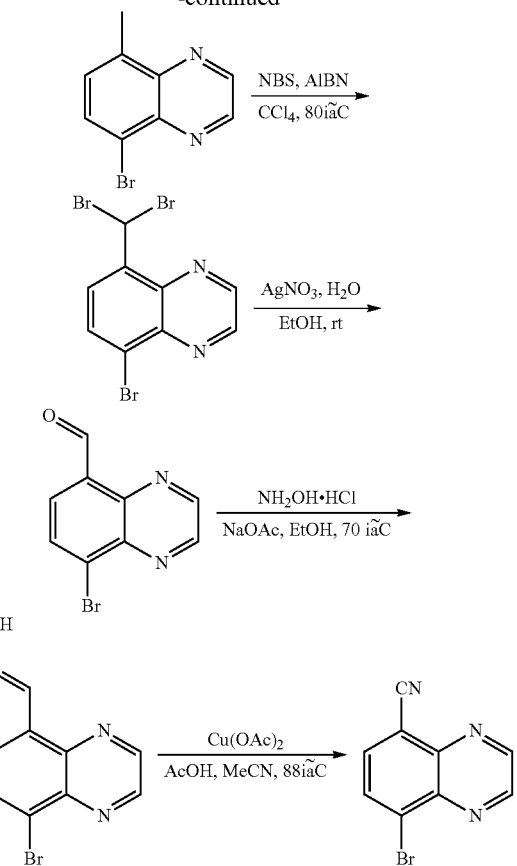

5-Bromo-8-methylquinoxaline

To a solution of 5-methylquinoxaline (9.50 g, 65.97 mmol) in CH$_3$CN (80 mL) was added 1-bromopyrrolidine-2,5-dione (27.00 g, 151.74 mmol) at room temperature. The resulting solution was stirred for 16 h at 60° C. After cooling to room temperature, the reaction mixture was concentrated under reduced pressure and the residue was diluted with ethyl acetate (500 mL). The insoluble solids in the mixture were filtered out and the filtrate was washed with brine and dried over Na$_2$SO$_4$. The solvent was removed under reduced pressure to yield 5-bromo-8-methylquinoxaline as brown solid (6.00 g, 41%). MS: m/z=222.9 [M+H]$^+$.

5-Bromo-8-(dibromomethyl)quinoxaline

To a solution of 5-bromo-8-methylquinoxaline (6.00 g, 27.02 mmol) in CCl$_4$ (200 mL) was added NBS (19.23 g, 108.08 mmol) and AIBN (0.71 g, 4.32 mmol) at room temperature. The resulting solution was then stirred for 16 h at 80° C. After cooling to room temperature, the reaction mixture was concentrated under reduced pressure and the residue was diluted with ethyl acetate (500 mL). The insoluble solids in the mixture were filtered out, and then the filtrate was washed with brine and dried over Na$_2$SO$_4$. The solvent was removed under reduced pressure and the residue was purified by flash chromatography eluting with EtOAc in petroleum ether (0% to 5% gradient) to yield 5-bromo-8-(dibromomethyl)quinoxaline as light yellow solid (7.15 g, 70%). MS: m/z=378.7 [M+H]$^+$.

8-Bromoquinoxaline-5-carbaldehye

To a solution of 5-bromo-8-(dibromomethyl)quinoxaline (13.50 g, 35.71 mmol) in ethanol (290 mL) was added a solution of AgNO$_3$ (24.27 g, 142.86 mmol) in water (90 mL) dropwise at room temperature. The resulting mixture was then stirred for 1 h at room temperature. When the reaction was done, the reaction mixture was diluted with CH$_3$CN (300 mL) and precipitation happened. The precipitates were filtered out and the filtrate was concentrated under reduced pressure to yield 8-bromoquinoxaline-5-carbaldehyde as yellow solid (10.00 g, crude). MS: m/z=236.8 [M+H]$^+$.

(E)-8-Bromoquinoxaline-5-carbaldehyde Oxime

To a solution of 8-bromoquinoxaline-5-carbaldehyde (10 g, crude) in ethanol (100 mL) was added NaOAc (6.34 g, 73.42 mmol) and NH$_2$OH—HCl (3.12 g, 42.65 mmol) at room temperature. The resulting mixture was stirred for 3 h at 70° C. When the reaction was done, the insoluble solids in the reaction mixture were filtered out at 70° C., and then the filtrate was cooled to 0° C. and precipitation happened. The precipitates were collected by filtration and dried in oven to yield (E)-N-[(8-bromoquinoxalin-5-yl)methylidene]hydroxylamine as yellow solid (2.96 g, 33% for 2 steps). MS: m/z=253.9 [M+H]$^+$.

8-Bromoquinoxaline-5-carbonitrile

To a solution of (E)-N-[(8-bromoquinoxalin-5-yl)methylidene]hydroxylamine (3.47 g, 13.82 mmol) in acetonitrile (20 mL) was added Cu(OAc)$_2$ (577 mg, 3.18 mmol) and acetic acid (1.24 g, 20.73 mmol) at room temperature. The resulting mixture was stirred for 15 h at 88° C. After cooling to room temperature, the reaction mixture was diluted with acetonitrile (10 mL). The insoluble solids in the mixture were filtered out and the filtrate was concentrated under reduced pressure. The residue was purified by flash chromatography eluting with EtOAc in petroleum ether (0% to 15% gradient) to yield 8-bromoquinoxaline-5-carbonitrile as yellow solid (1.22 g, 38%). MS: m/z=235.8 [M+H]$^+$.

Intermediate 2:
5-Bromo-7-fluoro-8-methyl-quinoline

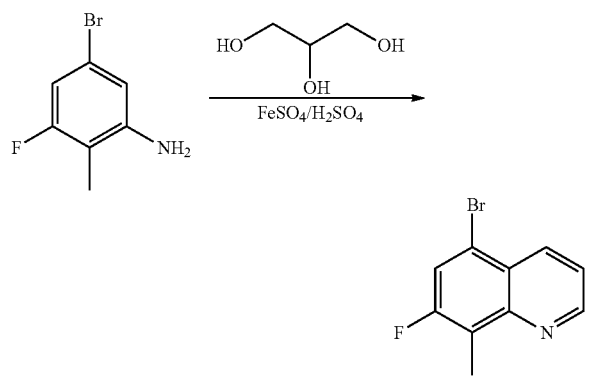

5-Bromo-7-fluoro-8-methyl-quinoline

To 5-Bromo-3-fluoro-2-methyl-phenylamine (10.00 g; 49.01 mmol) in 200 ml flask was added glycerol (14.44 ml; 196.04 mmol), iron(ii) sulfate heptahydrate (2.73 g; 9.80 mmol), and sulfuric acid (15.99 ml; 294.06 mmol). The mixture was stirred at 125° C. for 4 hr. The completed reaction was cooled to room temperature and diluted with 200 ml of DCM. 2N Sodium hydroxide (269 ml; 539.11 mmol) was added slowly to the mixture cooled with ice bath, followed by another 100 ml of DCM. The mixture was stirred for 30 mins at rt. The separated organic layer was washed with brine, dried and concentrated. The crude brown oil was purified by Biotage silica gel column (340 g, eluted with EA/Hexane 10-35%) to yield the title compound as white solid (6.0 g, yield 51%). MS: m/z=241 [M+H]$^+$.

Intermediate 3:
5-Bromo-7-fluoro-quinoline-8-carbonitrile

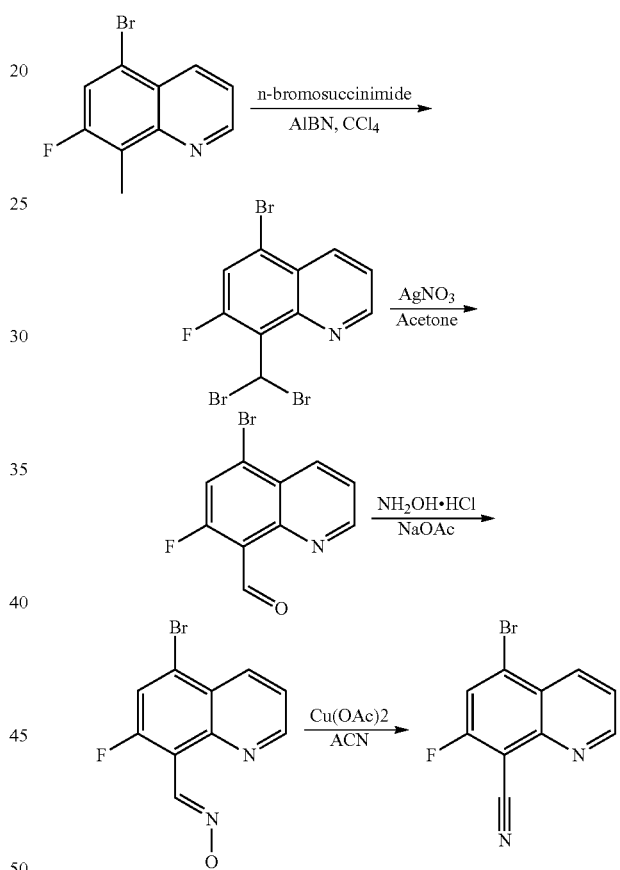

5-Bromo-8-dibromomethyl-7-fluoro-quinoline

To 5-Bromo-7-fluoro-8-methyl-quinoline (2000 mg; 8.33 mmol) and n-bromosuccinimide (3744 mg; 20.83 mmol) was added 60 ml of CCl$_4$, followed by 2,2'-azobis(2-methylpropionitrile) (205 mg; 1.25 mmol). The mixture was stirred at 80° C. overnight. The reaction mixture was cooled to rt and filtered to remove the solid. The filtrate was concentrated to yield the title compound as a white solid (2800 mg, yield 84.5%). LC-MS (M+1)=397/399.

5-Bromo-7-fluoro-quinoline-8-carbaldehyde

To a stirred solution of 5-Bromo-8-dibromomethyl-7-fluoro-quinoline (11.00 g; 27.65 mmol) in acetone (200 ml)

and water (40 ml) was added AgNO$_3$ (11.74 g; 69.12 mmol) at RT. The mixture was stirred at RT for 15 min. The precipitate was removed by filtration and washed with DCM (100 ml). The filtrate was concentrated to ⅓ volume and then extracted with DCM (100 ml×2). The combined organic phases was concentrated to yield the title compound as a yellow solid (7.0 g, 99%), which was directly used for the next step reaction. LC-MS (M+1)=255.

5-Bromo-7-fluoro-quinoline-8-carbaldehyde Oxime

To 5-Bromo-7-fluoro-quinoline-8-carbaldehyde (7.00 g; 27.55 mmol) in ethanol (300 ml) was added NaOAc (4.52 g; 55.11 mmol) followed by NH$_2$OH.HCl (2.30 g; 33.06 mmol). The mixture was stirred at 70° C. for 2 hr. The completed reaction was cooled, filtered and washed with ethanol to remove solid. The filtrate was concentrated to yield the title compound as a light yellow solid (7.2 g, yield 97%), which was directly used for the next step reaction. LC-MS (M+1)=270.

5-Bromo-7-fluoro-quinoline-8-carbonitrile

To 5-Bromo-7-fluoro-quinoline-8-carbaldehyde oxime (6.00 g; 22.30 mmol) in ACN (20 ml) was added Cu(OAc)$_2$ (1.01 g; 5.57 mmol) and CH$_3$COOH (1.28 ml; 22.30 mmol). The mixture was refluxed for 2 hr. LCMS showed the formation of the desired product (60%) and by-product. The reaction mixture was cooled and concentrated. The residue was dissolved in 100 ml of EA and 30 ml of 5% aq. NaHCO$_3$. The separated aqueous layer was extracted with 50 ml of EA. The combined organic layers was washed with brine, dried, and concentrated. The crude was purified with Biotage silica gel column (200 g, eluting with EA/hexane 0-60%) to yield the title compound (1230 mg, yield 22%). LC-MS (M+1)=252.

Intermediate 4:
5-bromo-8-methyl-[1,7]naphthyridine

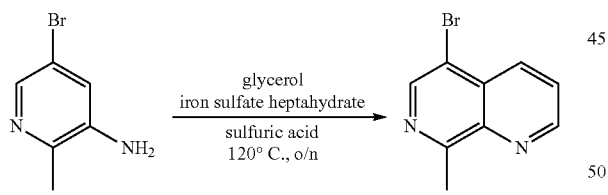

5-bromo-8-methyl-[1,7]naphthyridine

To a mixture of 5-bromo-2-methyl-pyridin-3-ylamine (3.00 g; 16.0 mmo), glycerol (4.7 mL; 64.1 mmol), iron(II) sulfate heptahydrate (892 mg; 3.2 mmol) was added sulfuric acid (5.6 mL; 96.2 mmol) dropwise. The resulting mixture was heated at 120° C. overnight. The reaction mixture was treated with ice, a solution 2N of sodium hydroxide, ethyl acetate and dichloromethane. After filtration to remove the dark brown solid, the organic layer was separated and washed with brine, dried and concentrated. The crude was purified by chromatography on silica gel, eluting with ethyla acetate and hexanes, to afford 5-bromo-8-methyl-[1,7]naphthyridine (470 mg, 13%). MS: m/z=224 [M+H]$^+$. $^1$H NMR (400 MHz, DMSO-d6) δ 9.14 (dd, J=4.2, 1.6 Hz, 1H), 8.72 (s, 1H), 8.50 (dd, J=8.6, 1.6 Hz, 1H), 7.96 (dd, J=8.5, 4.1 Hz, 1H), 2.95 (s, 3H).

Example 1: Synthesis of Compound 1 (cis-5-Methyl-1-[2-(1-methyl-piperidin-4-yl)-acetyl]-piperidin-3-yl}-quinoline-8-carbonitrile) and Compound 2 (trans-5-Methyl-1-[2-(1-methyl-piperidin-4-yl)-acetyl]-piperidin-3-yl}-quinoline-8-carbonitrile)

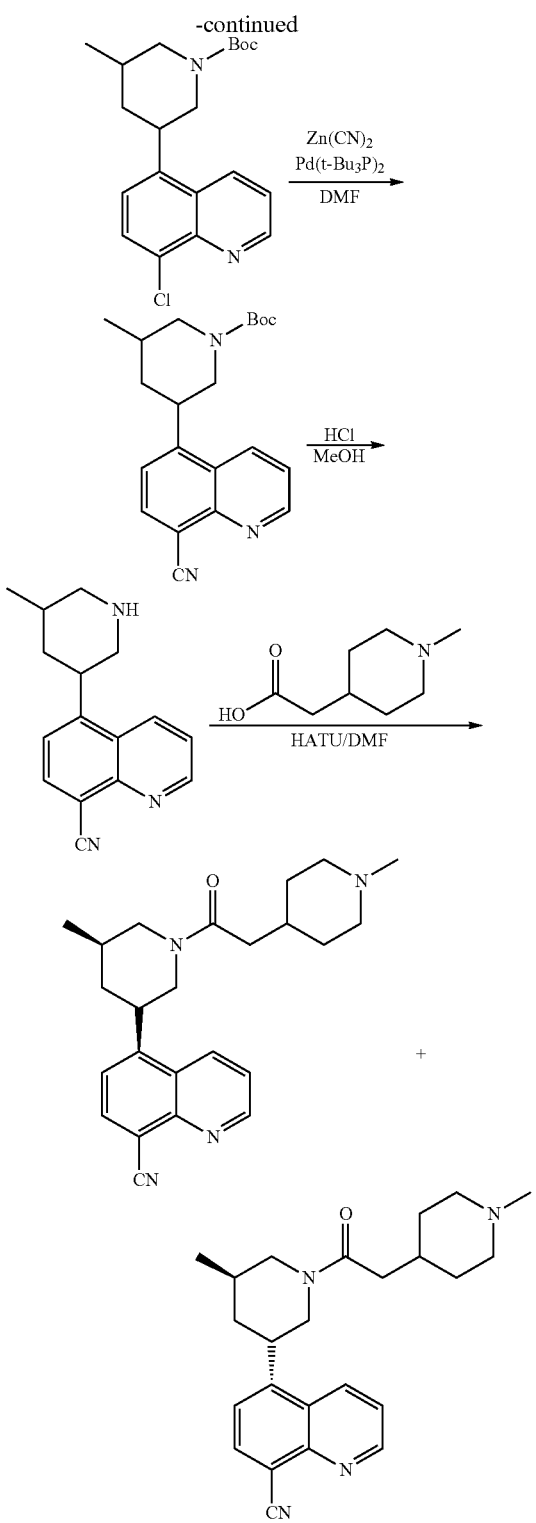

Trifluoro-methanesulfonic acid
1-benzyl-5-methyl-1, 4, 5, 6-tetrahydro-pyridin-3-yl
Ester A solution of 1-Benzyl-5-methyl-piperidin-3-one (7.00 g; 34.44 mmol) in THF (100 ml) was cooled to −78° C., added [bis(trimethylsilyl)amino] lithium (37.88 ml; 37.88 mmol) (1.0M in hexane) dropwise during 30 mins, and the mixture was stirred for about 30 min, a solution of N,N-bis(trifluoromethylsulfonyl) aniline (12.917 g, 36.16 mmol) in 50 ml of THF was added at −78° C. After the addition was completed, the result mixture was stirred for approximately an additional 10 mins at the same temperature and then allowed to warm to about 0° C. for about 3 hr. The reaction was quenched with 1 ml of saturated NaHCO₃ solution and the mixture was concentrated. The residue was purified by Biotage silica gel column (340 g, eluted with hexane/EA 0-20%) to yield the title compound (12 g, quantitative yield). LC-MS (M+1)=336.

5-(1-Benzyl-5-methyl-1, 4, 5, 6-tetrahydro-pyridin-3-yl)-2-chloro-phenylamine

A mixture of trifluoro-methanesulfonic acid 1-benzyl-5-methyl-1,4,5,6-tetrahydro-pyridin-3-yl ester (6097 mg; 18.18 mmol), 2-Chloro-5-(4,4,5,5-tetramethyl-[1,3,2]dioxaborolan-2-yl)-phenylamine (4.61 g; 18.18 mmol), sodium carbonate (3.85 g; 36.36 mmol) in dioxane (150 ml) and water (15 ml) was degassed, added bis(tri-tert-butylphosphine) palladium (0) (464 mg; 0.91 mmol). The mixture was stirred at 45° C. overnight. The reaction mixture was filtered and the filtrate was concentrated. The crude was purified by Biotage silica gel column (340 g, eluting with hex/EA 0-35) to yield the title compound (2700 mg, yield 47.5%) LC-MS (M+1)=313/315.

3-(3-Amino-4-chloro-phenyl)-5-methyl-piperidine-1-carboxylic acid tert-butyl Ester To a solution of 5-(1-Benzyl-5-methyl-1,4,5,6-tetrahydro-pyridin-3-yl)-2-chloro-phenylamine (3210 mg; 10.26 mmol) in EA (50 ml), was added di-tert-butyl bicarbonate (2463 mg; 11.29 mmol) and Pd (OH) 2/C (wet) (2800 mg). The reaction mixture was put on par shaker at 70-60 psi for 5.5 hours. The reaction mixture was filtered. The filtrate was concentrated to yield the title compound as a white solid, which was directly used for the next step reaction. LC-MS (M+1)=325.

8-Chloro-5-(5-methyl-piperidin-3-yl)-quinoline

To 3-(3-Amino-4-chloro-phenyl)-5-methyl-piperidine-1-carboxylic acid tert-butyl ester (3400 mg; 10.47 mmol) in 50 ml flask was added glycerol (3.08 ml; 41.87 mmol), iron(ii) sulfate heptahydrate (581 mg; 2.09 mmol), and sulfuric acid (3.64 ml; 62.80 mmol). The reaction mixture was stirred at 120° C. for 3 hr. The completed reaction was quenched with ice water (100 g) with 3.2 g of NaOH and extracted with DCM (3×100 ml). The combined organic layer was washed with small amount brine, dried and concentrated to yield the title compound (2290 mg, yield 83.3%). LC-MS (M+1)=261.

3-(8-Chloro-quinolin-5-yl)-5-methyl-piperidine-1-carboxylic Acid tert-butyl Ester To 8-Chloro-5-(5-methyl-piperidin-3-yl)-quinoline (2290 mg; 8.78 mmol) in DCM (20 ml) was added DIEA (2.36 ml; 13.17 mmol) and di-tert-butyl dicarbonate (2299 mg; 10.54 mmol). The resulting mixture was stirred at rt for 2 hr. The reaction mixture was concentrated and purified by Biotage silica gel column (50 g, eluting with hexane/EA 0-35%) to yield the title compound (1000 mg, yield 31.6%). LC-MS (M+1)=361.

3-(8-Cyano-quinolin-5-yl)-5-methyl-piperidine-1-carboxylic Acid tert-butyl Ester To 3-(8-Chloro-quinolin-5-yl)-5-methyl-piperidine-1-carboxylic acid tert-butyl ester (900 mg; 2.49 mmol) in DMF (10 ml), was added zinc cyanide (585 mg; 4.99 mmol) and degassed, followed by adding palladium tritert-butylphosphane (254 mg; 0.50 mmol). The reaction mixture was placed in microwave at 130° C. for 1 hr. The completed reaction was filtered. The filtrate was concentrated and purified by Biotage silica gel column (50 g, eluting with hexane/EA 0-50%) to yield the title compound (730 mg, yield 83.3%). LC-MS (M+1)=352.

5-(5-Methyl-Piperidin-3-Yl)-Quinoline-8-Carbonitrile Dihydrochloride

To a solution of 3-(8-Cyano-quinolin-5-yl)-5-methyl-piperidine-1-carboxylic acid tert-butyl ester (730.00 mg; 2.08 mmol) in methanol (1 ml) was added hydrogen chloride (5.19 ml; 20.77 mmol). The resulting mixture was stirred at RT for 1 hr. The completed reaction was concentrated to yield the title compound as an off-white solid, which was directly used for the next step reaction. LC-MS (M+1)=252

Cis- & Trans-5-Methyl-1-[2-(1-methyl-piperidin-4-yl)-acetyl]-piperidin-3-yl}-quinoline-8-carbonitrile To (1-Methyl-piperidin-4-yl)-acetic acid (218.18 mg; 1.39 mmol) in DMF (8 ml) was added HATU (492.51 mg; 1.30 mmol). The mixture was stirred for 10 mins and then added DIEA (0.66 ml; 3.70 mmol), and 5-(5-Methyl-piperidin-3-yl)-quinoline-8-carbonitrile dihydrochloride (300 mg; 0.93 mmol). The reaction mixture was stirred at RT for 1 hr. The completed reaction was concentrated and the crude was purified prep HPLC (basic, with 20-70% ACN/water) to yield cis-5-Methyl-1-[2-(1-methyl-piperidin-4-yl)-acetyl]-piperidin-3-yl}-quinoline-8-carbonitrile (185 mg, Yield 51.2%) and trans-5-Methyl-1-[2-(1-methyl-piperidin-4-yl)-acetyl]-piperidin-3-yl}-quinoline-8-carbonitrile (30 mg, yield 8.3%).

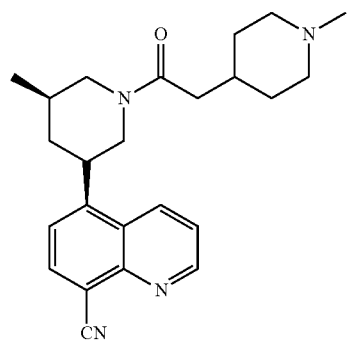

Compound 1

LC-MS (M+1)=391.1H NMR (400 MHz, DMSO-d6) δ 9.12 (dd, J=4.2, 1.5 Hz, 1H), 8.85 (td, J=8.9, 1.6 Hz, 1H), 8.36 (dd, J=7.6, 5.7 Hz, 1H), 7.86-7.59 (m, 2H), 4.58 (dd, J=28.7, 12.4 Hz, 2H), 3.98 (t, J=12.0 Hz, 1H), 3.48 (t, J=11.6 Hz, 1H), 2.86-2.57 (m, 3H), 2.45-2.18 (m, 3H), 2.12 (d, J=13.0 Hz, 3H), 2.01 (d, J=11.5 Hz, 1H), 1.93-1.73 (m, 3H), 1.71-1.57 (m, 3H), 1.32-1.03 (m, 2H), 0.95 (dd, J=20.5, 6.5 Hz, 3H).

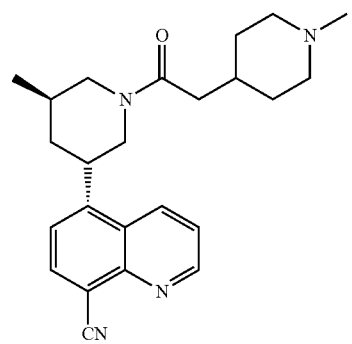

Compound 2

LC-MS (M+1)=391.1H NMR (400 MHz, DMSO-d6) δ 9.12 (td, J=4.6, 1.5 Hz, 1H), 8.76 (dd, J=8.8, 1.5 Hz, 1H), 8.34 (dd, J=12.9, 7.6 Hz, 1H), 7.80 (dd, J=8.7, 4.2 Hz, 1H), 7.69 (dd, J=26.5, 7.7 Hz, 1H), 4.26 (dd, J=12.9, 3.7 Hz, 2H), 3.91 (s, 1H), 3.76 (dq, J=9.0, 4.7, 4.0 Hz, 1H), 3.52 (qd, J=13.5, 3.9 Hz, 2H), 2.70 (dd, J=32.9, 11.1 Hz, 2H), 2.36 (dd, J=15.2, 6.7 Hz, 1H), 2.24 (ddd, J=15.3, 6.4, 4.3 Hz, 1H), 2.20-1.96 (m, 5H), 1.93-1.73 (m, 3H), 1.73-1.40 (m, 3H), 1.25-1.11 (m, 1H), 1.07 (dd, J=6.9, 2.9 Hz, 3H).

The following compounds were synthesized in an analogous manner:

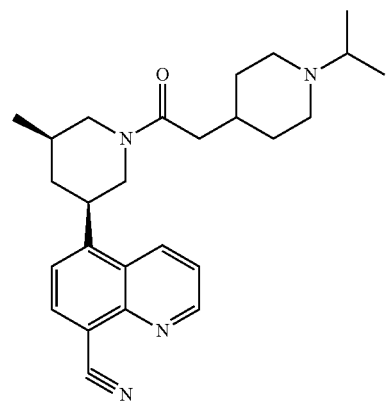 [SMILES: CC(C)N1CCC(CC(=O)N2C[C@H](C)C[C@H](c3ccc(C#N)c4ncccc34)C2)CC1]

Compound 19 (cis-1-[2-(1-Isopropyl-piperidin-4-yl)-acetyl]-5-methyl-piperidin-3-yl}-quinoline-8-carbonitrile)

From 5-(5-Methyl-piperidin-3-yl)-quinoline-8-carbonitrile dihydrochloride and (1-Isopropyl-piperidin-4-yl)-acetic acid. LC-MS (M+1)=419. ¹H NMR (400 MHz, DMSO-d₆) δ 9.12 (dd, J=4.2, 1.5 Hz, 1H), 8.92-8.81 (m, 1H), 8.36 (dd, J=7.6, 5.6 Hz, 1H), 7.85-7.53 (m, 2H), 4.58 (dd, J=28.0, 12.8 Hz, 1H), 4.06-3.90 (m, 1H), 3.66 (t, J=11.6 Hz, 1H), 3.49 (d, J=11.8 Hz, 1H), 2.86-2.54 (m, 4H), 2.39-2.15 (m, 2H), 2.06 (dt, J=21.1, 11.6 Hz, 3H), 1.80 (d, J=30.2 Hz, 1H), 1.62 (ddd, J=38.7, 24.1, 12.9 Hz, 4H), 1.33-1.04 (m, 3H), 1.04-0.78 (m, 9H).

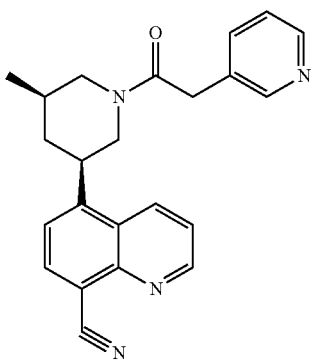

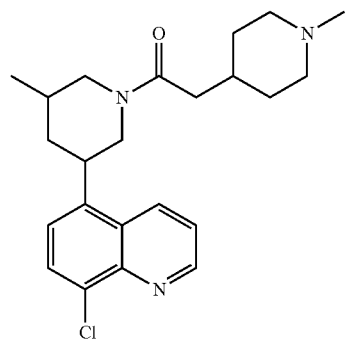

Compound 22 (1-[3-(8-Chloro-quinolin-5-yl)-5-methyl-piperidin-1-yl]-2-(1-methyl-piperidin-4-yl)-ethanone)

From 1-[3-(8-Chloro-quinolin-5-yl)-5-methyl-piperidin-1-yl]-2-(1-methyl-piperidin-4-yl)-ethanone and 1-methyl-4-piperidineacetic acid. LC-MS (M+1)=400. $^1$H NMR (400 MHz, DMSO-$d_6$) δ 9.05 (s, 1H), 8.76 (d, J=8.7 Hz, 1H), 8.00-7.89 (m, 1H), 7.72 (s, 1H), 7.54 (dd, J=18.0, 8.1 Hz, 1H), 4.58 (dd, J=31.6, 12.6 Hz, 1H), 3.97 (d, J=13.6 Hz, 1H), 3.56 (s, 1H), 3.20 (s, 1H), 2.79-2.64 (m, 3H), 2.59 (d, J=12.8 Hz, 1H), 2.41-2.19 (m, 3H), 2.11 (s, 2H), 2.00 (s, 1H), 1.82 (d, J=14.3 Hz, 3H), 1.64 (dd, J=31.6, 12.3 Hz, 4H), 1.48 (d, J=12.5 Hz, 1H), 1.20 (q, J=25.5, 21.3 Hz, 3H), 0.96 (dd, J=19.4, 6.4 Hz, 3H).

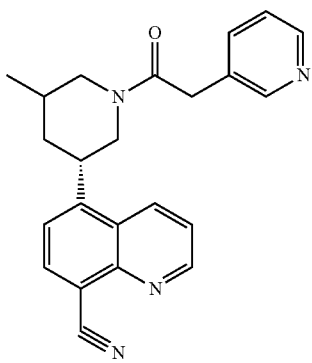

Compound 20 (cis-5-Methyl-1-(2-pyridin-3-yl-acetyl)-piperidin-3-yl]-quinoline-8-carbonitrile) and Compound 21 (trans-5-Methyl-1-(2-pyridin-3-yl-acetyl)-piperidin-3-yl]-quinoline-8-carbonitrile)

From 5-(5-Methyl-piperidin-3-yl)-quinoline-8-carbonitrile dihydrochloride and Pyridin-3-yl-acetic acid.

Compound 20

LC-MS (M+1)=371. $^1$H NMR (400 MHz, Methanol-$d_4$) δ 9.05 (dt, J=4.2, 1.7 Hz, 1H), 8.84 (dd, J=8.9, 1.6 Hz, 1H), 8.58-8.39 (m, 4H), 8.24 (d, J=7.6 Hz, 2H), 7.89-7.78 (m, 1H), 7.78-7.59 (m, 4H), 7.52-7.30 (m, 2H), 4.80-4.63 (m, 2H), 4.25-4.06 (m, 2H), 3.99 (s, 2H), 3.94-3.79 (m, 2H), 3.68-3.50 (m, 2H), 3.49-3.37 (m, 2H), 2.93 (dd, J=13.6, 11.5 Hz, 1H), 2.81-2.68 (m, 1H), 2.43 (t, J=12.3 Hz, 1H), 2.13 (t, J=14.2 Hz, 2H), 1.88 (s, 2H), 1.74 (q, J=11.9 Hz, 1H), 1.59 (q, J=12.0 Hz, 1H), 1.06 (dd, J=10.7, 6.6 Hz, 4H).

Compound 21

LC-MS (M+1)=371 $^1$H NMR (400 MHz, Methanol-$d_4$) δ 9.04 (td, J=4.6, 1.5 Hz, 2H), 8.77 (dd, J=8.8, 1.6 Hz, 1H), 8.57-8.48 (m, 1H), 8.48-8.35 (m, 3H), 8.20 (dd, J=7.7, 6.1 Hz, 1H), 7.82 (dt, J=7.9, 1.9 Hz, 1H), 7.78-7.61 (m, 4H), 7.53-7.29 (m, 2H), 4.43 (dd, J=12.8, 3.8 Hz, 1H), 4.31-4.06 (m, 1H), 4.06-3.84 (m, 4H), 3.84-3.57 (m, 4H), 3.43-3.35 (m, 1H), 3.26 (dd, J=13.3, 3.6 Hz, 1H), 2.31-2.01 (m, 3H), 2.01-1.73 (m, 2H), 1.17 (dd, J=9.9, 6.9 Hz, 4H).

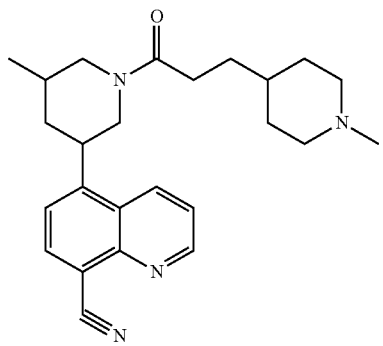

Compound 23 (5-Methyl-1-[3-(1-methyl-piperidin-4-yl)-propionyl]-piperidin-3-yl}-quinoline-8-carbonitrile)

From 5-(5-Methyl-piperidin-3-yl)-quinoline-8-carbonitrile dihydrochloride and 3-(1-Methyl-piperidin-4-yl)-propionic acid hydrochloride. LC-MS (M+1)=405. $^1$H NMR (400 MHz, DMSO-$d_6$) δ 9.11 (dd, J=4.2, 1.5 Hz, 1H), 8.93-8.79 (m, 1H), 8.36 (dd, J=7.6, 5.8 Hz, 1H), 7.83-7.62 (m, 2H), 4.56 (dd, J=27.2, 12.3 Hz, 1H), 4.09-3.86 (m, 1H), 3.68 (t, J=11.8 Hz, 1H), 3.59-3.38 (m, 1H), 2.87-2.57 (m, 3H), 2.47-2.28 (m, 2H), 2.23 (t, J=12.1 Hz, 1H), 2.11 (d, J=20.0 Hz, 3H), 1.99 (s, 1H), 1.79 (td, J=22.5, 20.3, 12.4 Hz, 3H), 1.72-1.61 (m, 2H), 1.57 (dd, J=11.0, 5.6 Hz, 1H), 1.45 (dt, J=23.8, 7.8 Hz, 3H), 1.29-1.02 (m, 3H), 0.95 (dd, J=19.3, 6.5 Hz, 3H).

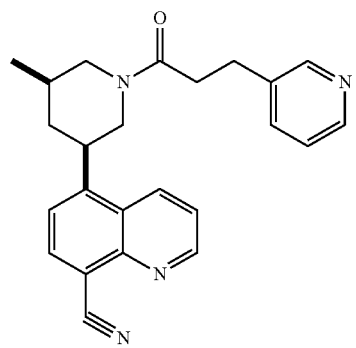

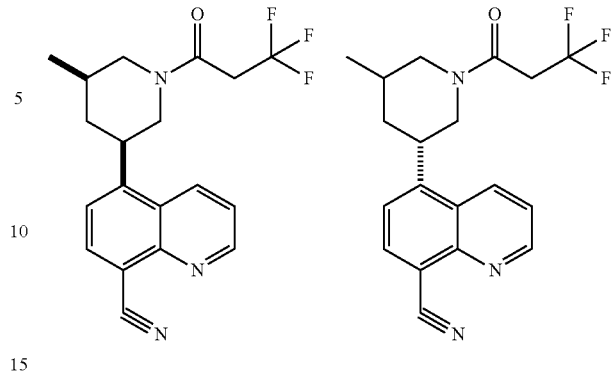

Compound 26 (cis-5-Methyl-1-(3,3,3-trifluoro-propionyl)-piperidin-3-yl]-quinoline-8-carbonitrile) and Compound 27 (trans-5-Methyl-1-(3,3,3-trifluoro-propionyl)-piperidin-3-yl]-quinoline-8-carbonitrile)

From 5-(5-Methyl-piperidin-3-yl)-quinoline-8-carbonitrile dihydrochloride and 3,3,3-Trifluoro-propionic acid.

Compound 26

LC-MS (M+1)=362. $^1$H NMR (400 MHz, DMSO-d$_6$) δ 9.12 (ddd, J=4.1, 2.5, 1.5 Hz, 1H), 8.92 (d, J=8.4 Hz, 1H), 8.81 (dd, J=8.9, 1.5 Hz, 1H), 8.37 (dd, J=7.7, 4.9 Hz, 1H), 7.88-7.64 (m, 2H), 4.55 (dd, J=27.6, 11.9 Hz, 1H), 3.94 (t, J=11.8 Hz, 1H), 3.72 (dtp, J=29.8, 11.6, 6.0 Hz, 2H), 3.54 (t, J=11.9 Hz, 1H), 2.92-2.57 (m, 1H), 2.33 (t, J=12.3 Hz, 1H), 2.05-1.42 (m, 3H), 0.96 (dd, J=13.4, 6.5 Hz, 3H).

Compound 27

LC-MS (M+1)=362. $^1$H NMR (400 MHz, Methanol-d$_4$) δ 9.06 (td, J=3.9, 1.6 Hz, 1H), 8.76 (ddd, J=18.3, 8.8, 1.6 Hz, 1H), 8.22 (dd, J=13.2, 7.7 Hz, 1H), 7.82-7.60 (m, 2H), 4.48-4.24 (m, 1H), 4.14-3.84 (m, 2H), 3.76-3.54 (m, 3H), 3.54-3.37 (m, 2H), 2.36-2.07 (m, 2H), 2.02-1.85 (m, 1H), 1.49-1.34 (m, 1H), 1.20 (dd, J=15.4, 6.9 Hz, 3H).

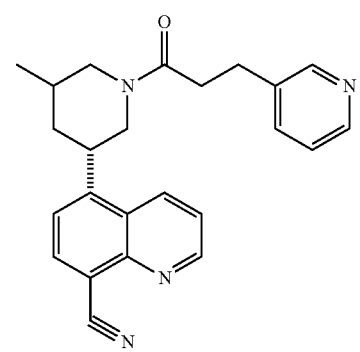

Compound 24 (cis-5-Methyl-1-(3-pyridin-3-yl-propionyl)-piperidin-3-yl]-quinoline-8-carbonitrile) and Compound 25 (trans-5-Methyl-1-(3-pyridin-3-yl-propionyl)-piperidin-3-yl]-quinoline-8-carbonitrile)

From 5-(5-Methyl-piperidin-3-yl)-quinoline-8-carbonitrile dihydrochloride and 3-Pyridin-3-yl-propionic acid.

Compound 24

LC-MS (M+1)=385. $^1$H NMR (400 MHz, Methanol-d$_4$) δ 9.03 (ddd, J=7.6, 4.2, 1.5 Hz, 1H), 8.75 (ddd, J=40.4, 8.8, 1.6 Hz, 1H), 8.55-8.29 (m, 2H), 8.20 (dd, J=7.6, 6.3 Hz, 1H), 7.91-7.61 (m, 3H), 7.36 (dddd, J=30.4, 7.8, 4.9, 0.9 Hz, 1H), 4.81-4.57 (m, 1H), 4.19-3.94 (m, 1H), 3.68-3.40 (m, 1H), 3.14-2.95 (m, 2H), 2.95-2.73 (m, 3H), 2.66 (dd, J=12.7, 11.5 Hz, 1H), 2.16-2.00 (m, 1H), 1.93-1.43 (m, 2H), 1.03 (dd, J=6.4, 3.6 Hz, 3H).

Compound 25

LC-MS (M+1)=385. $^1$H NMR (400 MHz, Methanol-d$_4$) δ 9.04 (dd, J=4.2, 1.7 Hz, 1H), 8.76 (dd, J=8.8, 1.6 Hz, 1H), 8.59-8.34 (m, 2H), 8.27-8.13 (m, 1H), 7.88-7.61 (m, 3H), 7.36 (ddd, J=26.9, 7.9, 4.9 Hz, 1H), 4.42 (dd, J=13.2, 3.8 Hz, 1H), 4.24-3.94 (m, 1H), 3.85 (td, J=9.9, 9.3, 4.5 Hz, 1H), 3.69-3.45 (m, 2H), 3.30-3.16 (m, 1H), 3.05 (t, J=7.3 Hz, 1H), 2.99-2.58 (m, 3H), 2.25-1.99 (m, 2H), 1.97-1.76 (m, 1H), 1.21-0.98 (m, 3H).

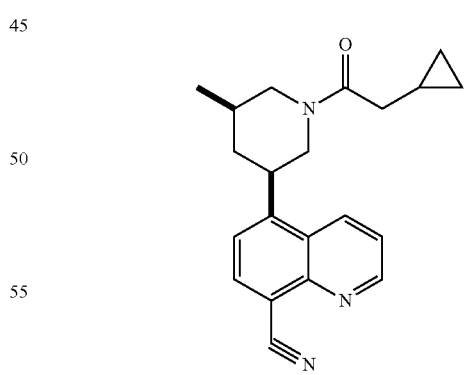

Compound 28 (Cis 5-[1-(2-Cyclopropyl-acetyl)-5-methyl-piperidin-3-yl]-quinoline-8-carbonitrile)

From 5-(5-Methyl-piperidin-3-yl)-quinoline-8-carbonitrile dihydrochloride and Cyclopropyl-acetic acid. LC-MS (M+1)=334. $^1$H NMR (400 MHz, Methanol-d$_4$) δ 9.16-8.98 (m, 1H), 8.69-8.51 (m, 1H), 8.29-8.20 (m, 1H), 7.77-7.50

(m, 2H), 4.56 (dt, J=18.2, 2.3 Hz, 1H), 4.34 (q, J=2.2 Hz, 1H), 4.24-4.08 (m, 1H), 4.00 (dd, J=13.5, 5.0 Hz, 1H), 3.45-3.36 (m, 1H), 2.82-2.56 (m, 1H), 2.49 (d, J=6.8 Hz, 1H), 2.41 (d, J=6.7 Hz, 1H), 1.20 (dd, J=9.7, 7.0 Hz, 3H), 1.14-0.95 (m, 1H), 0.57 (dddd, J=23.3, 8.1, 5.8, 4.2 Hz, 2H), 0.35-0.09 (m, 2H).

d₄) δ 9.14-8.98 (m, 1H), 8.79 (ddd, J=8.9, 4.3, 1.5 Hz, 1H), 8.22 (ddd, J=18.8, 7.7, 1.9 Hz, 1H), 7.85-7.62 (m, 2H), 4.35 (dd, J=13.1, 3.9 Hz, 1H), 4.29-4.16 (m, 1H), 4.13-3.98 (m, 1H), 3.91 (dt, J=8.9, 4.7 Hz, 1H), 3.71-3.61 (m, 1H), 3.61-3.47 (m, 1H), 3.41 (ddd, J=14.4, 9.1, 4.6 Hz, 1H), 3.27 (d, J=14.5 Hz, 1H), 3.18 (dd, J=13.0, 3.7 Hz, 1H), 3.05 (d, J=13.6 Hz, 1H), 2.68 (s, 3H), 2.44 (s, 2H), 2.32 (s, 2H), 2.25-2.06 (m, 2H), 2.04-1.88 (m, 1H), 1.48-1.35 (m, 1H), 1.20 (t, J=7.4 Hz, 3H).

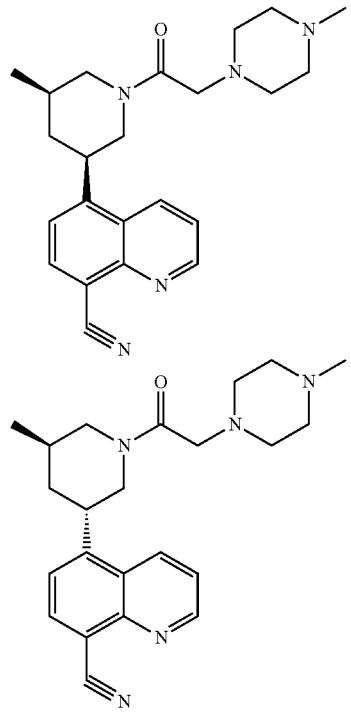

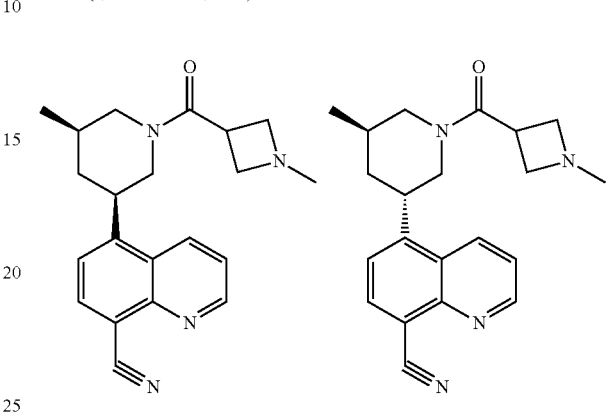

Compound 31 (cis-5-Methyl-1-(1-methyl-azetidine-3-carbonyl)-1,2,5,6-tetrahydro-pyridin-3-yl]-quinoline-8-carbonitrile) and Compound 32 (trans-5-Methyl-1-(1-methyl-azetidine-3-carbonyl)-1,2,5,6-tetrahydro-pyridin-3-yl]-quinoline-8-carbonitrile)

From 5-(5-Methyl-piperidin-3-yl)-quinoline-8-carbonitrile dihydrochloride and 1-Methyl-azetidine-3-carboxylic acid.

Compound 31

LC-MS (M+1)=392. ¹H NMR (400 MHz, Methanol-d₄) δ 9.06 LC-MS (M+1)=349. ¹H NMR (400 MHz, DMSO-d₆) δ 9.11 (dt, J=4.3, 1.5 Hz, 1H), 8.85 (ddd, J=8.9, 7.2, 1.6 Hz, 1H), 8.35 (dd, J=7.6, 1.6 Hz, 1H), 7.87-7.62 (m, 2H), 4.52 (dd, J=24.3, 11.6 Hz, 1H), 3.62 (d, J=13.3 Hz, 1H), 3.59-3.37 (m, 3H), 3.27-3.16 (m, 1H), 3.12 (t, J=6.2 Hz, 1H), 2.76-2.63 (m, 1H), 2.27 (t, J=12.2 Hz, 1H), 2.19 (s, 2H), 2.13 (s, 1H), 1.98 (d, J=11.7 Hz, 1H), 1.78 (q, J=7.6, 5.9 Hz, 1H), 1.67-1.39 (m, 1H), 0.94 (t, J=6.4 Hz, 3H).

Compound 32

LC-MS (M+1)=392. ¹H NMR (400 MHz, Methanol-d₄) δ 9.06 LC-MS (M+1)=349. ¹H NMR (400 MHz, Methanol-d₄) δ 9.06 (ddd, J=6.9, 4.2, 1.6 Hz, 1H), 8.77 (ddd, J=15.3, 8.9, 1.6 Hz, 1H), 8.23 (dd, J=7.7, 6.3 Hz, 1H), 7.86-7.62 (m, 2H), 4.42 (dd, J=13.1, 3.9 Hz, 1H), 4.15 (d, J=11.8 Hz, 1H), 4.00-3.86 (m, 1H), 3.86-3.76 (m, 1H), 3.71-3.61 (m, 2H), 3.59-3.40 (m, 3H), 3.30-3.16 (m, 1H), 2.67 (s, 1H), 2.38 (s, 2H), 2.30 (s, 1H), 2.26-2.09 (m, 2H), 2.00-1.89 (m, 1H), 1.17 (dd, J=24.8, 6.9 Hz, 3H).

Compound 29 (cis-5-Methyl-1-[2-(4-methyl-piperazin-1-yl)-acetyl]-piperidin-3-yl}-quinoline-8-carbonitrile) and Compound 30 (trans-5-Methyl-1-[2-(4-methyl-piperazin-1-yl)-acetyl]-piperidin-3-yl}-quinoline-8-carbonitrile)

From 5-(5-Methyl-piperidin-3-yl)-quinoline-8-carbonitrile dihydrochloride and (4-Methyl-piperazin-1-yl)-acetic acid.

Compound 29

LC-MS (M+1)=392. ¹H NMR (400 MHz, Methanol-d₄) δ 9.06 (ddd, J=9.1, 4.2, 1.6 Hz, 1H), 8.88 (ddd, J=19.2, 8.8, 1.6 Hz, 1H), 8.25 (dd, J=7.7, 6.5 Hz, 1H), 7.82-7.66 (m, 2H), 4.80-4.71 (m, 1H), 4.71-4.58 (m, 1H), 4.30 (d, J=13.0 Hz, 1H), 4.25-4.12 (m, 1H), 3.84-3.69 (m, 1H), 3.60 (ddd, J=11.8, 8.5, 3.4 Hz, 1H), 3.53-3.38 (m, 1H), 3.28 (d, J=14.2 Hz, 1H), 3.09 (d, J=13.6 Hz, 1H), 2.82 (dd, J=13.4, 11.5 Hz, 1H), 2.78-2.64 (m, 1H), 2.38 (t, J=12.3 Hz, 1H), 2.32 (s, 3H), 2.18 (d, J=28.1 Hz, 2H), 2.09-1.96 (m, 1H), 1.96-1.81 (m, 1H), 1.73 (q, J=12.0 Hz, 1H), 1.58 (q, J=12.2 Hz, 1H), 1.06 (dd, J=16.2, 6.6 Hz, 3H).

Compound 30

LC-MS (M+1)=392. ¹H NMR (400 MHz, Methanol-d₄) δ 9.06 LC-MS (M+1)=392. ¹H NMR (400 MHz, Methanol-

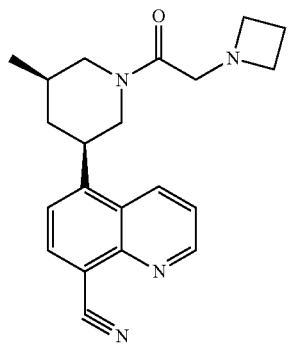 [SMILES: C[C@@H]1C[C@H](c2ccc(C#N)c3ncccc23)CN(C(=O)CN2CCC2)C1]

Compound 33 (cis-1-(2-Azetidin-1-yl-acetyl)-5-methyl-piperidin-3-yl]-quinoline-8-carbonitrile)

From 5-(5-Methyl-piperidin-3-yl)-quinoline-8-carbonitrile dihydrochloride and Azetidin-1-yl-acetic acid hydrochloride. LC-MS (M+1)=349. $^1$H NMR (400 MHz, DMSO-$d_6$) δ 9.24-9.01 (m, 2H), 8.36 (dd, J=9.4, 7.6 Hz, 1H), 7.89-7.64 (m, 2H), 4.48 (dd, J=31.0, 12.7 Hz, 1H), 4.14-4.00 (m, 1H), 3.95 (dd, J=10.4, 6.7 Hz, 1H), 3.70 (d, J=12.3 Hz, 1H), 3.54-3.37 (m, 1H), 3.19 (dq, J=20.5, 6.9 Hz, 4H), 3.09-2.94 (m, 1H), 2.68 (dt, J=23.8, 12.1 Hz, 1H), 2.22 (t, J=11.6 Hz, 1H), 2.10-1.86 (m, 3H), 1.77-1.46 (m, 2H), 0.96 (d, J=5.9 Hz, 3H).

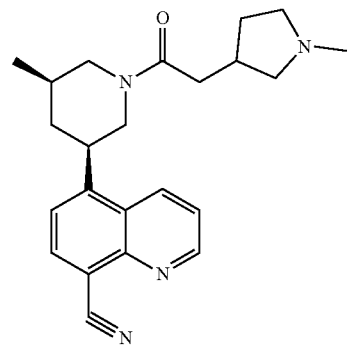

Compound 35 (cis-5-Methyl-1-[2-(1-methyl-pyrrolidin-3-yl)-acetyl]-piperidin-3-yl-quinoline-8-carbonitrile)

From 5-(5-Methyl-piperidin-3-yl)-quinoline-8-carbonitrile dihydrochloride and (1-Methyl-pyrrolidin-3-yl)-acetic acid. LC-MS (M+1)=377. UPLC (% area): 99.0%. 1H NMR (400 MHz, DMSO-d6) δ 9.11 (dd, J=4.2, 1.5 Hz, 1H), 8.85 (dd, J=18.4, 6.2 Hz, 1H), 8.35 (dd, J=7.6, 4.5 Hz, 1H), 7.82-7.75 (m, 1H), 7.70 (dd, J=13.3, 7.7 Hz, 1H), 4.56 (dd, J=28.1, 12.5 Hz, 1H), 3.96 (t, J=14.0 Hz, 1H), 3.48 (s, 1H), 2.75 (dd, J=13.5, 11.5 Hz, 1H), 2.72-2.55 (m, 2H), 2.49-2.31 (m, 5H), 2.20 (dd, J=19.3, 6.0 Hz, 4H), 2.13-2.05 (m, 1H), 2.05-1.94 (m, 2H), 1.60 (q, J=12.0 Hz, 1H), 1.35 (s, 2H), 0.95 (dd, J=19.6, 6.5 Hz, 3H).

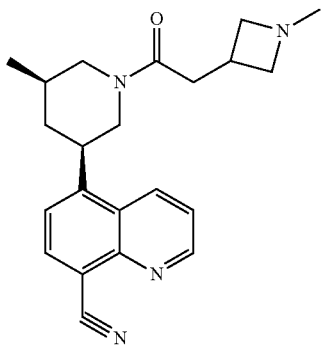

Compound 34 (cis-5-Methyl-1-[2-(1-methyl-azetidin-3-yl)-acetyl]-piperidin-3-yl-quinoline-8-carbonitrile)

From 5-(5-Methyl-piperidin-3-yl)-quinoline-8-carbonitrile dihydrochloride and (1-Methyl-azetidin-3-yl)-acetic acid hydrochloride. LC-MS (M+1)=363. $^1$H NMR (400 MHz, DMSO-$d_6$) δ 9.11 (dd, J=4.2, 1.5 Hz, 1H), 8.93-8.76 (m, 1H), 8.35 (t, J=7.3 Hz, 1H), 7.81-7.63 (m, 2H), 4.53 (dd, J=28.2, 12.3 Hz, 1H), 3.94 (dd, J=16.1, 11.9 Hz, 1H), 3.68 (t, J=11.9 Hz, 1H), 3.46 (q, J=16.8, 14.2 Hz, 1H), 2.83-2.53 (m, 5H), 2.15 (d, J=19.9 Hz, 3H), 2.00 (d, J=12.4 Hz, 1H), 1.81 (d, J=43.4 Hz, 2H), 1.59 (q, J=12.0 Hz, 1H), 1.46 (q, J=12.1 Hz, 1H), 0.94 (dd, J=23.0, 6.5 Hz, 3H).

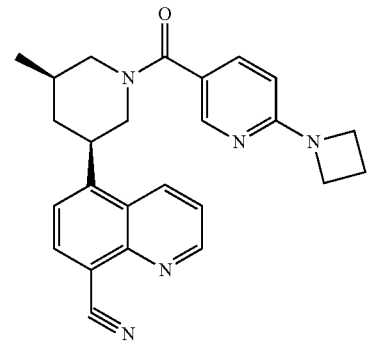 [SMILES: C[C@@H]1C[C@H](c2ccc(C#N)c3ncccc23)CN(C(=O)c2ccc(N3CCC3)nc2)C1]

Compound 36 (cis-5-[1-(6-Azetidin-1-yl-pyridine-3-carbonyl)-5-methyl-piperidin-3-yl]-quinoline-8-carbonitrile)

From 5-(5-Methyl-piperidin-3-yl)-quinoline-8-carbonitrile dihydrochloride and 6-Azetidin-1-yl-nicotinic acid. LC-MS (M+1)=412.5. UPLC (% area): 95.0%. 1H NMR (400 MHz, DMSO-d6) δ 9.11 (dd, J=4.2, 1.5 Hz, 1H), 8.86 (s, 1H), 8.35 (d, J=7.7 Hz, 1H), 8.24 (d, J=2.3 Hz, 1H), 7.76 (s, 1H), 7.70 (d, J=7.6 Hz, 1H), 7.64 (dd, J=8.5, 2.4 Hz, 1H), 6.35 (d, J=8.6 Hz, 1H), 4.02-3.95 (m, 3H), 3.72 (d, J=12.0 Hz, 2H), 2.70 (s, 1H), 2.34 (d, J=14.5 Hz, 2H), 2.04 (d, J=12.3 Hz, 1H), 1.89 (d, J=18.0 Hz, 2H), 1.64 (d, J=13.9 Hz, 2H), 1.52 (d, J=14.1 Hz, 1H), 1.48-1.37 (m, 1H), 0.95-0.90 (m, 2H).

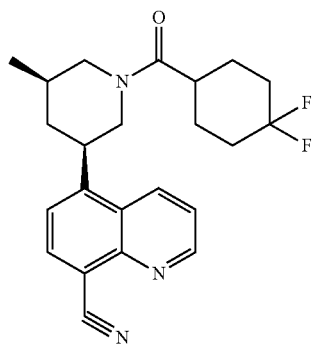 [SMILES: C[C@@H]1C[C@H](c2ccc(C#N)c3ncccc23)CN(C(=O)C2CCC(F)(F)CC2)C1]

Compound 37 (cis-5-[1-(4,4-Difluoro-cyclohexanecarbonyl)-5-methyl-piperidin-3-yl]-quinoline-8-carbonitrile)

From 5-(5-Methyl-piperidin-3-yl)-quinoline-8-carbonitrile dihydrochloride and 4,4-difluorocyclohexanecarboxylic acid. LC-MS (M+1)=398.2. UPLC (% area): 100.0%. 1H NMR (400 MHz, DMSO-d6) δ 9.12 (dd, J=4.3, 1.5 Hz, 1H), 8.85 (t, J=8.9 Hz, 1H), 8.36 (t, J=8.3 Hz, 1H), 7.80 (dd, J=8.5, 4.2 Hz, 1H), 7.76 (dd, J=8.9, 5.9 Hz, 1H), 7.69 (d, J=7.7 Hz, 1H), 4.57 (dd, J=26.5, 12.4 Hz, 1H), 4.10 (dd, J=23.3, 13.2 Hz, 1H), 3.58 (dt, J=70.6, 11.0 Hz, 1H), 2.93 (d, J=12.5 Hz, 1H), 2.87-2.63 (m, 2H), 1.91 (d, J=85.3 Hz, 9H), 1.74-1.54 (m, 4H), 1.00 (d, J=6.5 Hz, 2H), 0.92 (d, J=6.5 Hz, 1H).

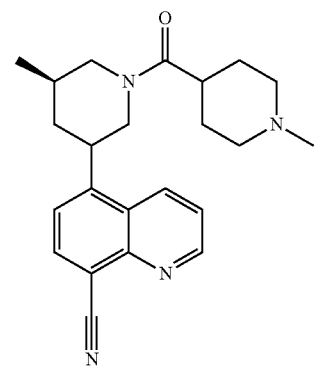

Compound 39 (cis-5-[5-Methyl-1-(1-methyl-piperidine-4-carbonyl)-piperidin-3-yl]-quinoline-8-carbonitrile)

From 5-(5-Methyl-piperidin-3-yl)-quinoline-8-carbonitrile dihydrochloride and 1-Methyl-piperidine-4-carboxylic acid. LC-MS (M+1)=377.4. UPLC (% area): 100.0%.

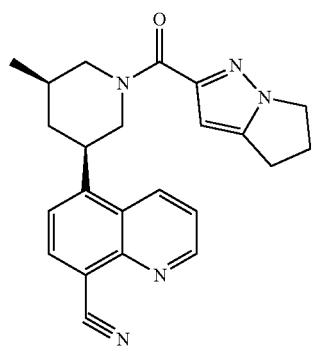 [SMILES: C[C@@H]1C[C@H](c2ccc(C#N)c3ncccc23)CN(C(=O)c2cc3n(n2)CCC3)C1]

Compound 38 (cis-5-[1-(5,6-Dihydro-4H-pyrrolo[1,2-b]pyrazole-2-carbonyl)-5-methyl-piperidin-3-yl]-quinoline-8-carbonitrile)

From 5-(5-Methyl-piperidin-3-yl)-quinoline-8-carbonitrile dihydrochloride and 5,6-dihydro-4h-pyrrolo[1,2-b]pyrazole-2-carboxylic acid. LC-MS (M+1)=386.4. UPLC (% area): 100.0%. 1H NMR (400 MHz, DMSO-d6) δ 9.12 (d, J=4.0 Hz, 1H), 8.91 (s, 1H), 8.36 (d, J=7.9 Hz, 1H), 7.84-7.77 (m, 1H), 7.74 (d, J=7.7 Hz, 1H), 6.35 (d, J=17.9 Hz, 1H), 4.95 (d, J=14.4 Hz, 1H), 4.63 (t, J=16.3 Hz, 1H), 4.20-4.07 (m, 2H), 3.98 (s, 1H), 3.69 (d, J=39.0 Hz, 2H), 3.09 (t, J=11.9 Hz, 1H), 2.93-2.78 (m, 3H), 2.04 (d, J=12.5 Hz, 1H), 1.87 (d, J=14.8 Hz, 1H), 1.72 (dd, J=25.4, 12.3 Hz, 1H), 1.02 (d, J=6.2 Hz, 1H), 0.95 (d, J=6.6 Hz, 1H), 0.92 (d, J=6.6 Hz, 1H).

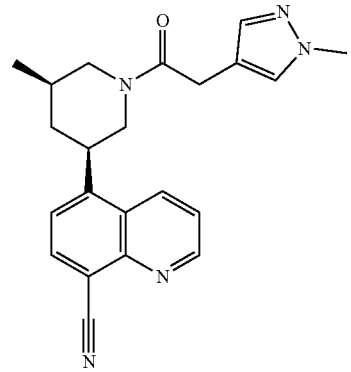

Compound 107 (cis-5-Methyl-1-[2-(1-methyl-1H-pyrazol-4-yl)-acetyl]-piperidin-3-yl-quinoline-8-carbonitrile)

From 5-(5-Methyl-piperidin-3-yl)-quinoline-8-carbonitrile dihydrochloride and (1-Methyl-1H-pyrazol-4-yl)-acetic acid. LC-MS (M+1)=374.4. UPLC (% area): 99.0%. 1H NMR (400 MHz, DMSO-d6) δ 9.12-9.09 (m, 1H), 8.83 (d, J=7.9 Hz, 1H), 8.35 (d, J=7.6 Hz, 1H), 7.79 (dd, J=8.7, 4.1 Hz, 1H), 7.76-7.67 (m, 2H), 7.61-7.18 (m, 3H), 4.64-4.49 (m, 1H), 4.08-3.95 (m, 1H), 3.78 (d, J=23.7 Hz, 3H), 3.68-3.44 (m, 4H), 2.72 (dt, J=38.7, 12.4 Hz, 2H), 2.28 (t, J=12.1 Hz, 1H), 1.97 (t, J=15.9 Hz, 1H), 1.55 (dq, J=44.2, 12.0 Hz, 2H), 0.94 (t, J=6.7 Hz, 3H).

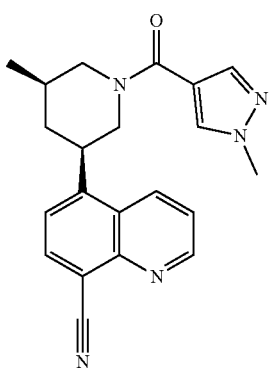 [SMILES: C[C@@H]1C[C@H](c2ccc(C#N)c3ncccc23)CN(C(=O)c2cnn(C)c2)C1]

Compound 108 (cis-5-Methyl-1-(1-methyl-1H-pyrazole-4-carbonyl)-piperidin-3-yl-quinoline-8-carbonitrile)

From 5-(5-Methyl-piperidin-3-yl)-quinoline-8-carbonitrile dihydrochloride and 1-Methyl-1H-pyrazole-4-carboxylic acid. LC-MS (M+1)=360.4. UPLC (% area): 100.0%. 1H NMR (400 MHz, DMSO-d6) δ 9.11 (dd, J=4.1, 1.5 Hz, 1H), 8.36 (d, J=7.6 Hz, 1H), 8.08 (s, 1H), 7.73 (t, J=9.8 Hz, 3H), 3.86 (s, 3H), 3.66 (s, 1H), 2.04 (d, J=12.4 Hz, 1H), 1.89 (s, 1H), 1.66 (s, 2H), 0.96 (d, J=6.5 Hz, 3H).

Example 2: Synthesis of Compound 3 (2-(1-Methyl-piperidin-4-yl)-1-[3-methyl-5-(8-trifluoromethyl-quinolin-5-yl)-piperidin-1-yl]-ethanone) and Compound 4 (cis-2-(1-Methyl-piperidin-4-yl-1-[3-methyl-5-(8-trifluoromethyl-quinolin-5-yl)-piperidin-1-yl]-ethanone)

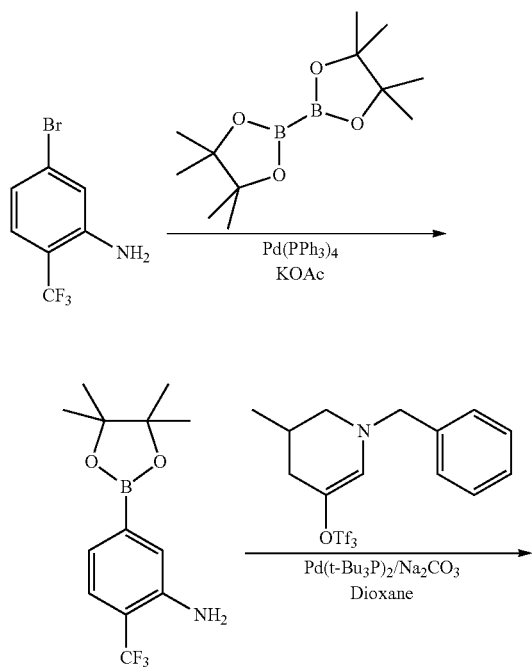

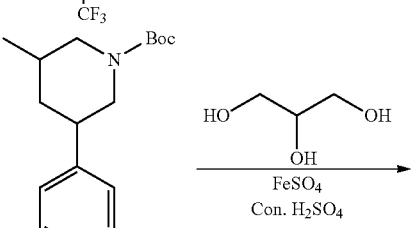

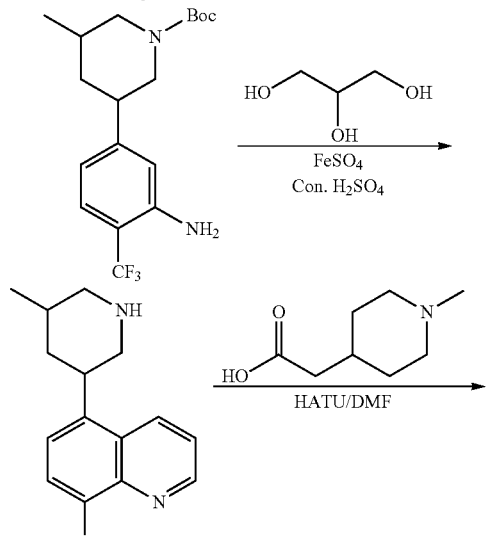

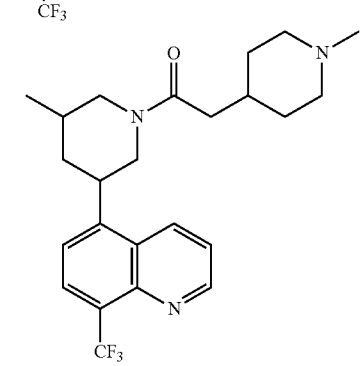

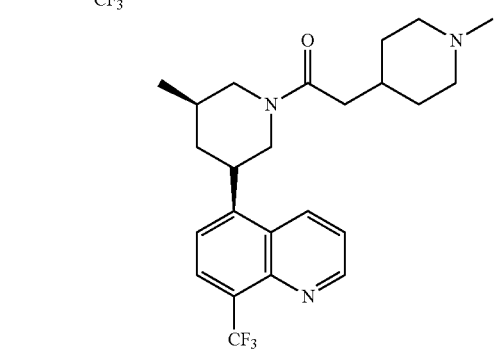

5-(4, 4, 5, 5-Tetramethyl-[1, 3, 2] dioxaborolan-2-yl)-2-trifluoromethyl-phenylamine A mixture of 5-Bromo-2-trifluoromethyl-phenylamine (1151 mg; 4.80 mmol), 4,4,5,5,4',4',5',5'-Octamethyl-[2,2']bi[[1,3,2]dioxaborolanyl] (1339 mg; 5.27 mmol), and potassium acetate (941 mg; 9.59 mmol) in dioxane (15 ml) was degassed, and then added tetrakis(triphenylphosphine)palladium(0). The reaction mixture was stirred at 100° C. for 18 hrs. The completed reaction was filtered. The filtrate was concentrated. The crude was purified by Biotage silica gel column (100 g, eluting with EA in hexane 0-30%) to yield the title compound (966 mg, yield 70%). LC-MS (M+1)=288.

5-(1-Benzyl-5-methyl-1, 4, 5, 6-tetrahydro-pyridin-3-yl)-2-trifluoromethyl-phenylamine A mixture of trifluoro-methanesulfonic acid 1-benzyl-5-methyl-1,4,5,6-tetrahydro-pyridin-3-yl ester (6000 mg; 17.89 mmol), 5-(4,4,5,5-Tetramethyl-[1,3,2]dioxaborolan-2-yl)-2-trifluoromethyl-phenylamine (4622 mg; 16.10 mmol) and sodium carbonate (2275 mg; 21.47 mmol) in dioxane (100 ml) and water (10 ml) was degassed, and then added bis(tri-tert-butylphosphine)palladium(0) (457.19 mg; 0.89 mmol). The mixture was stirred at 45° C. overnight. The completed reaction was filtered and the filtrate was concentrate. The crude was purified by Biotage silica gel column (eluted with DMC containing 2% methanol and 0.01% TEA) to yield the title compound (3300 mg, yield 54%). LC-MS (M+1)=347.

3-(3-Amino-4-trifluoromethyl-phenyl)-5-methyl-piperidine-1-carboxylic Acid tert-butyl Ester To 5-(1-Benzyl-5-methyl-1,4,5,6-tetrahydro-pyridin-3-yl)-2-trifluoromethyl-phenylamine (2250 mg; 6.50 mmol) in ethanol (30 ml) was added tert-butoxycarbonyl methyl carbonate (1487 mg; 8.44 mmol), Pd(OH)$_2$ (2 g, wet, 10% on carbon). The reaction mixture was put on par shaker at 75 psi for 6 hours. The completed reaction was filtered and concentrated to yield the title compound, which was directly used for the next step reaction. LC-MS (M+1)=359

5-Methyl-piperidin-3-yl)-8-trifluoromethyl-quinoline

To 3-(3-Amino-4-trifluoromethyl-phenyl)-5-methyl-piperidine-1-carboxylic acid tert-butyl ester (2329 mg; 6.50 mmol) in 50 ml flask was added glycerol (1.92 ml; 26.00 mmol), iron(ii) sulfate heptahydrate (361 mg; 1.30 mmol) and sulfuric acid (2.26 ml; 39.00 mmol). The resulting mixture was stirred at 120° C. for 2 hr. The completed reaction was cooled to rt and poured into ice water (100 g) and aqueous 2N NaOH (13 ml), extracted with DCM (2×100 ml). The combined organic layers were washed with small brine (20 ml), dried, and concentrated to yield the title compound, which was directly used for the next step reaction. LC-MS (M+1)=295.

2-(1-Methyl-piperidin-4-yl)-1-[3-methyl-5-(8-trifluoromethyl-quinolin-5-yl)-piperidin-1-yl]-ethanone & cis 2-(1-Methyl-piperidin-4-yl)-1-[3-methyl-5-(8-trifluoromethyl-quinolin-5-yl)-piperidin-1-yl]-ethanone To a solution of (1-Methyl-piperidin-4-yl)-acetic acid (64.10 mg; 0.41 mmol) in DMF (2 ml) was added HATU (142 mg; 0.37 mmol). After stirring for 10 mins, DIEA (0.12 ml; 0.68 mmol) was added followed by 5-(5-Methyl-piperidin-3-yl)-8-trifluoromethyl-quinoline (100 mg; 0.34 mmol). The reaction mixture was stirred at RT for 1 hr. The completed reaction was concentrated. The crude was purified by prep HPLC (Basic, eluting with 20%-70% ACN/water) to yield 2-(1-Methyl-piperidin-4-yl)-1-[3-methyl-5-(8-trifluoromethyl-quinolin-5-yl)-piperidin-1-yl]-ethanone and cis-2-(1-Methyl-piperidin-4-yl)-1-[3-methyl-5-(8-trifluoromethyl-quinolin-5-yl)-piperidin-1-yl]-ethanone.

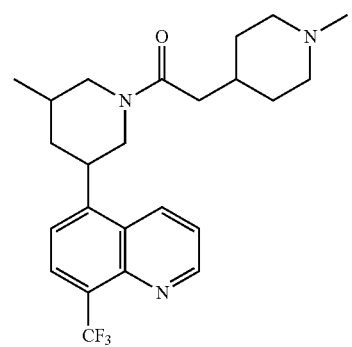

Compound 3

LC-MS (M+1)=434. 1H NMR (400 MHz, DMSO-d6) δ 9.08 (dd, J=4.1, 1.6 Hz, 1H), 8.82 (ddd, J=8.8, 4.5, 1.7 Hz, 1H), 8.16 (dd, J=7.8, 2.8 Hz, 1H), 7.82-7.61 (m, 2H), 4.64 (d, J=12.8 Hz, 1H), 3.99 (t, J=13.3 Hz, 1H), 3.64 (t, J=11.8 Hz, 2H), 2.83-2.52 (m, 4H), 2.41-2.21 (m, 2H), 2.15 (d, J=12.6 Hz, 3H), 2.03 (d, J=12.4 Hz, 1H), 1.94-1.78 (m, 3H), 1.74-1.52 (m, 4H), 1.21 (dd, J=33.8, 16.8 Hz, 2H), 0.99-0.84 (m, 3H).

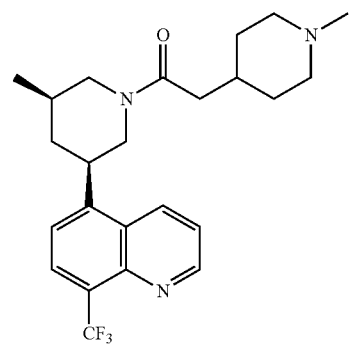

Compound 4

LC-MS (M+1)=434. 1H NMR (400 MHz, DMSO-d6) δ 9.09 (d, J=4.4 Hz, 1H), 8.74 (d, J=8.5 Hz, 1H), 8.14 (dd, J=13.2, 7.8 Hz, 1H), 7.80-7.61 (m, 2H), 4.31 (d, J=12.5 Hz, 1H), 3.85 (d, J=77.1 Hz, 2H), 3.60-3.44 (m, 1H), 2.69 (d, J=27.9 Hz, 2H), 2.36 (dd, J=15.3, 6.6 Hz, 2H), 2.17-1.92 (m, 5H), 1.91-1.35 (m, 6H), 1.25-0.88 (m, 5H).

The following compounds were synthesized in an analogous manner:

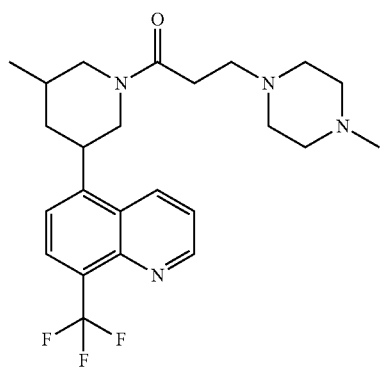

Compound 11 (3-(4-Methyl-piperazin-1-yl)-1-[3-methyl-5-(8-trifluoromethyl-quinolin-5-yl)-piperidin-1-yl]-propan-1-one)

From 5-(5-Methyl-piperidin-3-yl)-8-trifluoromethyl-quinoline and 3-(4-Methyl-piperazin-1-yl)-propionic acid. LC-MS (M+1)=449. ¹H NMR (400 MHz, DMSO-d$_6$) δ 9.08 (dd, J=4.1, 1.6 Hz, 1H), 8.84 (dd, J=21.4, 8.8 Hz, 1H), 8.17 (d, J=7.9 Hz, 1H), 7.84-7.59 (m, 2H), 4.58 (dd, J=34.2, 12.1 Hz, 1H), 4.10-3.89 (m, H), 3.68 (s, 1H), 3.49 (d, J=11.5 Hz, 1H), 2.84-2.67 (m, 2H), 2.59 (s, 2H), 2.31 (dd, J=61.9, 26.9 Hz, 6H), 2.16 (s, 3H), 2.04 (d, J=28.2 Hz, 2H), 1.83 (d, J=53.8 Hz, 2H), 1.69-1.53 (m, 2H), 0.96 (dd, J=20.9, 6.5 Hz, 3H).

Compound 12 (cis-3-Methyl-5-(8-trifluoromethyl-quinolin-5-yl)-piperidin-1-yl]-3-pyrazol-1-yl-propan-1-one) and Compound 13 (trans-3-Methyl-5-(8-trifluoromethyl-quinolin-5-yl)-piperidin-1-yl]-3-pyrazol-1-yl-propan-1-one)

From 5-(5-Methyl-piperidin-3-yl)-8-trifluoromethyl-quinoline and 3-(1h-pyrazol-1-yl) propanoic acid.

Compound 12

LC-MS (M+1)=417. ¹H NMR (400 MHz, Methanol-d$_4$) δ 9.01 (dt, J=4.1, 1.8 Hz, 1H), 8.76 (ddd, J=21.3, 8.8, 1.7 Hz, 1H), 8.12 (d, J=7.7 Hz, 1H), 7.75-7.67 (m, 2H), 7.67-7.60 (m, 1H), 7.54 (dd, J=2.0, 0.7 Hz, 1H), 6.29 (dt, J=14.4, 2.1 Hz, 1H), 4.61-4.41 (m, 2H), 4.10-3.90 (m, 1H), 3.61-3.41 (m, 1H), 3.26-2.96 (m, 2H), 2.85-2.57 (m, 1H), 2.18-2.03 (m, 1H), 1.87-1.50 (m, 2H), 1.03 (dd, J=6.5, 5.4 Hz, 3H).

Compound 13

LC-MS (M+1)=417. ¹H NMR (400 MHz, Methanol-d$_4$) δ 9.01 (ddd, J=6.0, 4.2, 1.6 Hz, 1H), 8.71 (ddd, J=12.6, 8.9, 1.7 Hz, 1H), 8.09 (dd, J=12.3, 7.7 Hz, 1H), 7.78-7.66 (m, 1H), 7.66-7.56 (m, 1H), 7.56-7.38 (m, 1H), 6.28 (dt, J=9.1, 2.1 Hz, 1H), 4.58-4.48 (m, 2H), 4.48-4.33 (m, 1H), 4.25-4.13 (m, 1H), 4.07-3.90 (m, 1H), 3.87-3.73 (m, 1H), 3.55 (t, J=3.2 Hz, 1H), 3.46 (dd, J=13.5, 10.2 Hz, 1H), 3.22-3.06 (m, 1H), 3.01 (dt, J=16.3, 6.4 Hz, 1H), 2.83 (dt, J=15.9, 6.0 Hz, 1H), 2.29-2.02 (m, 2H), 1.96-1.83 (m, 1H), 1.10 (t, J=6.8 Hz, 3H).

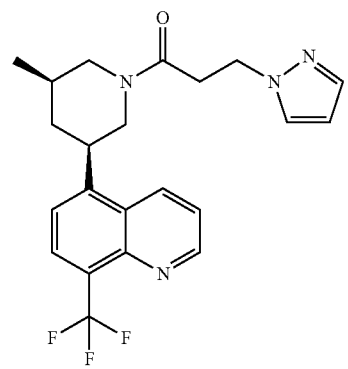

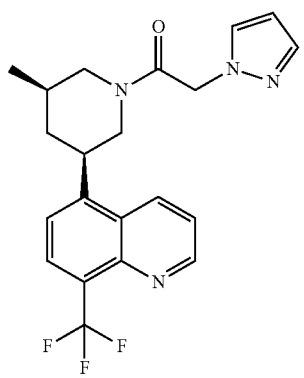

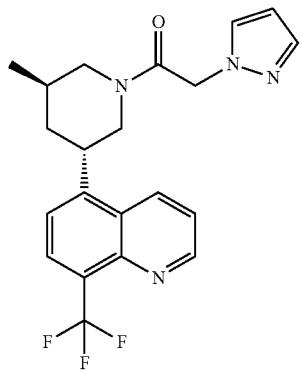

Compound 14 (cis-3-Methyl-5-(8-trifluoromethyl-quinolin-5-yl)-piperidin-1-yl]-2-pyrazol-1-yl-ethanone) and Compound 15 (trans-3-Methyl-5-(8-trifluoromethyl-quinolin-5-yl)-piperidin-1-yl]-2-pyrazol-1-yl-ethanone)

From 5-(5-Methyl-piperidin-3-yl)-8-trifluoromethyl-quinoline and 2-(1H-pyrazol-1-yl)acetic acid.

Compound 14

LC-MS (M+1)=404. $^1$H NMR (400 MHz, Methanol-$d_4$) δ 9.07-8.95 (m, 1H), 8.86-8.75 (m, 1H), 8.14 (t, J=7.6 Hz, 1H), 7.68 (ddt, J=15.7, 7.0, 3.2 Hz, 2H), 7.63-7.48 (m, 1H), 6.36 (dt, J=19.4, 2.1 Hz, 1H), 5.39-5.17 (m, 2H), 5.08 (d, J=16.2 Hz, 1H), 4.79-4.58 (m, 1H), 4.25-3.96 (m, 1H), 3.69 (dt, J=42.5, 11.9 Hz, 1H), 3.54-3.38 (m, 1H), 2.94 (dd, J=13.7, 11.7 Hz, 1H), 2.85-2.66 (m, 1H), 2.45 (t, J=12.3 Hz, 1H), 2.18 (d, J=12.7 Hz, 1H), 2.01 (d, J=34.9 Hz, 1H), 1.70 (dq, J=57.8, 12.1 Hz, 1H), 1.08 (dd, J=23.6, 6.6 Hz, 3H).

Compound 15

LC-MS (M+1)=404. $^1$H NMR (400 MHz, Methanol-$d_4$) δ 9.01 (dd, J=10.4, 4.2 Hz, 1H), 8.75 (d, J=8.8 Hz, 1H), 8.12 (dd, J=17.1, 7.8 Hz, 1H), 7.78-7.60 (m, 3H), 7.60-7.46 (m, 1H), 6.45-6.27 (m, 1H), 5.35-5.14 (m, 2H), 4.41 (d, J=12.4 Hz, 1H), 4.32-4.07 (m, 2H), 4.02-3.77 (m, 2H), 3.64 (d, J=27.3 Hz, 2H), 3.43 (s, 1H), 2.29-2.09 (m, 2H), 1.96 (s, 1H), 1.23 (dd, J=13.0, 6.9 Hz, 3H).

Compound 16 (cis-3-Methyl-5-(8-trifluoromethyl-quinolin-5-yl)-piperidin-1-yl]-2-morpholin-4-yl-ethanone) and Compound 17 (trans-3-Methyl-5-(8-trifluoromethyl-quinolin-5-yl)-piperidin-1-yl]-2-morpholin-4-yl-ethanone)

From 5-(5-Methyl-piperidin-3-yl)-8-trifluoromethyl-quinoline and 2-morpholinoacetic acid hydrochloride.

Compound 16

LC-MS (M+1)=422. $^1$H NMR (400 MHz, Methanol-$d_4$) δ 9.02 (ddd, J=9.3, 4.2, 1.6 Hz, 1H), 8.85 (ddd, J=25.5, 8.8, 1.7 Hz, 1H), 8.14 (t, J=7.1 Hz, 1H), 7.70 (qd, J=8.1, 7.5, 3.6 Hz, 2H), 4.72-4.47 (m, 1H), 4.41-4.08 (m, 1H), 3.76 (t, J=4.7 Hz, 3H), 3.70-3.52 (m, 2H), 3.43 (dd, J=13.8, 5.6 Hz, 1H), 3.28 (d, J=14.1 Hz, 1H), 3.11 (d, J=13.6 Hz, 1H), 2.83 (dd, J=13.3, 11.5 Hz, 1H), 2.71 (t, J=12.2 Hz, 1H), 2.60 (q, J=5.2 Hz, 2H), 2.53-2.30 (m, 2H), 2.17 (d, J=13.0 Hz, 1H), 2.11-1.82 (m, 2H), 1.68 (dq, J=52.1, 12.1 Hz, 2H), 1.07 (dd, J=17.0, 6.6 Hz, 3H).

Compound 17

LC-MS (M+1)=422. $^1$H NMR (400 MHz, Methanol-$d_4$) δ 9.02 (ddd, J=11.6, 4.1, 1.6 Hz, 1H), 8.83-8.69 (m, 1H), 8.11 (dd, J=20.7, 7.8 Hz, 1H), 7.80-7.55 (m, 2H), 4.40 (d, J=15.7 Hz, 1H), 4.28-4.16 (m, 1H), 4.05 (t, J=10.7 Hz, 1H), 3.98-3.83 (m, 1H), 3.77-3.50 (m, 6H), 3.45-3.36 (m, 2H), 3.03 (d, J=13.7 Hz, 1H), 2.57 (t, J=4.7 Hz, 2H), 2.53-2.46 (m, 1H), 2.46-2.34 (m, 1H), 2.34-2.08 (m, 2H), 1.96 (d, J=13.4 Hz, 1H), 1.21 (d, J=6.9 Hz, 3H).

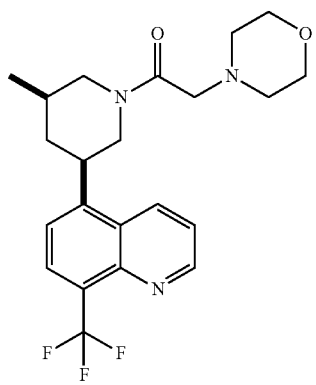

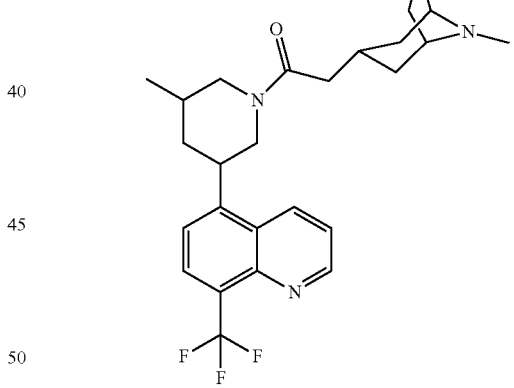

Compound 18 (2-(8-Methyl-8-aza-bicyclo[3.2.1]oct-3-yl)-1-[3-methyl-5-(8-trifluoromethyl-quinolin-5-yl)-piperidin-1-yl]-ethanone)

From 5-(5-Methyl-piperidin-3-yl)-8-trifluoromethyl-quinoline and 2-(8-methyl-8-azabicyclo[3.2.1]octan-3-yl)acetic acid hydrochloride. LC-MS (M+1)=460. $^1$H NMR (400 MHz, DMSO-$d_6$) δ 9.12-9.03 (m, 1H), 8.74 (d, J=9.6 Hz, 1H), 8.14 (dd, J=13.4, 7.8 Hz, 1H), 7.79-7.61 (m, 2H), 4.31 (d, J=12.6 Hz, 1H), 3.90 (d, J=14.8 Hz, 1H), 3.74 (s, 1H), 3.61-3.38 (m, 2H), 3.17 (t, J=11.2 Hz, 2H), 3.00 (d, J=35.2 Hz, 2H), 2.26-1.91 (m, 9H), 1.85 (d, J=19.8 Hz, 2H), 1.64 (dt, J=19.8, 9.8 Hz, 2H), 1.33-1.14 (m, 2H), 1.08 (dd, J=11.2, 6.7 Hz, 3H).

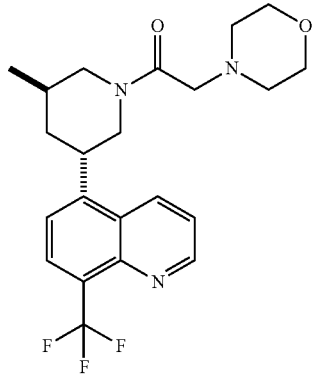

Example 3: Synthesis of Compound 5 (Cis-(5-Methyl-piperidin-3-yl)-8-trifluoromethyl-quinoline) and Compound 6 (Trans-(5-Methyl-piperidin-3-yl)-8-trifluoromethyl-quinoline

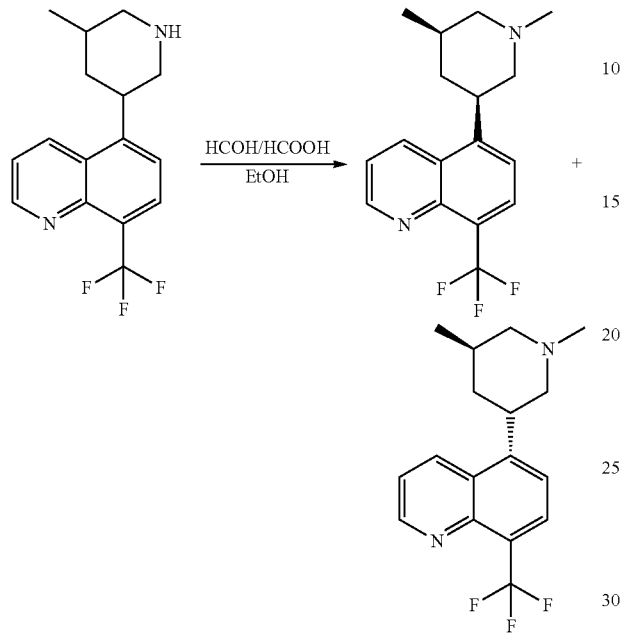

To a solution of 5-(5-Methyl-piperidin-3-yl)-8-trifluoromethyl-quinoline (200 mg; 0.68 mmol) in ethanol (2 ml) was added formic acid (0.06 ml; 1.70 mmol) and formaldehyde (0.07 ml; 0.82 mmol). The mixture was stirred at 80° C. for 2 hr. The completed reaction was concentrated and the crude was purified by prep HPLC (basic, eluting with 10-70% ACN in water) to yield cis-(5-Methyl-piperidin-3-yl)-8-trifluoromethyl-quinoline (major product) and trans-(5-Methyl-piperidin-3-yl)-8-trifluoromethyl-quinoline (minor product).

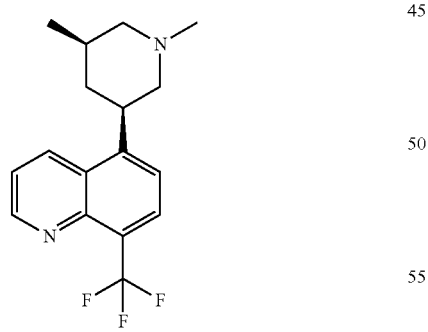

Compound 5

LC-MS (M+1)=309. $^1$H NMR (400 MHz, Methanol-$d_4$) δ 9.00 (dd, J=4.2, 1.7 Hz, 1H), 8.75 (dd, J=8.9, 1.7 Hz, 1H), 8.11 (d, J=7.7 Hz, 1H), 7.73-7.58 (m, 2H), 3.78 (ddd, J=15.1, 7.7, 3.3 Hz, 1H), 3.14-2.95 (m, 2H), 2.40 (s, 3H), 2.18 (t, J=11.3 Hz, 1H), 2.13-1.95 (m, 2H), 1.82 (t, J=11.2 Hz, 1H), 1.49-1.31 (m, 1H), 1.04 (d, J=6.4 Hz, 3H).

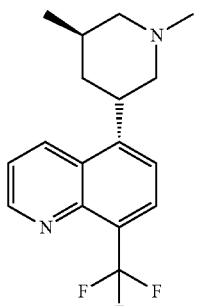

Compound 6

LC-MS (M+1)=309. $^1$H NMR (400 MHz, Methanol-$d_4$) δ 9.00 (dd, J=4.2, 1.6 Hz, 1H), 8.75 (dd, J=8.8, 1.7 Hz, 1H), 8.12 (d, J=7.7 Hz, 1H), 7.75-7.59 (m, 2H), 3.77 (t, J=11.7 Hz, 1H), 3.05 (t, J=13.9 Hz, 2H), 2.39 (s, 3H), 2.16 (t, J=11.3 Hz, 1H), 2.04 (d, J=8.7 Hz, 2H), 1.81 (t, J=11.2 Hz, 1H), 1.51-1.30 (m, 3H), 1.03 (dd, J=12.2, 6.4 Hz, 3H).

The following compounds were synthesized in an analogous manner:

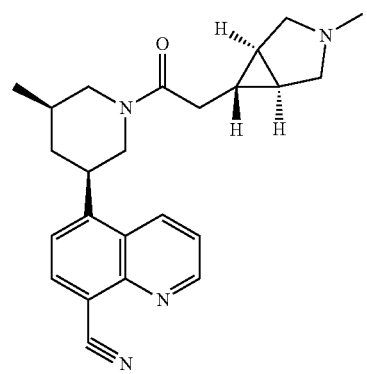

Compound 78 (cis-5-Methyl-1-[2-((1S,5R,6S)-3-methyl-3-aza-bicyclo[3.1.0]hex-6-yl)-acetyl]-piperidin-3-yl}-quinoline-8-carbonitrile)

From cis-1-((1S,5R,6S)-2-3-Aza-bicyclo[3.1.0]hex-6-yl-acetyl)-5-methyl-piperidin-3-yl]-quinoline-8-carbonitrile.
LC-MS (M+1)=389. $^1$H NMR (400 MHz, DMSO-$d_6$) δ 9.11 (d, J=2.7 Hz, 1H), 8.85 (d, J=8.6 Hz, 1H), 8.36 (dd, J=7.7, 2.1 Hz, 1H), 7.86-7.61 (m, 2H), 4.56 (dd, J=26.4, 12.4 Hz, 1H), 3.98-3.83 (m, 1H), 3.65 (s, 1H), 3.51 (d, J=11.4 Hz, 1H), 2.99-2.81 (m, 2H), 2.70 (dt, J=37.7, 12.2 Hz, 2H), 2.42-2.24 (m, 2H), 2.24-2.07 (m, 5H), 2.00 (s, 1H), 1.81 (d, J=33.2 Hz, 1H), 1.55 (dq, J=45.6, 12.0 Hz, 2H), 1.38-1.10 (m, 3H), 0.95 (dd, J=14.1, 6.5 Hz, 3H).

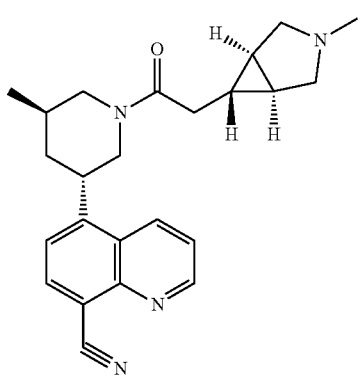

Compound 79 (cis-5-Methyl-1-[2-((1S,5R,6S)-3-methyl-3-aza-bicyclo[3.1.0]hex-6-yl)-acetyl]-piperidin-3-yl}-quinoline-8-carbonitrile)

From trans-1-((1S,5R,6S)-2-3-Aza-bicyclo[3.1.0]hex-6-yl-acetyl)-5-methyl-piperidin-3-yl]-quinoline-8-carbonitrile. LC-MS (M+1)=389. $^1$H NMR (400 MHz, DMSO-$d_6$) δ 9.20-9.09 (m, 1H), 8.85 (d, J=8.7 Hz, 1H), 8.36 (dd, J=7.6, 2.1 Hz, 1H), 7.86-7.66 (m, 2H), 4.56 (dd, J=26.7, 12.6 Hz, 1H), 3.91 (t, J=11.6 Hz, 1H), 3.66 (s, 1H), 3.49 (t, J=11.8 Hz, 1H), 2.98-2.80 (m, 2H), 2.75 (t, J=12.4 Hz, 1H), 2.66 (t, J=11.9 Hz, 1H), 2.40-2.24 (m, 2H), 2.24-2.07 (m, 4H), 2.00 (s, 1H), 1.81 (d, J=33.4 Hz, 1H), 1.55 (dq, J=45.7, 12.0 Hz, 1H), 1.42-1.10 (m, 3H), 0.95 (dd, J=14.1, 6.5 Hz, 3H).

Example 4: Synthesis of Compound 7 (cis-3-Methyl-5-(8-trifluoromethyl-quinolin-5-yl)-piperidin-1-yl]-ethanol-2) and Compound 8 (trans-3-Methyl-5-(8-trifluoromethyl-quinolin-5-yl)-piperidin-1-yl]-ethanol-2

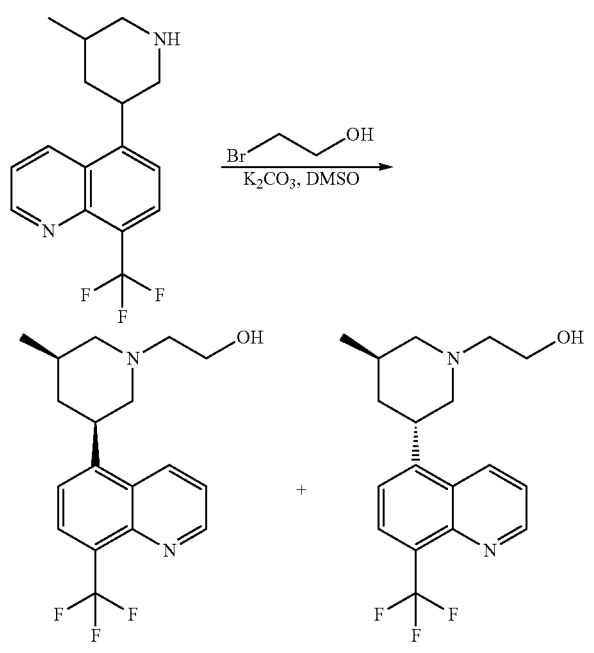

A reaction mixture of 5-(5-Methyl-piperidin-3-yl)-8-trifluoromethyl-quinoline (100 mg; 0.34 mmol), 2-Bromoethanol (0.02 ml; 0.34 mmol) and potassium carbonate (56.35 mg; 0.41 mmol) in DMSO (1 ml) at seal tube was stirred at 80° C. overnight. The completed reaction was purified by prep HPLC to yield cis-3-Methyl-5-(8-trifluoromethyl-quinolin-5-yl)-piperidin-1-yl]-ethanol-2 (major product) and trans-3-Methyl-5-(8-trifluoromethyl-quinolin-5-yl)-piperidin-1-yl]-ethanol-2 (minor product).

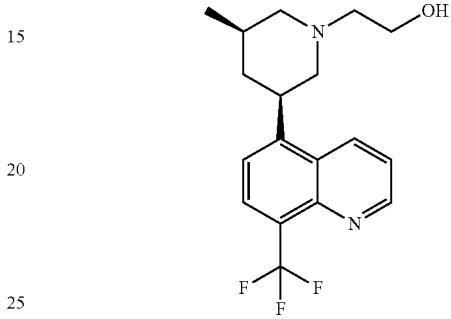

Compound 7

LC-MS (M+1)=339. $^1$H NMR (400 MHz, Methanol-$d_4$) δ 8.99 (dd, J=4.2, 1.6 Hz, 1H), 8.78 (dd, J=8.8, 1.6 Hz, 1H), 8.10 (d, J=7.7 Hz, 1H), 7.72-7.54 (m, 2H), 3.84-3.65 (m, 3H), 3.14 (dddt, J=18.1, 11.1, 3.5, 1.7 Hz, 2H), 2.80 (d, J=5.9 Hz, 1H), 2.72-2.57 (m, 2H), 2.21 (t, J=11.2 Hz, 1H), 2.14-1.92 (m, 2H), 1.85 (t, J=11.1 Hz, 1H), 1.50-1.35 (m, 1H), 1.03 (d, J=6.4 Hz, 3H).

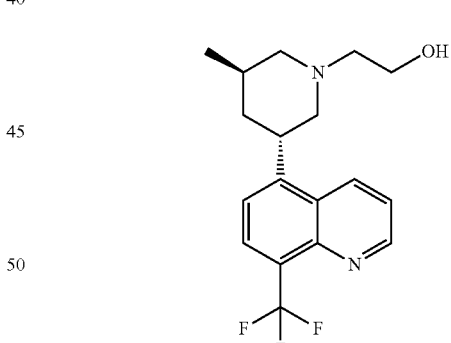

Compound 8

LC-MS (M+1)=339. $^1$H NMR (400 MHz, Methanol-$d_4$) δ 9.02-8.90 (m, 1H), 8.72 (dd, J=8.8, 1.7 Hz, 1H), 8.21-7.98 (m, 2H), 7.67 (dd, J=8.7, 4.2 Hz, 1H), 3.96 (tt, J=7.6, 4.4 Hz, 1H), 3.75 (t, J=5.9 Hz, 2H), 2.88 (dd, J=11.5, 3.7 Hz, 1H), 2.79 (s, 1H), 2.72-2.60 (m, 1H), 2.57 (dt, J=7.4, 5.9 Hz, 2H), 2.45-2.36 (m, 1H), 2.04-1.87 (m, 2H), 1.81-1.66 (m, 1H), 1.12 (d, J=6.8 Hz, 3H).

Example 5: Synthesis of Compound 9 (trans-1-[3-Methyl-5-(8-trifluoromethyl-quinolin-5-yl)-piperidin-1-yl]-ethanone) and Compound 10 (cis-1-[3-Methyl-5-(8-trifluoromethyl-quinolin-5-yl)-piperidin-1-yl]-ethanone

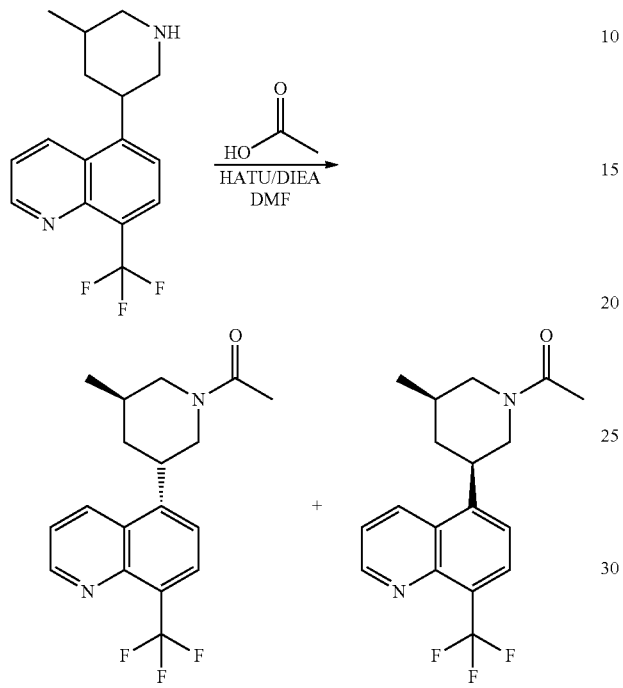

To a solution of acetic acid (40 mg; 0.68 mmol) in DMF (2 ml) was added HATU (232 mg; 0.61 mmol; 1.80 eq.). After stirring for 10 mins, DIEA (0.12 ml; 0.68 mmol) was added followed by 5-(5-Methyl-piperidin-3-yl)-8-trifluoromethyl-quinoline (100 mg; 0.34 mmol). The resulting mixture was stirred at RT for 1 hr. The completed reaction was concentrated and the crude was purified by prep HPLC (basic, eluting with 10-70% ACN in water) to yield trans-1-[3-Methyl-5-(8-trifluoromethyl-quinolin-5-yl)-piperidin-1-yl]-ethanone (major product) and cis-1-[3-Methyl-5-(8-trifluoromethyl-quinolin-5-yl)-piperidin-1-yl]-ethanone (minor product).

Compound 9

LC-MS (M+1)=337. $^1$H NMR (400 MHz, DMSO-d6) δ 9.07 (dd, J=4.1, 1.6 Hz, 1H), 8.84 (ddd, J=30.3, 8.8, 1.6 Hz, 1H), 8.16 (dd, J=7.8, 2.0 Hz, 1H), 7.78-7.60 (m, 2H), 4.57 (dd, J=33.1, 11.7 Hz, 1H), 3.92 (t, J=14.3 Hz, 1H), 3.50 (s, 1H), 2.79 (dd, J=13.4, 11.6 Hz, 1H), 2.63 (t, J=12.0 Hz, 1H), 2.23 (t, J=12.2 Hz, 1H), 2.11 (s, 2H), 2.04 (s, 2H), 1.57 (dq, J=35.9, 12.0 Hz, 1H), 0.96 (dd, J=15.6, 6.5 Hz, 3H).

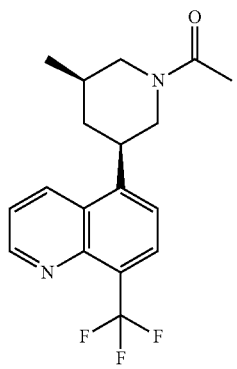 [SMILES: CC(=O)N1C[C@H](C)C[C@H](c2ccc(C(F)(F)F)c3ncccc23)C1]

Compound 10

LC-MS (M+1)=337. $^1$H NMR (400 MHz, Methanol-d$_4$) δ 9.01 (ddd, J=5.9, 4.1, 1.6 Hz, 1H), 8.75 (ddd, J=8.8, 3.6, 1.7 Hz, 1H), 8.12 (dd, J=10.6, 7.7 Hz, 1H), 7.78-7.55 (m, 2H), 4.52 (ddt, J=13.0, 3.5, 1.6 Hz, 1H), 4.02 (ddd, J=18.6, 11.7, 4.0 Hz, 1H), 3.85 (td, J=9.7, 4.7 Hz, 1H), 3.73-3.63 (m, 1H), 3.63-3.48 (m, 1H), 3.29-3.11 (m, 1H), 2.26-2.16 (m, 4H), 2.12 (s, 1H), 2.01-1.82 (m, 1H), 1.31 (d, J=6.6 Hz, 1H), 1.20 (dd, J=7.0, 4.7 Hz, 3H).

Example 6: Synthesis of Compound 40 (cis-Cyclopropyl-3-methyl-5-[8-(trifluoromethyl)-5-quinolyl] piperidine-1-carboxamide) and Compound 41 (trans-Cyclopropyl-3-methyl-5-[8-(trifluoromethyl)-5-quinolyl] piperidine-1-carboxamide)

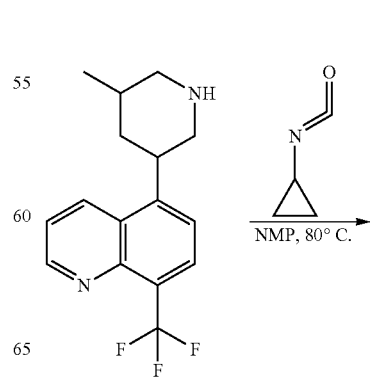

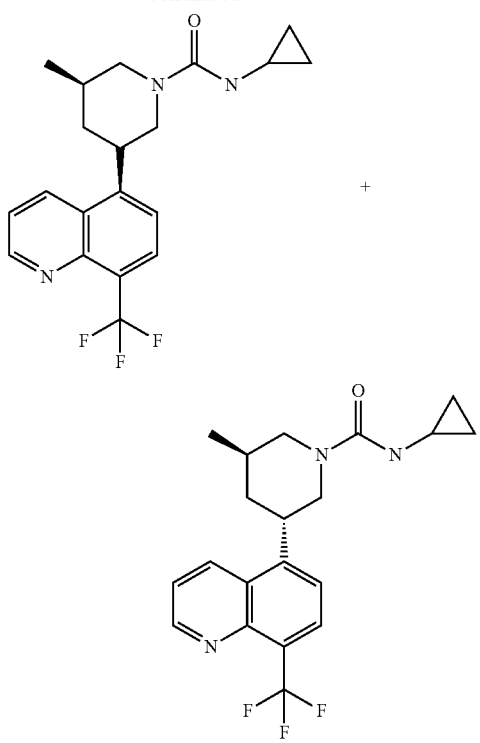

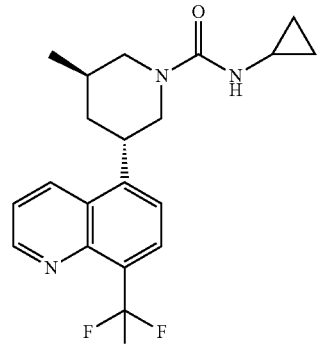

To a solution of 5-(5-Methyl-piperidin-3-yl)-8-trifluoromethyl-quinoline (100.00 mg; 0.34 mmol) in NMP (2 ml) was added Isocyanato-cyclopropane (56 mg; 0.68 mmol). The mixture was stirred at 80° C. overnight. The completed reaction was purified by prep HPLC (basic, eluted with ACN/water 30-80%) to yield cis-Cyclopropyl-3-methyl-5-[8-(trifluoromethyl)-5-quinolyl] piperidine-1-carboxamide as the major product and trans-Cyclopropyl-3-methyl-5-[8-(trifluoromethyl)-5-quinolyl] piperidine-1-carboxamide as the minor product.

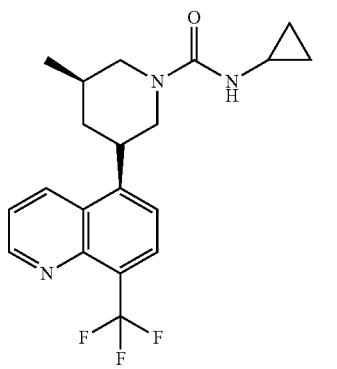

Compound 40: LC-MS (M+1)=378. $^1$H NMR (400 MHz, Methanol-d$_4$) δ 9.00 (d, J=4.3 Hz, 1H), 8.88 (d, J=8.7 Hz, 1H), 8.12 (d, J=7.7 Hz, 1H), 7.75-7.57 (m, 2H), 4.43-4.24 (m, 1H), 4.10-3.94 (m, 1H), 3.68-3.48 (m, 1H), 2.81 (t, J=12.2 Hz, 1H), 2.69-2.46 (m, 2H), 2.12 (d, J=12.9 Hz, 1H), 1.97-1.78 (m, 1H), 1.64 (q, J=12.1 Hz, 1H), 1.04 (d, J=6.5 Hz, 3H), 0.70 (h, J=4.6 Hz, 2H), 0.52 (q, J=3.8, 2.7 Hz, 2H).

Compound 41

LC-MS (M+1)=378. $^1$H NMR (400 MHz, Methanol-d$_4$) δ 9.00 (dd, J=4.2, 1.6 Hz, 1H), 8.81 (dd, J=8.9, 1.6 Hz, 1H), 8.10 (d, J=7.7 Hz, 1H), 7.78-7.61 (m, 2H), 4.18-4.07 (m, 1H), 3.97-3.83 (m, 1H), 3.62-3.46 (m, 1H), 3.39 (dd, J=13.4, 3.5 Hz, 2H), 3.30-3.22 (m, 1H), 2.60 (tt, J=7.1, 3.7 Hz, 1H), 2.12 (dddd, J=20.1, 11.3, 8.5, 4.3 Hz, 2H), 1.91 (dd, J=12.8, 4.8 Hz, 1H), 1.15 (d, J=6.9 Hz, 2H), 0.74-0.62 (m, 2H), 0.55-0.42 (m, 2H).

Example 7: Separation of compound 42 (2-(1-Methyl-piperidin-4-yl)-1-[(3R,5R)-3-methyl-5-(8-trifluoromethyl-quinolin-5-yl)-piperidin-1-yl]-ethanone) and Compound 43 (2-(1-Methyl-piperidin-4-yl)-1-[(3S,5S)-3-methyl-5-(8-trifluoromethyl-quinolin-5-yl)-piperidin-1-yl]-ethanone)

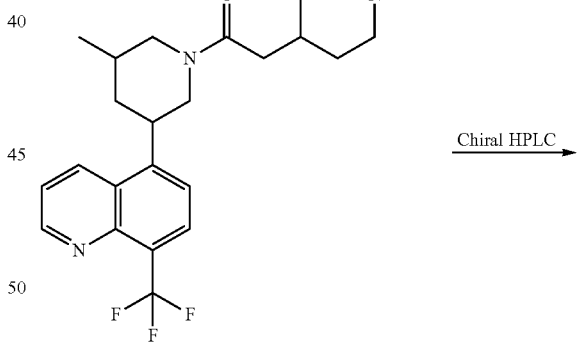

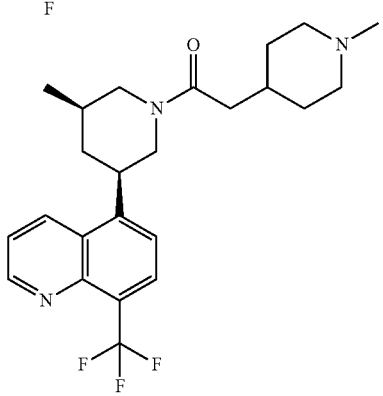

-continued

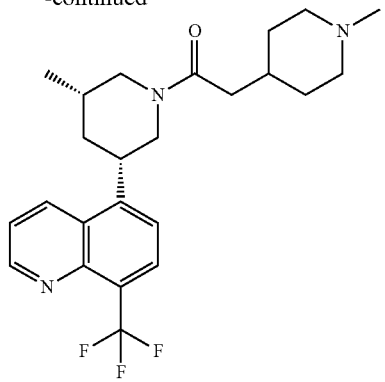

The title compounds were isolated via chiral SFC chromatography of Compound 4 on CHIRALPAK IA-3 column, (0.46×10 cm, 3 um); mobile phase, hexane (with 0.1% DMEA) in MeOH, 50% isocratic in 15 min; detector, UV 220 nm.

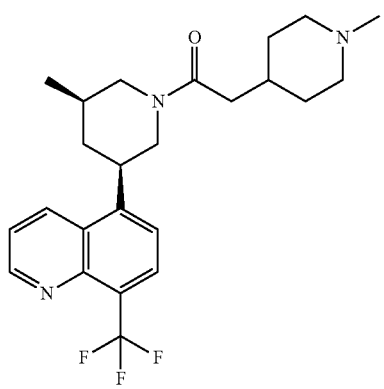 [SMILES: C[C@@H]1C[C@H](c2ccc(C(F)(F)F)c3ncccc23)CN(C(=O)CC2CCN(C)CC2)C1]

Compound 42

LC-MS (M+1)=378. ¹H NMR (400 MHz, Methanol-d₄) δ 9.00 LC-MS (M+1)=434. ¹H NMR (400 MHz, DMSO-d₆) δ 9.08 (dd, J=4.2, 1.5 Hz, 1H), 8.83 (dd, J=8.9, 5.3 Hz, 1H), 8.17 (dd, J=7.9, 2.7 Hz, 1H), 7.83-7.61 (m, 2H), 4.60 (dd, J=35.9, 12.7 Hz, 2H), 4.00 (t, J=13.0 Hz, 1H), 3.65 (s, 1H), 3.47 (s, 2H), 2.75 (dd, J=26.5, 12.4 Hz, 3H), 2.63 (t, J=12.0 Hz, 1H), 2.42-2.32 (m, 1H), 2.29 (dd, J=11.1, 5.6 Hz, 1H), 2.19 (d, J=12.0 Hz, 2H), 2.07-1.84 (m, 3H), 1.67 (dd, J=30.8, 12.5 Hz, 4H), 1.36-1.05 (m, 2H), 0.96 (dd, J=20.2, 6.5 Hz, 3H).

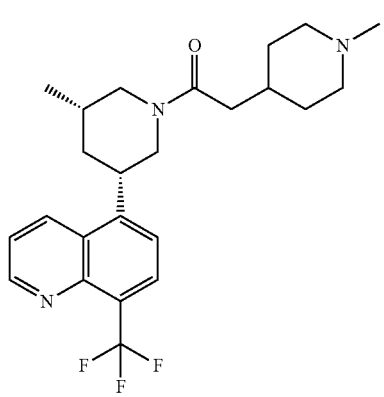 [SMILES: C[C@H]1C[C@@H](c2ccc(C(F)(F)F)c3ncccc23)CN(C(=O)CC2CCN(C)CC2)C1]

Compound 43

LC-MS (M+1)=434. ¹H NMR (400 MHz, DMSO-d₆) δ 9.08 (dd, J=4.2, 1.5 Hz, 1H), 8.83 (dd, J=8.9, 5.3 Hz, 1H), 8.17 (dd, J=7.9, 2.7 Hz, 1H), 7.83-7.61 (m, 2H), 4.60 (dd, J=35.9, 12.7 Hz, 2H), 4.00 (t, J=13.0 Hz, 1H), 3.65 (s, 1H), 3.47 (s, 2H), 2.75 (dd, J=26.5, 12.4 Hz, 3H), 2.63 (t, J=12.0 Hz, 1H), 2.42-2.32 (m, 1H), 2.29 (dd, J=11.1, 5.6 Hz, 1H), 2.19 (d, J=12.0 Hz, 2H), 2.07-1.84 (m, 3H), 1.67 (dd, J=30.8, 12.5 Hz, 4H), 1.36-1.05 (m, 2H), 0.96 (dd, J=20.2, 6.5 Hz, 3H).

The following compounds were prepared in an analogous manner:

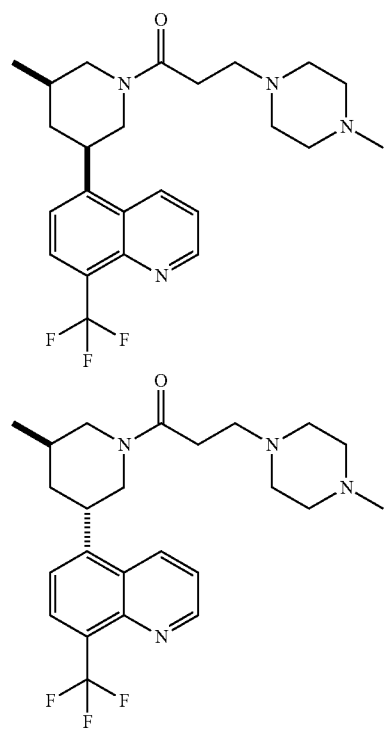

Compound 44 (3-(4-Methyl-piperazin-1-yl)-1-[(3R, 5R)-3-methyl-5-(8-trifluoromethyl-quinolin-5-yl)-piperidin-1-yl]-propan-1-one) and Compound 45 (3-(4-Methyl-piperazin-1-yl)-1-[(3S,5S)-3-methyl-5-(8-trifluoromethyl-quinolin-5-yl)-piperidin-1-yl]-propan-1-one)

From SFC chiral isolation of compound 11.

Compound 44

LC-MS (M+1)=449. ¹H NMR (400 MHz, DMSO-d₆) δ 9.08 (dd, J=4.1, 1.6 Hz, 1H), 8.84 (dd, J=21.4, 8.8 Hz, 1H), 8.17 (d, J=7.9 Hz, 1H), 7.84-7.59 (m, 2H), 4.58 (dd, J=34.2, 12.1 Hz, 1H), 4.10-3.89 (m, H), 3.68 (s, 1H), 3.49 (d, J=11.5 Hz, 1H), 2.84-2.67 (m, 2H), 2.59 (s, 2H), 2.31 (dd, J=61.9, 26.9 Hz, 6H), 2.16 (s, 3H), 2.04 (d, J=28.2 Hz, 2H), 1.83 (d, J=53.8 Hz, 2H), 1.69-1.53 (m, 2H), 0.96 (dd, J=20.9, 6.5 Hz, 3H).

Compound 45

LC-MS (M+1)=434. ¹H NMR (400 MHz, DMSO-d₆) δ 9.08 (dd, LC-MS (M+1)=449. ¹H NMR (400 MHz, DMSO- $d_6$) δ 9.08 (dd, J=4.1, 1.6 Hz, 1H), 8.84 (dd, J=21.4, 8.8 Hz, 1H), 8.17 (d, J=7.9 Hz, 1H), 7.84-7.59 (m, 2H), 4.58 (dd, J=34.2, 12.1 Hz, 1H), 4.10-3.89 (m, H), 3.68 (s, 1H), 3.49 (d, J=11.5 Hz, 1H), 2.84-2.67 (m, 2H), 2.59 (s, 2H), 2.31 (dd, J=61.9, 26.9 Hz, 6H), 2.16 (s, 3H), 2.04 (d, J=28.2 Hz, 2H), 1.83 (d, J=53.8 Hz, 2H), 1.69-1.53 (m, 2H), 0.96 (dd, J=20.9, 6.5 Hz, 3H).

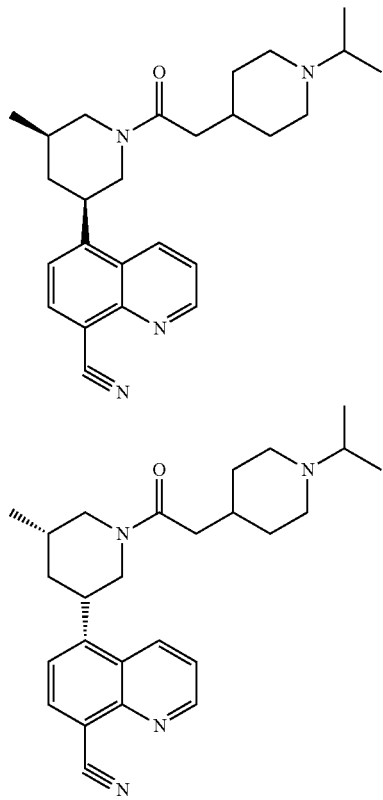

Compound 46 (5-{(3R,5R)-1-[2-(1-Isopropyl-piperidin-4-yl)-acetyl]-5-methyl-piperidin-3-yl}-quinoline-8-carbonitrile) and Compound 47 (5-{(3S,5S)-1-[2-(1-Isopropyl-piperidin-4-yl)-acetyl]-5-methyl-piperidin-3-yl}-quinoline-8-carbonitrile)

From SFC chiral isolation of compound 19.

Compound 46

LC-MS (M+1)=419. $^1$H NMR (400 MHz, DMSO-$d_6$) δ 9.12 (dd, J=4.2, 1.5 Hz, 1H), 8.92-8.81 (m, 1H), 8.36 (dd, J=7.6, 5.6 Hz, 1H), 7.85-7.53 (m, 2H), 4.58 (dd, J=28.0, 12.8 Hz, 1H), 4.06-3.90 (m, 1H), 3.66 (t, J=11.6 Hz, 1H), 3.49 (d, J=11.8 Hz, 1H), 2.86-2.54 (m, 4H), 2.39-2.15 (m, 2H), 2.06 (dt, J=21.1, 11.6 Hz, 3H), 1.80 (d, J=30.2 Hz, 1H), 1.62 (ddd, J=38.7, 24.1, 12.9 Hz, 4H), 1.33-1.04 (m, 3H), 1.04-0.78 (m, 9H).

Compound 47

LC-MS (M+1)=419. $^1$H NMR (400 MHz, DMSO-$d_6$) δ 9.12 (dd, J=4.2, 1.5 Hz, 1H), 8.92-8.81 (m, 1H), 8.36 (dd, J=7.6, 5.6 Hz, 1H), 7.85-7.53 (m, 2H), 4.58 (dd, J=28.0, 12.8 Hz, 1H), 4.06-3.90 (m, 1H), 3.66 (t, J=11.6 Hz, 1H), 3.49 (d, J=11.8 Hz, 1H), 2.86-2.54 (m, 4H), 2.39-2.15 (m, 2H), 2.06 (dt, J=21.1, 11.6 Hz, 3H), 1.80 (d, J=30.2 Hz, 1H), 1.62 (ddd, J=38.7, 24.1, 12.9 Hz, 4H), 1.33-1.04 (m, 3H), 1.04-0.78 (m, 9H).

Example 8: Synthesis of Compound 48 (3-[3-(8-Cyano-quinolin-5-yl)-5-methyl-piperidin-1-yl]-propionic Acid Methyl Ester)

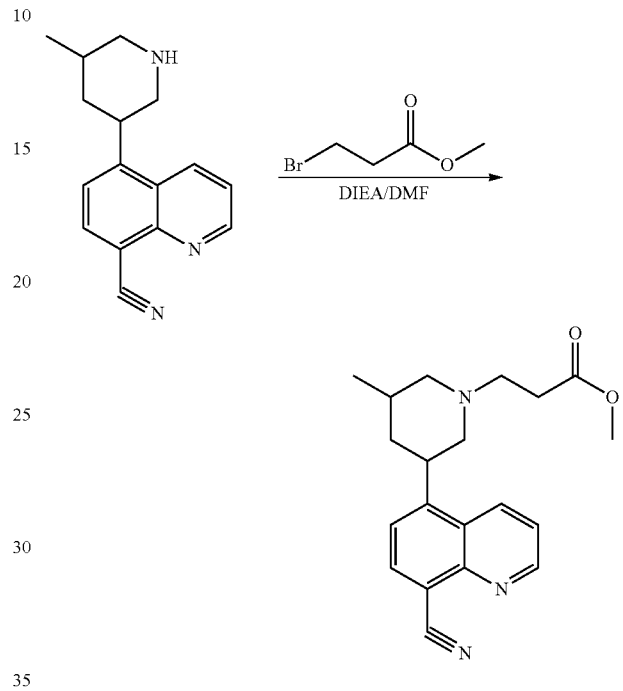

A mixture of 5-(5-Methyl-piperidin-3-yl)-quinoline-8-carbonitrile dihydrochloride (300 mg; 0.93 mmol), 3-Bromo-propionic acid methyl ester (0.15 ml; 1.39 mmol) and DIEA (0.83 ml; 4.63 mmol) in DMF (1.5 ml) was stirred at 80° C. for 1 h. The completed reaction was concentrated and the crude was purified by prep HPLC (basic, eluting with ACN/water 20-70%) to yield the title compound (185 mg, yield 59%).

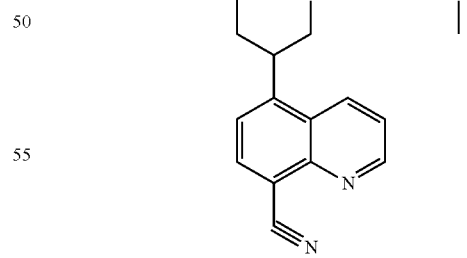

Compound 48

LC-MS (M+1)=338. $^1$H NMR (400 MHz, Methanol-$d_4$) δ 9.10-9.01 (m, 1H), 8.63 (dd, J=8.6, 1.7 Hz, 1H), 8.28-8.20 (m, 1H), 7.81-7.64 (m, 2H), 3.78 (d, J=12.4 Hz, 1H), 3.70 (d, J=3.5 Hz, 3H), 3.18-2.99 (m, 1H), 2.96-2.85 (m, 1H), 2.85-2.75 (m, 1H), 2.67-2.53 (m, 1H), 2.29 (dd, J=11.4, 8.3 Hz, 1H), 2.20 (t, J=11.2 Hz, 1H), 2.10-1.92 (m, 2H), 1.85 (t, J=11.0 Hz, 1H), 1.41 (q, J=12.4 Hz, 1H), 1.14 (dd, J=22.0, 6.9 Hz, 2H), 1.03 (d, J=6.4 Hz, 3H).

Example 9: Synthesis of Compound 49 (3-[3-(8-Cyano-quinolin-5-yl)-5-methyl-piperidin-1-yl]-propionamide)

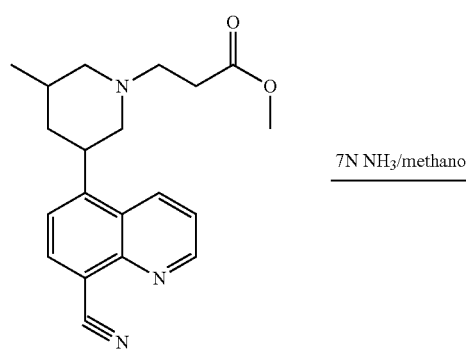

7N NH₃/methanol

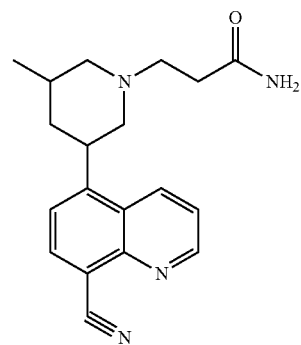 [SMILES: CC1CC(c2ccc(C#N)c3ncccc23)CN(CCC(N)=O)C1]

A reaction of mixture of 3-[3-(8-Cyano-quinolin-5-yl)-5-methyl-piperidin-1-yl]-propionic acid methyl ester (30.00 mg; 0.09 mmol) and ammonia (0.44 ml; 2.67 mmol; 7N in methanol) was stirred at 60° C. overnight and 80° C. for 8 hr. The completed reaction was concentrated and the crude was purified by prep HPLC (Basic, eluting with ACN/water 20-70%) to yield the title compound.

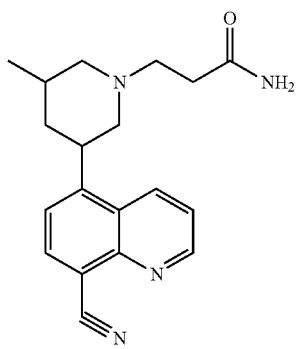

Compound 49

LC-MS (M+1)=323. ¹H NMR (400 MHz, Methanol-d₄) δ 9.05 (dd, J=4.2, 1.6 Hz, 1H), 8.79 (dd, J=9.0, 1.6 Hz, 1H), 8.22 (d, J=7.7 Hz, 1H), 7.82-7.61 (m, 2H), 3.79 (t, J=11.7 Hz, 2H), 3.10 (d, J=12.2 Hz, 2H), 2.85-2.71 (m, 2H), 2.47 (t, J=7.2 Hz, 2H), 2.21 (t, J=11.2 Hz, 1H), 2.04 (d, J=12.8 Hz, 2H), 1.85 (t, J=11.0 Hz, 1H), 1.41 (q, J=12.5 Hz, 1H), 1.04 (d, J=6.4 Hz, 3H).

Example 10: Synthesis of Compound 50 (3-(8-Cyano-quinolin-5-yl)-5-methyl-piperidin-1-yl]-N-methyl-propionamide)

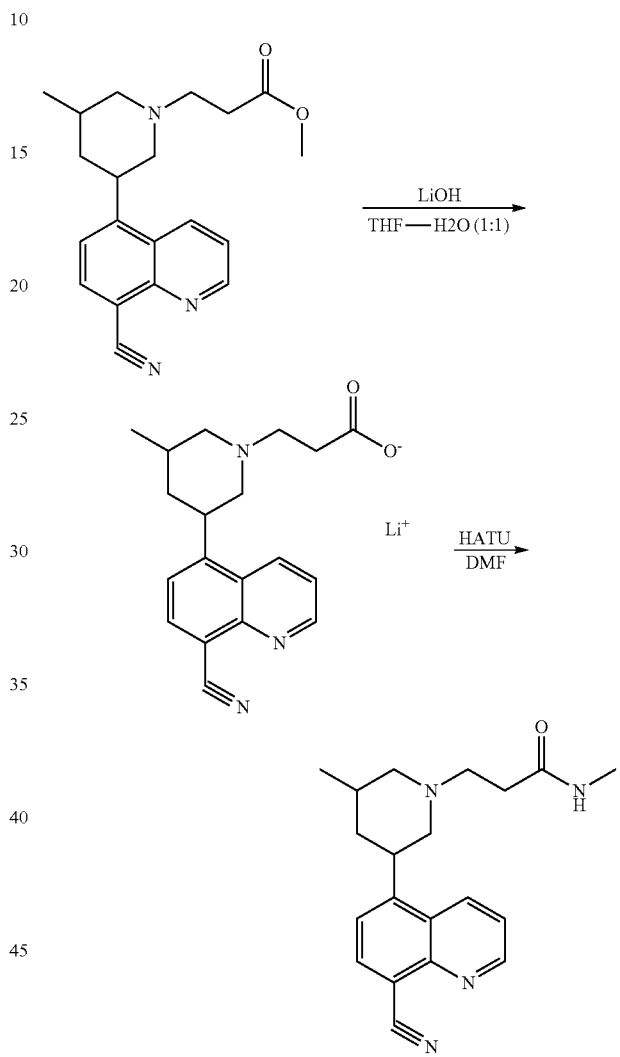

Lithium Salt of 3-[3-(8-Cyano-quinolin-5-yl)-5-methyl-piperidin-1-yl]-propionic Acid To a solution of 3-[3-(8-Cyano-quinolin-5-yl)-5-methyl-piperidin-1-yl]-propionic acid methyl ester (150.00 mg; 0.44 mmol) in THF (1 ml), was added water (1 ml) and lithium hydroxide (21.29 mg; 0.89 mmol). The resulting mixture was stirred at rt for 3 hr. The completed reaction was concentrated to yield the title compound as a yellow solid, which was directly used for the next step reaction without purification. LC-MS (M+1)=323.

3-(8-Cyano-quinolin-5-yl)-5-methyl-piperidin-1-yl]-N-methyl-propionamide

To a solution of lithium salt of 3-[3-(8-Cyano-quinolin-5-yl)-5-methyl-piperidin-1-yl]-propionic acid (75 mg; 0.23 mmol) in DMF (2 ml) was added HATU (129 mg; 0.34 mmol). After stirring for 10 mins, DIEA (0.25 ml; 1.37 mmol) was added, followed by Methanamine hydrochloride (30 mg; 0.46 mmol). The resulting mixture was stirred at RT overnight. The reaction was concentrated. The crude was purified by prep HPLC (basic, eluting with ACN/water 20-70%) to yield the title compound.

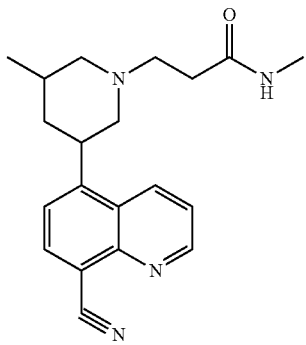

Compound 50

LC-MS (M+1)=327. $^1$H NMR (400 MHz, DMSO-d$_6$) δ 9.10 (dd, J=4.2, 1.5 Hz, 1H), 8.77 (dd, J=8.8, 1.6 Hz, 1H), 8.32 (d, J=7.7 Hz, 1H), 7.77 (dd, J=8.7, 4.1 Hz, 2H), 7.66 (d, J=7.7 Hz, 1H), 3.68 (t, J=11.6 Hz, 2H), 2.97 (dd, J=25.1, 11.0 Hz, 2H), 2.69-2.61 (m, 1H), 2.61-2.52 (m, 3H), 2.26 (t, J=7.4 Hz, 2H), 2.12 (t, J=10.9 Hz, 1H), 1.92 (t, J=13.3 Hz, 2H), 1.71 (t, J=10.9 Hz, 1H), 1.26 (q, J=12.1 Hz, 1H), 0.92 (d, J=6.4 Hz, 3H).

The following compounds were prepared in an analogous manner:

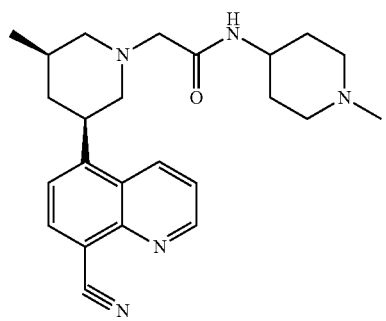

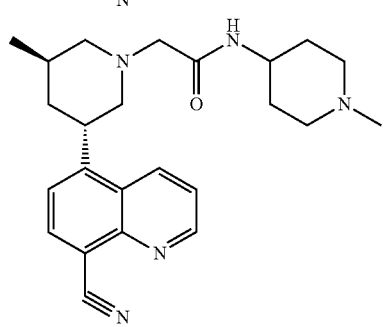

Compound 68 (cis-2-[3-(8-Cyano-quinolin-5-yl)-5-methyl-piperidin-1-yl]-N-(1-methyl-piperidin-4-yl)-acetamide) and Compound 69 (trans-2-[3-(8-Cyano-quinolin-5-yl)-5-methyl-piperidin-1-yl]-N-(1-methyl-piperidin-4-yl)-acetamide)

From [3-(8-Cyano-quinolin-5-yl)-5-methyl-piperidin-1-yl]-acetic acid methyl ester and 1-Methyl-piperidin-4-ylamine.

Compound 68

LC-MS (M+1)=406. $^1$H NMR (400 MHz, Methanol-d$_4$) δ 9.05 (dd, J=4.2, 1.6 Hz, 1H), 8.84 (dd, J=8.9, 1.6 Hz, 1H), 8.22 (d, J=7.6 Hz, 1H), 7.74 (dd, J=8.7, 4.2 Hz, 1H), 7.68 (d, J=7.6 Hz, 1H), 3.97-3.83 (m, 1H), 3.74 (td, J=10.9, 5.4 Hz, 1H), 3.19-2.93 (m, 4H), 2.86 (d, J=11.8 Hz, 2H), 2.30 (s, 3H), 2.29-2.09 (m, 4H), 1.99-1.81 (m, 3H), 1.62 (qd, J=11.8, 3.9 Hz, 2H), 1.42 (q, J=12.0 Hz, 1H), 1.03 (d, J=6.5 Hz, 3H).

Compound 69

LC-MS (M+1)=406. $^1$H NMR (400 MHz, Methanol-d$_4$) δ 9.04 (d, J=4.2 Hz, 1H), 8.77 (d, J=8.7 Hz, 1H), 8.23 (d, J=7.6 Hz, 1H), 8.08 (d, J=7.6 Hz, 1H), 7.74 (dd, J=8.8, 4.1 Hz, 1H), 4.06 (s, 1H), 3.72 (d, J=11.6 Hz, 2H), 3.15 (d, J=15.3 Hz, 1H), 2.93 (dt, J=39.2, 14.8 Hz, 4H), 2.76 (s, 1H), 2.65 (d, J=10.6 Hz, 1H), 2.41 (d, J=10.0 Hz, 1H), 2.31 (s, 3H), 2.17 (t, J=11.8 Hz, 2H), 2.05 (s, 1H), 1.98-1.73 (m, 4H), 1.59 (q, J=13.1, 12.5 Hz, 2H), 1.21 (d, J=6.9 Hz, 3H).

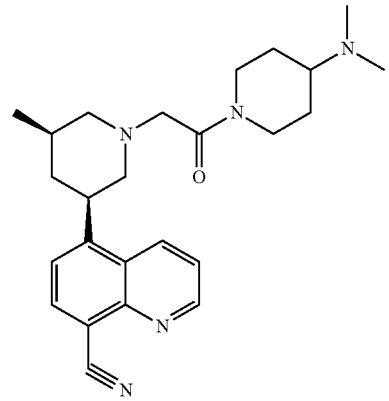

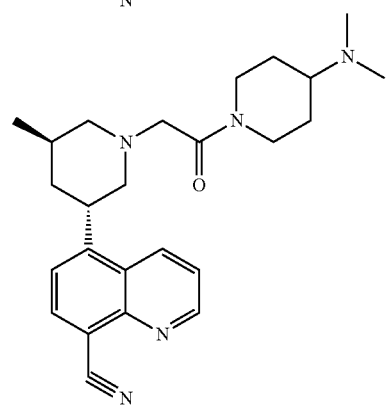

Compound 70 (cis-5-(1-{2-[4-(dimethylamino) piperidin-1-yl]-2-oxoethyl}-5-methylpiperidin-3-yl) quinoline-8-carbonitrile) and Compound 71 (trans-5-(1-{2-[4-(dimethylamino) piperidin-1-yl]-2-oxoethyl}-5-methylpiperidin-3-yl) quinoline-8-carbonitrile)

From [3-(8-Cyano-quinolin-5-yl)-5-methyl-piperidin-1-yl]-acetic acid methyl ester and dimethyl-piperidin-4-yl-amine.

Compound 70

LC-MS (M+1)=419. $^1$H NMR (400 MHz, Methanol-$d_4$) δ 9.04 (dd, J=4.2, 1.6 Hz, 1H), 8.81 (dd, J=8.8, 1.6 Hz, 1H), 8.21 (d, J=7.7 Hz, 1H), 7.74 (dt, J=8.3, 4.0 Hz, 1H), 7.67 (d, J=7.7 Hz, 1H), 4.57 (t, J=9.5 Hz, 1H), 4.20 (s, 1H), 3.93-3.77 (m, 1H), 3.42 (t, J=14.2 Hz, 1H), 3.35-3.20 (m, 3H), 3.19-2.94 (m, 3H), 2.64 (t, J=13.3 Hz, 1H), 2.47 (dt, J=11.3, 5.7 Hz, 1H), 2.31 (d, J=1.7 Hz, 6H), 2.27-2.18 (m, 1H), 2.16-1.81 (m, 5H), 1.55-1.22 (m, 3H), 1.02 (d, J=6.5 Hz, 3H).

Compound 71

LC-MS (M+1)=419. $^1$H NMR (400 MHz, Methanol-$d_4$) δ 9.04 LC-MS (M+1)=419. $^1$H NMR (400 MHz, Methanol-$d_4$) δ 9.03 (dd, J=4.2, 1.5 Hz, 1H), 8.71 (dd, J=8.7, 4.3 Hz, 1H), 8.28-8.11 (m, 2H), 7.78-7.66 (m, 1H), 4.56 (s, 1H), 4.38-4.21 (m, 1H), 3.99 (d, J=6.5 Hz, 1H), 3.32-3.05 (m, 3H), 2.86 (d, J=21.3 Hz, 2H), 2.74-2.57 (m, 2H), 2.57-2.37 (m, 2H), 2.33 (d, J=2.4 Hz, 6H), 2.12-1.84 (m, 4H), 1.76 (dt, J=12.6, 5.9 Hz, 1H), 1.57-1.43 (m, 1H), 1.32 (td, J=13.0, 8.4 Hz, 2H), 1.13 (dd, J=18.9, 6.7 Hz, 3H).

Compound 72 (cis-2-[3-(8-Cyano-quinolin-5-yl)-5-methyl-piperidin-1-yl]-N-[2-(4-methyl-piperazin-1-yl)-ethyl]-acetamide) and Compound 73 (trans-2-[3-(8-Cyano-quinolin-5-yl)-5-methyl-piperidin-1-yl]-N-[2-(4-methyl-piperazin-1-yl)-ethyl]-acetamide)

From [3-(8-Cyano-quinolin-5-yl)-5-methyl-piperidin-1-yl]-acetic acid methyl ester and 2-(4-Methyl-piperazin-1-yl)-ethylamine Compound 72

LC-MS (M+1)=435. $^1$H NMR (400 MHz, Methanol-$d_4$) δ 9.05 (dd, J=4.2, 1.6 Hz, 1H), 8.82 (dd, J=8.9, 1.6 Hz, 1H), 8.22 (d, J=7.6 Hz, 1H), 7.75 (dd, J=8.7, 4.2 Hz, 1H), 7.68 (d, J=7.7 Hz, 1H), 3.96-3.79 (m, 1H), 3.40 (q, J=6.5 Hz, 2H), 3.35 (d, J=6.3 Hz, 2H), 3.21-3.06 (m, 3H), 3.06-2.95 (m, 1H), 2.51 (t, J=6.4 Hz, 4H), 2.34 (t, J=11.0 Hz, 3H), 2.17 (s, 3H), 2.10-2.02 (m, 1H), 1.96 (t, J=11.0 Hz, 1H), 1.45-1.28 (m, 1H), 1.02 (d, J=6.5 Hz, 3H).

Compound 73

LC-MS (M+1)=435. $^1$H NMR (400 MHz, Methanol-$d_4$) δ 9.05 (dd, J=4.2, 1.6 Hz, 1H), 8.74 (dd, J=8.9, 1.6 Hz, 1H), 8.23 (d, J=7.7 Hz, 1H), 8.04 (d, J=7.7 Hz, 1H), 7.75 (dd, J=8.7, 4.2 Hz, 1H), 4.05 (dt, J=8.1, 4.0 Hz, 1H), 3.40 (td, J=6.3, 2.0 Hz, 2H), 3.08 (d, J=3.0 Hz, 2H), 2.95 (dd, J=11.2, 3.6 Hz, 1H), 2.79 (d, J=9.4 Hz, 1H), 2.68 (dd, J=11.1, 3.5 Hz, 1H), 2.51 (td, J=6.4, 1.1 Hz, 6H), 2.18 (s, 3H), 2.12-1.96 (m, 2H), 1.92 (ddd, J=12.9, 8.7, 4.3 Hz, 1H), 1.88-1.72 (m, 1H), 1.25 (d, J=6.9 Hz, 3H).

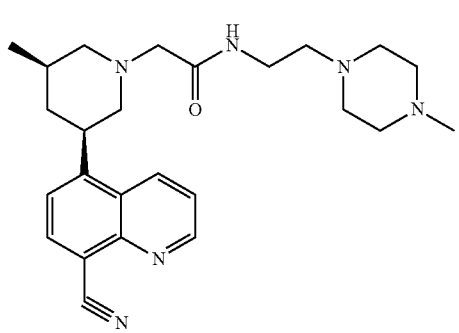

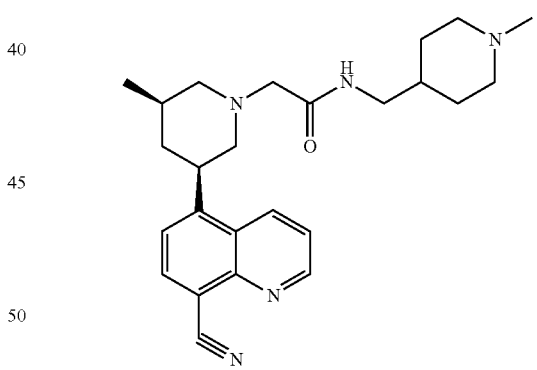

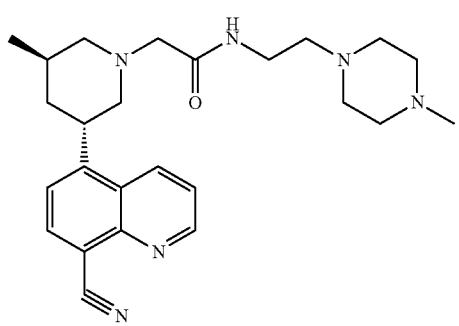

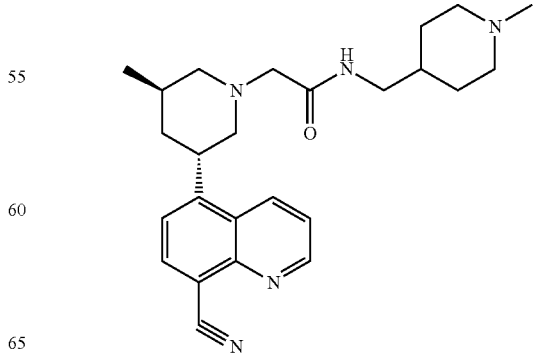

Compound 74 (cis-2-[3-(8-Cyano-quinolin-5-yl)-5-methyl-piperidin-1-yl]-N-(1-methyl-piperidin-4-ylmethyl)-acetamide) and Compound 75 (trans-2-[3-(8-Cyano-quinolin-5-yl)-5-methyl-piperidin-1-yl]-N-(1-methyl-piperidin-4-ylmethyl)-acetamide)

From [3-(8-Cyano-quinolin-5-yl)-5-methyl-piperidin-1-yl]-acetic acid methyl ester and C-(1-Methyl-piperidin-4-yl)-methylamine.

Compound 74

LC-MS (M+1)=420. $^1$H NMR (400 MHz, Methanol-$d_4$) δ 9.05 (dd, J=4.2, 1.6 Hz, 1H), 8.85 (dd, J=8.9, 1.6 Hz, 1H), 8.22 (d, J=7.6 Hz, 1H), 7.74 (dd, J=8.7, 4.2 Hz, 1H), 7.68 (d, J=7.7 Hz, 1H), 3.91 (t, J=11.6 Hz, 1H), 3.19-3.09 (m, 3H), 3.09-2.94 (m, 2H), 2.81 (t, J=10.0 Hz, 2H), 2.36-2.26 (m, 1H), 2.24 (s, 3H), 2.08 (dd, J=32.9, 9.9 Hz, 2H), 1.94 (dt, J=18.1, 10.6 Hz, 2H), 1.68 (d, J=13.1 Hz, 1H), 1.54 (td, J=8.9, 7.6, 5.2 Hz, 1H), 1.41 (q, J=12.1 Hz, 1H), 1.34-1.22 (m, 2H), 1.02 (d, J=6.6 Hz, 3H).

Compound 75

LC-MS (M+1)=420. $^1$H NMR (400 MHz, Methanol-$d_4$) δ 9.04 (dd, J=4.2, 1.6 Hz, 1H), 8.77 (dd, J=8.9, 1.6 Hz, 1H), 8.22 (d, J=7.7 Hz, 1H), 8.07 (d, J=7.7 Hz, 1H), 7.74 (dd, J=8.7, 4.2 Hz, 1H), 4.06 (d, J=5.3 Hz, 1H), 3.24-2.99 (m, 4H), 2.97-2.80 (m, 3H), 2.80-2.58 (m, 2H), 2.44 (s, 1H), 2.26 (s, 2H), 2.08 (s, 1H), 2.03-1.87 (m, 2H), 1.85-1.74 (m, 1H), 1.68 (s, 3H), 1.49 (s, 1H), 1.39-1.26 (m, 1H), 1.21 (d, J=6.9 Hz, 3H).

Compound 76 (cis-2-[3-(8-Cyano-quinolin-5-yl)-5-methyl-piperidin-1-yl]-N-(1-methyl-1H-pyrazol-4-yl)-acetamide) and Compound 77 (trans-2-[3-(8-Cyano-quinolin-5-yl)-5-methyl-piperidin-1-yl]-N-(1-methyl-1H-pyrazol-4-yl)-acetamide)

From [3-(8-Cyano-quinolin-5-yl)-5-methyl-piperidin-1-yl]-acetic acid methyl ester and 1-Methyl-1H-pyrazol-4-ylamine.

Compound 76

LC-MS (M+1)=389. $^1$H NMR (400 MHz, Methanol-$d_4$) δ 9.03 (dd, J=4.2, 1.6 Hz, 1H), 8.83 (dd, J=9.0, 1.6 Hz, 1H), 8.22 (d, J=7.6 Hz, 1H), 7.94 (d, J=0.7 Hz, 1H), 7.76-7.63 (m, 2H), 7.60 (d, J=0.8 Hz, 1H), 4.04-3.91 (m, 1H), 3.88 (s, 3H), 3.30-3.15 (m, 1H), 3.15-2.98 (m, 2H), 2.32 (t, J=11.1 Hz, 1H), 2.25-2.12 (m, 1H), 2.02 (dt, J=22.1, 12.0 Hz, 2H), 1.43 (q, J=12.1 Hz, 1H), 1.36-1.21 (m, 1H), 1.04 (d, J=6.6 Hz, 3H).

Compound 77

LC-MS (M+1)=389. $^1$H NMR (400 MHz, DMSO-$d_6$) δ 9.80 (d, J=9.3 Hz, 1H), 9.08 (dd, J=4.1, 1.6 Hz, 1H), 8.75 (d, J=7.4 Hz, 1H), 8.39-8.18 (m, 2H), 7.91 (s, 1H), 7.83-7.65 (m, 1H), 7.47 (d, J=0.7 Hz, 1H), 4.09-3.88 (m, 2H), 3.79 (d, J=1.1 Hz, 2H), 3.23 (d, J=14.9 Hz, 1H), 3.07 (d, J=14.9 Hz, 1H), 2.79 (s, 2H), 2.74-2.59 (m, 2H), 2.26 (s, 2H), 1.96-1.72 (m, 2H), 1.65 (s, 1H), 1.00 (dd, J=41.6, 6.6 Hz, 3H).

Example 11: Synthesis of Compound 51 (5-Methyl-1-(1-methyl-pyrrolidin-3-ylmethyl)-piperidin-3-yl]-quinoline-8-carbonitrile

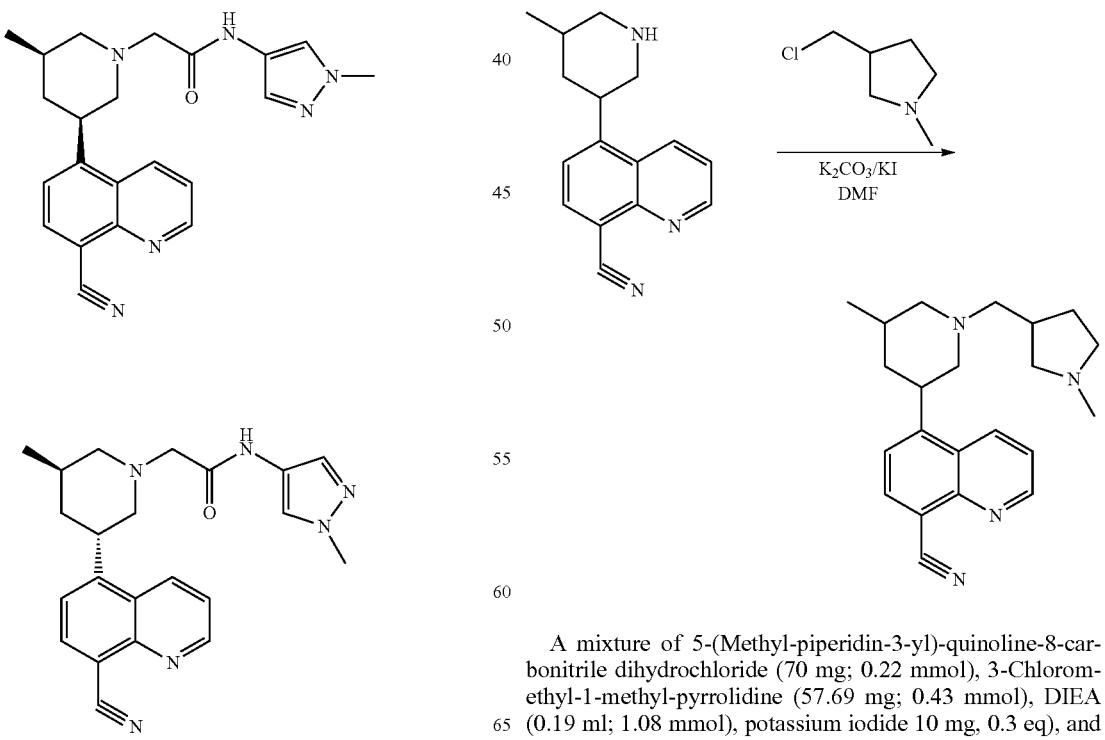

A mixture of 5-(Methyl-piperidin-3-yl)-quinoline-8-carbonitrile dihydrochloride (70 mg; 0.22 mmol), 3-Chloromethyl-1-methyl-pyrrolidine (57.69 mg; 0.43 mmol), DIEA (0.19 ml; 1.08 mmol), potassium iodide 10 mg, 0.3 eq), and potassium carbonate (35 mg, 0.26 mmol) in DMF (1.5 ml) was placed in microwave at 140° C. for 2 hr. The reaction mixture was concentrated and the residue was purified by prep HPLC (basic, eluting with ACN/water 20-70%) to yield the title compound.

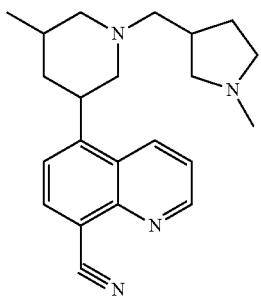 [SMILES: CC1CC(c2ccc(C#N)c3ncccc23)CN(CC2CCN(C)C2)C1]

Compound 51

LC-MS (M+1)=349. ¹H NMR (400 MHz, Methanol-$d_4$) δ 9.03 (ddd, J=5.0, 3.4, 1.6 Hz, 1H), 8.77 (dt, J=8.8, 2.1 Hz, 1H), 8.21 (dd, J=7.6, 1.7 Hz, 1H), 7.79-7.62 (m, 2H), 3.79 (tt, J=11.8, 3.7 Hz, 1H), 3.24-2.95 (m, 2H), 2.90-2.75 (m, 1H), 2.75-2.61 (m, 2H), 2.61-2.42 (m, 4H), 2.42 (s, 3H), 2.18-1.95 (m, 4H), 1.76 (dt, J=18.1, 11.1 Hz, 1H), 1.65-1.48 (m, 1H), 1.47-1.27 (m, 1H), 1.02 (dd, J=6.4, 1.2 Hz, 3H).

The following compounds were synthesized in an analogous manner:

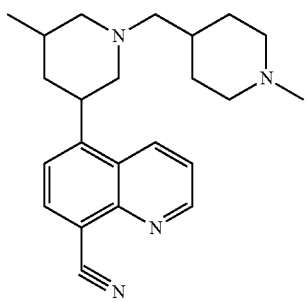

Compound 52 (5-Methyl-1-(1-methyl-piperidin-4-ylmethyl)-piperidin-3-yl]-quinoline-8-carbonitrile)

From 5-(Methyl-piperidin-3-yl)-quinoline-8-carbonitrile dihydrochloride and 4-Chloromethyl-1-methyl-piperidine hydrochloride. LC-MS (M+1)=363. ¹H NMR (400 MHz, Methanol-$d_4$) δ 9.03 (td, J=3.9, 1.6 Hz, 1H), 8.77 (dd, J=8.8, 1.6 Hz, 1H), 8.21 (dd, J=7.5, 1.9 Hz, 1H), 7.78-7.66 (m, 2H), 3.77 (tt, J=11.8, 3.2 Hz, 1H), 3.15-3.04 (m, 2H), 2.85 (tdd, J=8.4, 6.8, 3.7 Hz, 1H), 2.78-2.63 (m, 1H), 2.61-2.39 (m, 3H), 2.36 (dd, J=2.8, 1.7 Hz, 3H), 2.26-2.10 (m, 4H), 2.10-1.95 (m, 2H), 1.82-1.58 (m, 3H), 1.56-1.33 (m, 2H), 1.03 (d, J=6.4 Hz, 3H).

Example 12: Synthesis of Compound 53 (5-{(3R,5R)-5-Methyl-1-[2-(1-methyl-piperidin-4-yl)-acetyl]-piperidin-3-yl}-quinoline-8-carbonitrile) and Compound 54 (5-{(3S,5R)-5-Methyl-1-[2-(1-methyl-piperidin-4-yl)-acetyl]-piperidin-3-yl}-quinoline-8-carbonitrile)

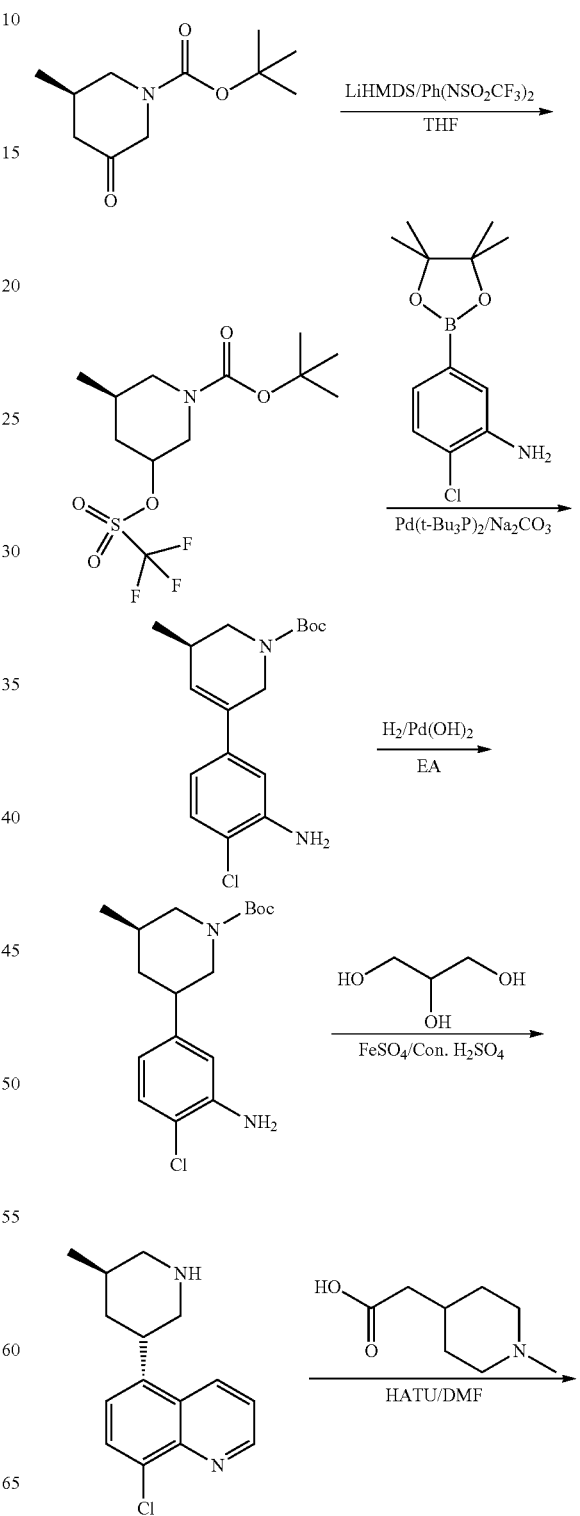

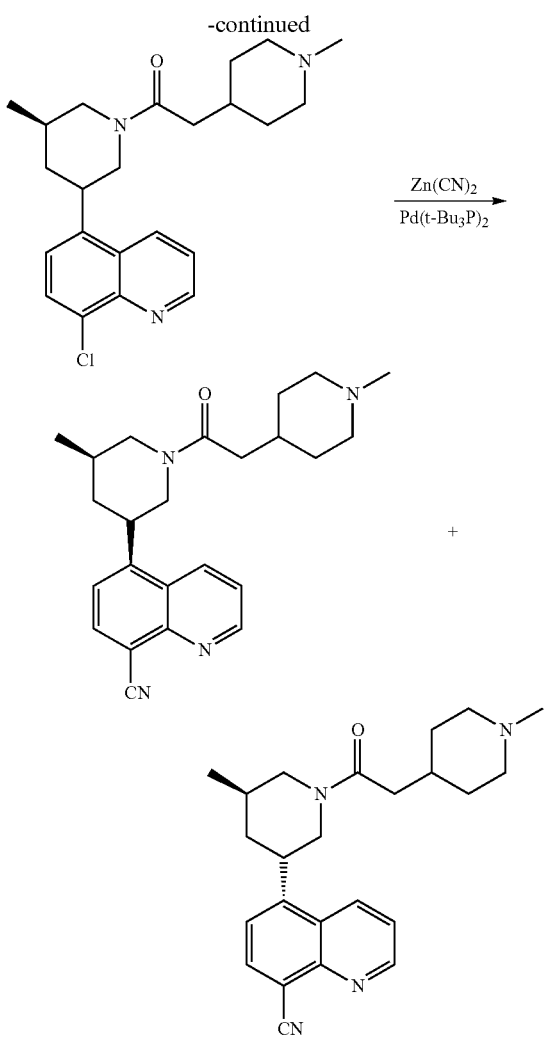

(R)-3-Methyl-5-trifluoromethanesulfonyloxy-3,4-dihydro-2H-pyridine-1-carboxylic acid tert-butyl ester To a solution of (R)-3-Methyl-5-oxo-piperidine-1-carboxylic acid tert-butyl ester (2000 mg, 9.38 mmol) in THF (50 ml) cooled at −78° C., was added [bis(trimethylsilyl)amino]lithium (10.32 ml; 10.32 mmol) dropwise. The mixture was stirred for about 30 min, a solution of N,N-bis(trifluoromethylsulfonyl)aniline (3517 mg; 9.85 mmol) in 25 ml THF was added. After the addition was completed, the mixture was stirred for approximately an additional 10 mins at −78° C., then allowed to warm to about 0° C. and stirred for about 2 hr. The reaction was quenched with 1 ml of 5% NaHCO$_3$ solution and the mixture was concentrated. The residue was added with 250 ml of hexane and stirred for 10 min and filtered. The filtrate was concentrated to yield the title compound as yellow oil, which was directly used for the next step reaction.

(R)-5-(3-Amino-4-chloro-phenyl)-3-methyl-3,4-dihydro-2H-pyridine-1-carboxylic acid tert-butyl ester A mixture of 3-Methyl-5-trifluoromethanesulfonyloxy-3,4-dihydro-2H-pyridine-1-carboxylic acid tert-butyl ester (3237 mg; 9.37 mmol), 2-Chloro-5-(4,4,5,5-tetramethyl-[1,3,2]dioxaborolan-2-yl)-phenylamine (1.90 g; 7.50 mmol) and sodium carbonate (1.99 g; 18.75 mmol) in dioxane (150 ml) and water (15 ml) was degassed, and then added bis(tri-tert-butylphosphine)palladium(0) (239.52 mg; 0.47 mmol). The mixture was stirred at 45° C. overnight. The reaction mixture was filtered. The filtrate was concentrated. The curde was purified by Biotage silica gel column (150 g, eluted with hex/EA 0-35%) to yield (R)-5-(3-Amino-4-chloro-phenyl)-3-methyl-3,6-dihydro-2H-pyridine-1-carboxylic acid tert-butyl ester as the major product (526 mg, 18%). LC-MS (M+1)=323. 1HNMR (400 MHz, Chloroform-d) δ 7.41 (ddt, J=8.9, 6.7, 1.8 Hz, 1H), 7.37-7.30 (m, 1H), 7.22-7.12 (m, 1H), 6.87-6.68 (m, 2H), 4.11-3.74 (m, 3H), 2.51-2.40 (m, 1H), 2.10-1.94 (m, 2H), 1.55 (s, 9H), 1.10 (d, J=6.1 Hz, 3H) and (R)-5-(3-Amino-4-chloro-phenyl)-3-methyl-3,4-dihydro-2H-pyridine-1-carboxylic acid tert-butyl ester (300 mg, 10%). LC-MS (M+1)=323. 1HNMR (400 MHz, Chloroform-d) δ 7.21 (d, J=8.3 Hz, 1H), 6.76 (dd, J=22.4, 5.2 Hz, 2H), 6.01 (dt, J=3.6, 1.9 Hz, 1H), 4.32 (d, J=17.5 Hz, 1H), 4.09 (d, J=23.5 Hz, 2H), 2.93 (d, J=51.9 Hz, 1H), 2.50 (s, 1H), 1.52 (s, 9H), 1.33-1.24 (m, 3H), 1.08 (d, J=7.1 Hz, 3H).

(R)-3-(3-Amino-4-chloro-phenyl)-5-methyl-piperidine-1-carboxylic acid tert-butyl ester To a solution of (R)-5-(3-Amino-4-chloro-phenyl)-3-methyl-3,6-dihydro-2H-pyridine-1-carboxylic acid tert-butyl ester (526.00 mg; 1.63 mmol) in 12 ml of EA, was added 10% Pd/C (500 mg). After degas, put two H$_2$ balloons on and the reaction mixture was stirred at 40° C. for 5 hr. LCMS showed 60-70% convertion. The reaction was stopped due to the formation of by-product. The reaction mixture was degassed, and purged with N$_2$ and filtered. The filtrate was concentrated. The crude was purified by Biotage silica gel column (50 g, eluted with hex/EA 0-35%) to yield the title compound (190 mg, yield 36%). LC-MS (M+1)=323. $^1$H NMR (400 MHz, Chloroform-d) δ 7.18 (d, J=8.2 Hz, 1H), 6.64 (d, J=2.0 Hz, 1H), 6.57 (dd, J=8.2, 2.1 Hz, 1H), 4.33-3.92 (m, 4H), 2.60 (d, J=9.2 Hz, 2H), 2.41-2.17 (m, 1H), 1.97 (ddq, J=12.8, 3.5, 1.7 Hz, 1H), 1.69 (ddd, J=17.8, 12.5, 7.2 Hz, 2H), 1.32-1.16 (m, 2H), 1.11-1.00 (m, 1H), 1.00-0.88 (m, 4H).

8-Chloro-5-((R)-5-methyl-piperidin-3-yl)-quinoline

To (R)-3-(3-Amino-4-chloro-phenyl)-5-methyl-piperidine-1-carboxylic acid tert-butyl ester (180 mg; 0.55 mmol) in 10 ml flask was added glycerol (0.16 ml; 2.22 mmol), iron(ii) sulfate heptahydrate (30 mg; 0.11 mmol) and sulfuric acid (0.26 ml; 4.43 mmol). The resulting mixture was stirred at 120° C. for 2 hr. Ice (10 g) and sodium hydroxide (398 mg; 9.97 mmol) was added. The mixture was stirred for 30 mins and extracted with DCM (30 ml×2). The combined organic layer was washed with brine (10 ml), dried over MgSO$_4$ and concentrated to yield the title compound as a yellow oil, which was directly used for the next step reaction. LC-MS (M+1)=261.

1-[(R)-3-(8-Chloro-quinolin-5-yl)-5-methyl-piperidin-1-yl]-2-(1-methyl-piperidin-4-yl)-ethanone A mixture of 8-Chloro-5-((R)-5-methyl-piperidin-3-yl)-quinoline (100 mg; 0.28 mmol), (1-Methyl-piperidin-4-yl)-acetic acid (52 mg; 0.34 mmol) and DIEA (0.15 ml; 0.84 mmol) in DMSO (2 ml) was stirred at RT for 5 min. After adding BOP (148 mg; 0.34 mmol), the resulting mixture was stirred at RT for 1 hr. The completed reaction was diluted with EA, washed with brine, dried and concentrated to yield the title compound, which was directly carried for the next step reaction. LC-MS (M+1)=400.

5-{(3R,5R)-5-Methyl-1-[2-(1-methyl-piperidin-4-yl)-acetyl]-piperidin-3-yl}-quinoline-8-carbonitrile & 5-{(3S,5R)-5-Methyl-1-[2-(1-methyl-piperidin-4-yl)-acetyl]-piperidin-3-yl}-quinoline-8-carbonitrile To a solution of 1-[(R)-3-(8-Chloro-quinolin-5-yl)-5-methyl-piperidin-1-yl]-2-(1-methyl-piperidin-4-yl)-ethanone (350 mg; 0.88 mmol) in 2 ml of DMF, was added zinc cyanide (205.52 mg; 1.75 mmol). The mixture was degassed and then added palladium tritert-butylphosphane (89 mg; 0.18 mmol). The resulting mixture was placed on microwave at 130° C. for 1 hr. The completed reaction was purified by prep HPLC (basic, ACN/water 20-60%) to yield 5-{(3R,5R)-1-[2-(1-Isopropyl-piperidin-4-yl)-acetyl]-5-methyl-piperidin-3-yl}-quinoline-8-carbonitrile (50 mg, yield 15%) and 5-{(3S,5R)-1-[2-(1-Isopropyl-piperidin-4-yl)-acetyl]-5-methyl-piperidin-3-yl}-quinoline-8-carbonitrile (15 mg, 4.4%).

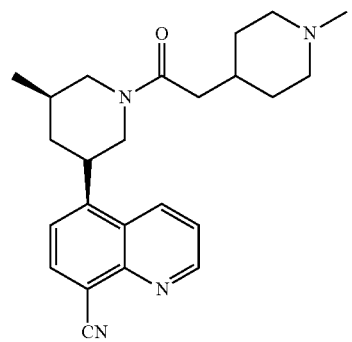

Compound 53

LC-MS (M+1)=391. 1H NMR (400 MHz, DMSO-d6) δ 9.12 (dd, J=4.2, 1.5 Hz, 1H), 8.85 (td, J=8.9, 1.6 Hz, 1H), 8.36 (dd, J=7.6, 5.7 Hz, 1H), 7.86-7.59 (m, 2H), 4.58 (dd, J=28.7, 12.4 Hz, 2H), 3.98 (t, J=12.0 Hz, 1H), 3.48 (t, J=11.6 Hz, 1H), 2.86-2.57 (m, 3H), 2.45-2.18 (m, 3H), 2.12 (d, J=13.0 Hz, 3H), 2.01 (d, J=11.5 Hz, 1H), 1.93-1.73 (m, 3H), 1.71-1.57 (m, 3H), 1.32-1.03 (m, 2H), 0.95 (dd, J=20.5, 6.5 Hz, 3H).

Compound 54

LC-MS (M+1)=391. 1H NMR (400 MHz, DMSO-d6) δ 9.12 (td, J=4.6, 1.5 Hz, 1H), 8.76 (dd, J=8.8, 1.5 Hz, 1H), 8.34 (dd, J=12.9, 7.6 Hz, 1H), 7.80 (dd, J=8.7, 4.2 Hz, 1H), 7.69 (dd, J=26.5, 7.7 Hz, 1H), 4.26 (dd, J=12.9, 3.7 Hz, 2H), 3.91 (s, 1H), 3.76 (dq, J=9.0, 4.7, 4.0 Hz, 1H), 3.52 (qd, J=13.5, 3.9 Hz, 2H), 2.70 (dd, J=32.9, 11.1 Hz, 2H), 2.36 (dd, J=15.2, 6.7 Hz, 1H), 2.24 (ddd, J=15.3, 6.4, 4.3 Hz, 1H), 2.20-1.96 (m, 5H), 1.93-1.73 (m, 3H), 1.73-1.40 (m, 3H), 1.25-1.11 (m, 1H), 1.07 (dd, J=6.9, 2.9 Hz, 3H).

The following compounds were synthesized in an analogous manner:

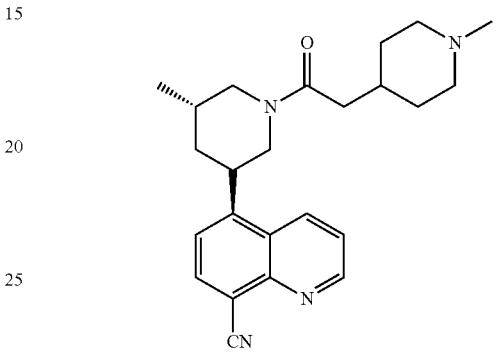

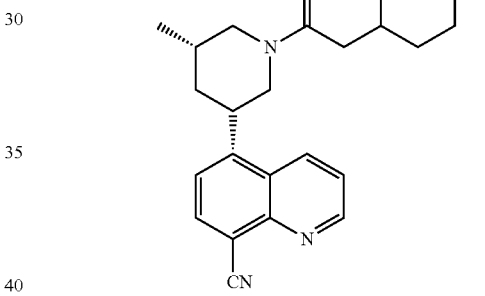

Compound 55 (5-{(3S,5R)-5-Methyl-1-[2-(1-methyl-piperidin-4-yl)-acetyl]-piperidin-3-yl}-quinoline-8-carbonitrile) and Compound 56 (5-{(3S,5S)-5-Methyl-1-[2-(1-methyl-piperidin-4-yl)-acetyl]-piperidin-3-yl}-quinoline-8-carbonitrile)

From (S)-3-Methyl-5-oxo-piperidine-1-carboxylic acid tert-butyl ester.

Compound 55

LC-MS (M+1)=391. 1H NMR (400 MHz, DMSO-d6) δ 9.12 (td, J=4.6, 1.5 Hz, 1H), 8.76 (dd, J=8.8, 1.5 Hz, 1H), 8.34 (dd, J=12.9, 7.6 Hz, 1H), 7.80 (dd, J=8.7, 4.2 Hz, 1H), 7.69 (dd, J=26.5, 7.7 Hz, 1H), 4.26 (dd, J=12.9, 3.7 Hz, 2H), 3.91 (s, 1H), 3.76 (dq, J=9.0, 4.7, 4.0 Hz, 1H), 3.52 (qd, J=13.5, 3.9 Hz, 2H), 2.70 (dd, J=32.9, 11.1 Hz, 2H), 2.36 (dd, J=15.2, 6.7 Hz, 1H), 2.24 (ddd, J=15.3, 6.4, 4.3 Hz, 1H), 2.20-1.96 (m, 5H), 1.93-1.73 (m, 3H), 1.73-1.40 (m, 3H), 1.25-1.11 (m, 1H), 1.07 (dd, J=6.9, 2.9 Hz, 3H).

Compound 56

LC-MS (M+1)=391. 1H NMR (400 MHz, DMSO-d6) δ 9.12 (dd, LC-MS (M+1)=391. 1H NMR (400 MHz, DMSO-d6) δ 9.12 (dd, J=4.2, 1.5 Hz, 1H), 8.85 (td, J=8.9, 1.6 Hz, 1H), 8.36 (dd, J=7.6, 5.7 Hz, 1H), 7.86-7.59 (m, 2H), 4.58 (dd, J=28.7, 12.4 Hz, 2H), 3.98 (t, J=12.0 Hz, 1H), 3.48 (t, J=11.6 Hz, 1H), 2.86-2.57 (m, 3H), 2.45-2.18 (m, 3H), 2.12 (d, J=13.0 Hz, 3H), 2.01 (d, J=11.5 Hz, 1H), 1.93-1.73 (m, 3H), 1.71-1.57 (m, 3H), 1.32-1.03 (m, 2H), 0.95 (dd, J=20.5, 6.5 Hz, 3H).

Example 13: Synthesis of Compound 57 (5-(1-Isoxazol-3-yl-5-methyl-piperidin-3-yl)-8-trifluoromethyl-quinoline

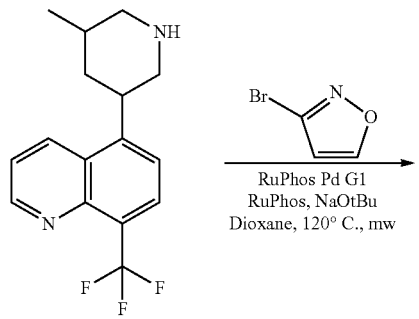

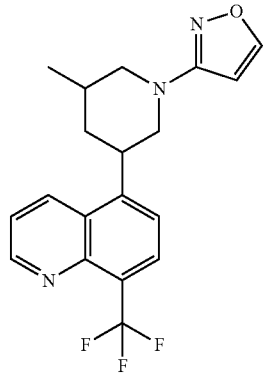 [SMILES: CC1CC(c2ccc(C(F)(F)F)c3ncccc23)CN(c2ccon2)C1]

Compound 57

LC-MS (M+1)=362. ¹H NMR (400 MHz, DMSO-d₆) δ 9.08 (ddd, J=4.4, 3.0, 1.6 Hz, 1H), 8.90 (dd, J=8.8, 1.7 Hz, 1H), 8.79 (dd, J=8.8, 1.7 Hz, 1H), 8.18 (d, J=7.6 Hz, 1H), 7.84-7.62 (m, 3H), 4.51 (dd, J=31.9, 11.8 Hz, 1H), 4.24-3.94 (m, 2H), 3.77 (t, J=12.0 Hz, 1H), 3.57 (t, J=11.9 Hz, 1H), 2.95-2.63 (m, 1H), 2.37 (t, J=12.2 Hz, 1H), 2.04 (d, J=32.0 Hz, 1H), 1.79 (d, J=17.2 Hz, 1H), 1.58 (dq, J=41.6, 12.0 Hz, 1H), 0.96 (dd, J=7.8, 6.4 Hz, 3H).

The following compounds were synthesized in an analogous manner:

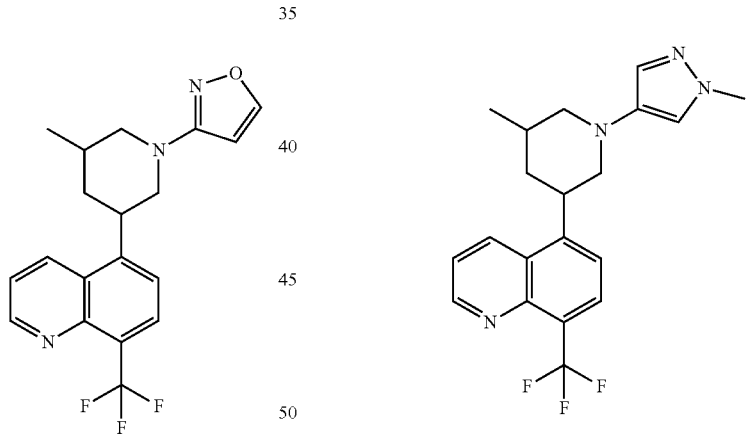

A reaction mixture of 5-(5-Methyl-piperidin-3-yl)-8-trifluoromethyl-quinoline (150 mg; 0.51 mmol), 3-Bromo-isoxazole (150.82 mg; 1.02 mmol), 2-dicyclohexylphosphino-2',6'-di-i-propoxy-1,1'-biphenyl (11.89 mg; 0.03 mmol), chloro(2-dicyclohexylphosphino-2',6'-di-i-propoxy-1,1'-biphenyl)[2-(2-aminoethylphenyl)]palladium(ii), methyl-t-butylether adduct (20.82 mg; 0.03 mmol), and sodium tert-butoxide (97.96 mg; 1.02 mmol) in dioxane (2 ml) in 10 ml microwave tube, was place in microwave at 120° C. for 3 hr. The completed reaction was purified by prep HPLC (eluted with 30-70% ACN/water) to yield the title compound.

Compound 58 (5-[5-Methyl-1-(1-methyl-1H-pyrazol-4-yl)-piperidin-3-yl]-8-trifluoromethyl-quinoline)

From 5-(5-Methyl-piperidin-3-yl)-8-trifluoromethyl-quinoline and 4-Bromo-1-methyl-1H-pyrazole. LC-MS (M+1)= 374. ¹H NMR (400 MHz, Methanol-d₄) δ 9.01 (s, 1H), 8.79 (d, J=8.8 Hz, 1H), 8.13 (d, J=7.8 Hz, 1H), 7.71 (d, J=7.6 Hz, 2H), 7.30 (d, J=9.3 Hz, 2H), 3.89 (d, J=11.0 Hz, 1H), 3.81 (d, J=1.8 Hz, 2H), 3.57 (s, 3H), 2.79-2.63 (m, 2H), 2.34 (t, J=11.1 Hz, 1H), 2.25-2.00 (m, 2H), 1.54 (t, J=12.1 Hz, 1H), 1.09 (d, J=6.3 Hz, 2H).

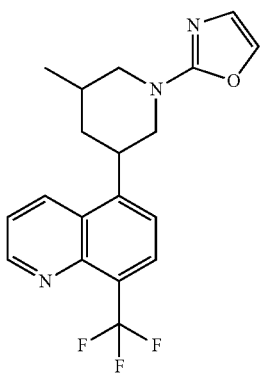 [SMILES: CC1CC(c2ccc(C(F)(F)F)c3ncccc23)CN(c2ncco2)C1]

Compound 59 (5-(5-Methyl-1-oxazol-2-yl-piperidin-3-yl)-8-trifluoromethyl-quinoline)

From 5-(5-Methyl-piperidin-3-yl)-8-trifluoromethyl-quinoline and 2-Bromo-oxazole. LC-MS (M+1)=362. ¹H NMR (400 MHz, DMSO-d₆) δ 9.09 (dd, J=4.1, 1.6 Hz, 1H), 8.92 (dd, J=9.0, 1.6 Hz, 1H), 8.18 (d, J=7.7 Hz, 1H), 7.79-7.67 (m, 2H), 7.61 (d, J=1.0 Hz, 1H), 6.92 (d, J=1.0 Hz, 1H), 4.21-4.10 (m, 1H), 4.10-3.96 (m, 1H), 3.75 (t, J=11.8 Hz, 1H), 3.10 (dd, J=12.8, 11.4 Hz, 1H), 2.85-2.65 (m, 1H), 2.11-1.85 (m, 2H), 1.66 (q, J=11.9 Hz, 1H), 0.99 (d, J=6.5 Hz, 3H).

Example 14: Synthesis of Compound 60 (trans-1-((S)-2-Amino-2-cyclopropyl-acetyl)-5-methyl-piperidin-3-yl]-quinoline-8-carbonitrile) and Compound 61 (cis-1-((S)-2-Amino-2-cyclopropyl-acetyl)-5-methyl-piperidin-3-yl]-quinoline-8-carbonitrile)

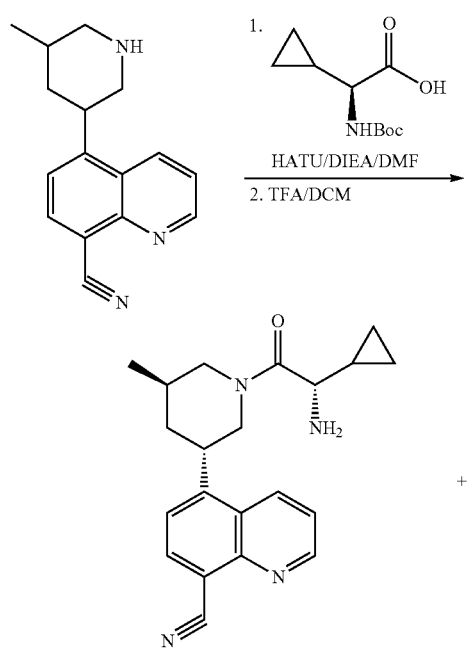

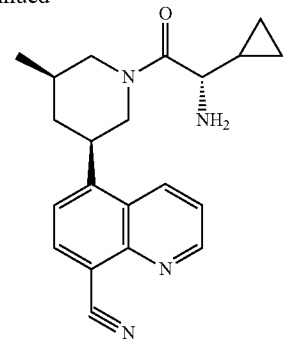

To Boc-1-cyclopropylglycine (62 mg, 0.28 mmol) in DMF (1.0 ml) was added HATU (98 mg; 0.26 mmol). After stirring for 10 mins, DIEA was added (0.13 ml; 0.74 mmol), followed by 5-(5-Methyl-piperidin-3-yl)-quinoline-8-carbonitrile dihydrochloride (60 mg; 0.19 mmol). The resulting mixture was stirred at RT for 1 hr. The completed reaction was diluted with water (10 ml) and extracted with DCM (20×2). The combined organic layer was washed with 5 ml of brine, dried and concentrated to leave about 1-2 ml solution to yield a DCM solution of a mixture of tert-butyl N-[(1S)-2-[trans-3-(8-cyanoquinolin-5-yl)-5-methylpiperidin-1-yl]-1-cyclopropyl-2-oxoethyl]carbamate & tert-butyl N-[(1S)-2-[cis-3-(8-cyanoquinolin-5-yl)-5-methylpiperidin-1-yl]-1-cyclopropyl-2-oxoethyl]carbamate.

To the above solution was added 0.5 ml of TFA. The mixture was stirred at RT for 30 min. The completed reaction was diluted with 20 ml of DCM and washed with 5% NaHCO₃ aq. The organic phase was concentrated and the crude was purified by prep HPLC (basic, eluted with 10-60% CAN in water) to yield the title compounds.

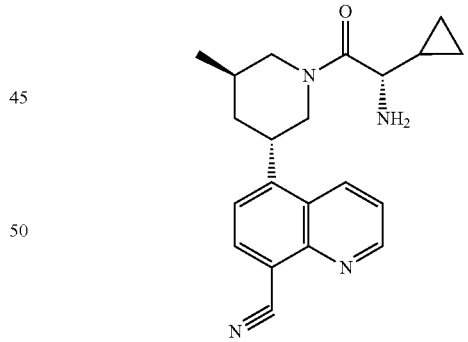

Compound 60

LC-MS (M+1)=349. ¹H NMR (400 MHz, Methanol-d₄) δ 9.11-8.98 (m, 1H), 8.92-8.82 (m, 1H), 8.29-8.19 (m, 1H), 7.78-7.68 (m, 2H), 4.11 (d, J=14.1 Hz, 1H), 3.64 (d, J=16.9 Hz, 1H), 3.43 (dd, J=31.6, 11.1 Hz, 1H), 2.90 (t, J=12.7 Hz, 1H), 2.78 (t, J=12.1 Hz, 1H), 2.43 (t, J=12.4 Hz, 1H), 2.17 (d, J=12.8 Hz, 1H), 2.00 (s, 1H), 1.76 (q, J=11.9 Hz, 1H), 1.27-1.13 (m, 1H), 1.07 (dd, J=11.7, 6.6 Hz, 3H), 0.66-0.26 (m, 4H).

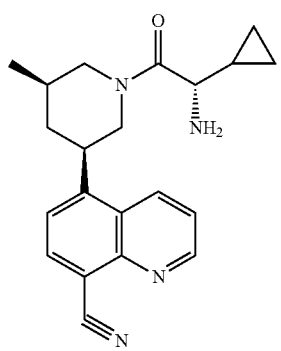 [SMILES: C[C@@H]1C[C@H](c2ccc(C#N)c3ncccc23)CN(C(=O)[C@@H](N)C2CC2)C1]

Compound 61

LC-MS (M+1)=349. $^1$H NMR (400 MHz, Methanol-d$_4$) δ 9.11-8.99 (m, 1H), 8.87 (t, J=7.6 Hz, 1H), 8.25 (d, J=7.6 Hz, 1H), 7.75 (ddt, J=10.1, 5.5, 2.8 Hz, 2H), 4.68 (d, J=12.8 Hz, 1H), 4.14 (dd, J=27.0, 13.6 Hz, 1H), 3.79 (d, J=12.0 Hz, 1H), 3.70-3.54 (m, 1H), 3.51-3.40 (m, 1H), 3.00-2.84 (m, 1H), 2.77 (t, J=12.1 Hz, 1H), 2.44 (t, J=12.2 Hz, 1H), 2.20 (d, J=23.9 Hz, 1H), 1.95 (d, J=35.6 Hz, 1H), 1.69 (dq, J=48.5, 13.0, 12.5 Hz, 1H), 1.28-1.13 (m, 1H), 1.13-0.96 (m, 3H), 0.80-0.16 (m, 4H).

The following compounds were synthesized in an analogous manner:

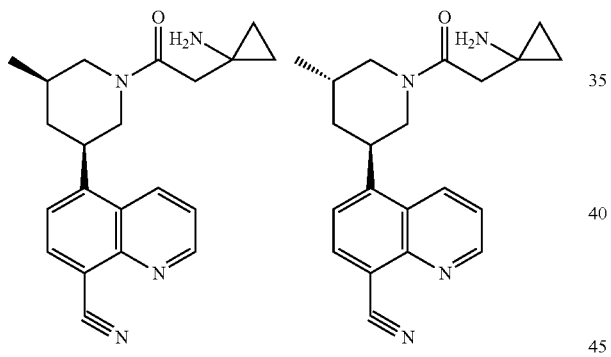

Compound 62 (Cis-1-[2-(1-Amino-cyclopropyl)-acetyl]-5-methyl-piperidin-3-yl-quinoline-8-carbonitrile) and Compound 63 (Trans-1-[2-(1-Amino-cyclopropyl)-acetyl]-5-methyl-piperidin-3-yl-quinoline-8-carbonitrile)

From 5-(5-Methyl-piperidin-3-yl)-quinoline-8-carbonitrile dihydrochloride and 2-(1-((tert-butoxycarbonyl)amino)cyclopropyl)acetic acid.

Compound 62

LC-MS (M+1)=349 1H NMR (400 MHz, Methanol-d$_4$) δ 9.06 (dd, J=4.2, 1.5 Hz, 1H), 8.93-8.77 (m, 1H), 8.25 (d, J=7.6 Hz, 1H), 7.74 (ddd, J=15.6, 8.1, 3.9 Hz, 2H), 4.75 (dd, J=24.9, 13.0 Hz, 1H), 4.02 (dd, J=24.9, 13.0 Hz, 1H), 3.75 (t, J=11.7 Hz, 1H), 3.63 (s, 1H), 2.90-2.77 (m, 1H), 2.36 (t, J=12.3 Hz, 1H), 2.15 (d, J=12.6 Hz, 1H), 1.94 (s, 1H), 1.82-1.51 (m, 2H), 1.06 (dd, J=10.9, 6.5 Hz, 3H).

Compound 63

LC-MS (M+1)=349 1H NMR (400 MHz, Methanol-d$_4$) δ 9.06 LC-MS (M+1)=349 1H NMR (400 MHz, Methanol-d$_4$) δ 9.06 (dd, J=4.2, 1.6 Hz, 1H), 8.86 (ddd, J=20.9, 8.8, 1.6 Hz, 1H), 8.24 (d, J=7.7 Hz, 1H), 7.74 (ddd, J=15.9, 8.1, 3.9 Hz, 2H), 4.14-3.90 (m, 1H), 3.62 (tt, J=11.8, 3.4 Hz, 1H), 2.83 (dd, J=13.6, 11.6 Hz, 1H), 2.76-2.49 (m, 3H), 2.15 (d, J=13.0 Hz, 1H), 1.93 (s, 1H), 1.65 (dq, J=52.3, 12.1 Hz, 1H), 1.06 (dd, J=11.1, 6.6 Hz, 3H), 0.75-0.35 (m, 4H).

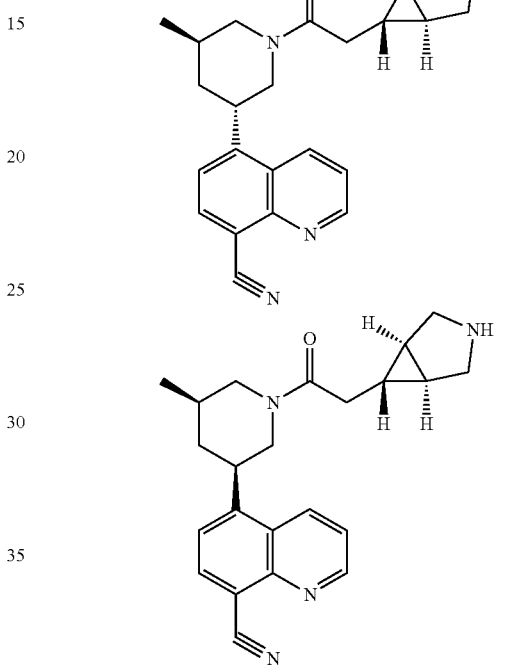

Compound 64 (trans-5-Methyl-1-[2-((1S,5R,6S)-3-methyl-3-aza-bicyclo[3.1.0]hex-6-yl)-acetyl]-piperidin-3-yl}-quinoline-8-carbonitrile) and Compound 65 (cis-5-Methyl-1-[2-((1S,5R,6S)-3-methyl-3-aza-bicyclo[3.1.0]hex-6-yl)-acetyl]-piperidin-3-yl}-quinoline-8-carbonitrile)

From 5-(5-Methyl-piperidin-3-yl)-quinoline-8-carbonitrile dihydrochloride and 2-((1r,5s,6s)-3-(tert-butoxycarbonyl)-3-azabicyclo[3.1.0]hexan-6-yl)acetic acid.

Compound 64

LC-MS (M+1)=389 $^1$H NMR (400 MHz, DMSO-d$_6$) δ 9.11 (dd, J=4.1, 1.7 Hz, 1H), 8.77 (t, J=8.3 Hz, 1H), 8.35 (dd, J=11.9, 7.6 Hz, 1H), 7.83-7.59 (m, 2H), 4.19 (d, J=13.3 Hz, 1H), 4.03 (d, J=12.4 Hz, 1H), 3.95-3.69 (m, 2H), 3.47 (d, J=11.5 Hz, 2H), 3.04-2.89 (m, 2H), 2.88-2.69 (m, 2H), 2.45-2.13 (m, 2H), 2.06 (dd, J=26.5, 13.1 Hz, 2H), 1.81 (d, J=10.8 Hz, 1H), 1.42-1.27 (m, 1H), 1.21 (d, J=14.0 Hz, 1H), 1.11-0.93 (m, 3H).

Compound 65

LC-MS (M+1)=389 $^1$H NMR (400 MHz, DMSO-d$_6$) δ 9.11 (dd, J=4.2, 1.7 Hz, 1H), 8.91-8.77 (m, 1H), 8.36 (dd,

J=7.6, 2.7 Hz, 1H), 7.85-7.65 (m, 2H), 4.56 (dd, J=26.7, 12.8 Hz, 1H), 3.92 (t, J=12.7 Hz, 1H), 3.67 (s, 1H), 3.48 (t, J=13.4 Hz, 2H), 2.89-2.70 (m, 2H), 2.70-2.53 (m, 2H), 2.43-2.19 (m, 2H), 2.00 (s, 1H), 1.82 (d, J=37.3 Hz, 1H), 1.55 (dq, J=53.3, 12.1 Hz, 2H), 1.22 (dt, J=7.3, 3.4 Hz, 1H), 1.10 (d, J=7.9 Hz, 1H), 0.95 (dd, J=16.1, 6.5 Hz, 3H).

Example 15: Synthesis of Compound 66 (trans-3-(8-Cyano-quinolin-5-yl)-5-methyl-piperidin-1-yl]-acetamide) and Compound 67 (cis-3-(8-Cyano-quinolin-5-yl)-5-methyl-piperidin-1-yl]-acetamide)

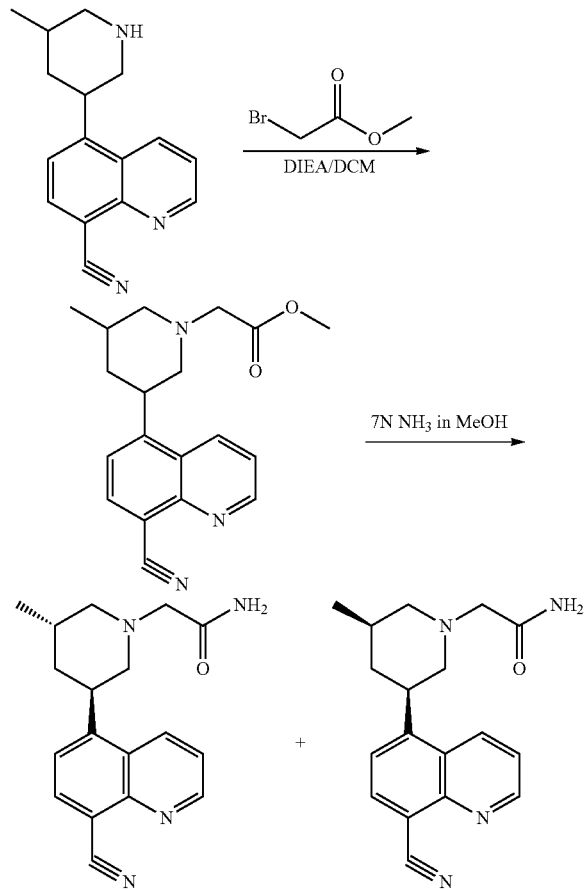

[3-(8-Cyano-quinolin-5-yl)-5-methyl-piperidin-1-yl]-acetic acid methyl ester

A reaction mixture of 5-(5-Methyl-piperidin-3-yl)-quinoline-8-carbonitrile dihydrochloride (350 mg; 1.08 mmol), Bromo-acetic acid methyl ester (0.11 ml; 1.19 mmol) and DIEA (0.78 ml; 4.32 mmol) in DCM (5 ml) was stirred at RT for 1 h. The completed reaction was diluted with DCM, washed with brine, dried and concentrate to yield the crude [3-(8-Cyano-quinolin-5-yl)-5-methyl-piperidin-1-yl]-acetic acid methyl ester, which was directly used for the next step reaction without purification. LC-MS (M+1)=324.

Trans & cis-3-(8-Cyano-quinolin-5-yl)-5-methyl-piperidin-1-yl]-acetamide

A solution of [3-(8-Cyano-quinolin-5-yl)-5-methyl-piperidin-1-yl]-acetic acid methyl ester (45.00 mg; 0.14 mmol) in 7 N ammonia in methanol (2.00 ml; 14.00 mmol) was stirred at RT overnight. LCMS showed around 20% conversion. The reaction mixture was then stirred at 70° C. for 24 hr. The reaction mixture was concentrated and the crude was purified by prep HPLC (basic, eluted with ACN/water 10-50%) to yield the title compounds.

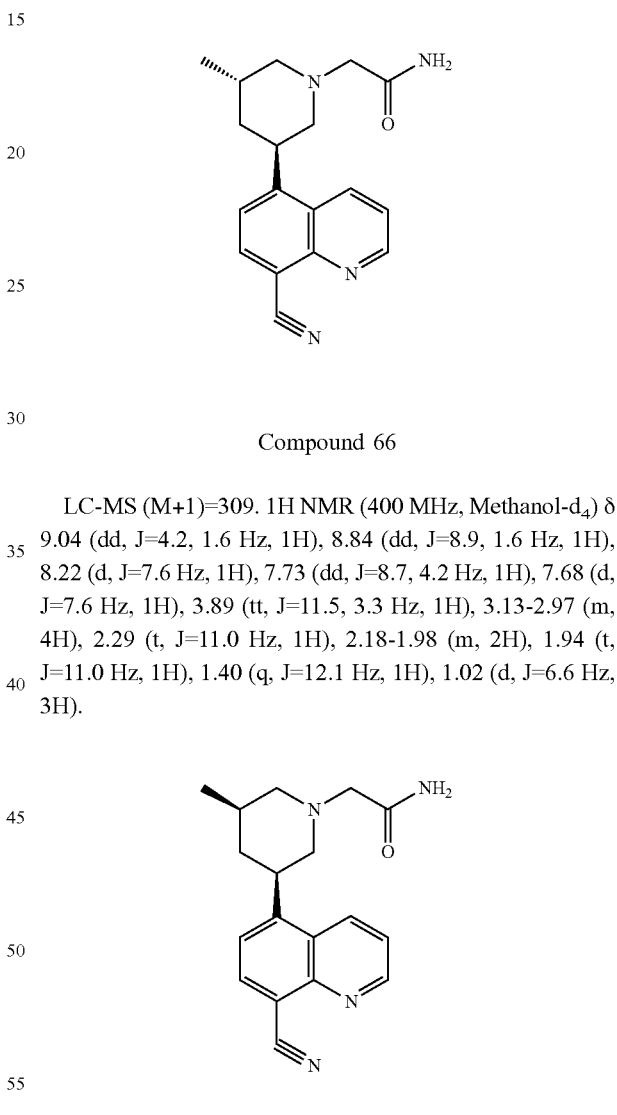

Compound 66

LC-MS (M+1)=309. 1H NMR (400 MHz, Methanol-$d_4$) δ 9.04 (dd, J=4.2, 1.6 Hz, 1H), 8.84 (dd, J=8.9, 1.6 Hz, 1H), 8.22 (d, J=7.6 Hz, 1H), 7.73 (dd, J=8.7, 4.2 Hz, 1H), 7.68 (d, J=7.6 Hz, 1H), 3.89 (tt, J=11.5, 3.3 Hz, 1H), 3.13-2.97 (m, 4H), 2.29 (t, J=11.0 Hz, 1H), 2.18-1.98 (m, 2H), 1.94 (t, J=11.0 Hz, 1H), 1.40 (q, J=12.1 Hz, 1H), 1.02 (d, J=6.6 Hz, 3H).

Compound 67

LC-MS (M+1)=309. $^1$H NMR (400 MHz, Methanol-$d_4$) δ 9.03 (dd, J=4.2, 1.6 Hz, 1H), 8.77 (dd, J=8.9, 1.6 Hz, 1H), 8.22 (d, J=7.7 Hz, 1H), 8.07 (s, 1H), 7.73 (dd, J=8.7, 4.2 Hz, 1H), 4.07 (dt, J=8.3, 4.1 Hz, 2H), 3.06 (s, 2H), 2.95 (d, J=11.7 Hz, 1H), 2.78-2.64 (m, 2H), 2.47 (s, 1H), 2.05 (s, 1H), 1.99-1.86 (m, 1H), 1.79 (dd, J=12.3, 6.2 Hz, 1H), 1.22 (d, J=6.9 Hz, 3H).

Example 16: Synthesis of Compound 80 (1-[(3R,5S)-3-Methyl-5-(8-methyl-quinolin-5-yl)-piperidin-1-yl]-2-(1-methyl-piperidin-4-yl)-ethanone) and Compound 81 (1-[(3R,5R)-3-Methyl-5-(8-methyl-quinolin-5-yl)-piperidin-1-yl]-2-(1-methyl-piperidin-4-yl)-ethanone)

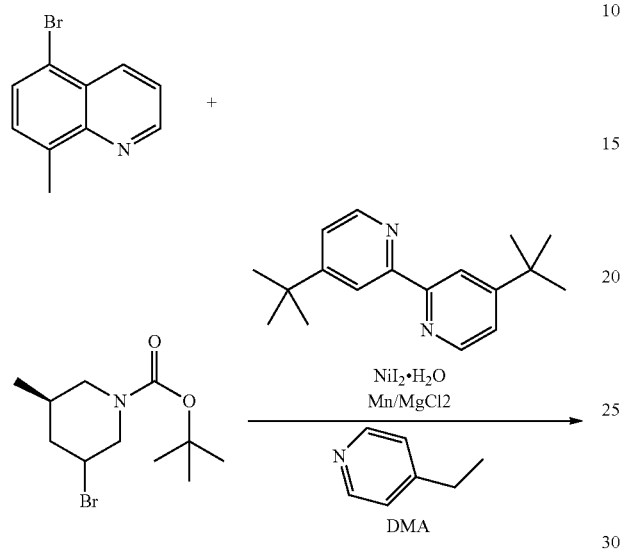

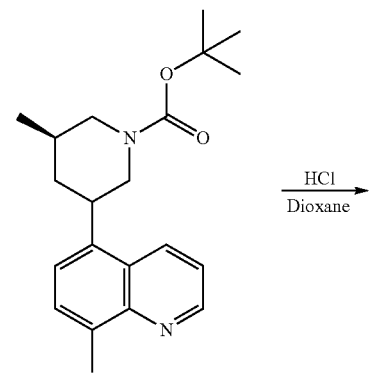

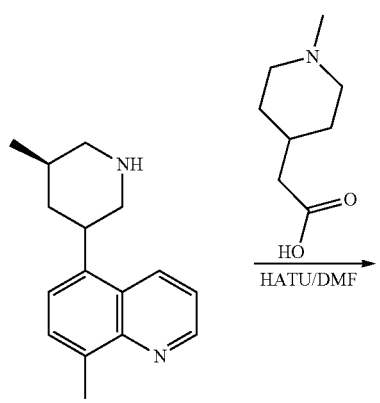

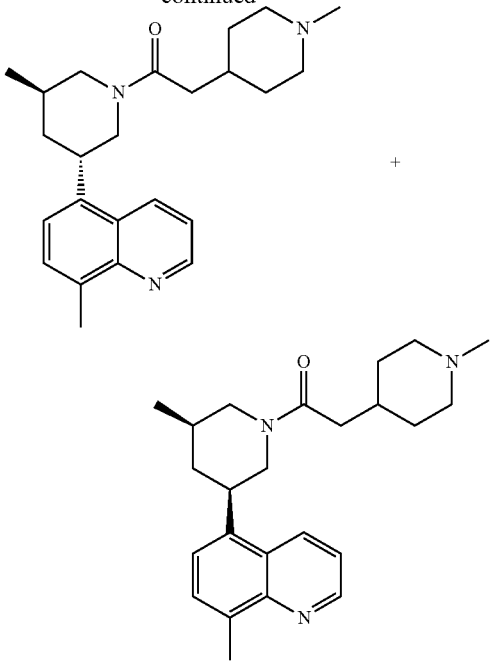

(R)-3-Methyl-5-(8-methyl-quinolin-5-yl)-piperidine-1-carboxylic acid tert-butyl ester A mixture of 5-bromo-8-methylquinoline (222 mg; 1.00 mmol), (R)-3-Bromo-5-methyl-piperidine-1-carboxylic acid tert-butyl ester (305 mg; 1.10 mmol), 4-ethylpyridine (0.11 ml; 1.00 mmol), 4,4'-di-tert-butyl-2,2'-bipyridine (26 mg; 0.10 mmol) and magnesium chloride (95 mg; 1.00 mmol) in DMA (5 ml) was purged with argon, and nickel(ii) iodide hydrate (42.04 mg; 0.10 mmol) was added, followed by manganese (109.84 mg; 2.00 mmol). The reaction mixture was stirred at 60° C. overnight. The completed reaction was filtered and washed with EA, The filtrate was concentrated and the residue was purified by Biotage silica gel column (50 G, eluted with 0-50% hex/EA) to yield the title compound (140 mg, yield 41%). LC-MS (M+1)=341.

8-Methyl-5-((R)-5-methyl-piperidin-3-yl)-quinoline dihydrochloride

To (R)-3-Methyl-5-(8-methyl-quinolin-5-yl)-piperidine-1-carboxylic acid tert-butyl ester (140.00 mg; 0.41 mmol) in methanol (1 ml) was added 4M hydrogen chloride in dioxane (1.54 ml; 6.17 mmol). The mixture was stirred at RT for 1 hr. The completed reaction was concentrated to yield the title compound, which was directly carried for the next step reaction. LC-MS (M+1)=241.

1-[(3R,5S)-3-Methyl-5-(8-methyl-quinolin-5-yl)-piperidin-1-yl]-2-(1-methyl-piperidin-4-yl)-ethanone & 1-[(3R,5R)-3-Methyl-5-(8-methyl-quinolin-5-yl)-piperidin-1-yl]-2-(1-methyl-piperidin-4-yl)-ethanone To (1-Methyl-piperidin-4-yl)-acetic acid (49 mg, 0.31 mmol) in DMF (1 ml) was added HATU (110.74 mg; 0.29 mmol). After stirring for 10 mins, DIEA (0.07 ml; 0.42 mmol) was added, followed by 8-Methyl-5-((R)-5-methyl-piperidin-3-yl)-quinoline (50.00 mg; 0.21 mmol). The mixture was stirred at rt for 1 hr. the completed reaction was concentrated and the crude was purified by prep HPLC (basic, 10-50% ACN/water) to yield the title compounds.

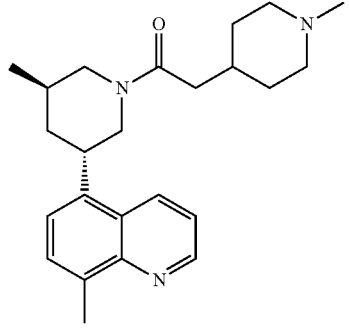

Compound 80

LC-MS (M+1)=380. $^1$H NMR (400 MHz, DMSO-$d_6$) δ 9.02-8.88 (m, 1H), 8.56 (t, J=6.8 Hz, 1H), 7.65-7.51 (m, 2H), 7.43 (dd, J=23.0, 7.4 Hz, 1H), 4.35 (d, J=12.7 Hz, 1H), 4.00-3.82 (m, 1H), 3.75 (s, 1H), 3.60 (d, J=12.9 Hz, 1H), 3.52-3.37 (m, 1H), 3.14 (d, J=16.2 Hz, 1H), 3.10-2.94 (m, 1H), 2.70 (d, J=3.9 Hz, 3H), 2.67-2.58 (m, 1H), 2.36 (dd, J=15.1, 6.6 Hz, 1H), 2.23 (p, J=7.4 Hz, 1H), 2.18-1.93 (m, 4H), 1.90-1.60 (m, 4H), 1.53 (dd, J=22.7, 12.5 Hz, 1H), 1.32-1.15 (m, 1H), 1.07 (dd, J=8.6, 6.8 Hz, 3H).

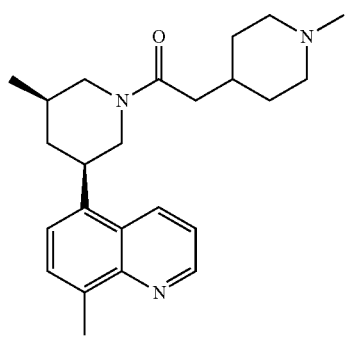

Compound 81

LC-MS (M+1)=380. $^1$H NMR (400 MHz, DMSO-$d_6$) δ 8.95 (dd, J=4.1, 1.7 Hz, 1H), 8.64 (dd, J=8.8, 1.6 Hz, 1H), 7.67-7.51 (m, 2H), 7.43 (dd, J=18.2, 7.4 Hz, 1H), 4.58 (dd, J=34.3, 12.3 Hz, 1H), 3.96 (d, J=11.9 Hz, 1H), 3.49 (d, J=12.0 Hz, 1H), 3.25-3.06 (m, 1H), 2.79-2.60 (m, 5H), 2.40-2.15 (m, 2H), 2.12 (d, J=11.6 Hz, 3H), 1.99 (d, J=12.8 Hz, 1H), 1.91-1.71 (m, 3H), 1.72-1.42 (m, 4H), 1.20 (td, J=30.6, 29.0, 13.4 Hz, 2H), 0.96 (dd, J=18.3, 6.5 Hz, 3H).

The following compounds were synthesized in an analogous manner:

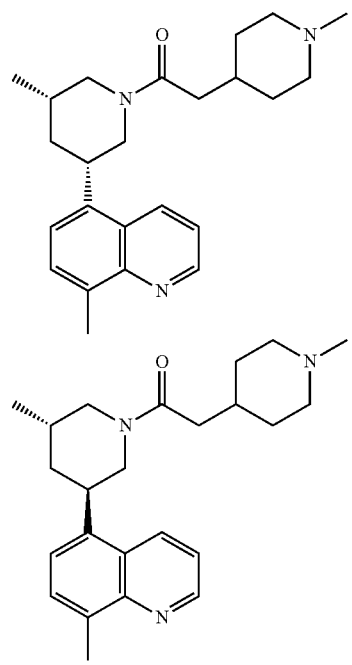

Compound 82 (1-[(3S,5S)-3-Methyl-5-(8-methyl-quinolin-5-yl)-piperidin-1-yl]-2-(1-methyl-piperidin-4-yl)-ethanone) and Compound 83 (1-[(3S,5R)-3-Methyl-5-(8-methyl-quinolin-5-yl)-piperidin-1-yl]-2-(1-methyl-piperidin-4-yl)-ethanone)

From (S)-3-Bromo-5-methyl-piperidine-1-carboxylic acid tert-butyl ester.

Compound 82

LC-MS (M+1)=380. $^1$H NMR (400 MHz, DMSO-$d_6$) δ 8.94 (dt, J=3.9, 1.8 Hz, 1H), 8.63 (dd, J=8.7, 1.7 Hz, 1H), 7.59 (qd, J=6.7, 2.9 Hz, 2H), 7.42 (dd, J=18.8, 7.4 Hz, 1H), 4.67-4.49 (m, 1H), 3.94 (dt, J=12.0, 5.2 Hz, 1H), 3.50 (ddt, J=12.0, 8.7, 3.5 Hz, 0H), 3.22-3.11 (m, 0H), 2.77-2.63 (m, 5H), 2.54 (s, 0H), 2.40-2.28 (m, 1H), 2.31-2.17 (m, 1H), 2.12 (d, J=11.7 Hz, 3H), 1.98 (d, J=12.7 Hz, 1H), 1.81 (dtt, J=20.1, 8.9, 2.5 Hz, 3H), 1.73-1.40 (m, 4H), 1.31-1.07 (m, 1H), 0.95 (dd, J=17.5, 6.5 Hz, 3H).

Compound 83

LC-MS (M+1)=380. $^1$H NMR (400 MHz, DMSO-$d_6$) δ 8.99-8.89 (m, 1H), 8.63-8.50 (m, 1H), 7.67-7.51 (m, 2H), 7.43 (dd, J=22.9, 7.4 Hz, 1H), 4.34 (d, J=11.5 Hz, 1H), 4.00-3.82 (m, 1H), 3.75 (s, 1H), 3.60 (d, J=13.2 Hz, 1H), 3.52-3.36 (m, 2H), 3.20-3.09 (m, 1H), 3.04 (dd, J=12.8, 9.6 Hz, 1H), 2.70 (d, J=3.9 Hz, 4H), 2.36 (dd, J=15.0, 6.7 Hz, 1H), 2.23 (dt, J=14.7, 7.0 Hz, 1H), 2.16-1.94 (m, 4H), 1.88-1.60 (m, 4H), 1.53 (dd, J=22.2, 12.4 Hz, 1H), 1.34-1.15 (m, 1H), 1.07 (dd, J=8.6, 6.8 Hz, 3H).

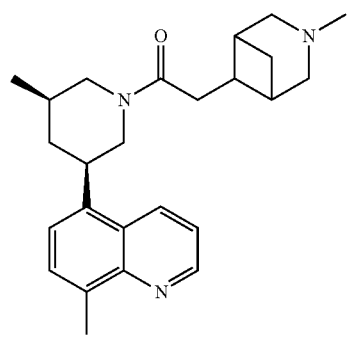

Compound 84 (2-(3-Methyl-3-aza-bicyclo [3.1.1]
hept-6-yl)-1-[(3R,5R)-3-methyl-5-(8-methyl-quino-
lin-5-yl)-piperidin-1-yl]-ethanone)

From 8-Methyl-5-((R)-5-methyl-piperidin-3-yl)-quino-
line coupled with (3-Methyl-3-aza-bicyclo[3.1.1]hept-6-yl)-
acetic acid. LC-MS (M+1)=392. $^{1}$H NMR (400 MHz,
DMSO-$d_6$) δ 8.94 (d, J=3.2 Hz, 1H), 8.65 (t, J=7.8 Hz, 1H),
7.60 (t, J=8.2 Hz, 2H), 7.44 (dd, J=23.3, 7.4 Hz, 1H), 4.56
(dd, J=34.5, 12.9 Hz, 1H), 3.95 (d, J=12.3 Hz, 1H), 3.52 (d,
J=12.0 Hz, 1H), 3.24-3.02 (m, 1H), 2.94-2.74 (m, 3H), 2.70
(d, J=2.4 Hz, 3H), 2.48-2.36 (m, 2H), 2.33 (s, 3H), 2.20 (s,
2H), 2.00 (d, J=12.8 Hz, 1H), 1.80 (p, J=8.5, 8.1 Hz, 2H),
1.68-1.39 (m, 2H), 0.96 (dd, J=19.8, 6.5 Hz, 3H).

Example 17: Synthesis of Compound 85 (7-Fluoro-
5-{(3R,5R)-5-methyl-1-[2-(1-methyl-piperidin-4-yl)-
acetyl]-piperidin-3-yl}-quinoline-8-carbonitrile

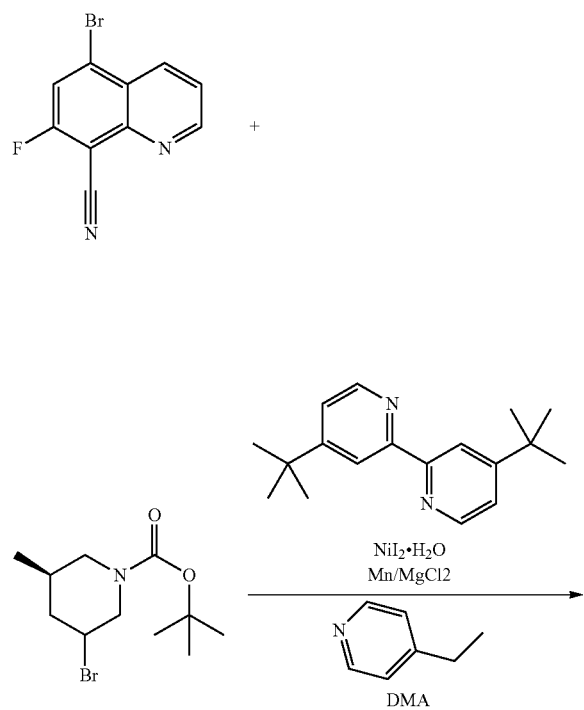

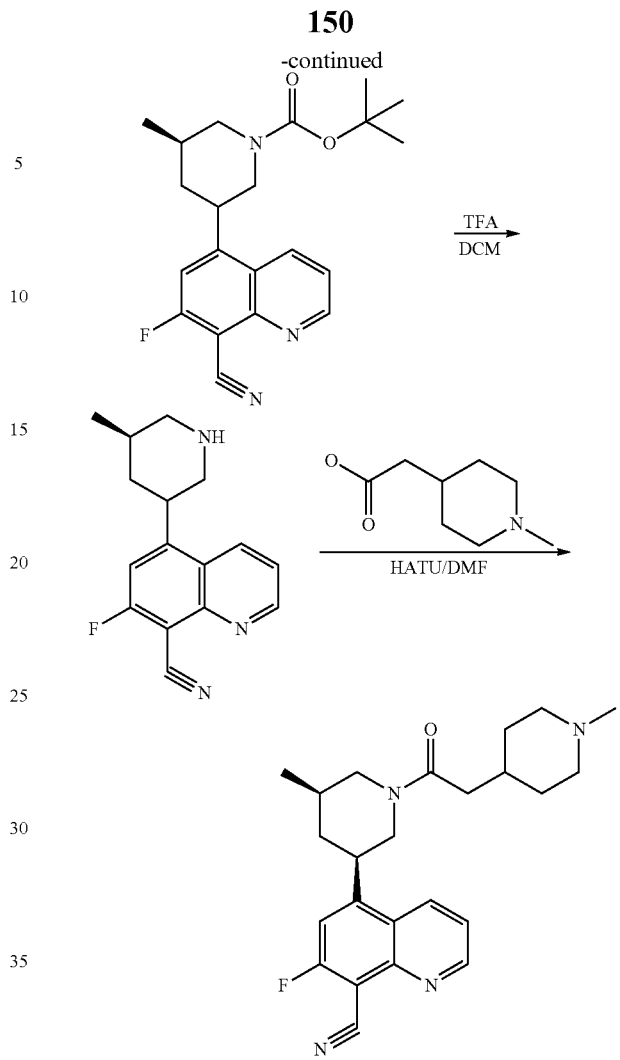

(R)-3-(8-Cyano-7-fluoro-quinolin-5-yl)-5-methyl-
piperidine-1-carboxylic Acid tert-butyl Ester A mixture of (R)-3-Bromo-5-methyl-piperidine-1-car-
boxylic acid tert-butyl ester (250.00 mg; 0.90 mmol),
5-Bromo-7-fluoro-quinoline-8-carbonitrile (248.18 mg;
0.99 mmol), 4,4'-di-tert-butyl-2,2'-bipyridine (24.12 mg;
0.09 mmol), magnesium chloride (85.56 mg; 0.90 mmol),
manganese (98.74 mg; 1.80 mmol) and diiodonickel (28.08
mg; 0.09 mmol) was degased, added DMA 5 ml, degas,
added 4-ethylpyridine (0.10 ml; 0.90 mmol). The mixture
was stirred at 80° C. for 18 hr. The completed reaction was
diluted with CAN and filtered. The filtrate was concentrated.
The crude was purified by Biotage silica gel column (25 g,
eluted with hexane/EA 0-50%) to yield the title compound.
LC-MS (M+1)=370.

7-Fluoro-5-((R)-5-methyl-piperidin-3-yl)-quinoline-
8-carbonitrile

To a solution of (R)-3-(8-Cyano-7-fluoro-quinolin-5-yl)-
5-methyl-piperidine-1-carboxylic acid tert-butyl ester (90
mg; 0.26 mmol) in DCM (2 ml) was added Trifluoro-acetic
acid (584 mg; 5.12 mmol). The mixture was stirred at RT for
30 min. The completed reaction was concentrated. The
residue was dissolved in DCM (30 ml) and 5% aq NaHCO$_3$ (10 ml). The separated organic layer was washed with brine, dried and concentrated to yield the title compound as a yellow solid, which was directly used for the next step reaction without purification. LC-MS (M+1)=270.

7-Fluoro-5-{(3R,5R)-5-methyl-1-[2-(1-methyl-piperidin-4-yl)-acetyl]-piperidin-3-yl}-quinoline-8-carbonitrile To a mixture of (1-Methyl-piperidin-4-yl)-acetic acid (16 mg; 0.10 mmol) in DMF (1 ml) was added HATU (36 mg; 0.09 mmol). After stirring for 10 mins, DIEA was added (0.02 ml; 0.14 mmol), followed by 7-Fluoro-5-((R)-5-methyl-piperidin-3-yl)-quinoline-8-carbonitrile (25.00 mg; 0.07 mmol). The reaction mixture was stirred at RT for 1 hr. The completed reaction was concentrated. The crude was purified by prep HPLC (basic, eluted with 10-50% ACN/water) to yield the title compound.

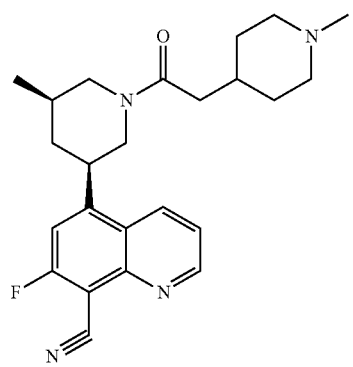

Compound 85

LC-MS (M+1)=409. $^1$H NMR (400 MHz, Methanol-d$_4$) δ 9.10-9.03 (m, 1H), 8.84 (dd, J=17.3, 8.2 Hz, 2H), 7.80-7.69 (m, 2H), 7.69-7.59 (m, 1H), 4.29-4.04 (m, 2H), 3.68 (d, J=52.6 Hz, 2H), 2.97-2.79 (m, 2H), 2.74-2.63 (m, 1H), 2.55-2.43 (m, 1H), 2.37 (s, 1H), 2.31-2.20 (m, 4H), 2.20-2.04 (m, 3H), 1.91-1.69 (m, 4H), 1.46-1.17 (m, 2H), 1.07 (dd, J=20.5, 6.6 Hz, 3H).

The following compounds were synthesized in an analogous manner:

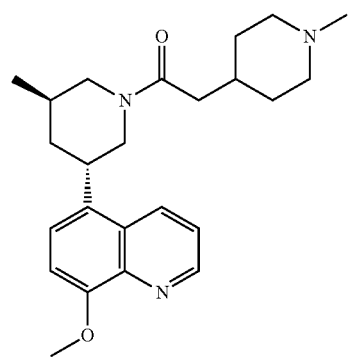

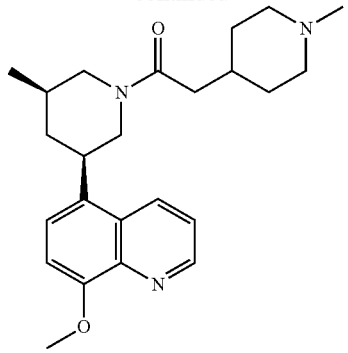

Compound 86 (1-[(3S,5R)-3-(8-Methoxy-quinolin-5-yl)-5-methyl-piperidin-1-yl]-2-(1-methyl-piperidin-4-yl)-ethanone) and Compound 87 (1-[(3R,5R)-3-(8-Methoxy-quinolin-5-yl)-5-methyl-piperidin-1-yl]-2-(1-methyl-piperidin-4-yl)-ethanone)

From (R)-3-Bromo-5-methyl-piperidine-1-carboxylic acid tert-butyl ester, 5-Bromo-8-methoxy-quinoline and (1-Methyl-piperidin-4-yl)-acetic acid.

Compound 86

LC-MS (M+1)=396. $^1$H NMR (400 MHz, Methanol-d$_4$) δ 8.84 (ddd, J=9.2, 4.2, 1.6 Hz, 1H), 8.69-8.58 (m, 1H), 7.73-7.59 (m, 1H), 7.52 (dd, J=23.0, 8.2 Hz, 1H), 7.19 (dd, J=15.5, 8.2 Hz, 1H), 4.51 (d, J=12.2 Hz, 1H), 4.06 (t, J=5.1 Hz, 3H), 4.02-3.91 (m, 1H), 3.89-3.61 (m, 2H), 3.61-3.48 (m, 1H), 3.12 (dd, J=13.0, 9.8 Hz, 1H), 3.00-2.78 (m, 2H), 2.50 (dd, J=15.1, 6.9 Hz, 1H), 2.43-2.35 (m, 1H), 2.35-2.16 (m, 4H), 2.15-2.03 (m, 2H), 2.03-1.75 (m, 4H), 1.61 (s, 1H), 1.39 (q, J=14.7, 12.9 Hz, 1H), 1.18 (t, J=7.0 Hz, 3H).

Compound 87

LC-MS (M+1)=396. $^1$H NMR (400 MHz, Methanol-d$_4$) δ 8.84 (ddd, J=5.9, 4.2, 1.5 Hz, 1H), 8.69 (ddd, J=19.5, 8.8, 1.6 Hz, 1H), 7.65 (td, J=8.7, 4.2 Hz, 1H), 7.52 (dd, J=16.4, 8.1 Hz, 1H), 7.21 (dd, J=10.4, 8.2 Hz, 1H), 4.07 (d, J=3.0 Hz, 4H), 3.53 (t, J=11.8 Hz, 1H), 3.39 (d, J=11.9 Hz, 1H), 2.98-2.68 (m, 3H), 2.63-2.52 (m, 1H), 2.46 (t, J=6.8 Hz, 1H), 2.41-2.35 (m, 1H), 2.29 (d, J=13.5 Hz, 3H), 2.22-1.98 (m, 3H), 1.97-1.53 (m, 5H), 1.35 (dt, J=34.8, 11.6 Hz, 2H), 1.07 (dd, J=17.3, 6.6 Hz, 3H).

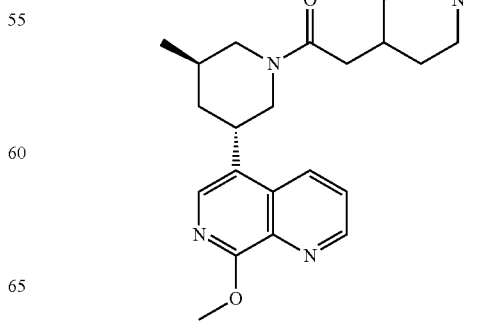

-continued

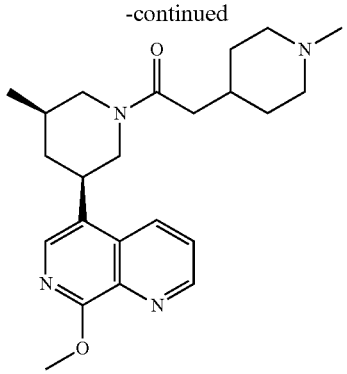

Compound 88 (1-[(3S,5R)-3-(8-Methoxy-[1,7]naphthyridin-5-yl)-5-methyl-piperidin-1-yl]-2-(1-methyl-piperidin-4-yl)-ethanone) and Compound 89 (1-[(3R,5R)-3-(8-Methoxy-[1,7]naphthyridin-5-yl)-5-methyl-piperidin-1-yl]-2-(1-methyl-piperidin-4-yl)-ethanone)

From (R)-3-Bromo-5-methyl-piperidine-1-carboxylic acid tert-butyl ester, 5-bromo-8-methoxy-1,7-naphthyridine and (1-Methyl-piperidin-4-yl)-acetic acid.

Compound 88

LC-MS (M+1)=397. $^1$H NMR (400 MHz, Methanol-$d_4$) δ 8.99-8.89 (m, 1H), 8.67-8.57 (m, 1H), 8.06 (d, J=25.0 Hz, 1H), 7.92-7.74 (m, 1H), 4.40 (d, J=12.5 Hz, 1H), 4.00 (dd, J=26.5, 14.5 Hz, 2H), 3.80-3.54 (m, 3H), 3.40 (d, J=10.2 Hz, 1H), 2.86 (d, J=27.1 Hz, 3H), 2.50 (dd, J=15.2, 6.8 Hz, 1H), 2.41-2.13 (m, 5H), 2.07 (d, J=11.7 Hz, 2H), 2.01-1.89 (m, 2H), 1.89-1.72 (m, 2H), 1.63 (d, J=13.3 Hz, 1H), 1.44-1.23 (m, 3H), 1.16 (dd, J=6.9, 2.2 Hz, 3H).

Compound 89

LC-MS (M+1)=397. $^1$H NMR (400 MHz, Methanol-$d_4$) δ 8.94 (td, J=4.4, 1.5 Hz, 1H), 8.71-8.58 (m, 1H), 8.07 (d, J=19.5 Hz, 1H), 7.86 (dt, J=8.8, 4.7 Hz, 1H), 4.13-4.00 (m, 2H), 3.43 (t, J=12.1 Hz, 1H), 3.31-3.22 (m, 1H), 3.02-2.81 (m, 4H), 2.71-2.56 (m, 1H), 2.53-2.35 (m, 2H), 2.29 (d, J=12.8 Hz, 4H), 2.24-1.99 (m, 3H), 1.97-1.67 (m, 4H), 1.60 (q, J=12.1 Hz, 1H), 1.34 (dq, J=34.1, 11.3, 10.7 Hz, 2H), 1.17-0.99 (m, 3H).

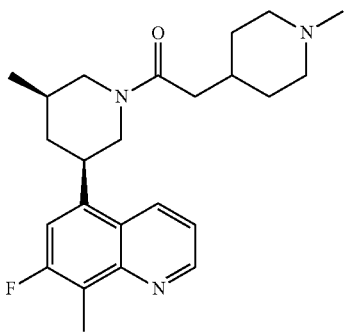

Compound 90 (1-[(3R,5R)-3-(7-Fluoro-8-methyl-quinolin-5-yl)-5-methyl-piperidin-1-yl]-2-(1-methyl-piperidin-4-yl)-ethanone)

From (R)-3-Bromo-5-methyl-piperidine-1-carboxylic acid tert-butyl ester, 5-Bromo-7-fluoro-8-methyl-quinoline and (1-Methyl-piperidin-4-yl)-acetic acid. LC-MS (M+1) =398. $^1$H NMR (400 MHz, DMSO-$d_6$) δ 8.97 (d, J=4.0 Hz, 1H), 8.71-8.62 (m, 1H), 7.57 (td, J=9.0, 4.0 Hz, 1H), 7.44 (dd, J=26.9, 11.0 Hz, 1H), 4.56 (dd, J=28.6, 12.6 Hz, 1H), 3.94 (d, J=13.5 Hz, 1H), 3.39 (d, J=11.7 Hz, 1H), 3.23 (t, J=12.4 Hz, 1H), 2.71 (q, J=13.8, 12.6 Hz, 2H), 2.49 (d, J=42.2 Hz, 2H), 2.41-2.17 (m, 3H), 2.17-2.05 (m, 3H), 1.97 (d, J=12.6 Hz, 1H), 1.81 (q, J=18.9, 15.2 Hz, 3H), 1.71-1.50 (m, 4H), 1.15 (dq, J=28.4, 16.4, 14.2 Hz, 2H), 0.94 (dd, J=19.3, 6.5 Hz, 3H).

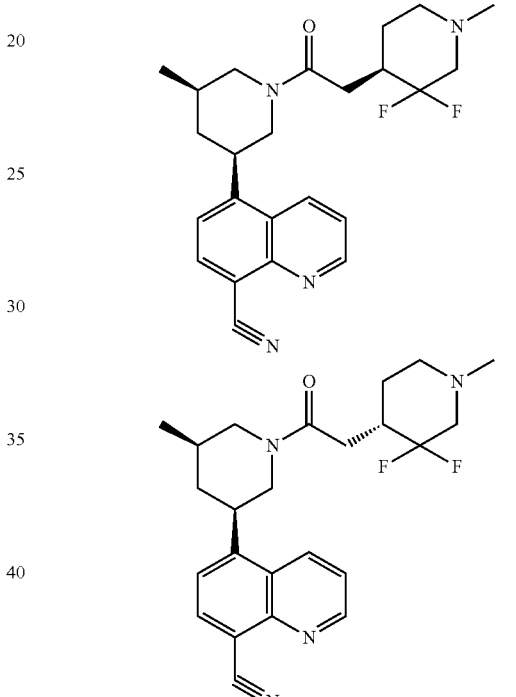

Compound 91 (5-{(3R,5R)-1-[2-((R)-3,3-Difluoro-1-methyl-piperidin-4-yl)-acetyl]-5-methyl-piperidin-3-yl}-quinoline-8-carbonitrile) and Compound 92 (5-{(3R,5R)-1-[2-((S)-3,3-Difluoro-1-methyl-piperidin-4-yl)-acetyl]-5-methyl-piperidin-3-yl}-quinoline-8-carbonitrile)

From (R)-3-Bromo-5-methyl-piperidine-1-carboxylic acid tert-butyl ester, 5-Bromo-quinoline-8-carbonitrile and (3,3-Difluoro-1-methyl-piperidin-4-yl)-acetic acid.

Compound 91

LC-MS (M+1)=427. 1H NMR (400 MHz, DMSO-d6) δ 9.11 (dd, J=4.2, 1.6 Hz, 1H), 8.93-8.77 (m, 1H), 8.36 (dd, J=7.6, 4.5 Hz, 1H), 7.89-7.61 (m, 2H), 4.57 (dd, J=28.0, 12.5 Hz, 1H), 3.97 (d, J=15.3 Hz, 1H), 3.52 (t, J=11.5 Hz, 1H), 2.96 (d, J=35.8 Hz, 1H), 2.80-2.58 (m, 3H), 2.29 (dd, J=12.6, 5.1 Hz, 1H), 2.25-2.11 (m, 3H), 2.00 (d, J=12.2 Hz, 2H), 1.92-1.69 (m, 2H), 1.03-0.83 (m, 3H).

Compound 92

LC-MS (M+1)=427. 1H NMR (400 MHz, DMSO-d6) δ 9.11 (dd, J=4.2, 1.6 Hz, 1H), 8.94-8.78 (m, 1H), 8.36 (dd, J=7.6, 4.5 Hz, 1H), 7.84-7.65 (m, 2H), 4.57 (dd, J=28.0, 12.5 Hz, 2H), 3.97 (d, J=15.3 Hz, 1H), 3.52 (t, J=11.5 Hz, 1H), 2.96 (d, J=35.8 Hz, 2H), 2.84-2.60 (m, 3H), 2.29 (dd, J=12.6, 5.1 Hz, 1H), 2.25-2.11 (m, 3H), 2.00 (d, J=12.2 Hz, 2H), 1.95-1.71 (m, 2H), 1.06-0.85 (m, 3H).

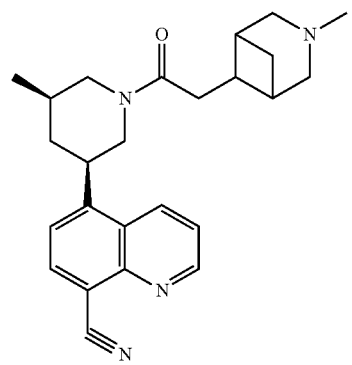

Compound 93 (5-[(3R,5R)-5-methyl-1-[2-(3-methyl-3-azabicyclo[3.1.1]heptan-6-yl)acetyl]-3-piperidyl]quinoline-8-carbonitrile)

From (R)-3-Bromo-5-methyl-piperidine-1-carboxylic acid tert-butyl ester, 5-Bromo-quinoline-8-carbonitrile and racemic (3-Methyl-3-aza-bicyclo[3.1.1]hept-6-yl)-acetic acid. LC-MS (M+1)=403. ¹H NMR (400 MHz, Methanol-d₄) δ 9.06 (ddd, J=5.8, 4.1, 1.5 Hz, 1H), 8.85 (dt, J=8.2, 1.9 Hz, 1H), 8.25 (t, J=7.7 Hz, 1H), 7.83-7.65 (m, 2H), 4.81-4.58 (m, 1H), 4.21-4.00 (m, 1H), 3.83-3.49 (m, 1H), 3.17-2.99 (m, 2H), 2.99-2.82 (m, 3H), 2.82-2.48 (m, 4H), 2.43 (d, J=2.8 Hz, 3H), 2.34 (d, J=12.6 Hz, 1H), 2.28 (s, 1H), 2.16 (d, J=13.3 Hz, 1H), 2.06-1.82 (m, 2H), 1.82-1.52 (m, 2H), 1.07 (dd, J=23.9, 6.6 Hz, 3H).

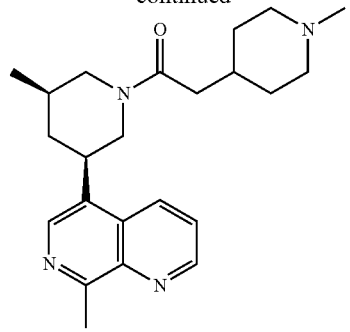

Compound 94 (1-[(3R,5S)-3-Methyl-5-(8-methyl-[1,7]naphthyridin-5-yl)-piperidin-1-yl]-2-(1-methyl-piperidin-4-yl)-ethanone) and Compound 95 (1-[(3R,5R)-3-Methyl-5-(8-methyl-[1,7]naphthyridin-5-yl)-piperidin-1-yl]-2-(1-methyl-piperidin-4-yl)-ethanone)

From (R)-3-Bromo-5-methyl-piperidine-1-carboxylic acid tert-butyl ester, 5-Bromo-8-methyl-[1,7]naphthyridine and (1-Methyl-piperidin-4-yl)-acetic acid.

Compound 94

LC-MS (M+1)=381. ¹H NMR (400 MHz, Methanol-d₄) δ 9.06 (ddd, J=8.9, 4.1, 1.5 Hz, 1H), 8.64 (ddd, J=17.9, 8.7, 1.6 Hz, 1H), 8.35 (d, J=23.1 Hz, 1H), 7.84 (ddd, J=9.8, 8.7, 4.1 Hz, 1H), 4.42 (dd, J=13.1, 3.8 Hz, 1H), 4.20-3.96 (m, 1H), 3.91-3.78 (m, 1H), 3.78-3.67 (m, 1H), 3.67-3.57 (m, 1H), 3.37 (d, J=9.3 Hz, 1H), 3.02 (d, J=6.7 Hz, 3H), 2.87 (dq, J=21.6, 11.8, 11.1 Hz, 2H), 2.50 (dd, J=15.2, 6.9 Hz, 1H), 2.44-2.32 (m, 1H), 2.28 (d, J=16.3 Hz, 4H), 2.19 (dt, J=11.0, 4.6 Hz, 1H), 2.08 (td, J=11.9, 10.3, 5.5 Hz, 1H), 1.96 (dd, J=10.9, 6.9 Hz, 1H), 1.92-1.61 (m, 3H), 1.48-1.30 (m, 2H), 1.17 (d, J=6.8 Hz, 3H).

Compound 95

LC-MS (M+1)=381. ¹H NMR (400 MHz, DMSO-d₆) δ 9.09-9.01 (m, 1H), 8.67 (d, J=7.8 Hz, 1H), 8.40 (d, J=22.0 Hz, 2H), 7.82 (ddd, J=11.6, 8.5, 4.0 Hz, 2H), 4.58 (dd, J=37.7, 12.5 Hz, 1H), 3.97 (t, J=12.8 Hz, 1H), 3.45 (s, 1H), 2.93 (s, 3H), 2.82-2.58 (m, 3H), 2.39-2.17 (m, 2H), 2.11 (d, J=12.6 Hz, 3H), 2.01 (t, J=11.8 Hz, 2H), 1.81 (q, J=10.1, 8.2 Hz, 2H), 1.74-1.53 (m, 4H), 1.34-1.05 (m, 3H), 0.95 (dd, J=19.7, 6.5 Hz, 5H).

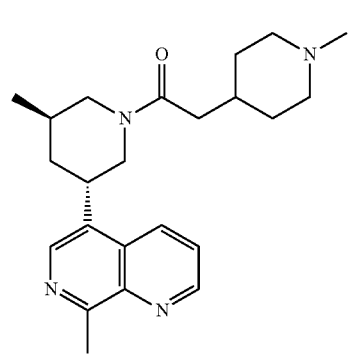

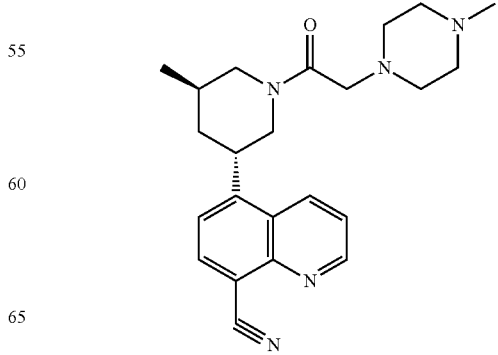

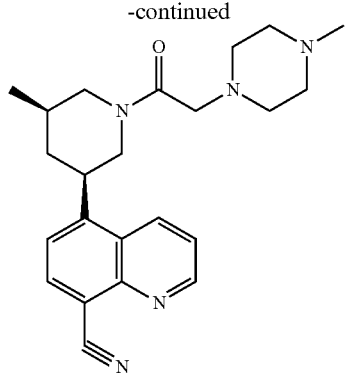

Compound 96 (5-{(3S,5R)-5-Methyl-1-[2-(4-methyl-piperazin-1-yl)-acetyl]-piperidin-3-yl}-quinoline-8-carbonitrile) and Compound 97 (5-{(3R,5R)-5-Methyl-1-[2-(4-methyl-piperazin-1-yl)-acetyl]-piperidin-3-yl}-quinoline-8-carbonitrile)

From (R)-3-Bromo-5-methyl-piperidine-1-carboxylic acid tert-butyl ester, 5-Bromo-quinoline-8-carbonitrile and (4-Methyl-piperazin-1-yl)-acetic acid.

Compound 96

LC-MS (M+1)=392. $^1$H NMR (400 MHz, DMSO-d$_6$) δ 9.12 (dd, J=12.6, 4.1 Hz, 1H), 8.76 (t, J=9.6 Hz, 1H), 8.34 (dd, J=23.3, 7.7 Hz, 1H), 7.86-7.72 (m, 1H), 7.65 (d, J=7.7 Hz, 1H), 4.11 (t, J=10.7 Hz, 1H), 4.03-3.74 (m, 2H), 3.55 (d, J=4.1 Hz, 1H), 3.48-3.33 (m, 2H), 3.28-3.24 (m, 1H), 3.13-2.95 (m, 2H), 2.82 (d, J=12.9 Hz, 1H), 2.43 (s, 3H), 2.27 (d, J=32.2 Hz, 3H), 2.11 (d, J=33.0 Hz, 4H), 1.79 (d, J=12.4 Hz, 1H), 1.08 (d, J=6.8 Hz, 3H).

Compound 97

LC-MS (M+1)=392. $^1$H NMR (400 MHz, DMSO-d$_6$) δ 9.12 (ddd, J=6.6, 4.2, 1.5 Hz, 1H), 8.86 (ddd, J=40.3, 8.8, 1.6 Hz, 1H), 8.36 (t, J=8.1 Hz, 1H), 7.89-7.66 (m, 2H), 4.51 (dd, J=29.3, 11.6 Hz, 1H), 4.16 (t, J=15.3 Hz, 1H), 3.68 (t, J=11.8 Hz, 1H), 3.49 (t, J=11.8 Hz, 1H), 3.35 (d, J=1.4 Hz, 1H), 3.29-3.17 (m, 1H), 3.08 (d, J=13.3 Hz, 1H), 2.88 (d, J=12.9 Hz, 1H), 2.69 (q, J=12.5 Hz, 1H), 2.45-2.20 (m, 5H), 2.11 (d, J=40.9 Hz, 3H), 2.00 (d, J=12.7 Hz, 1H), 1.83 (d, J=61.2 Hz, 1H), 1.57 (dq, J=36.5, 12.1 Hz, 1H), 0.95 (dd, J=11.5, 6.5 Hz, 3H).

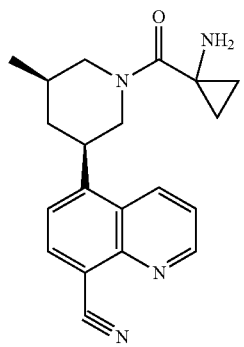 [SMILES: C[C@@H]1C[C@H](c2ccc(C#N)c3ncccc23)CN(C(=O)C2(N)CC2)C1]

Compound 98 (5-[(3R,5R)-1-(1-Amino-cyclopropanecarbonyl)-5-methyl-piperidin-3-yl]-quinoline-8-carbonitrile)

From (R)-3-Bromo-5-methyl-piperidine-1-carboxylic acid tert-butyl ester, 5-Bromo-quinoline-8-carbonitrile and 1-tert-Butoxycarbonylamino-cyclopropanecarboxylic acid, followed by the depretection of Boc. LC-MS (M+1)=335. $^1$H NMR (400 MHz, DMSO-d$_6$) δ 9.11 (dd, J=4.2, 1.5 Hz, 1H), 8.90 (d, J=8.7 Hz, 1H), 8.36 (d, J=7.6 Hz, 1H), 7.86-7.67 (m, 2H), 4.48 (dd, J=31.0, 12.5 Hz, 2H), 3.65 (s, 1H), 2.94 (s, 1H), 2.54 (s, 1H), 2.26 (s, 2H), 1.99 (d, J=12.7 Hz, 1H), 1.87 (s, 1H), 1.61 (q, J=12.1 Hz, 1H), 0.97 (d, J=6.5 Hz, 4H), 0.93-0.78 (m, 1H), 0.63 (s, 2H).

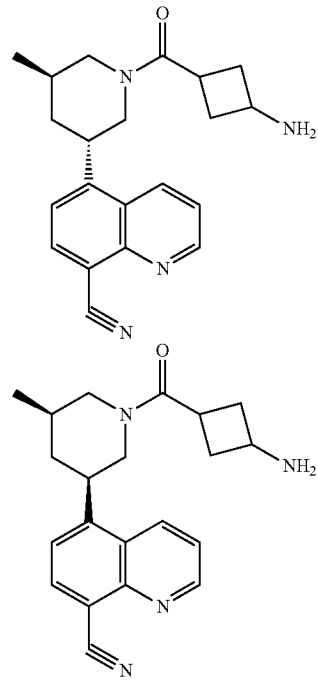

Compound 99 (5-[(3S,5R)-1-(3-aminocyclobutanecarbonyl)-5-methyl-3-piperidyl]quinoline-8-carbonitrile) and Compound 100 (5-[(3R,5R)-1-(3-aminocyclobutanecarbonyl)-5-methyl-3-piperidyl]quinoline-8-carbonitrile)

From (R)-3-Bromo-5-methyl-piperidine-1-carboxylic acid tert-butyl ester, 5-Bromo-quinoline-8-carbonitrile and racemic 3-tert-Butoxycarbonylamino-cyclobutanecarboxylic acid, followed by the depretection of Boc.

Compound 99

LC-MS (M+1)=392. $^1$H NMR (400 MHz, DMSO-d$_6$) δ 9.12 LC-MS (M+1)=349. $^1$H NMR (400 MHz, Methanol-d$_4$) δ 9.06 (ddd, J=5.9, 4.2, 1.6 Hz, 1H), 8.85-8.72 (m, 1H), 8.23 (t, J=7.9 Hz, 1H), 7.82-7.62 (m, 2H), 4.41 (d, J=11.0 Hz, 1H), 4.18-4.08 (m, 1H), 4.03-3.81 (m, 2H), 3.65-3.52 (m, 2H), 3.45-3.37 (m, 1H), 3.27 (dd, J=13.4, 5.4 Hz, 1H), 3.18-3.06 (m, 1H), 3.00 (t, J=8.7 Hz, 1H), 2.55 (qd, J=7.4, 3.8 Hz, 1H), 2.45 (d, J=9.9 Hz, 1H), 2.39-2.26 (m, 1H), 2.26-2.05 (m, 3H), 2.07-1.90 (m, 2H), 1.17 (dd, J=16.3, 6.9 Hz, 3H).

Compound 100

LC-MS (M+1)=349. ¹H NMR (400 MHz, Methanol-$d_4$) δ 9.06 (ddd, J=4.3, 2.7, 1.6 Hz, 1H), 8.83 (ddd, J=25.0, 8.8, 1.6 Hz, 1H), 8.24 (dd, J=7.7, 4.1 Hz, 1H), 7.83-7.57 (m, 2H), 4.79-4.54 (m, 1H), 4.08-3.91 (m, 1H), 3.74-3.49 (m, 1H), 3.46-3.34 (m, 1H), 3.21-2.95 (m, 1H), 2.82 (dd, J=13.6, 11.5 Hz, 1H), 2.75-2.63 (m, 1H), 2.55 (dddd, J=14.5, 12.4, 7.7, 3.7 Hz, 1H), 2.47-2.34 (m, 1H), 2.22-1.95 (m, 3H), 1.95-1.82 (m, 1H), 1.65 (dq, J=57.8, 12.1 Hz, 1H), 1.06 (dd, J=16.4, 6.6 Hz, 3H).

Compound 102

LC-MS (M+1)=392. 1H NMR (400 MHz, Methanol-$d_4$) δ 9.12-9.00 (m, 1H), 8.40-8.20 (m, 2H), 7.97-7.88 (m, 1H), 4.38-4.19 (m, 1H), 3.93 (ddd, J=13.6, 10.1, 4.0 Hz, 1H), 3.76 (ddd, J=26.9, 13.3, 3.9 Hz, 1H), 3.67-3.51 (m, 1H), 2.80 (ddd, J=50.2, 28.6, 13.5 Hz, 2H), 2.61-2.39 (m, 2H), 2.40-2.25 (m, 4H), 1.96-1.59 (m, 5H), 1.43-1.20 (m, 2H), 1.18-1.02 (m, 4H).

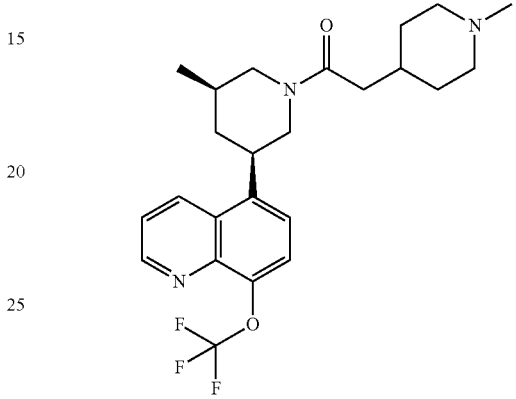

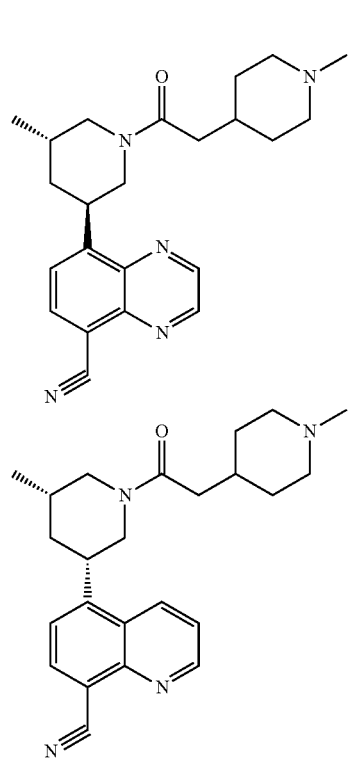

Compound 101 (8-{(3R,5S)-5-Methyl-1-[2-(1-methyl-piperidin-4-yl)-acetyl]-piperidin-3-yl}-quinoxaline-5-carbonitrile) and Compound 102 (8-{(3S,5S)-5-Methyl-1-[2-(1-methyl-piperidin-4-yl)-acetyl]-piperidin-3-yl}-quinoxaline-5-carbonitrile)

From (S)-3-Bromo-5-methyl-piperidine-1-carboxylic acid tert-butyl ester, 8-Bromo-quinoxaline-5-carbonitrile and (1-Methyl-piperidin-4-yl)-acetic acid.

Compound 101

LC-MS (M+1)=392. 1H NMR (400 MHz, Methanol-$d_4$) δ 9.09 (d, J=6.7 Hz, 1H), 8.34 (dddd, J=27.9, 10.8, 7.9, 1.4 Hz, 2H), 7.92 (ddd, J=10.0, 8.5, 7.3 Hz, 1H), 4.47 (dd, J=13.3, 4.8 Hz, 1H), 4.20-3.92 (m, 1H), 3.83 (dd, J=13.5, 4.2 Hz, 1H), 3.77-3.57 (m, 2H), 3.49 (dd, J=13.0, 6.6 Hz, 1H), 3.22-3.07 (m, 2H), 2.78-2.57 (m, 3H), 2.53-2.30 (m, 4H), 2.01-1.74 (m, 4H), 1.21-1.13 (m, 1H), 1.10 (dd, J=6.9, 1.7 Hz, 4H).

Compound 103 (2-(1-Methyl-piperidin-4-yl)-1-[(3R,5R)-3-methyl-5-(8-trifluoromethoxy-quinolin-5-yl)-piperidin-1-yl]-ethanone)

From (S)-3-Bromo-5-methyl-piperidine-1-carboxylic acid tert-butyl ester, 5-Bromo-8-trifluoromethoxy-quinoline and (1-Methyl-piperidin-4-yl)-acetic acid. LC-MS (M+1)=450. 1H NMR (400 MHz, Methanol-$d_4$) δ 9.02-8.91 (m, 1H), 8.85-8.71 (m, 1H), 7.78-7.58 (m, 3H), 4.10 (t, J=15.3 Hz, 1H), 3.52 (s, 2H), 2.99-2.78 (m, 3H), 2.66 (t, J=12.2 Hz, 1H), 2.53-2.44 (m, 2H), 2.44-2.33 (m, 2H), 2.13 (d, J=12.7 Hz, 3H), 1.99-1.68 (m, 4H), 1.48-1.23 (m, 3H), 1.07 (dd, J=18.6, 6.6 Hz, 3H).

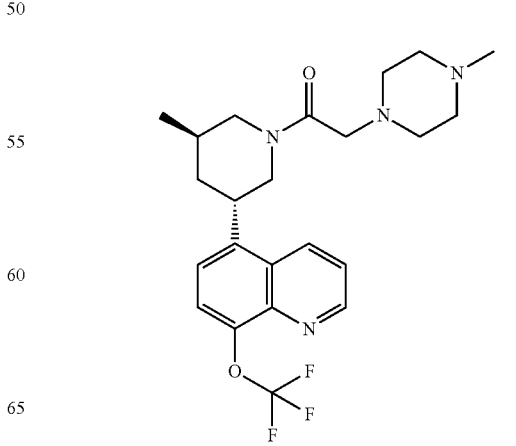

161

-continued

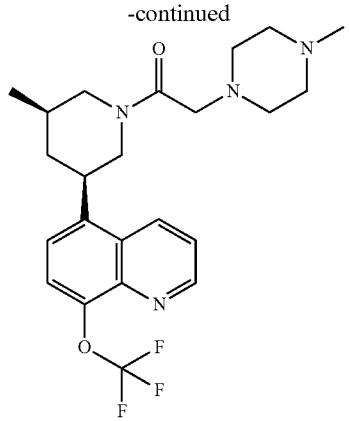

Compound 104 (2-(4-Methyl-piperazin-1-yl)-1-
[(3R,5S)-3-methyl-5-(8-trifluoromethoxy-quinolin-
5-yl)-piperidin-1-yl]-ethanone) and Compound 105
(2-(4-Methyl-piperazin-1-yl)-1-[(3R,5R)-3-methyl-
5-(8-trifluoromethoxy-quinolin-5-yl)-piperidin-1-yl]-
ethanone)

From (S)-3-Bromo-5-methyl-piperidine-1-carboxylic acid tert-butyl ester, 5-Bromo-8-trifluoromethoxy-quinoline and (4-Methyl-piperazin-1-yl)-acetic acid.

Compound 104

LC-MS (M+1)=451.

Compound 105

LC-MS (M+1)=451. 1H NMR (400 MHz, DMSO-d6) δ 9.06 (ddd, J=5.9, 4.2, 1.5 Hz, 1H), 8.85 (d, J=8.5 Hz, 1H), 8.74 (d, J=8.5 Hz, 1H), 7.85-7.69 (m, 2H), 7.62 (dd, J=16.8, 8.1 Hz, 1H), 4.52 (dd, J=34.0, 11.8 Hz, 1H), 4.13 (td, J=26.6, 10.4 Hz, 1H), 3.69-3.47 (m, 1H), 3.45-3.31 (m, 4H), 3.23-2.96 (m, 2H), 2.87 (d, J=12.8 Hz, 1H), 2.78-2.55 (m, 2H), 2.28 (dd, J=27.6, 15.5 Hz, 4H), 1.91 (s, 1H), 1.74 (s, 1H), 1.57 (dq, J=36.0, 12.0 Hz, 2H), 0.96 (dd, J=11.1, 6.5 Hz, 3H).

Example 18: Synthesis of Compound 106 (5-[(3R, 5R)-5-methyl-1-[(1-methylpyrazol-4-yl)methyl]-3-piperidyl]quinoline-8-carbonitrile)

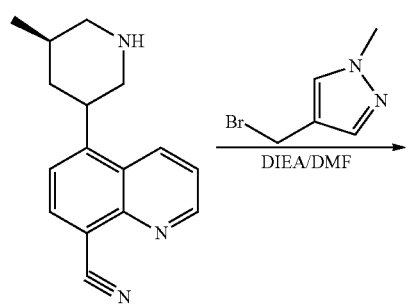

162

-continued

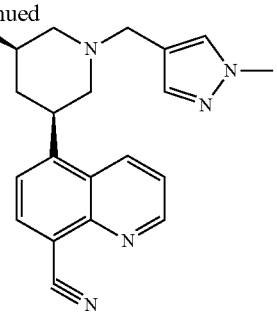

To a solution of 4-Bromomethyl-1-methyl-1H-pyrazole hydrobromide (45.83 mg; 0.18 mmol) and DIEA (0.07 ml; 0.40 mmol) in DMF (1 ml) was added 5-((R)-5-Methyl-piperidin-3-yl)-quinoline-8-carbonitrile (50.00 mg; 0.20 mmol). The mixture was stirred at RT for 30 min. The completed reaction was purified by prep HPLC to yield the title compound.

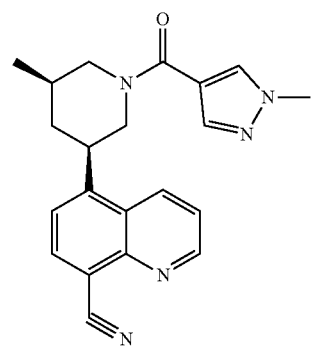

Compound 106

LC-MS (M+1)=346.1H NMR (400 MHz, Methanol-d4) δ 9.04 (dd, J=4.3, 1.6 Hz, 1H), 8.74 (dd, J=8.8, 1.6 Hz, 1H), 8.21 (d, J=7.6 Hz, 1H), 7.72 (dd, J=8.7, 4.2 Hz, 1H), 7.66 (d, J=7.7 Hz, 1H), 7.56 (s, 1H), 7.44 (s, 1H), 3.86 (s, 2H), 3.83-3.68 (m, 1H), 3.58 (s, 3H), 3.08 (t, J=11.9 Hz, 2H), 2.14 (t, J=11.2 Hz, 1H), 2.03 (d, J=11.9 Hz, 2H), 1.80 (t, J=11.1 Hz, 1H), 1.38 (q, J=12.5 Hz, 1H), 1.02 (d, J=6.4 Hz, 3H).

Example 19: Synthesis of Compound 109 (3-(8-Cyano-quinolin-5-yl)-5-methyl-piperidine-1-carboxylic acid (1-methyl-piperidin-4-yl)-amide)

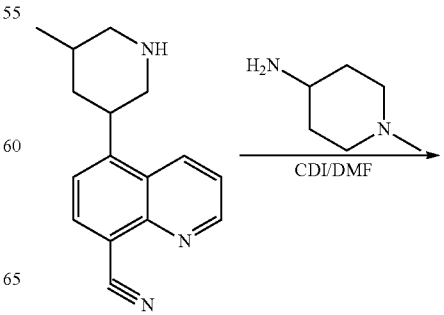

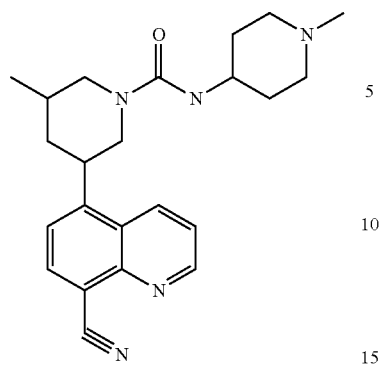

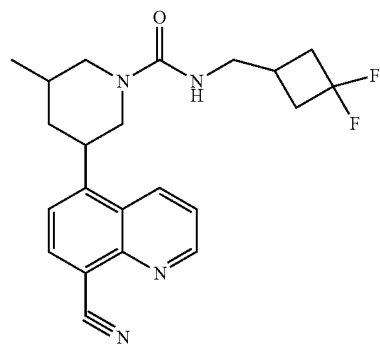 [SMILES: CC1CC(c2ccc(C#N)c3ncccc23)CN(C(=O)NCC2CC(F)(F)C2)C1]

To a solution of 1-Methyl-piperidin-4-ylamine (28.31 mg; 0.25 mmol) in DMF (1 ml) was added CDI (40.21 mg; 0.25 mmol). After stirring at rt for 1 h, a solution of DIEA (72 ul, 0.41 mmol, 2.0 eq) and 5-(5-Methyl-piperidin-3-yl)-quinoline-8-carbonitrile dihydrochloride (67.00 mg; 0.21 mmol) in DMF (1 mL) was added. The mixture was continued stirred for 1 hr. The completed reaction was purified by prep HPLC (Basic, eluted with 10-50% ACN/water) to yield the title compound.

Compound 110 (3-(8-Cyano-quinolin-5-yl)-5-methyl-piperidine-1-carboxylic acid (3,3-difluoro-cyclobutylmethyl)-amide)

From 5-(5-Methyl-piperidin-3-yl)-quinoline-8-carbonitrile dihydrochloride and C-(3,3-Difluoro-cyclobutyl)-methylamine hydrochloride. LC-MS (M+1)=400. UPLC (% area)= 100%. 1H NMR (400 MHz, DMSO-d6) δ 9.11 (dd, J=4.2, 1.5 Hz, 1H), 8.89 (dd, J=8.8, 1.6 Hz, 1H), 8.35 (d, J=7.6 Hz, 1H), 7.78 (dd, J=8.7, 4.2 Hz, 1H), 7.68 (d, J=7.7 Hz, 1H), 6.78 (t, J=5.7 Hz, 1H), 4.10 (dd, J=56.1, 13.6 Hz, 3H), 3.52 (s, 1H), 3.19 (h, J=7.5 Hz, 2H), 2.80 (dd, J=12.9, 11.3 Hz, 1H), 2.63-2.53 (m, 2H), 2.30 (s, 4H), 1.99 (d, J=12.6 Hz, 1H), 1.54 (q, J=12.0 Hz, 2H), 0.93 (d, J=6.6 Hz, 3H).

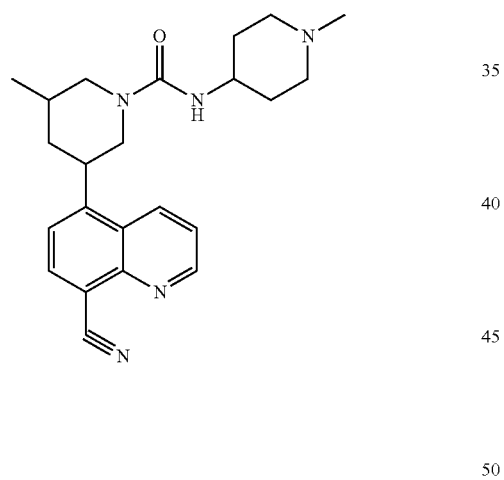

Compound 109

LC-MS (M+1)=392. $^1$H NMR (400 MHz, DMSO-d$_6$) δ 9.11 (dd, J=4.2, 1.5 Hz, 1H), 8.91 (dd, J=8.9, 1.6 Hz, 1H), 8.34 (d, J=7.6 Hz, 1H), 7.78 (dd, J=8.6, 4.2 Hz, 1H), 7.72-7.54 (m, 1H), 6.31 (d, J=7.6 Hz, 1H), 4.19 (d, J=13.3 Hz, 1H), 4.05 (d, J=13.4 Hz, 1H), 3.60-3.37 (m, 3H), 2.81-2.67 (m, 3H), 2.40 (dd, J=13.4, 11.4 Hz, 1H), 2.14 (s, 3H), 1.97 (d, J=12.4 Hz, 1H), 1.88 (td, J=11.8, 2.5 Hz, 2H), 1.82-1.65 (m, 3H), 1.61-1.39 (m, 3H), 0.99-0.87 (m, 3H).

The following compounds were synthesized in an analogous manner:

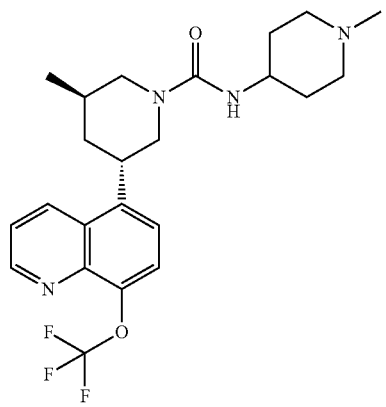

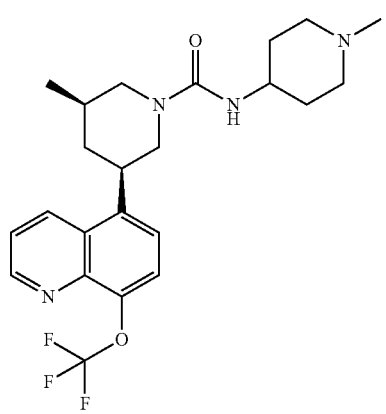

Compound 111 ((3R,5S)-3-Methyl-5-(8-trifluoromethoxy-quinolin-5-yl)-piperidine-1-carboxylic acid (1-methyl-piperidin-4-yl)-amide) and Compound 112 ((3R,5R)-3-Methyl-5-(8-trifluoromethoxy-quinolin-5-yl)-piperidine-1-carboxylic acid (1-methyl-piperidin-4-yl)-amide)

From 5-((R)-5-Methyl-piperidin-3-yl)-8-trifluoromethoxy-quinoline and 1-Methyl-piperidin-4-ylamine.

Compound 111

LC-MS (M+1)=451. $^1$H NMR (400 MHz, DMSO-d6) δ 9.04 (d, J=3.8 Hz, 1H), 8.77 (d, J=8.7 Hz, 1H), 7.83-7.72 (m, 1H), 7.59 (d, J=8.1 Hz, 1H), 6.21 (d, J=7.5 Hz, 1H), 3.99 (d, J=13.2 Hz, 2H), 2.72 (d, J=11.5 Hz 2H), 2.13 (s, 3H), 2.01 (dd, J=24.3, 11.2 Hz, 2H), 1.88 (t, J=11.3 Hz, 2H), 1.73 (d, J=36.1 Hz, 2H), 1.55-1.33 (m, 2H), 1.24 (s, 2H), 1.05 (d, J=6.8 Hz, 3H).

Compound 112: LC-MS (M+1)=451. $^1$H NMR (400 MHz, DMSO-d6) δ 9.04 (dd, J=4.1, 1.5 Hz, 1H), 8.83 (dd, J=8.9, 1.6 Hz, 1H), 7.83 7.68 (m, 2H), 7.57 (d, J=8.1 Hz, 1H), 6.29 (d, J=7.6 Hz, 1H), 4.25-3.97 (m, 2H), 3.44 (d, J=10.7 Hz, 2H), 2.78-2.56 (m, 3H), 2.45-2.29 (m, 3H), 2.14 (s, 3H), 2.05-1.81 (m, 3H), 1.74 (d, J=28.9 Hz, 2H), 1.59-1.36 (m, 3H), 0.93 (d, J=6.5 Hz, 3H).

Compound 113 ((3R,5R)-3-(8-Cyano-quinolin-5-yl)-5-methyl-piperidine-1-carboxylic acid (1-methyl-piperidin-4-yl)-amid From 5-((R)-5-Methyl-piperidin-3-yl)-quinoline-8-carbonitrile and 1-Methyl-piperidin-4-ylamine. LC-MS (M+1)=392. $^1$H NMR (400 MHz, Methanol-d$_4$) δ 9.05 (dd, J=4.2, 1.6 Hz, 1H), 8.91 (dd, J=8.8, 1.6 Hz, 1H), 8.23 (d, J=7.7 Hz, 1H), 7.83-7.57 (m, 2H), 4.43-4.28 (m, 1H), 4.10 (d, J=13.2 Hz, 1H), 3.63 (ddt, J=11.5, 7.3, 3.8 Hz, 2H), 3.00-2.69 (m, 3H), 2.58 (dd, J=13.5, 11.5 Hz, 1H), 2.30 (s, 3H), 2.15 (t, J=12.7 Hz, 3H), 1.92 (d, J=12.7 Hz, 3H), 1.63 (dt, J=23.7, 12.0 Hz, 3H), 1.05 (d, J=6.5 Hz, 3H).

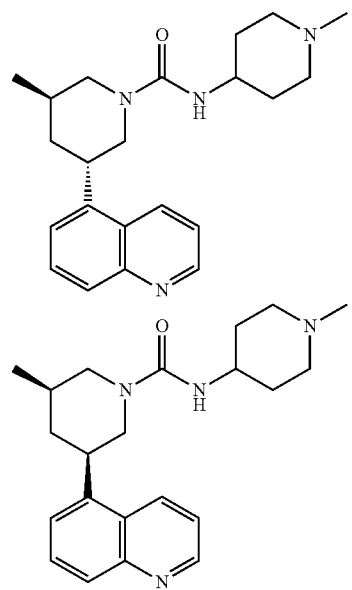

Compound 114 ((3R,5S)-3-Methyl-5-quinolin-5-yl-piperidine-1-carboxylic acid (1-methyl-piperidin-4-yl)-amide) and Compound 115 ((3R,5R)-3-Methyl-5-quinolin-5-yl-piperidine-1-carboxylic acid (1-methyl-piperidin-4-yl)-amide)

From 5-((R)-5-Methyl-piperidin-3-yl)-quinoline and 1-Methyl-piperidin-4-ylamine.

Compound 114

LC-MS (M+1)=451. $^1$H NMR (400 MHz, DMSO-d$_6$) δ 9.04 LC-MS (M+1)=392. $^1$H NMR (400 MHz, DMSO-d$_6$) δ 8.91 (dd, J=4.1, 1.6 Hz, 1H), 8.66 (d, J=8.7 Hz, 1H), 7.90 (d, J=8.4 Hz, 1H), 7.71 (dd, J=8.4, 7.2 Hz, 1H), 7.62-7.42 (m, 2H), 6.20 (d, J=7.6 Hz, 2H), 4.07-3.94 (m, 1H), 3.77-3.56 (m, 3H), 3.45 (dd, J=7.5, 3.9 Hz, 1H), 3.22 (dd, J=13.3, 3.3 Hz, 1H), 3.07 (dd, J=13.0, 9.4 Hz, 1H), 2.68 (dd, J=29.3, 10.9 Hz, 2H), 2.14 (s, 3H), 2.07-1.95 (m, 2H), 1.96-1.84 (m, 2H), 1.72 (dd, J=26.2, 12.0 Hz, 3H), 1.45 (q, J=11.9 Hz, 2H), 1.06 (d, J=6.8 Hz, 3H).

Compound 115

LC-MS (M+1)=451. $^1$H NMR (400 MHz, DMSO-d$_6$) δ 9.04 LC-MS (M+1)=392. $^1$H NMR (400 MHz, DMSO-d$_6$) δ 8.91 (dd, J=4.1, 1.6 Hz, 1H), 8.72 (dt, J=8.7, 1.3 Hz, 1H), 8.02-7.86 (m, 1H), 7.72 (dd, J=8.5, 7.2 Hz, 1H), 7.63-7.39 (m, 2H), 6.29 (d, J=7.7 Hz, 1H), 4.21 (d, J=12.9 Hz, 1H), 4.06 (d, J=11.5 Hz, 1H), 3.42 (ddt, J=11.7, 8.5, 4.0 Hz, 2H), 2.82-2.62 (m, 3H), 2.38 (dd, J=13.3, 11.4 Hz, 1H), 2.14 (s, 3H), 1.98 (d, J=12.5 Hz, 1H), 1.88 (td, J=11.8, 2.6 Hz, 2H), 1.84-1.62 (m, 3H), 1.61-1.31 (m, 3H), 0.93 (d, J=6.5 Hz, 3H).

Example 20: Synthesis of Compound 116 (5-[(3R,5R)-1-(2-2,5-Diaza-bicyclo[2.2.2]oct-2-yl-acetyl)-5-methyl-piperidin-3-yl]-quinoline-8-carbonitrile (racemic)

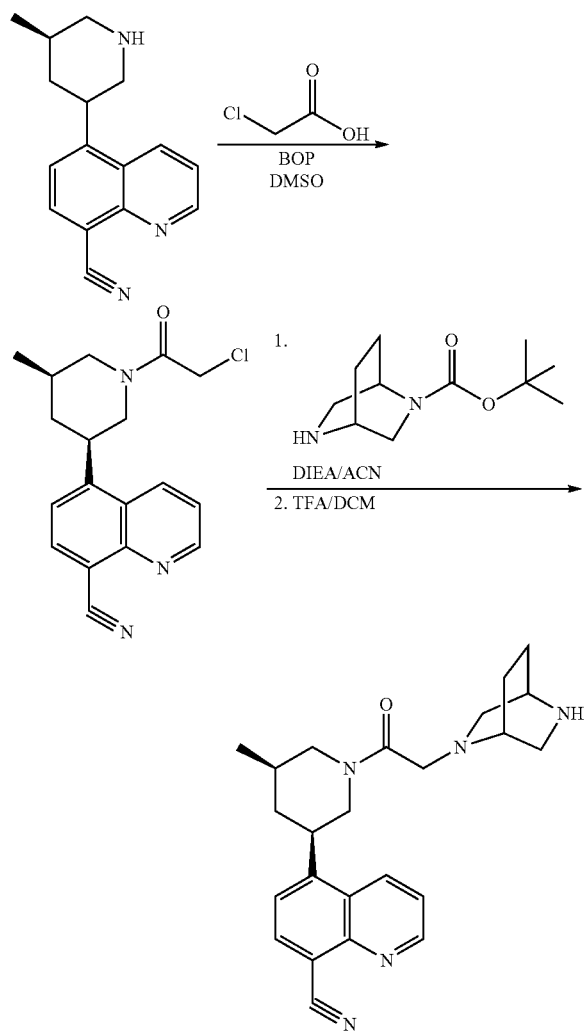

5-[(3R,5R)-1-(2-Chloro-acetyl)-5-methyl-piperidin-3-yl]-quinoline-8-carbonitrile To a mixture of 5-((R)-5-Methyl-piperidin-3-yl)-quinoline-8-carbonitrile (250.00 mg; 0.99 mmol), Chloro-acetic acid (121.13 mg; 1.24 mmol) and DIEA (0.36 ml; 1.99 mmol) in DMSO (1 ml) was added bop (549.93 mg; 1.24 mmol). The mixture was stirred at RT for 1 hr. The completed reaction was purified by prep HPLC (basic, 10-50% ACN/waters) to yield the title compound (90 mg, yield 25%). LC-MS (M+1)=328.

5-[(3R,5R)-1-(2-2,5-Diaza-bicyclo[2.2.2]oct-2-yl-acetyl)-5-methyl-piperidin-3-yl]-quinoline-8-carbonitrile (racemic)

To 5-[(3R,5R)-1-(2-Chloro-acetyl)-5-methyl-piperidin-3-yl]-quinoline-8-carbonitrile (50 mg; 0.15 mmol) in CAN (1 ml) was added DIEA (0.05 ml; 0.31 mmol) and tert-butyl 2,5-diazabicyclo[2.2.2]octane-2-carboxylate (39 mg, 0.18 mmol). The reaction mixture was stirred at 80° C. for 1 hr. The completed reaction was concentrated. The residue was added DCM (0.5 ml) and Trifluoro-acetic acid (347 mg; 3.05 mmol; 20.00 eq.). The mixture was stirred at RT for 1 hr. The completed reaction was concentrated. The residue was added 30 ml of DCM and 5 ml of 5% aq $Na_2HCO_3$. The separated organic layer was washed with brine, dried and concentrated to yield the title compound as a white wax solid.

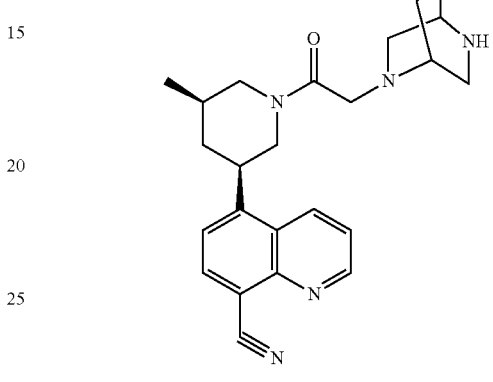

Compound 116

LC-MS (M+1)=404. NMR (400 MHz, Methanol-$d_4$) δ 9.05 (d, J=4.6 Hz, 1H), 8.93-8.80 (m, 1H), 8.25 (dd, J=7.7, 4.3 Hz, 1H), 7.83-7.65 (m, 2H), 4.77 (d, J=12.9 Hz, 1H), 4.29 (d, J=13.5 Hz, 1H), 4.24-4.07 (m, 1H), 3.87-3.69 (m, 1H), 3.65-3.52 (m, 2H), 3.52-3.38 (m, 2H), 3.15-2.95 (m, 3H), 2.95-2.76 (m, 2H), 2.76-2.57 (m, 1H), 2.45-2.31 (m, 1H), 2.16 (d, J=13.1 Hz, 2H), 2.08-1.95 (m, 1H), 1.80-1.64 (m, 2H), 1.17-1.01 (m, 3H).

The following compounds were synthesized in an analogous manner:

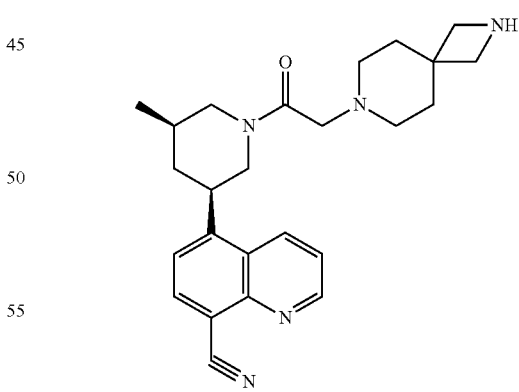

Compound 117 (5-[(3R,5R)-1-(2-2,7-Diaza-spiro[3.5]non-7-yl-acetyl)-5-methyl-piperidin-3-yl]-quinoline-8-carbonitrile)

From 5-[(3R,5R)-1-(2-Chloro-acetyl)-5-methyl-piperidin-3-yl]-quinoline-8-carbonitrile and tert-butyl 2,7-diazaspiro[3.5]nonane-2-carboxylate. LC-MS (M+1)=418. 1H NMR (400 MHz, DMSO-d6) δ 9.12 (dd, J=4.2, 1.6 Hz, 1H), 8.84 (dd, J=27.0, 8.7 Hz, 2H), 8.37 (dd, J=7.1, 2.1 Hz, 1H), 7.86-7.66 (m, 3H), 4.51 (dd, J=30.5, 12.0 Hz, 2H), 4.15 (t, J=15.5 Hz, 2H), 3.67 (s, 2H), 3.18-2.54 (m, 5H), 2.29 (dd, J=28.8, 16.6 Hz, 4H), 2.00 (d, J=12.3 Hz, 1H), 1.89 (s, 1H), 1.74 (s, 2H), 1.67-1.36 (m, 2H), 0.98-0.88 (m, 4H).

Example 21: Synthesis of Compound 118 ((3R,5R)-3-(8-Cyano-quinolin-5-yl)-5-methyl-piperidine-1-carboxylic acid amide) and Compound 119 ((3R,5R)-3-(8-Cyano-quinolin-5-yl)-5-methyl-piperidine-1-carboxamidine)

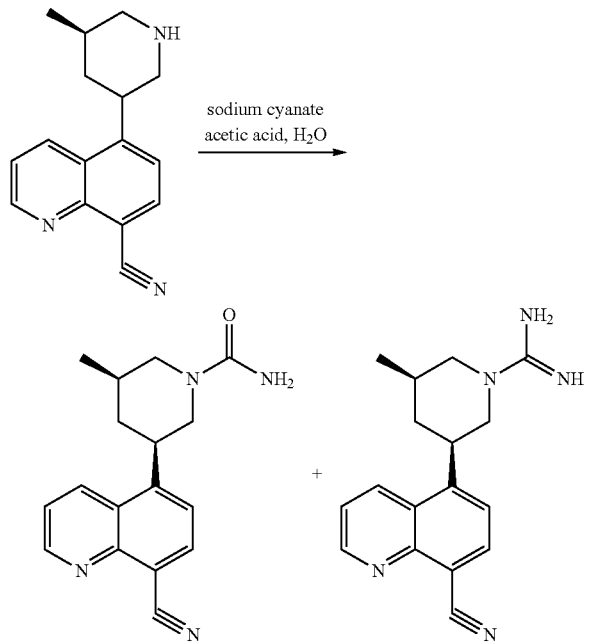

A mixture of 5-((R)-5-Methyl-piperidin-3-yl)-quinoline-8-carbonitrile (50 mg; 0.20 mmol) and sodium cyanate (38 mg; 0.60 mmol) in acetic acid (1.50 ml; 28.48 mmol) and water (0.50 ml; 27.75 mmol) was stirred at rt for 2 hr. The completed reaction was concentrated. The residue was dissolved in DMSO, neutralized with TEA to PH >7, and subjected to prep HPLC (basic, 10-70% ACN in water) to yield the title compounds.

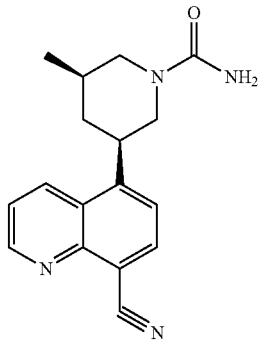 [SMILES: C[C@@H]1C[C@H](c2ccc(C#N)c3ncccc23)CN(C(N)=O)C1]

Compound 118

LC-MS (M+1)=295. $^1$H NMR (400 MHz, Methanol-d$_4$) δ 9.05 (dd, J=4.2, 1.6 Hz, 1H), 8.89 (dd, J=9.0, 1.5 Hz, 1H), 8.24 (d, J=7.7 Hz, 1H), 7.79-7.64 (m, 2H), 4.34 (d, J=13.6 Hz, 1H), 4.06 (d, J=12.7 Hz, 1H), 3.66 (tt, J=11.8, 3.5 Hz, 1H), 2.97-2.82 (m, 1H), 2.63 (dd, J=13.5, 11.6 Hz, 1H), 2.13 (d, J=12.7 Hz, 1H), 2.02-1.81 (m, 1H), 1.64 (q, J=12.0 Hz, 1H), 1.05 (d, J=6.6 Hz, 3H).

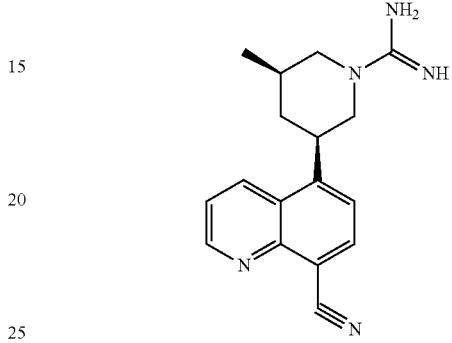

Compound 119

LC-MS (M+1)=294. $^1$H NMR (400 MHz, Methanol-d$_4$) δ 9.06 (ddd, J=4.2, 3.6, 1.6 Hz, 1H), 8.85 (dt, J=8.8, 1.7 Hz, 1H), 8.25 (dd, J=7.7, 4.3 Hz, 1H), 7.82-7.63 (m, 2H), 4.82-4.58 (m, 1H), 4.13-3.92 (m, 1H), 3.86-3.69 (m, 1H), 3.61 (tt, J=11.7, 3.4 Hz, 1H), 2.90 (dd, J=13.6, 11.7 Hz, 1H), 2.79-2.59 (m, 1H), 2.46-2.29 (m, 1H), 2.19 (d, J=26.0 Hz, 3H), 2.04-1.80 (m, 1H), 1.66 (dq, J=42.8, 12.1 Hz, 1H), 1.07 (dd, J=17.2, 6.6 Hz, 3H).

Example 22: Synthesis of Compound 120 (8-((1S,3R,5R)-3-amino-5-methylcyclohexyl) quinoxaline-5-carbonitrile)

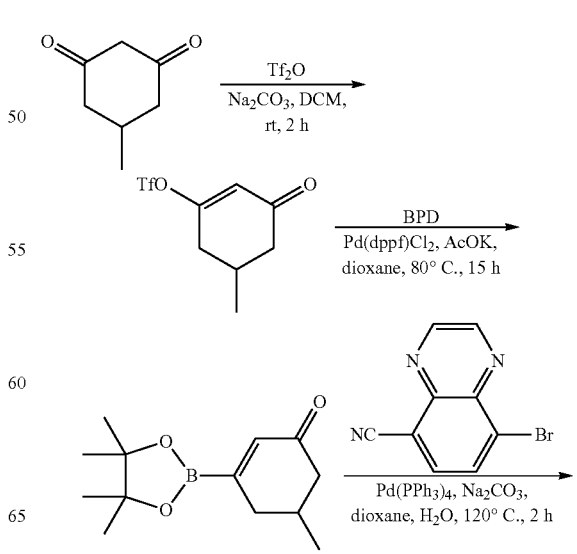

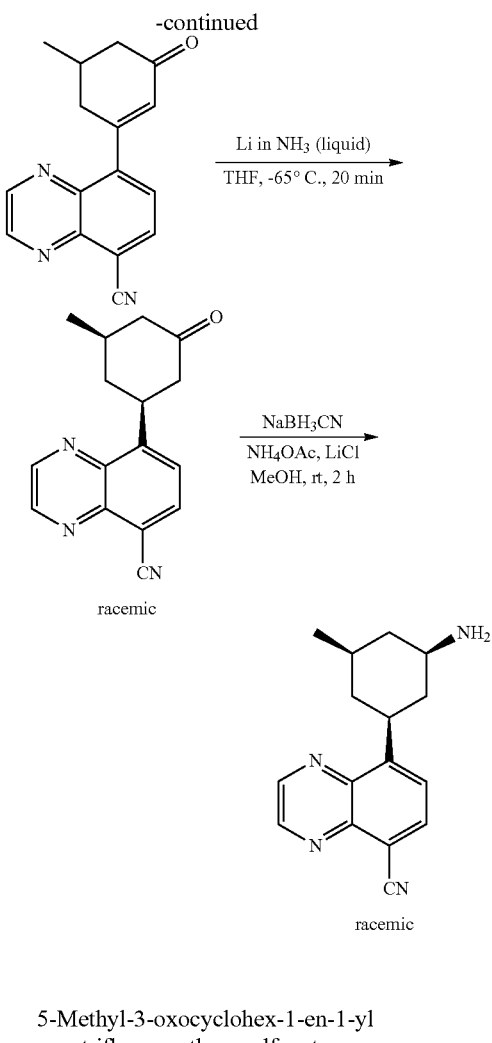

racemic

5-Methyl-3-oxocyclohex-1-en-1-yl trifluoromethanesulfonate

At 0° C., to a solution of 5-methylcyclohexane-1,3-dione (4.90 g, 38.84 mmol) in dichloromethane (100 mL) was added sodium carbonate (4.39 g, 41.41 mmol), to which was added a solution of Tf$_2$O (11.73 g, 41.58 mmol) in dichloromethane (10 mL) dropwise over 30 min period. The resulting solution was stirred for 2 h at room temperature. When the reaction was done, it was quenched by the addition of sat. sodium bicarbonate solution (500 mL). The resulting mixture was extracted with DCM (300 mL×3). The organic phases were combined, washed with brine and dried over Na$_2$SO$_4$. The solvent was removed under reduced pressure and the residue was purified by flash chromatography eluting with DCM in hexane (0% to 50% gradient) to yield 5-methyl-3-oxocyclohex-1-en-1-yl trifluoromethanesulfonate as yellow oil (5.00 g, crude). MS: m/z=258.8 [M+H]$^+$.

5-methyl-3-(tetramethyl-1,3,2-dioxaborolan-2-yl)cyclohex-2-en-1-one

To a solution of 5-methyl-3-oxocyclohex-1-en-1-yl trifluoromethanesulfonate (5.00 g, crude) in dioxane (50 mL) were added BPD (9.03 g, 35.54 mmol), AcOK (5.41 g, 55.17 mmol) and Pd(dppf)Cl$_2$ (1.50 g, 2.05 mmol) at room temperature. The resulting solution was then stirred for 15 h at 80° C. After cooling to room temperature, the reaction mixture was filtered to remove insoluable solids and the filtrate was concentrated under reduced pressure to yield 5-methyl-3-(tetramethyl-1,3,2-dioxaborolan-2-yl)cyclohex-2-en-1-one as yellow oil (5.00 g, crude). MS: m/z=237.0 [M+H]$^+$.

8-(5-Methyl-3-oxocyclohex-1-en-1-yl)quinoxaline-5-carbonitrile

To a solution of 5-methyl-3-(tetramethyl-1,3,2-dioxaborolan-2-yl)cyclohex-2-en-1-one (5.00 g, crude) in dioxane (50 mL) was added 8-bromoquinoxaline-5-carbonitrile (3.19 g, 13.61 mmol), Pd(dppf)Cl$_2$ (1.90 g, 2.60 mmol) and a solution of sodium carbonate (4.37 g, 41.23 mmol) in water (10 mL) at room temperature. The resulting mixture was stirred for 2 h at 120° C. After cooling to room temperature, the reaction mixture was quenched by the addition of water (100 mL). The resulting mixture was extracted with ethyl acetate (300 mL×3). The organic phases were combined, washed with brine and dried over Na$_2$SO$_4$. The solvent was removed under reduced pressure and the residue was purified by flash chromatography eluting with EtOAc in hexane (0% to 70% gradient) to yield 8-(5-methyl-3-oxocyclohex-1-en-1-yl)quinoxaline-5-carbonitrile as red solid (1.50 g, 15% for 3 steps). MS: m/z=263.9 [M+H]$^+$.

8-((cis-1,3)-3-methyl-5-oxocyclohexyl)quinoxaline-5-carbonitrile

At −65° C., Li (112 mg, 16.14 mmol) was added slowly into liquid NH$_3$ (30 mL), to which was added a solution of 8-(5-methyl-3-oxocyclohex-1-en-1-yl)quinoxaline-5-carbonitrile (850 mg, 3.23 mmol) in THF (5 mL) dropwise. The resulting solution was stirred for 20 min at −65° C. When the reaction was done, it was quenched by the addition of NH$_4$Cl (20.00 g, 0.38 mol) and NH$_3$ gas was allowed to evaporate. The remaining mixture was diluted with water (50 mL) and extracted with ethyl acetate (150 mL×3). The organic phases were combined, washed with brine and dried over Na$_2$SO$_4$. The solvent was removed under reduced pressure and the residue was first purified by flash chromatography eluting with EtOAc in hexane (0% to 17% gradient) to give a mixture of the cis and trans isomers. The obtained mixture was further purified by reverse phase flash chromatography eluting with acetonitrile in water (with 10 mmol/L NH$_4$HCO$_3$) (30% to 60% gradient in 50 min) to yield 8-[(cis-1,3)-3-methyl-5-oxocyclohexyl]quinoxaline-5-carbonitrile as white solid (220 mg, 26%). MS: m/z=266.0 [M+H]$^+$.

8-[(cis-1,3,5)-3-amino-5-methylcyclohexyl]quinoxaline-5-carbonitrile

To a solution of 8-[(1S,3R)-3-methyl-5-oxocyclohexyl]quinoxaline-5-carbonitrile (451 mg, 1.70 mmol) in methanol (20 mL) was added ammonia acetate (1.46 g, 18.98 mmol), LiCl (84 mg, 1.88 mmol, 1.11 equiv, 95%) and NaBH$_3$CN (124 mg, 1.97 mmol) at room temperature. The resulting mixture was then stirred for 2 h at room temperature. When the reaction was done, it was quenched by the addition of sat. sodium bicarbonate solution (30 mL). The resulting mixture was extracted with DCM (50 mL×3). The organic phases were combined, washed with brine and dried over Na$_2$SO$_4$. The solvent was removed under reduced pressure and the residue was purified by prep-HPLC under the following conditions: column, XBridge BEH130 Prep C18 OBD column, 150 mm, 5 um, 13 nm; mobile phase, acetonitrile in water (with 0.05% NH₄OH), 30% to 65% gradient in 10 min; detector, UV 254 nm. 8-[(cis-1,3,5)-3-amino-5-methylcyclohexyl]quinoxaline-5-carbonitrile was obtained white solid (20 mg, 4%).

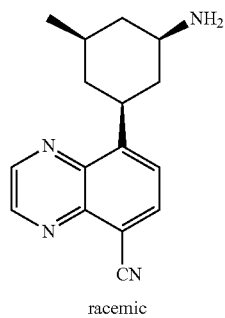 [SMILES: C[C@H]1C[C@@H](N)C[C@@H](c2ccc(C#N)c3nccnc23)C1]

racemic

Compound 120

HPLC: 99.7% purity, RT=1.22 min. MS: m/z=267.1 [M+H]⁺. ¹H NMR (300 MHz, DMSO-d₆, ppm) δ 9.15 (s, 2H), 8.43 (d, J=7.7 Hz, 1H), 7.87 (d, J=7.7 Hz, 1H), 4.09-3.95 (m, 1H), 2.90-2.76 (m, 1H), 1.98-1.62 (m, 6H), 1.38-1.08 (m, 2H), 0.98-0.74 (m, 4H).

Example 23: Synthesis of Compound 121 (8-[(1S,3R,5R)-3-amino-5-methylcyclohexyl]quinoxaline-5-carbonitrile) and Compound 122 (8-((1R,3S,5S)-3-amino-5-methylcyclohexyl)quinoxaline-5-carbonitrile)

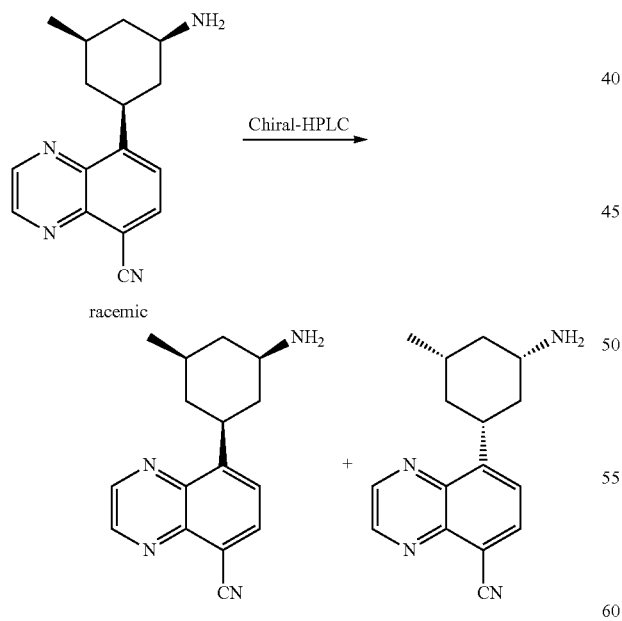

The two enantiomeric isomers of 8-[(cis-1,3,5)-3-amino-5-methylcyclohexyl]quinoxaline-5-carbonitrile were obtained by separation on chiral prep-HPLC under the following conditions: column, CHIRALPAK IF-3, 0.46×10 cm, 3 um; mobile phase, hexane (with 0.1% DEA) in MeOH, 50% isocratic in 15 min; detector, UV 220 nm.

Compound 121

(26 mg, 5%, white solid) HPLC: 94.8% purity, RT=1.31 min. MS: m/z=267.2 [M+H]⁺. ¹H NMR (300 MHz, DMSO-d₆, ppm) δ 9.15 (s, 2H), 8.43 (d, J=7.7 Hz, 1H), 7.87 (d, J=7.7 Hz, 1H), 4.09-3.95 (m, 1H), 2.90-2.76 (m, 1H), 1.98-1.62 (m, 6H), 1.38-1.08 (m, 2H), 0.98-0.74 (m, 4H).

Compound 122

(26 mg, 5%, white solid) HPLC: 93.6% purity, RT=1.13 min. MS: m/z=267.2 [M+H]⁺. ¹H NMR (300 MHz, DMSO-d₆, ppm) δ 9.15 (s, 2H), 8.43 (d, J=7.7 Hz, 1H), 7.87 (d, J=7.7 Hz, 1H), 4.09-3.95 (m, 1H), 2.90-2.76 (m, 1H), 1.98-1.62 (m, 6H), 1.38-1.08 (m, 2H), 0.98-0.74 (m, 4H).

Example 24: Synthesis of Compound 123 (8-[(1R,3R,5R)-3-amino-5-methylcyclohexyl]quinoxaline-5-carbonitrile) and Compound 124 (8-((1S,3S,5S)-3-amino-5-methylcyclohexyl)quinoxaline-5-carbonitrile)

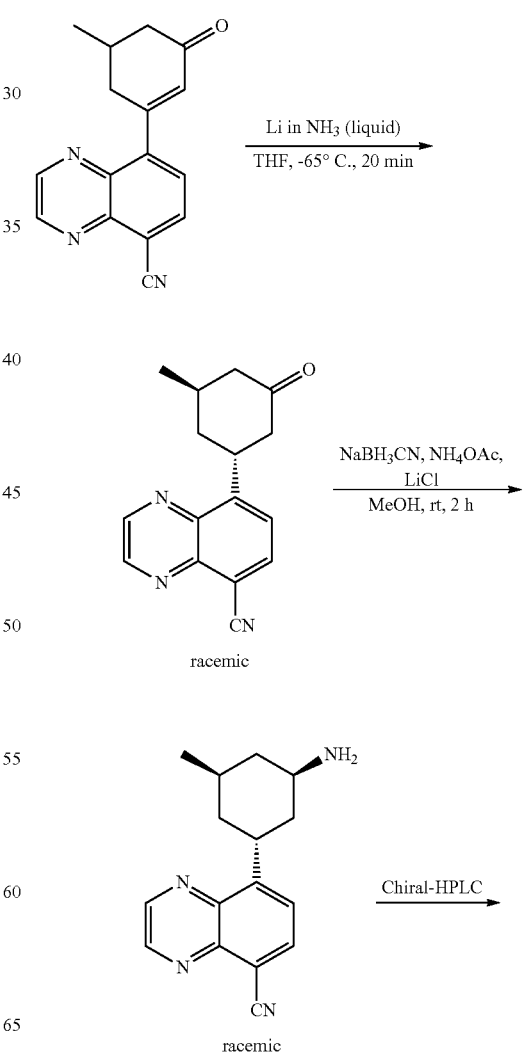

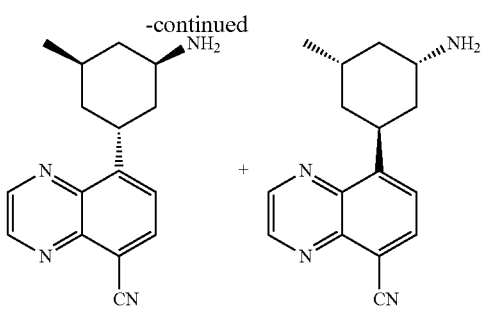

8-[(trans-1,3)-3-methyl-5-oxocyclohexyl]quinoxaline-5-carbonitrile

At −65° C., Li (651 mg, 93.75 mmol) was added slowly into liquid NH₃ (220 mL), to which was added a solution of 8-(5-methyl-3-oxocyclohex-1-en-1-yl)quinoxaline-5-carbonitrile (4.95 g, 18.80 mmol) in THF (110 mL) dropwise. The resulting solution was stirred for 20 min at −65° C. When the reaction was done, it was quenched by the addition of NH₄Cl (20.00 g, 0.38 mol) and NH₃ gas was allowed to evaporate. The remaining mixture was diluted with water (500 mL) and extracted with ethyl acetate (650 mL×3). The organic phases were combined, washed with brine and dried over Na₂SO₄. The solvent was removed under reduced pressure and the residue was first purified by flash chromatography eluting with EtOAc in hexane (0% to 17% gradient) to give a mixture of the cis and trans isomers. The obtained mixture was further purified by reverse phase flash chromatography eluting with acetonitrile in water (with 10 mM NH₄HCO₃) (30% to 60% gradient in 50 min) to yield 8-[(trans-1,3)-3-methyl-5-oxocyclohexyl]quinoxaline-5-carbonitrile as white solid (324 mg, 6%). MS: m/z=266.0 [M+H]⁺.

8-[(1,trans-3,cis-5,cis)-3-amino-5-methylcyclohexyl]quinoxaline-5-carbonitrile

To a solution of 8-[(1R,3R)-3-methyl-5-oxocyclohexyl]quinoxaline-5-carbonitrile (451 mg, 1.70 mmol) in methanol (20 mL) was added ammonia acetate (1.46 g, 18.98 mmol), LiCl (84 mg, 1.88 mmol) and NaBH₃CN (124 mg, 1.97 mmol) at room temperature. The resulting mixture was then stirred for 2 h at room temperature. When the reaction was done, it was quenched by the addition of sat. sodium bicarbonate solution (30 mL). The resulting mixture was extracted with DCM (50 mL×3). The organic phases were combined, washed with brine and dried over Na₂SO₄. The solvent was removed under reduced pressure and the residue was purified by prep-HPLC under the following conditions: column, XBridge BEH130 Prep C18 OBD column, 150 mm, 5 um, 13 nm; mobile phase, acetonitrile in water (with 0.05% NH₄OH), 30% to 65% gradient in 10 min; detector, UV 254 nm. 8-[(1,trans-3,cis-5)-3-amino-5-methylcyclohexyl]quinoxaline-5-carbonitrile was obtained as white solid (8 mg, 2%). HPLC: 91.3% purity, RT=1.20 min. MS: m/z=267.1 [M+H]⁺. ¹H NMR (300 MHz, DMSO-d₆, ppm) δ 9.16-9.08 (m, 2H), 8.38 (d, J=7.7 Hz, 1H), 7.94 (d, J=7.7 Hz, 1H), 4.49-4.37 (m, 1H), 2.98-2.83 (m, 1H), 2.19-2.08 (m, 1H), 2.05-1.94 (m, 1H), 1.85-1.40 (m, 4H), 0.95-0.76 (m, 4H).

8-[(1R,3R,5R)-3-amino-5-methylcyclohexyl]quinoxaline-5-carbonitrile and 8-((1S,3S,5S)-3-amino-5-methylcyclohexyl)quinoxaline-5-carbonitrile The two enantiomeric isomers of 8-[(1,trans-3,cis-5,cis)-3-amino-5-methylcyclohexyl]quinoxaline-5-carbonitrile were obtained by separation on chiral prep-HPLC under the following conditions: column, Lux Cellulose-3, 0.46×15 cm, 3 um; mobile phase, hexane (with 0.2% IPAmine) in EtOH, 85% isocratic in 15 min; detector, UV 220 nm.

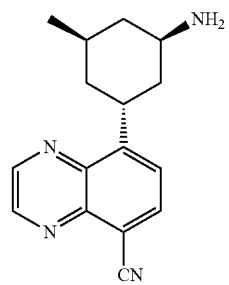 [SMILES: C[C@H]1C[C@@H](N)C[C@H](c2ccc(C#N)c3nccnc23)C1]

Compound 123

(5 mg, 1%, white solid) HPLC: 92.9% purity, RT=0.82 min. MS: m/z=267.1 [M+H]⁺. ¹H NMR (300 MHz, DMSO-d₆, ppm) δ 9.17-9.09 (m, 2H), 8.39 (d, J=7.7 Hz, 1H), 7.95 (d, J=7.7 Hz, 1H), 4.50-4.38 (m, 1H), 2.99-2.84 (m, 1H), 2.20-2.09 (m, 1H), 2.06-1.95 (m, 1H), 1.86-1.41 (m, 4H), 0.96-0.77 (m, 4H).

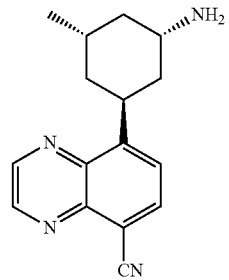 [SMILES: C[C@@H]1C[C@H](N)C[C@@H](c2ccc(C#N)c3nccnc23)C1]

Compound 124

(7 mg, 1%, white solid) HPLC: 94.4% purity, RT=0.83 min. MS: m/z=267.1 [M+H]⁺. ¹H NMR (300 MHz, DMSO-d₆, ppm) δ 9.16-9.09 (m, 2H), 8.38 (d, J=7.7 Hz, 1H), 7.94 (d, J=7.6 Hz, 1H), 4.49-4.37 (m, 1H), 2.98-2.83 (m, 1H), 2.19-2.08 (m, 1H), 2.06-1.94 (m, 2H), 1.85-1.41 (m, 4H), 0.96-0.75 (m, 4H).

Example 25: Synthesis of Compound 125 ((S)—N-((1R,3S,5R)-3-(8-cyanoquinoxalin-5-yl)-5-methylcyclohexyl)-2-hydroxy-3-methylbutanamide and Compound 126 ((S)—N-((1S,3R,5S)-3-(8-cyanoquinoxalin-5-yl)-5-methylcyclohexyl)-2-hydroxy-3-methylbutanamide)

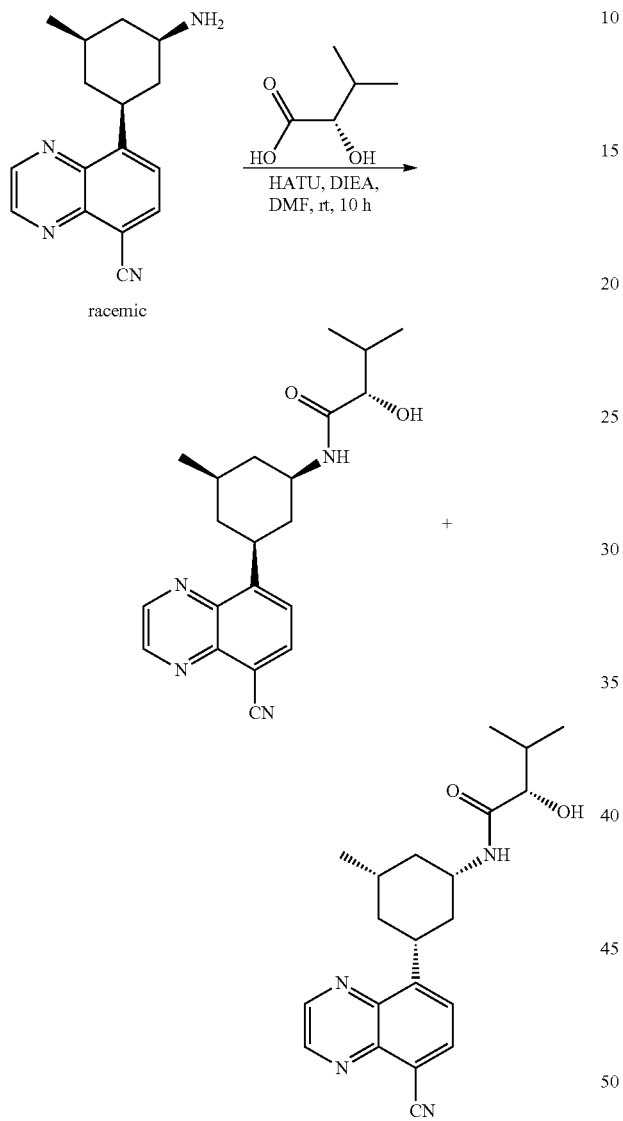

To a solution of (2S)-2-hydroxy-3-methylbutanoic acid (128 mg, 1.09 mmol) in N,N-dimethylformamide (15 mL) was added DIEA (346 mg, 2.68 mmol), HATU (306 mg, 0.80 mmol) and 8-[(cis-1,3,5)-3-amino-5-methylcyclohexyl]quinoxaline-5-carbonitrile (135 mg, 0.51 mmol) at room temperature. The resulting solution was stirred for 10 h at room temperature. When the reaction was done, it was quenched by the addition of water (15 mL). The resulting mixture was extracted with DCM (30 mL×3). The organic phases were combined, washed with brine and dried over Na$_2$SO$_4$. The solvent was removed under reduced pressure and the residue was purified by prep-HPLC under the following conditions: column, XBridge C18 OBD Prep Column, 150 mm, 5 um; mobile phase, acetonitrile in water (with 0.05% NH$_3$.H$_2$O), 30% to 65% gradient in 8 min; detector, UV 254 nm. Two diastereomeric products were separated and obtained.

Compound 125

(40 mg, 22%, white solid) HPLC: 96.1% purity, RT=2.31 min. MS: m/z=367.2 [M+H]$^+$. $^1$H NMR (300 MHz, Methanol-d4, ppm) δ 9.05-8.95 (m, 2H), 8.24 (d, J=7.7 Hz, 1H), 7.82 (d, J=7.7 Hz, 1H), 4.28-3.95 (m, 2H), 3.78 (d, J=3.7 Hz, 1H), 2.12-1.75 (m, 5H), 1.68-1.49 (m, 1H), 1.35-0.90 (m, 8H), 0.77 (d, J=6.8 Hz, 3H).

Compound 126

(8 mg, 13%, white solid) HPLC: 95.8% purity, RT=2.87 min. MS: m/z=367.3 [M+H]$^+$. $^1$H NMR (300 MHz, Methanol-d4, ppm) δ 9.05-8.95 (m, 2H), 8.25 (d, J=7.7 Hz, 1H), 7.82 (d, J=7.7 Hz, 1H), 4.26-4.10 (m, 1H), 4.11-3.97 (m, 1H), 3.77 (d, J=3.6 Hz, 1H), 2.12-1.85 (m, 5H), 1.70-1.51 (m, 1H), 1.36-0.91 (m, 8H), 0.83 (d, J=6.8 Hz, 3H).

The following compounds were synthesized in an analogous manner:

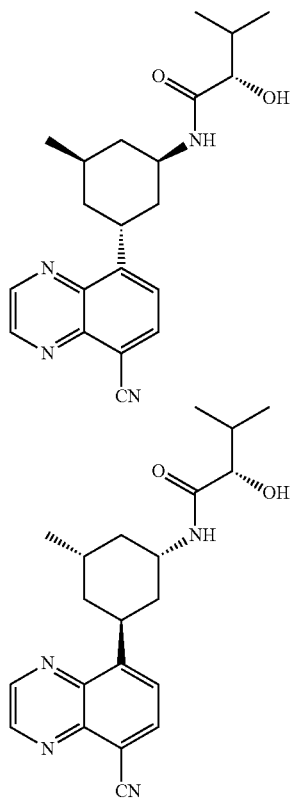

Compound 127 ((S)—N-((1R,3R,5R)-3-(8-cyanoquinoxalin-5-yl)-5-methylcyclohexyl)-2-hydroxy-3-methylbutanamide) and Compound 128 ((S)—N-((1S,3S,5S)-3-(8-cyanoquinoxalin-5-yl)-5-methylcyclohexyl)-2-hydroxy-3-methylbutanamide)

From racemic 8-[(1,trans-3,cis-5,cis)-3-amino-5-methylcyclohexyl]quinoxaline-5-carbonitrile and (2S)-2-hydroxy-3-methylbutanoic acid.

Compound 127

(5 mg, 6%, white solid) HPLC: 95.3% purity, RT=1.64 min. MS: m/z=367.3 [M+H]⁺. ¹H NMR (300 MHz, Methanol-d4, ppm) δ 9.06-8.94 (m, 2H), 8.25 (d, J=7.7 Hz, 1H), 8.06 (d, J=7.7, 0.9 Hz, 1H), 4.57-4.44 (m, 1H), 4.23-4.06 (m, 1H), 3.78 (d, J=3.6 Hz, 1H), 2.35-2.12 (m, 2H), 2.10-1.74 (m, 4H), 1.72-1.56 (m, 1H), 1.32-1.14 (m, 1H), 1.05-0.90 (m, 6H), 0.81 (d, J=6.8 Hz, 3H).

Compound 128

(6 mg, 6%, white solid) HPLC: 98.5% purity, RT=1.68 min. MS: m/z=367.2 [M+H]⁺. ¹H NMR (400 MHz, Methanol-d4, ppm) δ 9.07-8.98 (m, 2H), 8.28 (d, J=7.6 Hz, 1H), 8.09 (d, J=7.7 Hz, 1H), 4.58-4.48 (m, 1H), 4.21-4.08 (m, 1H), 3.79 (d, J=3.7 Hz, 1H), 2.38-2.29 (m, 1H), 2.21 (d, J=14.4 Hz, 1H), 2.12-1.99 (m, 1H), 1.97-1.79 (m, 3H), 1.72-1.60 (m, 1H), 1.33-1.13 (m, 1H), 1.06-0.95 (m, 6H), 0.85 (d, J=6.8 Hz, 3H).

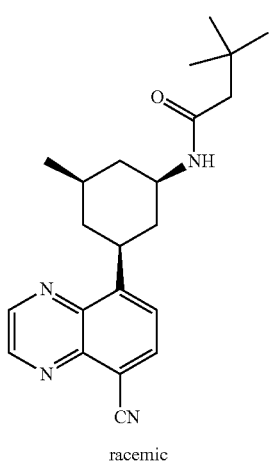 [SMILES: C[C@H]1C[C@@H](NC(=O)CC(C)(C)C)C[C@@H](c2ccc(C#N)c3nccnc23)C1]

racemic

Compound 129 (N-[(cis-1,3,5)-3-(8-cyanoquinoxalin-5-yl)-5-methylcyclohexyl]-3,3-dimethylbutanamide)

From racemic 8-[(cis-1,3,5)-3-amino-5-methylcyclohexyl]quinoxaline-5-carbonitrile and 3,3-dimethylbutanoic acid (12 mg, 45%, white solid). HPLC: 98.4% purity, RT=1.59 min. MS: r/z=365.1 [M+H]⁺. ¹H NMR (300 MHz, Methanol-d₄, ppm) δ 9.05-8.95 (m, 2H), 8.24 (d, J=7.7 Hz, 1H), 7.80 (d, J=7.7 Hz, 1H), 4.25-4.10 (m, 1H), 4.06-3.91 (m, 1H), 2.13-1.92 (m, 3H), 1.91-1.78 (m, 3H), 1.59-1.45 (m, 1H), 1.34-1.15 (m, 1H), 1.12-0.94 (m, 13H).

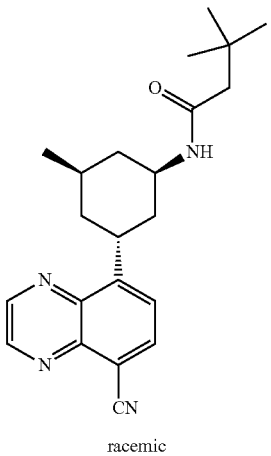 [SMILES: C[C@H]1C[C@@H](NC(=O)CC(C)(C)C)C[C@H](c2ccc(C#N)c3nccnc23)C1]

racemic

Compound 130 (N-[(1,cis-3,trans-5,cis)-3-(8-cyanoquinoxalin-5-yl)-5-methylcyclohexyl]-3,3-dimethylbutanamide)

From racemic 8-[(1,trans-3,cis-5,cis)-3-amino-5-methylcyclohexyl]quinoxaline-5-carbonitrile and 3,3-dimethylbutanoic acid (8 mg, 32%, white solid). HPLC: 99.3% purity, RT=1.90 min. MS: r/z=365.3 [M+H]⁺. ¹H NMR (400 MHz, Methanol-d4, ppm) δ 9.07-9.00 (m, 2H), 8.30 (d, J=7.6 Hz, 1H), 8.15 (d, J=7.7 Hz, 1H), 4.57-4.49 (m, 1H), 4.20-4.07 (m, 1H), 2.47-2.37 (m, 1H), 2.29-2.21 (m, 1H), 2.06 (br s, 2H), 1.98-1.88 (m, 1H), 1.88-1.71 (m, 2H), 1.70-1.57 (m, 1H), 1.18-1.00 (m, 10H), 0.96 (d, J=6.4 Hz, 3H).

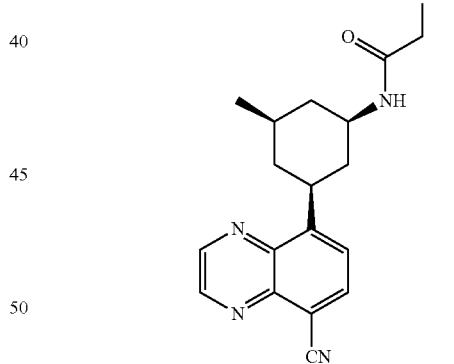

Compound 131 (N-[(cis-1,3,5)-3-(8-cyanoquinoxalin-5-yl)-5-methylcyclohexyl]-2-(dimethylamino)acetamide)

From racemic 8-[(cis-1,3,5)-3-amino-5-methylcyclohexyl]quinoxaline-5-carbonitrile and 2-(dimethylamino)acetic acid hydrochloride (22 mg, 61%, white solid). HPLC: 98.0% purity, RT=1.48 min. MS: m/z=352.2 [M+H]⁺. ¹H NMR (300 MHz, Methanol-d4, ppm) δ 9.05-8.95 (m, 2H), 8.24 (d, J=7.7 Hz, 1H), 7.82 (d, J=7.7 Hz, 1H), 4.26-3.94 (m, 2H), 2.93 (s, 2H), 2.25 (s, 6H), 2.15-1.75 (m, 4H), 1.65-1.47 (m, 1H), 1.35-0.96 (m, 5H).

181

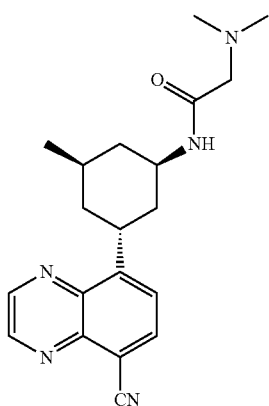 [SMILES: C[C@H]1C[C@@H](NC(=O)CN(C)C)C[C@H](c2ccc(C#N)c3nccnc23)C1]

Compound 132 (N-[(1,cis-3,trans-5,cis)-3-(8-cyano-quinoxalin-5-yl)-5-methylcyclohexyl]-2-(dimethyl-amino)acetamide)

From racemic 8-[(1,trans-3,cis-5,cis)-3-amino-5-methyl-cyclohexyl]quinoxaline-5-carbonitrile and 2-(dimethyl-amino)acetic acid hydrochloride (12 mg, 33%, white solid). HPLC: 99.4% purity, RT=1.63 min. MS: m/z=352.2 [M+H]$^+$. $^1$H NMR (300 MHz, Methanol-d4, ppm) δ 9.02-8.94 (m, 2H), 8.25 (d, J=7.7 Hz, 1H), 8.05 (dd, J=7.7, 0.9 Hz, 1H), 4.56-4.44 (m, 1H), 4.20-4.03 (m, 1H), 2.92 (s, 2H), 2.37-2.11 (m, 8H), 1.98-1.75 (m, 3H), 1.71-1.54 (m, 1H), 1.29-1.09 (m, 1H), 0.97 (d, J=6.5 Hz, 3H).

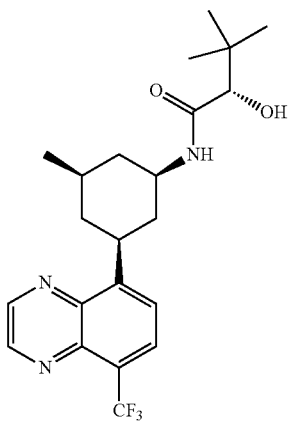 [SMILES: C[C@H]1C[C@@H](NC(=O)[C@@H](O)C(C)(C)C)C[C@@H](c2ccc(C(F)(F)F)c3nccnc23)C1]

Compound 154 ((S)-2-hydroxy-3,3-dimethyl-N-((1R,3R,5S)-3-methyl-5-(8-(trifluoromethyl)qui-noxalin-5-yl)cyclohexyl)butanamide)

From (1R,3R,5S)-3-methyl-5-(8-(trifluoromethyl)qui-noxalin-5-yl)cyclohexanamine and (2S)-2-hydroxy-3,3-di-methylbutanoic acid (9 mg, 7%, white solid). HPLC: 99.1% purity, RT=1.93 min. MS: m/z=424.2 [M+H]$^+$. $^1$H NMR (400 MHz, Methanol-d4, ppm) δ 9.04-8.96 (m, 2H), 8.18 (d, J=7.7 Hz, 1H), 7.83 (d, J=7.8 Hz, 1H), 4.29-4.16 (m, 1H), 4.15-4.02 (m, 1H), 3.64 (s, 1H), 2.16-2.08 (m, 1H), 2.08-1.85 (m, 3H), 1.68-1.58 (m, 1H), 1.37-1.23 (m, 1H), 1.29-1.01 (m, 4H), 0.97 (s, 9H).

182

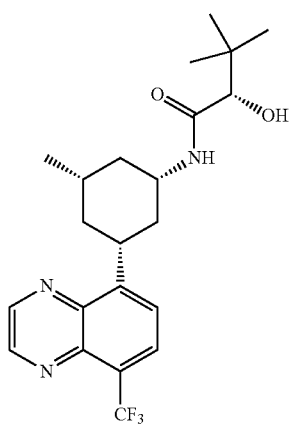 [SMILES: C[C@@H]1C[C@H](NC(=O)[C@@H](O)C(C)(C)C)C[C@H](c2ccc(C(F)(F)F)c3nccnc23)C1]

Compound 155 ((S)-2-hydroxy-3,3-dimethyl-N-((1S,3S,5R)-3-methyl-5-(8-(trifluoromethyl)qui-noxalin-5-yl)cyclohexyl)butanamide)

From (1S,3S,5R)-3-methyl-5-(8-(trifluoromethyl)qui-noxalin-5-yl)cyclohexanamine and (2S)-2-hydroxy-3,3-di-methylbutanoic acid (8 mg, 6%, white solid). HPLC: 98.2% purity, RT=2.21 min. MS: m/z=424.2 [M+H]$^+$. $^1$H NMR (400 MHz, Methanol-d$_4$, ppm) δ 9.04-8.96 (m, 2H), 8.18 (d, J=7.8 Hz, 1H), 7.84 (d, J=7.7 Hz, 1H), 4.28-4.15 (m, 1H), 4.15-4.03 (m, 1H), 3.64 (s, 1H), 2.16-2.08 (m, 1H), 2.08-1.85 (m, 3H), 1.72-1.58 (m, 1H), 1.39-1.25 (m, 1H), 1.21-1.00 (m, 4H), 0.98 (s, 9H).

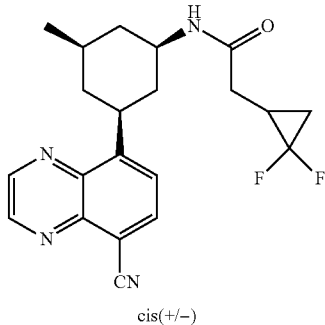 [SMILES: C[C@H]1C[C@@H](NC(=O)CC2CC2(F)F)C[C@@H](c2ccc(C#N)c3nccnc23)C1]

Compound 156 (N-[(cis-1,3,5)-3-(8-cyanoquinoxa-lin-5-yl)-5-methylcyclohexyl]-2-(2,2-difluorocyclo-propyl)acetamide)

From racemic 8-[(cis-1,3,5)-3-amino-5-methylcyclo-hexyl]quinoxaline-5-carbonitrile and 2-(2,2-difluorocyclo-propyl)acetic acid (30 mg, 55%, off-white solid). HPLC: 99.8% purity, RT=1.72 min. MS: m/z=385.2 [M+H]$^+$. $^1$H NMR (400 MHz, DMSO-d$_6$, ppm) δ 9.19-9.11 (m, 2H), 8.43 (d, J=7.7 Hz, 1H), 7.87 (d, J=7.7 Hz, 2H), 4.06 (t, J=12.1 Hz, 1H), 3.89-3.79 (m, 1H), 2.30-2.17 (m, 2H), 2.03-1.95 (m, 1H), 1.93-1.76 (m, 4H), 1.61-1.45 (m, 1H), 1.47-1.21 (m, 2H), 1.20-1.06 (m, 1H), 1.07-0.93 (m, 4H).

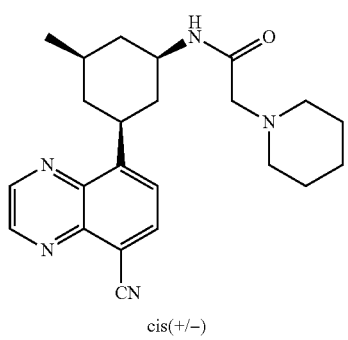 [SMILES: C[C@H]1C[C@@H](NC(=O)CN2CCCCC2)C[C@@H](c2ccc(C#N)c3nccnc23)C1]

Compound 157 (N-[(cis-1,3,5)-3-(8-cyanoquinoxalin-5-yl)-5-methylcyclohexyl]-2-(piperidin-1-yl)acetamide)

From racemic 8-[(cis-1,3,5)-3-amino-5-methylcyclohexyl]quinoxaline-5-carbonitrile and 2-(piperidin-1-yl)acetic acid (10 mg, 25%, light yellow solid). HPLC: 97.5% purity, RT=1.91 min. MS: m/z=392.2 [M+H]$^+$. $^1$H NMR (400 MHz, Methanol-d$_4$, ppm) δ 9.08-8.99 (m, 2H), 8.27 (d, J=7.7 Hz, 1H), 7.85 (d, J=7.7 Hz, 1H), 4.27-4.14 (m, 1H), 4.11-3.98 (m, 1H), 3.15 (d, J=11.7 Hz, 2H), 2.66-2.61 (m, 4H), 2.18-2.08 (m, 1H), 2.07-1.80 (m, 3H), 1.72-1.46 (m, 7H), 1.37-1.23 (m, 1H), 1.16-1.00 (m, 4H).

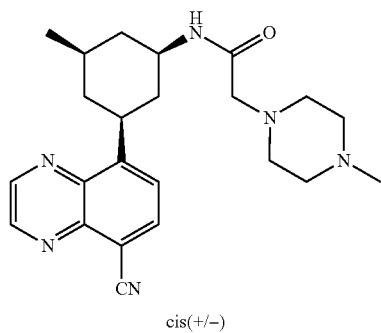 [SMILES: C[C@H]1C[C@@H](NC(=O)CN2CCN(C)CC2)C[C@@H](c2ccc(C#N)c3nccnc23)C1]

Compound 158 (N-[(cis-1,3,5)-3-(8-cyanoquinoxalin-5-yl)-5-methylcyclohexyl]-2-(4-methylpiperazin-1-yl)acetamide)

From racemic 8-[(cis-1,3,5)-3-amino-5-methylcyclohexyl]quinoxaline-5-carbonitrile and 2-(4-methylpiperazin-1-yl)acetic acid (10 mg, 24%, white solid). HPLC: 98.0% purity, RT=1.45 min. MS: m/z=407.2 [M+H]$^+$. $^1$H NMR (300 MHz, Methanol-d4, ppm) δ 9.04-8.95 (m, 2H), 8.24 (d, J=7.7 Hz, 1H), 7.81 (d, J=7.7 Hz, 1H), 4.26-4.09 (m, 1H), 4.10-3.93 (m, 1H), 2.97 (s, 2H), 2.53-2.43 (m, 8H), 2.24 (s, 3H), 2.14-2.02 (m, 1H), 2.03-1.74 (m, 3H), 1.64-1.46 (m, 1H), 1.36-1.17 (m, 1H), 1.17-0.96 (m, 4H).

Example 26: Synthesis of Compound 133 (8-[(cis-1,3,5)-3-[(2-methoxyethyl)amino]-5-methylcyclohexyl]quinoxaline-5-carbonitrile)

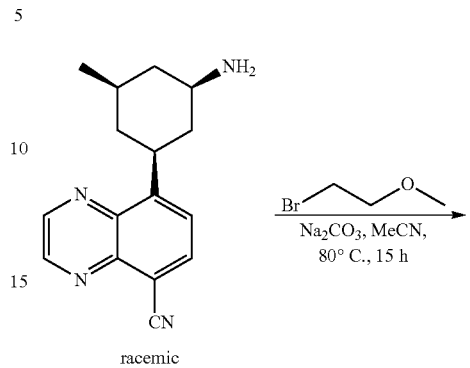

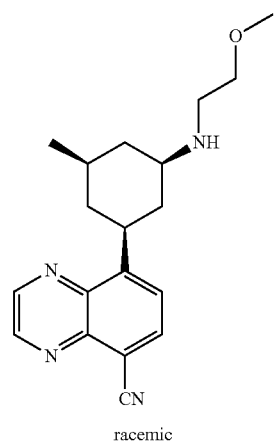

To a solution of 8-[(cis-1,3,5)-3-amino-5-methylcyclohexyl]quinoxaline-5-carbonitrile (45 mg, 0.17 mmol) in acetonitrile (10 mL) was added sodium carbonate (58 mg, 0.55 mmol), 1-bromo-2-methoxyethane (30 mg, 0.22 mmol) at room temperature. The resulting mixture was stirred for 15 h at 80° C. After cooling to room temperature, the solids were filtered out. Then the reaction was then quenched by the addition of water (15 mL). The resulting solution was extracted with DCM (30 mL×3). The organic phases were combined, washed with brine and dried over Na$_2$SO$_4$. The solvent was removed under reduced pressure and the residue was purified by prep-HPLC under the following conditions: column, XBridge C18 OBD Prep Column, 150 mm, 5 um; mobile phase, acetonitrile in water (with 10 mM NH$_4$HCO$_3$ and 0.05% NH$_3$.H$_2$O), 35% to 65% gradient in 8 min; detector, UV 254 nm. 8-[(cis-1,3,5)-3-[(2-methoxyethyl)amino]-5-methylcyclohexyl]quinoxaline-5-carbonitrile was obtained as white solid (15 mg, 28%).

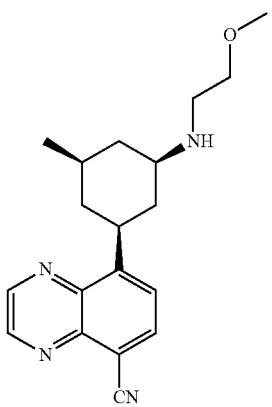 [SMILES: COCCN[C@@H]1C[C@H](C)C[C@H](c2ccc(C#N)c3nccnc23)C1]

Compound 133

HPLC: 97.4% purity, RT=1.37 min. MS: m/z=325.2 [M+H]+. 1H NMR (300 MHz, Methanol-d4, ppm) δ 9.00 (q, J=1.8 Hz, 2H), 8.25 (d, J=7.7 Hz, 1H), 7.83 (d, J=7.7 Hz, 1H), 4.21-4.04 (m, 1H), 3.50 (t, J=5.3 Hz, 2H), 3.33 (s, 3H), 3.03-2.81 (m, 3H), 2.25-2.14 (m, 1H), 2.13-1.71 (m, 3H), 1.53-1.18 (m, 2H), 1.07-0.88 (m, 4H).

The following compounds were synthesized in an analogous manner:

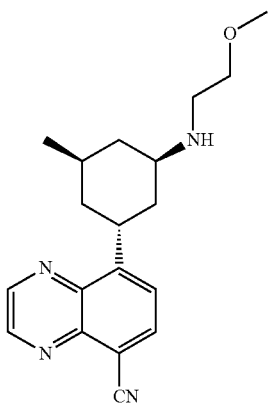 [SMILES: COCCN[C@@H]1C[C@H](C)C[C@@H](c2ccc(C#N)c3nccnc23)C1]

Compound 134 (8-[(1,trans-3,cis-5)-3-[(2-methoxyethyl)amino]-5-methylcyclohexyl]quinoxaline-5-carbonitrile)

From 8-[(1,trans-3,cis-5,cis)-3-amino-5-methylcyclohexyl]quinoxaline-5-carbonitrile and 1-bromo-2-methoxyethane (6 mg, 14%, white solid). HPLC: 95.1% purity, RT=2.42 min. MS: m/z=325.2 [M+H]+. 1H NMR (400 MHz, Methanol-d4, ppm) δ 9.06-9.01 (m, 2H), 8.26 (d, J=7.6 Hz, 1H), 7.98 (d, J=7.7 Hz, 1H), 4.65-4.52 (m, 1H), 3.51-3.45 (m, 2H), 3.31 (s, 3H), 3.02-2.76 (m, 3H), 2.49 (d, J=13.5 Hz, 1 H), 2.21 (d, J=13.9 Hz, 1H), 2.07 (d, J=12.4 Hz, 1H), 1.93-1.76 (m, 2H), 1.69-1.54 (m, 1H), 1.08-0.93 (m, 4H).

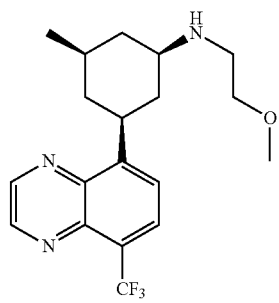 [SMILES: COCCN[C@@H]1C[C@H](C)C[C@H](c2ccc(C(F)(F)F)c3nccnc23)C1]

Compound 147 ((1R,3R,5S)—N-(2-methoxyethyl)-3-methyl-5-(8-(trifluoromethyl)quinoxalin-5-yl)cyclohexanamine)

From (1R,3R,5S)-3-methyl-5-(8-(trifluoromethyl)quinoxalin-5-yl)cyclohexanamine and 1-bromo-2-methoxyethane (7 mg, 5%, light yellow semi-solid). HPLC: 96.6% purity, RT=1.30 min. MS: m/z=368.1 [M+H]+. 1H NMR (400 MHz, DMSO-d6, ppm) δ 9.16-9.08 (m, 2H), 8.24 (d, J=7.6 Hz, 1H), 7.86 (d, J=7.7 Hz, 1H), 4.09-3.96 (m, 1H), 3.43-3.29 (m, 2H), 3.22 (s, 3H), 2.76-2.63 (m, 3H), 2.06 (d, J=12.6 Hz, 1H), 2.01-1.92 (m, 1H), 1.87-1.78 (m, 1H), 1.79-1.61 (m, 1H), 1.35-1.13 (m, 2H), 0.96 (d, J=6.5 Hz, 3H), 0.88-0.75 (m, 1H).

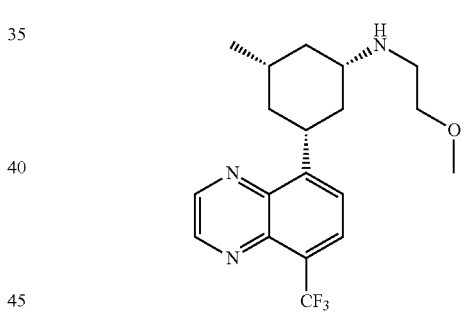

Compound 148 ((1S,3S,5R)—N-(2-methoxyethyl)-3-methyl-5-(8-(trifluoromethyl)quinoxalin-5-yl)cyclohexanamine)

From (1S,3S,5R)-3-methyl-5-(8-(trifluoromethyl)quinoxalin-5-yl)cyclohexanamine and 1-bromo-2-methoxyethane (7 mg, 5%, light yellow semi-solid). HPLC: 95.3% purity, RT=1.31 min. MS: m/z=368.0 [M+H]+. 1H NMR (400 MHz, DMSO-d6, ppm) δ 9.17-9.09 (m, 2H), 8.24 (d, J=7.7 Hz, 1H), 7.86 (d, J=7.7 Hz, 1H), 4.09-3.96 (m, 1H), 3.42-3.30 (m, 2H), 3.23 (s, 3H), 2.76-2.63 (m, 3H), 2.10-2.02 (m, 1H), 2.01-1.93 (m, 1H), 1.88-1.78 (m, 1H), 1.79-1.61 (m, 1H), 1.35-1.13 (m, 2H), 0.95 (d, J=6.5 Hz, 3H), 0.89-0.75 (m, 1H).

187

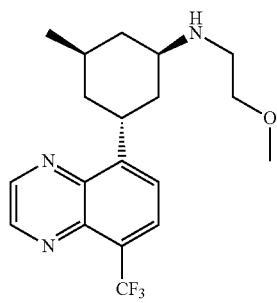 [SMILES: COCCN[C@@H]1C[C@H](C)C[C@@H](c2ccc(C(F)(F)F)c3nccnc23)C1]

Compound 149 ((1R,3R,5R)—N-(2-methoxyethyl)-3-methyl-5-(8-(trifluoromethyl)quinoxalin-5-yl)cyclohexanamine)

From (1S,3S,5R)-3-methyl-5-(8-(trifluoromethyl)quinoxalin-5-yl)cyclohexanamine and 1-bromo-2-methoxyethane (8 mg, 7%, light yellow semi-solid). HPLC: 97.3% purity, RT=1.71 min. MS: m/z=368.2 [M+H]$^+$. $^1$H NMR (400 MHz, Methanol-d4, ppm) δ 9.00 (dd, J=12.0, 1.7 Hz, 2H), 8.17 (d, J=7.7 Hz, 1H), 7.98 (d, J=7.7 Hz, 1H), 4.62-4.53 (m, 1H), 3.52-3.43 (m, 2H), 3.35 (s, 3H), 3.02-2.75 (m, 3H), 2.56-2.46 (m, 1H), 2.28-2.18 (m, 1H), 2.13-2.03 (m, 1H), 1.97-1.75 (m, 2H), 1.71-1.58 (m, 1H), 1.08-0.94 (m, 4H).

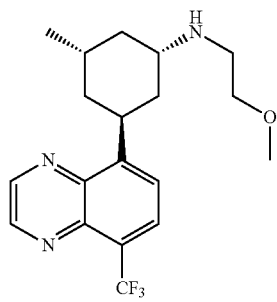 [SMILES: COCCN[C@H]1C[C@@H](C)C[C@H](c2ccc(C(F)(F)F)c3nccnc23)C1]

Compound 150 ((1S,3S,5S)—N-(2-methoxyethyl)-3-methyl-5-(8-(trifluoromethyl)quinoxalin-5-yl)cyclohexanamine)

From (1S,3S,5S)-3-methyl-5-(8-(trifluoromethyl)quinoxalin-5-yl)cyclohexanamine and 1-bromo-2-methoxyethane (8 mg, 7%, light yellow semi-solid). HPLC: 96.9% purity, RT=2.77 min. MS: m/z=368.2 [M+H]$^+$. $^1$H NMR (400 MHz, Methanol-d4, ppm) δ 9.00 (dd, J=12.0, 1.8 Hz, 2H), 8.17 (d, J=7.7 Hz, 1H), 7.98 (d, J=7.7 Hz, 1H), 4.62-4.53 (m, 1H), 3.53-3.43 (m, 2H), 3.37-3.29 (m, 3H), 3.03-2.76 (m, 3H), 2.56-2.46 (m, 1H), 2.28-2.18 (m, 1H), 2.13-2.03 (m, 1H), 1.98-1.75 (m, 2H), 1.71-1.58 (m, 1H), 1.08-0.95 (m, 4H).

188

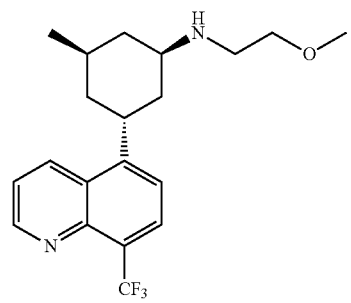

racemic

Compound 151 ((1,trans-3,trans-5,cis)-N-(2-methoxyethyl)-3-methyl-5-(8-(trifluoromethyl)quinolin-5-yl)cyclohexanamine)

From racemic (1,cis-3,cis-5,trans)-3-methyl-5-(8-(trifluoromethyl)quinolin-5-yl)cyclohexanamine and 1-bromo-2-methoxyethane (40 mg, 43%, light yellow oil). HPLC: 99.8% purity, RT=1.28 min. MS: m/z=367.1 [M+H]$^+$. $^1$H NMR (300 MHz, Methanol-d4, ppm) δ 8.97 (dd, J=4.2, 1.6 Hz, 1H), 8.69 (dd, J=8.9, 1.7 Hz, 1H), 8.13-8.04 (m, 1H), 7.83-7.61 (m, 2H), 4.25-4.13 (m, 1H), 3.56-3.41 (m, 2H), 3.41-3.29 (m, 3H), 3.06-2.71 (m, 3H), 2.41-2.27 (m, 1H), 2.17-1.99 (m, 2H), 1.97-1.61 (m, 3H), 1.11-0.92 (m, 4H).

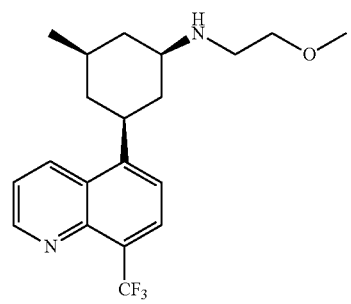 [SMILES: COCCN[C@@H]1C[C@H](C)C[C@H](c2ccc(C(F)(F)F)c3ncccc23)C1]

Compound 152 ((1R,3R,5S)—N-(2-methoxyethyl)-3-methyl-5-(8-(trifluoromethyl)quinolin-5-yl)cyclohexanamine)

From (1R,3R,5S)-3-methyl-5-(8-(trifluoromethyl)quinolin-5-yl)cyclohexanamine and 1-bromo-2-methoxyethane (15 mg, 16%, colorless oil). HPLC: 98.9% purity, RT=2.33 min. MS: m/z=367.1 [M+H]$^+$. $^1$H NMR (400 MHz, Methanol-d4, ppm) δ 8.99 (dd, J=4.2, 1.6 Hz, 1H), 8.73 (dd, J=8.9, 1.7 Hz, 1H), 8.11 (d, J=7.7 Hz, 1H), 7.71-7.62 (m, 2H), 3.67-3.52 (m, 3H), 3.38 (s, 3H), 3.08-2.85 (m, 3H), 2.28-2.08 (m, 2H), 2.02-1.81 (m, 2H), 1.55-1.41 (m, 1H), 1.38-1.24 (m, 1H), 1.10-0.94 (m, 4H).

189

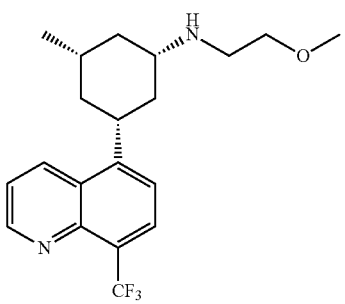 [SMILES: COCCN[C@H]1C[C@@H](C)C[C@@H](c2ccc(C(F)(F)F)c3ncccc23)C1]

Compound 153 ((1S,3S,5R)—N-(2-methoxyethyl)-3-methyl-5-(8-(trifluoromethyl)quinolin-5-yl)cyclohexanamine)

From (1S,3S,5R)-3-methyl-5-(8-(trifluoromethyl)quinolin-5-yl)cyclohexanamine and 1-bromo-2-methoxyethane (15 mg, 16%, colorless oil). HPLC: 97.1% purity, RT=1.30 min. MS: m/z=367.1 [M+H]$^+$. $^1$H NMR (400 MHz, Methanol-d4, ppm) δ 8.98 (dd, J=4.3, 1.7 Hz, 1H), 8.73 (dd, J=8.7, 1.9 Hz, 1H), 8.11 (d, J=7.8 Hz, 1H), 7.71-7.61 (m, 2H), 3.67-3.51 (m, 3H), 3.38 (s, 3H), 3.06-2.84 (m, 3H), 2.28-2.07 (m, 2H), 2.01-1.81 (m, 2H), 1.51-1.40 (m, 1H), 1.35-1.25 (m, 1H), 1.10-0.93 (m, 4H).

Example 27: Synthesis of Compound 135 ((1R,3R,5S)-3-methyl-5-(8-(trifluoromethyl)quinolin-5-yl)cyclohexanamine), compound 136 ((1S,3S,5R)-3-methyl-5-(8-(trifluoromethyl)quinolin-5-yl)cyclohexanamine), compound 137 ((1R,3R,5R)-3-methyl-5-(8-(trifluoromethyl)quinolin-5-yl)cyclohexanamine), and Compound 138 ((1S,3S,5S)-3-methyl-5-(8-(trifluoromethyl)quinolin-5-yl)cyclohexanamine)

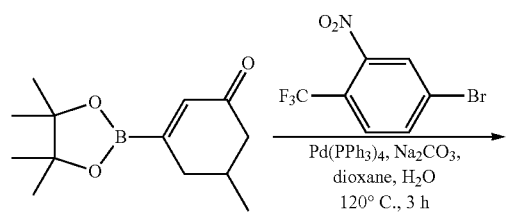

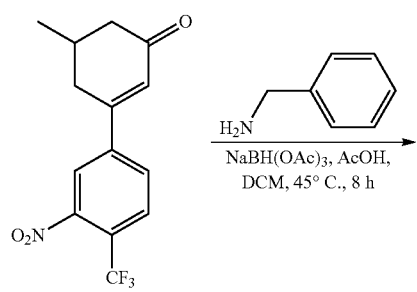

190

-continued

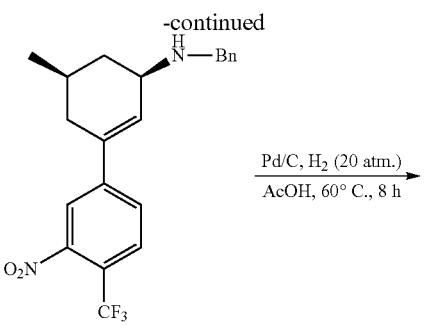

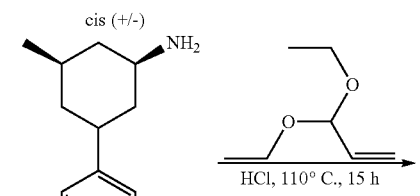

mixture of 4 isomers

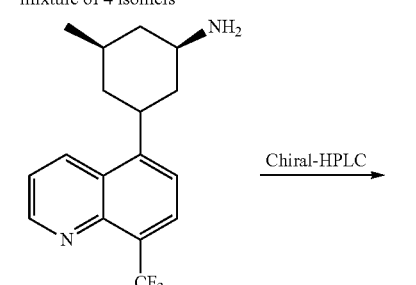

mixture of 4 isomers

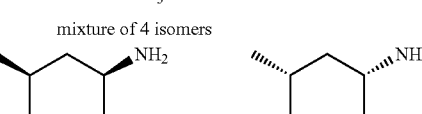
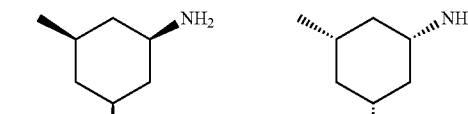
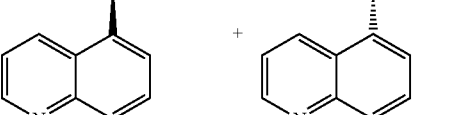
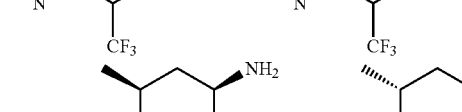
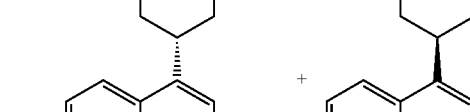
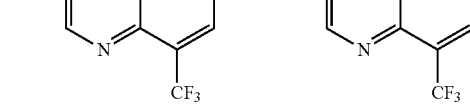

5-methyl-3-[3-nitro-4-(trifluoromethyl)phenyl]cyclohex-2-en-1-one

To a solution of 5-methyl-3-(tetramethyl-1,3,2-dioxaborolan-2-yl)cyclohex-2-en-1-one (18.00 g, 76.23 mmol) in dioxane (500 mL) was added 4-bromo-2-nitro-1-(trifluoromethyl)benzene (18.00 g, 66.67 mmol, 1.00 equiv, 90%), sodium carbonate solution (23.75 g in 50 mL water, 224.08 mmol) and Pd(dppf)Cl$_2$·CH$_2$Cl$_2$ (4.28 g, 5.23 mmol) at room temperature. The resulting mixture was stirred for 3 h at 120° C. When the reaction was done, it was quenched by the addition of water (150 mL). The resulting mixture was extracted with dichloromethane (500 mL×3). The organic phases were combined, washed with brine and dried over Na$_2$SO$_4$. The solvent was removed under reduced pressure and the residue was purified by flash chromatography eluting with EtOAc in hexane (0% to 10% gradient) to yield 5-methyl-3-[3-nitro-4-(trifluoromethyl)phenyl]cyclohex-2-en-1-one as yellow solid (16.94 g, 85%). MS: m/z=300.0 [M+H]$^+$.

(cis-1,5)-N-benzyl-5-methyl-3-(3-nitro-4-(trifluoromethyl)phenyl)cyclohex-2-enamine At 0° C., to a solution of 5-methyl-3-[3-nitro-4-(trifluoromethyl)phenyl]cyclohex-2-en-1-one (18.00 g, 60.15 mmol) in dichloromethane (500 mL) was added phenylmethanamine (8.55 g, 79.79 mmol) and AcOH (5 mL, 87.26 mmol). Then NaBH(OAc)$_3$ (39.90 g, 188.26 mmol) was added in several batchs. The resulting solution was stirred for 8 h at 45° C. When reaction was done, it was quenched by the addition of water (100 mL). The resulting mixture was extracted with EtOAc (200 mL×3). The organic phases were combined, washed with brine and dried over Na$_2$SO$_4$. The solvent was removed under reduced pressure and the residue was purified by flash chromatography eluting with EtOAc in hexane (0% to 40% gradient) to yield 25 g mixture of cis and trans isomers, which was purified by reverse phase flash chromatography eluting with acetonitrile in water (with 10 nM NH$_4$HCO$_3$), (0% to 55% gradient in 40 min), to yield (cis-1,5)-N-benzyl-5-methyl-3-(3-nitro-4-(trifluoromethyl)phenyl)cyclohex-2-enamine as yellow solid (13.45 g, 57%). MS: m/z=391.2 [M+H]$^+$.

5-((cis-3,5)-3-amino-5-methylcyclohexyl)-2-(trifluoromethyl)benzenamine

To a solution of (cis-1,5)-N-benzyl-5-methyl-3-(3-nitro-4-(trifluoromethyl)phenyl)cyclohex-2-enamine (13.45 g, 34.58 mmol) in methanol (300 mL) were added acetic acid (29 mL), palladium carbon (2.70 g, 25.37 mmol) under nitrogen atmosphere (20 atm). The reaction tank was vacuumed and flushed with hydrogen. Then the reaction mixture was hydrogenated for 15 h at 60° C. under 20 atm hydrogen pressures. When the reaction was done, the reaction mixture was filtered through a celite pad and the filtrate was concentrated under reduced pressure. The residue was purified by flash chromatography eluting with MeOH (with 1% TEA) in DCM (0% to 85% gradient) to yield 5-((cis-3,5)-3-amino-5-methylcyclohexyl)-2-(trifluoromethyl)benzenamine as yellow oil (6.22 g, 66%). MS: m/z=273.0 [M+H]$^+$.

(cis-1,3)-3-methyl-5-(8-(trifluoromethyl)quinolin-5-yl)cyclohexanamine

To a solution of 5-((cis-3,5)-3-amino-5-methylcyclohexyl)-2-(trifluoromethyl)benzenamine (6.23 g, 22.86 mmol) in hydrogen chloride solution (1 N, 250 mL, 8.23 mol) was added 3,3-diethoxyprop-1-ene (9.50 g, 72.97 mmol) at room temperature. The resulting mixture was stirred for 15 h at 110° C. When the reaction was done, the pH value of the reaction mixture was adjusted to 7-8 with saturated sodium bicarbonate solution and the resulting mixture was extracted with EtOAc (100 mL×3). The organic phases were combined, washed with brine and dried over Na$_2$SO$_4$. The solvent was removed under reduced pressure and the residue was purified by flash chromatography eluting with MeOH (1% TEA) in DCM (0% to 85% gradient) to yield (cis-1,3)-3-methyl-5-(8-(trifluoromethyl)quinolin-5-yl)cyclohexanamine as yellow solid (2.57 g, 36%). MS: m/z=309.3 [M+H]$^+$.

(1R,3R,5S)-3-methyl-5-(8-(trifluoromethyl)quinolin-5-yl)cyclohexanamine and (1S,3S,5R)-3-methyl-5-(8-(trifluoromethyl)quinolin-5-yl)cyclohexanamine and (1R,3R,5R)-3-methyl-5-(8-(trifluoromethyl)quinolin-5-yl)cyclohexanamine and (1S,3S,5S)-3-methyl-5-(8-(trifluoromethyl)quinolin-5-yl)cyclohexanamine The 4 stereoisomers of (cis-1,3)-3-methyl-5-(8-(trifluoromethyl)quinolin-5-yl)cyclohexanamine were obtained by separation on chiral prep-HPLC under the following conditions: column, Chiralpak IC, 2×25 cm, 5 um; mobile phase, hexane (with 0.1% DEA) in IPA, 70% isocratic in 15 min; detector, UV 220 nm.

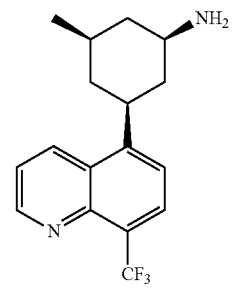

Compound 135

(13 mg, 1.9%, white solid) HPLC: 97.7% purity, RT=5.11 min. MS: m/z=309.2 [M+H]$^+$. $^1$H NMR (400 MHz, DMSO-d$_6$, ppm) δ 9.05 (dd, J=4.1, 1.6 Hz, 1H), 8.75 (dd, J=8.8, 1.6 Hz, 1H), 8.13 (d, J=7.7 Hz, 1H), 7.71 (dd, J=8.7, 4.1 Hz, 1H), 7.61 (d, J=7.7 Hz, 1H), 3.64-3.48 (m, 1H), 2.97-2.85 (m, 1H), 2.03-1.76 (m, 4H), 1.33-1.08 (m, 2H), 0.95 (d, J=6.3 Hz, 3H), 0.88-0.74 (m, 1H).

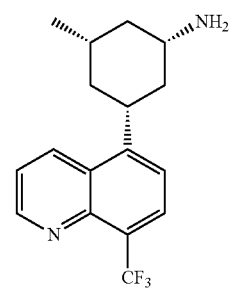 [SMILES: C[C@@H]1C[C@H](N)C[C@H](c2ccc(C(F)(F)F)c3ncccc23)C1]

Compound 136

(7 mg, 1%, white solid) HPLC: 97.6% purity, RT=4.22 min. MS: m/z=309.3 [M+H]+. 1H NMR (400 MHz, DMSO-d6, ppm) δ 9.05-9.01 (m, 1H), 8.75-8.64 (m, 1H), 8.13-8.08 (m, 1H), 7.79-7.68 (m, 2H), 4.15-4.07 (m, 1H), 3.03-2.94 (m, 1H), 2.18-2.01 (m, 1H), 1.97-1.50 (m, 5H), 1.18-0.89 (m, 4H).

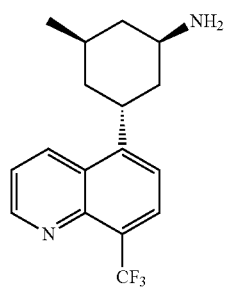 [SMILES: C[C@H]1C[C@@H](N)C[C@H](c2ccc(C(F)(F)F)c3ncccc23)C1]

Compound 137

(5 mg, 0.7%, white solid) HPLC: 98.8% purity, RT=3.88 min. MS: m/z=309.3 [M+H]+. 1H NMR (400 MHz, DMSO-d6, ppm) δ 9.05 (dd, J=4.1, 1.6 Hz, 1H), 8.75 (dd, J=8.8, 1.6 Hz, 1H), 8.13 (d, J=7.7 Hz, 1H), 7.71 (dd, J=8.7, 4.1 Hz, 1H), 7.61 (d, J=7.7 Hz, 1H), 3.64-3.48 (m, 1H), 2.97-2.85 (m, 1H), 2.03-1.76 (m, 4H), 1.33-1.08 (m, 2H), 0.95 (d, J=6.3 Hz, 3H), 0.88-0.74 (m, 1H).

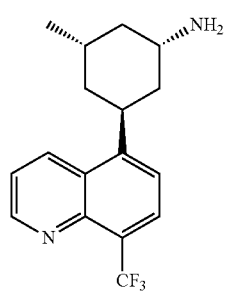

Compound 138

(7 mg, 1%, white solid) HPLC: 94.3% purity, RT=4.22 min. MS: m/z=309.3 [M+H]+. 1H NMR (400 MHz, DMSO-d6, ppm) δ 9.06-9.02 (m, 1H), 8.77-8.66 (m, 1 H), 8.14-8.10 (m, 1H), 7.79-7.67 (m, 2H), 4.15-4.08 (m, 1H), 3.03-2.95 (m, 1H), 2.17-2.09 (m, 1H), 1.96-1.50 (m, 5H), 1.16-0.90 (m, 4H).

Example 28: Synthesis of Compound 139 (1R,3R,5S)-3-methyl-5-(8-(trifluoromethyl)quinoxalin-5-yl)cyclohexanamine, compound 140 (1R,3R,5R)-3-methyl-5-(8-(trifluoromethyl)quinoxalin-5-yl)cyclohexanamine, compound 141 (1S,3S,5S)-3-methyl-5-(8-(trifluoromethyl)quinoxalin-5-yl)cyclohexanamine, and Compound 142 (1S,3S,5R)-3-methyl-5-(8-(trifluoromethyl)quinoxalin-5-yl)cyclohexanamine

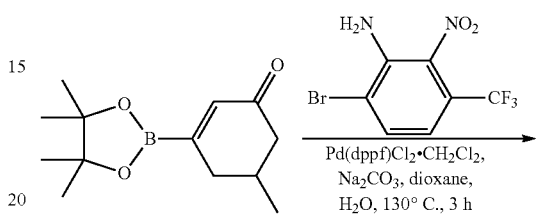

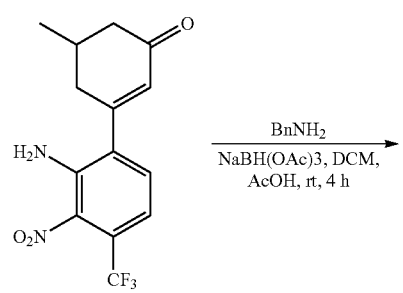

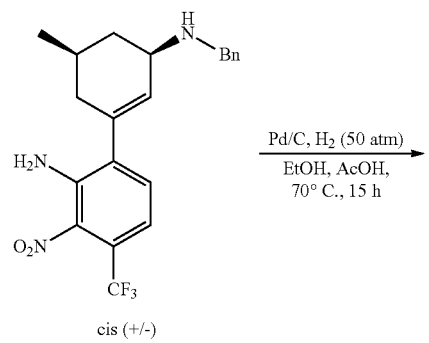

cis (+/−)

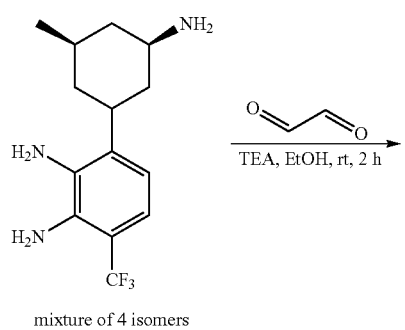

mixture of 4 isomers

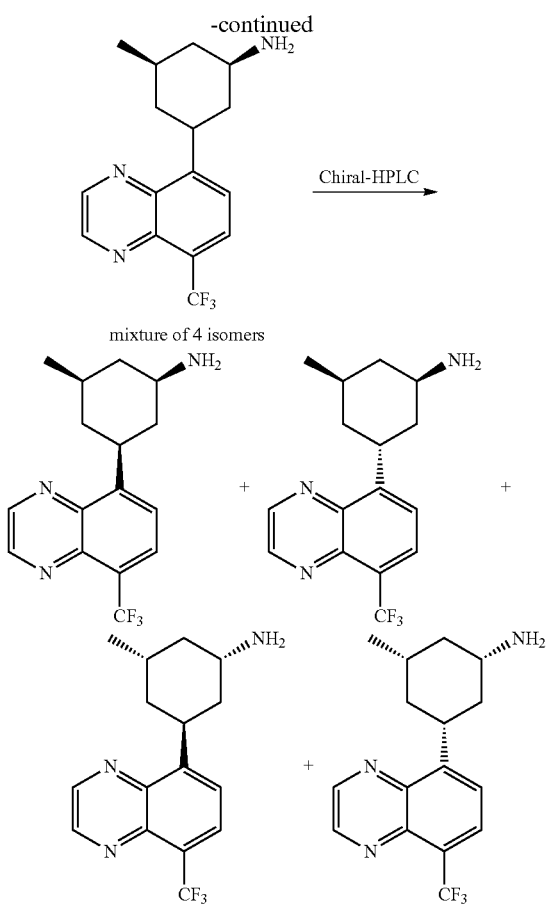

mixture of 4 isomers

3-[2-amino-3-nitro-4-(trifluoromethyl)phenyl]-5-methylcyclohex-2-en-1-one

To a solution of 6-bromo-2-nitro-3-(trifluoromethyl)aniline (3.20 g, 11.23 mmol) in dioxane (150 mL) were added 5-methyl-3-(tetramethyl-1,3,2-dioxaborolan-2-yl)cyclohex-2-en-1-one (3.88 g, 16.44 mmol), Pd(dppf)Cl$_2$·CH$_2$Cl$_2$ (720 mg, 0.88 mmol), sodium carbonate solution (4.27 g in 15 mL water, 40.33 mmol) at room temperature. The resulting mixture was stirred for 3 h at 130° C. When the reaction was done, it was quenched by the addition of water (150 mL). The resulting mixture was extracted with EtOAc (300 mL×3). The organic phases were combined, washed with brine and dried over Na$_2$SO$_4$. The solvent was removed under reduced pressure and the residue was purified by flash chromatography eluting with EtOAc in hexane (0% to 17% gradient) to yield 3-[2-amino-3-nitro-4-(trifluoromethyl)phenyl]-5-methylcyclohex-2-en-1-one as off-white solid (2.8 g, 79%). MS: m/z=315.0 [M+H]$^+$.

6-[(cis-3,5)-3-(benzylamino)-5-methylcyclohex-1-en-1-yl]-2-nitro-3-(trifluoromethyl)aniline At 0° C., to a solution of 3-[2-amino-3-nitro-4-(trifluoromethyl)phenyl]-5-methylcyclohex-2-en-1-one (1.87 g, 5.95 mmol) in dichloromethane (100 mL) was added phenylmethanamine (1.42 g, 13.30 mmol) and AcOH (50 mg, 0.83 mmol). The resulting solution was stirred for 1 h, and then was added by NaBH(OAc)$_3$ (4.23 g, 19.99 mmol) in several batchs at room temperature. The reaction mixture was stirred for 4 h at room temperature. When reaction was done, it was quenched by the addition of water (100 mL). The resulting mixture was extracted with dichloromethane (300 mL×3). The organic phases were combined, washed with brine and dried over Na$_2$SO$_4$. The solvent was removed under reduced pressure and the residue was purified by flash chromatography eluting with EtOAc in hexane (0% to 40% gradient) to yield 2.10 g cude, and then the crude was applied onto C18 gel column and purified by reverse phase flash chromatography eluting with acetonitrile in water (40% to 75% gradient in 35 min) to yield 6-[(cis-3,5)-3-(benzylamino)-5-methylcyclohex-1-en-1-yl]-2-nitro-3-(trifluoromethyl)aniline as yellow solid (1.05 g, 43%). MS: m/z=406.1 [M+H]$^+$.

3-[(cis-3,5)-3-amino-5-methylcyclohexyl]-6-(trifluoromethyl)benzene-1,2-diamine To a solution of 6-[(cis-3,5)-3-(benzylamino)-5-methylcyclohex-1-en-1-yl]-2-nitro-3-(trifluoromethyl)aniline (998 mg, 2.46 mmol) in ethanol (18 mL) was added palladium carbon (279 mg, 2.62 mmol) and HOAc (2 mL) under nitrogen atmosphere. The reaction tank was vacuumed and flushed with hydrogen. The reaction mixture was then hydrogenated for 15 h at 70° C. under 50 atm hydrogen pressures. When the reaction was done, the reaction mixture was filtered through a celite pad and the filtrate was concentrated under reduced pressure. The residue was purified by flash chromatography eluting with MeOH (with 1% TEA) in DCM (0% to 85% gradient) to yield 3-[(cis-3,5)-3-amino-5-methylcyclohexyl]-6-(trifluoromethyl)benzene-1,2-diamine as light brown oil (518 mg, 73%). MS: m/z=288.1 [M+H]$^+$.

(1R,3R,5S)-3-methyl-5-(8-(trifluoromethyl)quinoxalin-5-yl)cyclohexanamine and (1R,3R,5R)-3-methyl-5-(8-(trifluoromethyl)quinoxalin-5-yl)cyclohexanamine and (1S,3S,5S)-3-methyl-5-(8-(trifluoromethyl)quinoxalin-5-yl)cyclohexanamine and (1S,3S,5R)-3-methyl-5-(8-(trifluoromethyl)quinoxalin-5-yl)cyclohexanamine To a solution of 3-[(cis-3,5)-3-amino-5-methylcyclohexyl]-6-(trifluoromethyl)benzene-1,2-diamine (518 mg, 1.80 mmol) in ethanol (20 mL) were added oxaldehyde (200 mg, 3.45 mmol) and TEA (48 mg, 0.47 mmol) at room temperature. The resulting mixture was stirred for 6 h at room temperature. When the reaction was done, reaction mixture was concentrated under reduced pressure and the residue was purified by prep-HPLC under the following conditions: column, XBridge C18 OBD Prep Column, 150 mm, 5 um; mobile phase, acetonitrile in water (with 0.05% TFA), 29% to 33% gradient in 11 min; detector, UV 254 nm. 80 mg mixture of 4 stereoisomers was obtained. The 4 stereoisomers were obtained by separation on chiral prep-HPLC under the following conditions: column, CHIRALPAK IG, 2×25 cm, 5 um; mobile phase, hexane (with 0.1% DEA) in IPA, 90% isocratic in 30 min; detector, UV 220/254 nm.

197

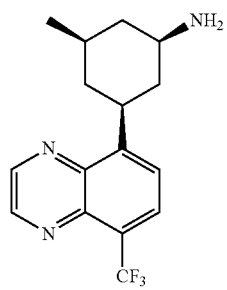

Compound 139

(12 mg, 2%, white solid) HPLC: 97.6% purity, RT=0.98 min. MS: m/z=310.1 [M+H]+. 1H HT-NMR (300 MHz, DMSO-d6, ppm, 353K) δ 9.13-9.00 (m, 2H), 8.18 (d, J=7.6 Hz, 1H), 7.94 (d, J=7.8 Hz, 1H), 4.52-4.43 (m, 1H), 3.03-2.96 (m, 1H), 2.24-2.12 (m, 1H), 2.09-1.97 (m, 1H), 1.91-1.71 (m, 2H), 1.66-1.46 (m, 2H), 1.04-0.87 (m, 4H).

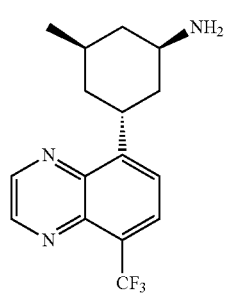 [SMILES: C[C@H]1C[C@@H](N)C[C@H](c2ccc(C(F)(F)F)c3nccnc23)C1]

Compound 140

(12 mg, 2%, white solid) HPLC: 97.2% purity, RT=2.08 min. MS: m/z=310.1 [M+H]+. 1H NMR (300 MHz, Methanol-d4, ppm) δ 9.00-8.91 (m, 2H), 8.14 (d, J=7.8 Hz, 1H), 7.79 (d, J=7.7 Hz, 1H), 4.20-4.03 (m, 1H), 3.15-2.98 (m, 1H), 2.20-2.06 (m, 1H), 2.06-1.71 (m, 3H), 1.53-1.35 (m, 1H), 1.34-1.15 (m, 1H), 1.07-0.89 (m, 4H).

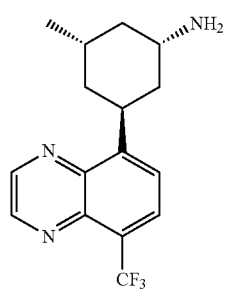

Compound 141

(11 mg, 1.8%, white solid) HPLC: 98.8% purity, RT=3.88 min. MS: m/z=310.1 [M+H]+. 1H NMR (400 MHz, DMSO-d6, ppm) δ 9.09-9.06 (m, 2H), 8.22 (dd, J=11.8, 7.7 Hz, 1H), 7.99 (dd, J=25.6, 7.8 Hz, 1H), 4.44-4.39 (m, 1H), 3.04-2.93 (m, 1H), 2.28-2.20 (m, 1H), 2.09-2.01 (m, 1H), 1.87-1.63 (m, 3H), 1.57-1.44 (m, 1H), 1.04-0.84 (m, 4H).

198

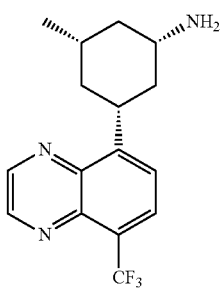 [SMILES: C[C@@H]1C[C@H](N)C[C@H](c2ccc(C(F)(F)F)c3nccnc23)C1]

Compound 142

(9 mg, 1.5%, light brown solid) HPLC: 97.9% purity, RT=1.00 min. MS: m/z=310.1 [M+H]+. 1H NMR (400 MHz, DMSO-d6, ppm) δ 9.16-9.07 (m, 2H), 8.24 (d, J=7.7 Hz, 1H), 7.85 (d, J=7.7 Hz, 1H), 4.09-3.96 (m, 1H), 2.93-2.81 (m, 1H), 1.96 (d, J=11.9 Hz, 1H), 1.92-1.65 (m, 3H), 1.37-1.10 (m, 2H), 1.00-0.78 (m, 4H).

Example 29: Synthesis of Compound 143 ((2R)-2-amino-N-((cis-1,3,5)-3-(8-cyanoquinoxalin-5-yl)-5-methylcyclohexyl)-3,3,3-trifluoropropanamide) and Compound 144 ((2S)-2-amino-N-((cis-1,3,5)-3-(8-cyanoquinoxalin-5-yl)-5-methylcyclohexyl)-3,3,3-trifluoropropanamide)

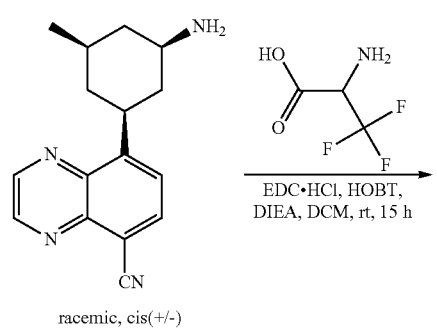

racemic, cis(+/-)

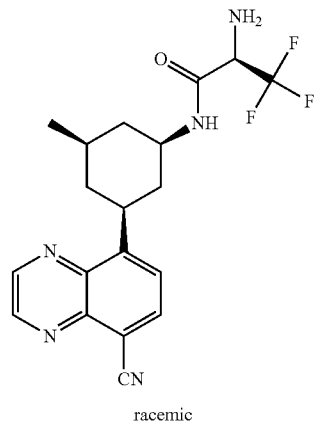

racemic

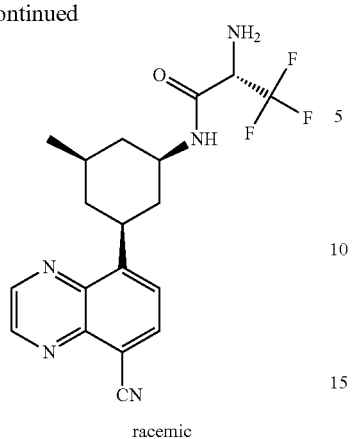

racemic

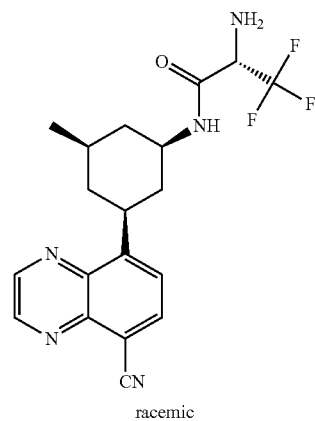 [SMILES: C[C@H]1C[C@@H](NC(=O)[C@H](N)C(F)(F)F)C[C@@H](c2ccc(C#N)c3nccnc23)C1]

racemic

To a solution of 2-amino-3,3,3-trifluoropropanoic acid hydrochloride (52 mg, 0.29 mmol) in dichloromethane (25 mL) was added EDC.HCl (43 mg, 0.22 mmol), HOBT (33 mg, 0.25 mmol) and DIEA (48 mg, 0.37 mmol) at room temperature. The resulting solution was stirred for 2 h at room temperature, and then was added by racemic 8-[(cis-1,3,5)-3-amino-5-methylcyclohexyl]quinoxaline-5-carbonitrile (45 mg, 0.17 mmol). The reaction mixture was stirred for 15 h at room temperature. When the reaction was done, it was quenched by the addition of water (10 mL). The resulting mixture was extracted with DCM (30 mL×3). The organic phases were combined, washed with brine and dried over Na$_2$SO$_4$. The solvent was removed under reduced pressure and the residue was purified by prep-HPLC under the following conditions: column, XBridge C18 OBD Prep Column, 150 mm, 5 um; mobile phase, acetonitrile in water (with 0.05% NH$_3$.H$_2$O), 36% to 42% gradient in 7 min; detector, UV 254 nm to yield the title compounds.

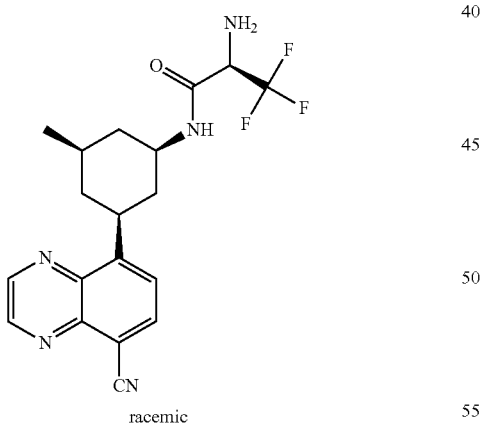

racemic

Compound 143

(10 mg, 15%, white solid) HPLC: 96.7% purity, RT=1.55 min. MS: m/z=392.2 [M+H]$^+$. $^1$H NMR (300 MHz, Methanol-d4, ppm) δ 9.06-8.93 (m, 2H), 8.24 (d, J=7.7 Hz, 1H), 7.81 (d, J=7.7 Hz, 1H), 4.26-3.93 (m, 2H), 3.92-3.78 (m, 1H), 2.17-1.79 (m, 4H), 1.61-1.42 (m, 1H), 1.40-1.18 (m, 1H), 1.17-0.94 (m, 4H).

Compound 144

(10 mg, 15%, white solid) HPLC: 99.6% purity, RT=1.62 min. MS: m/z=392.2 [M+H]$^+$. $^1$H NMR (400 MHz, Methanol-d4, ppm) δ 9.10-9.02 (m, 2H), 8.30 (d, J=7.6 Hz, 1H), 7.86 (d, J=7.6 Hz, 1H), 4.29-4.16 (m, 1H), 4.14-4.01 (m, 1H), 3.95-3.84 (m, 1H), 2.19 (d, J=12.1 Hz, 1H), 2.10-2.02 (m, 1H), 2.01-1.83 (m, 2H), 1.66-1.52 (m, 1H), 1.40-1.26 (m, 1H), 1.17-0.98 (m, 4H).

The following compounds were synthesized in an analogous manner:

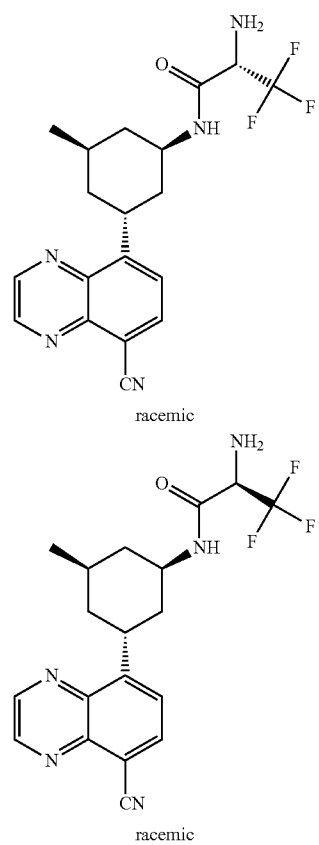

racemic racemic

Compound 145 ((2R)-2-amino-N-((1,cis-3cis-5, trans)-3-(8-cyanoquinoxalin-5-yl)-5-methylcyclohexyl)-3,3,3-trifluoropropanamide) and Compound 146 ((2S)-2-amino-N-((1,cis-3cis-5,trans)-3-(8-cyanoquinoxalin-5-yl)-5-methylcyclohexyl)-3,3,3-trifluoropropanamide)

From racemic 8-((1,cis-3,cis-5, trans)-3-amino-5-methylcyclohexyl)quinoxaline-5-carbonitrile and 2-amino-3,3,3-trifluoropropanoic acid hydrochloride.

Compound 145

(14 mg, 14%, white solid) HPLC: 95.4% purity, RT=2.25 min. MS: m/z=392.2 [M+H]$^+$. $^1$H NMR (400 MHz, Methanol-d4, ppm) δ 9.01 (dd, J=9.6, 1.8 Hz, 2H), 8.24 (d, J=7.6 Hz, 1H), 7.96 (d, J=7.7 Hz, 1H), 4.57-4.48 (m, 1H), 4.18-4.09 (m, 1H), 3.94-3.85 (m, 1H), 2.53-2.43 (m, 1H), 2.23-2.15 (m, 1H), 2.02-1.92 (m, 1H), 1.91-1.74 (m, 2H), 1.68-1.58 (m, 1H), 1.98-0.98 (m, 4H).

Compound 146

(6 mg, 6%, white solid) HPLC: 97.9% purity, RT=1.58 min. MS: m/z=392.2 [M+H]$^+$. $^1$H NMR (400 MHz, Methanol-d4, ppm) δ 9.05-8.99 (m, 2H), 8.29 (d, J=7.6 Hz, 1H), 8.09 (d, J=7.6 Hz, 1H), 4.61-4.50 (m, 1H), 4.18-4.06 (m, 1H), 3.94-3.83 (m, 1H), 2.48-2.39 (m, 1H), 2.27-2.19 (m, 1H), 1.99-1.78 (m, 3H), 1.72-1.59 (m, 1H), 1.22-1.09 (m, 1H), 0.98 (d, J=6.5 Hz, 3H).

Example 30: Synthesis of Compound 159 ((cis-1,3,5)-3-(8-fluoroquinoxalin-5-yl)-N-(2-methoxyethyl)-5-methylcyclohexan-1-amine)

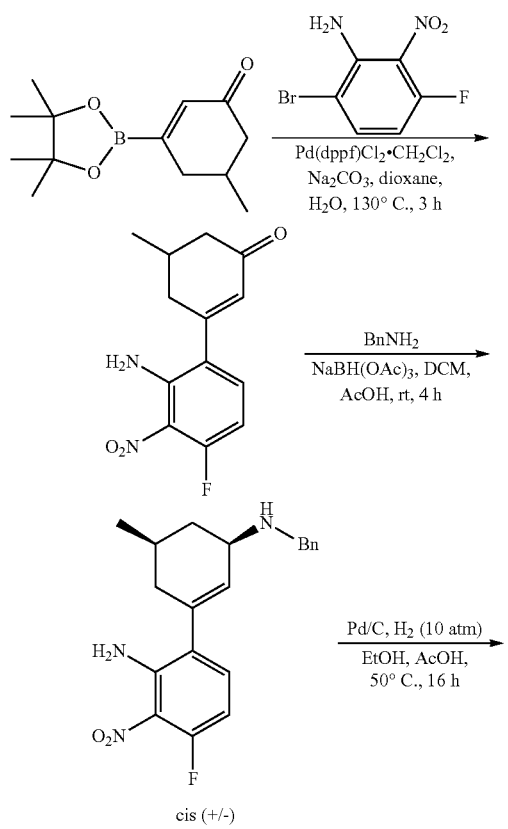

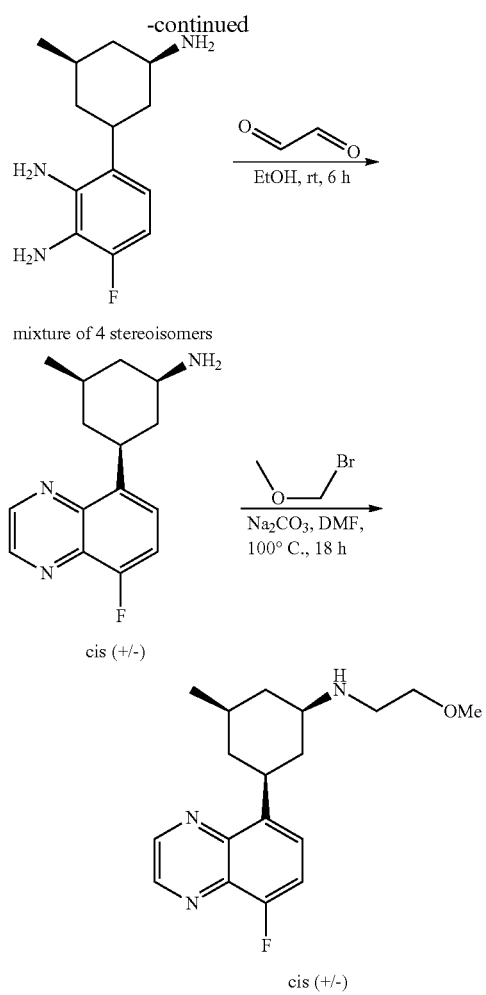

3-(2-amino-4-fluoro-3-nitrophenyl)-5-methylcyclohex-2-en-1-one

To a solution of 6-bromo-3-fluoro-2-nitroaniline (600 mg, 2.55 mmol) in dioxane (10 mL) were added 5-methyl-3-(tetramethyl-1,3,2-dioxaborolan-2-yl)cyclohex-2-en-1-one (720 mg, 3.05 mmol), Pd(dppf)Cl$_2$·CH$_2$Cl$_2$ (198 mg, 0.24 mmol) and sodium carbonate solution (771 mg in 1 mL water, 7.28 mmol) at room temperature. The resulting mixture was stirred for 3 h at 130° C. When the reaction was done, the reaction mixture was concentrated under reduced pressure and the residue was purified by flash chromatography eluting with petroleum ether in EtOAc (0% to 25% gradient) to yield 3-(2-amino-4-fluoro-3-nitrophenyl)-5-methylcyclohex-2-en-1-one as red solid (700 mg, 91%). MS: m/z=265.0 [M+H]$^+$.

3-[(cis-3,5)-3-amino-5-methylcyclohexyl]-6-fluorobenzene-1,2-diamine

To a solution of 3-(2-amino-4-fluoro-3-nitrophenyl)-5-methylcyclohex-2-en-1-one (440 mg, 1.66 mmol) in dichloromethane (15 mL) was added phenylmethanamine (481 mg, 4.49 mmol) at room temperature. The resulting mixture was stirred at room temperature for 30 min, and then were added by NaBH(AcO)$_3$ (1.14 g, 5.38 mmol) and AcOH (0.03 mL, 0.50 mmol) at room temperature. The reaction mixture was stirred for another 4 h at room temperature. When the reaction was done, it was quenched by the addition of water (5 mL). The resulting mixture was extracted with ethyl acetate (30 mL×3). The organic phases were combined, washed with brine and dried over Na$_2$SO$_4$. The solvent was removed under reduced pressure and the residue was purified by reverse phase flash chromatography eluting with acetonitrile in water (with 10 mmol/L NH$_4$HCO$_3$), (0% to 35% gradient in 45 min), to separate the cis isomer product. 6-[(cis-3,5)-3-(benzylamino)-5-methylcyclohex-1-en-1-yl]-3-fluoro-2-nitroaniline was obtained as yellow oil (298 mg, 35%). MS: m/z=356.3 [M+H]$^+$.

3-[(cis-3,5)-3-amino-5-methylcyclohexyl]-6-fluorobenzene-1,2-diamine

To a solution of 6-[(cis-3,5)-3-(benzylamino)-5-methylcyclohex-1-en-1-yl]-3-fluoro-2-nitroaniline (285 mg, 0.80 mmol) in EtOH (20 mL) was added palladium carbon (6 mg, 0.06 mmol) and AcOH (0.1 mL, 1.75 mmol) under nitrogen atmosphere at room temperature. The reaction tank was vacuumed and flushed with hydrogen. The reaction mixture was hydrogenated for 16 h at 50° C. under 10 atm hydrogen pressures. When the reaction was done, the reaction mixture was filtered through a celite pad and the filtrate was concentrated under reduced pressure. The residue was purified by flash chromatography eluting with MeOH (with 1% ammonia) in DCM (0% to 40% gradient) to yield 3-[(cis-3,5)-3-amino-5-methylcyclohexyl]-6-fluorobenzene-1,2-diamine as yellow oil (105 mg, 55%). MS: m/z=238.1 [M+H]$^+$.

(cis-1,3,5)-3-(8-fluoroquinoxalin-5-yl)-5-methylcyclohexanamine

To a solution of 3-[(3R,5R)-3-amino-5-methylcyclohexyl]-6-fluorobenzene-1,2-diamine (490 mg, 2.06 mmol) in ethanol (20 mL) was added TEA (143 mg, 1.41 mmol) and oxaldehyde (452 mg, 7.79 mmol) at room temperature. The resulting solution was stirred for 6 h at room temperature. When the reaction was done, the reaction mixture was concentrated under reduced pressure and the residue was purified by prep-HPLC under the following conditions: column, XBridge BEH130 Prep C18 OBD column, 150 mm, 5 um, 13 nm; mobile phase, acetonitrile in water (with 0.05% NH$_4$OH), 30% to 65% gradient in 10 min; detector, UV 254 nm. (cis-1,3,5)-3-(8-fluoroquinoxalin-5-yl)-5-methylcyclohexanamine was obtained as white solid (174 mg, 32%). MS: m/z=260.1 [M+H]$^+$.

(cis-1,3,5)-3-(8-fluoroquinoxalin-5-yl)-N-(2-methoxyethyl)-5-methylcyclohexan-1-amine To a solution of (1R,3S,5R)-3-(8-fluoroquinoxalin-5-yl)-5-methylcyclohexanamine (174 mg, 0.67 mmol) in MeCN (5 mL) were added sodium carbonate (105 mg, 0.99 mmol) and 1-bromo-2-methoxyethane (202 mg, 1.46 mmol) at room temperature. The resulting mixture was stirred for 18 h at 90° C. When the reaction was done, it was quenched by the addition of water (5 mL). The resulting mixture was extracted with DCM (30 mL×3). The organic phases were combined, washed with brine and dried over Na$_2$SO$_4$. The solvent was removed under reduced pressure and the residue was purified by prep-HPLC under the following conditions: column, XBridge BEH130 Prep C18 OBD column, 150 mm, 5 um, 13 nm; mobile phase, acetonitrile in water (with 10 mM NH$_4$HCO$_3$ and 0.1% NH$_3$.H$_2$O), 5% to 72% gradient in 7 min; detector, UV 254 nm. (cis-1,3,5)-3-(8-fluoroquinoxalin-5-yl)-N-(2-methoxyethyl)-5-methylcyclohexan-1-amine was obtained as white solid (5 mg, 2%).

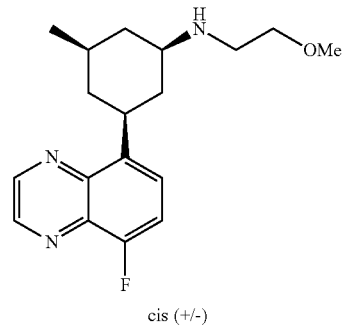 [SMILES: COCCN[C@@H]1C[C@H](C)C[C@H](c2ccc(F)c3nccnc23)C1]

Compound 159

HPLC: 97.3% purity, RT=3.56 min. MS: m/z=318.1 [M+H]$^+$. $^1$H NMR (300 MHz, DMSO-d$_6$, ppm) δ 9.05 (d, J=1.8 Hz, 1H), 9.00 (d, J=1.9 Hz, 1H), 7.72-7.62 (m, 2H), 3.96-3.79 (m, 1H), 3.44-3.32 (m, 3H), 3.21 (s, 3H), 2.73-2.60 (m, 2H), 2.07-1.89 (m, 2H), 1.83-1.59 (m, 2H), 1.34-1.07 (m, 3H), 0.97-0.68 (m, 4H).

Example 31: Synthesis of Compound 160 ((cis-1,3,5)-3-(8-fluoroquinolin-5-yl)-N-(2-methoxyethyl)-5-methylcyclohexan-1-amine)

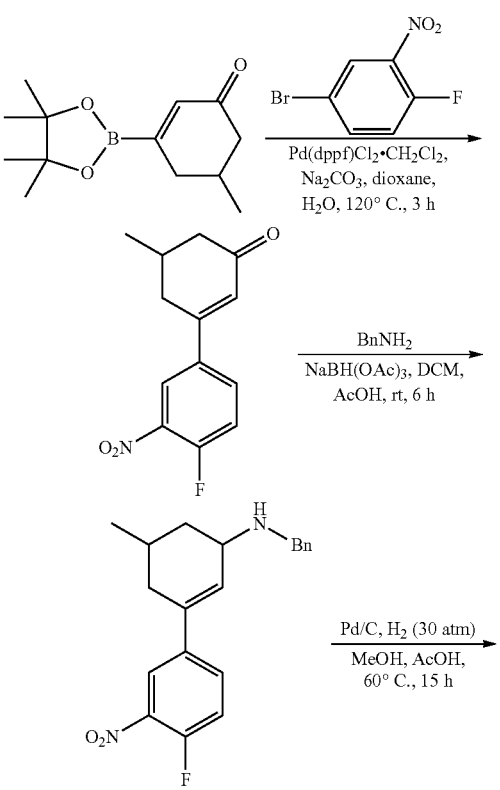

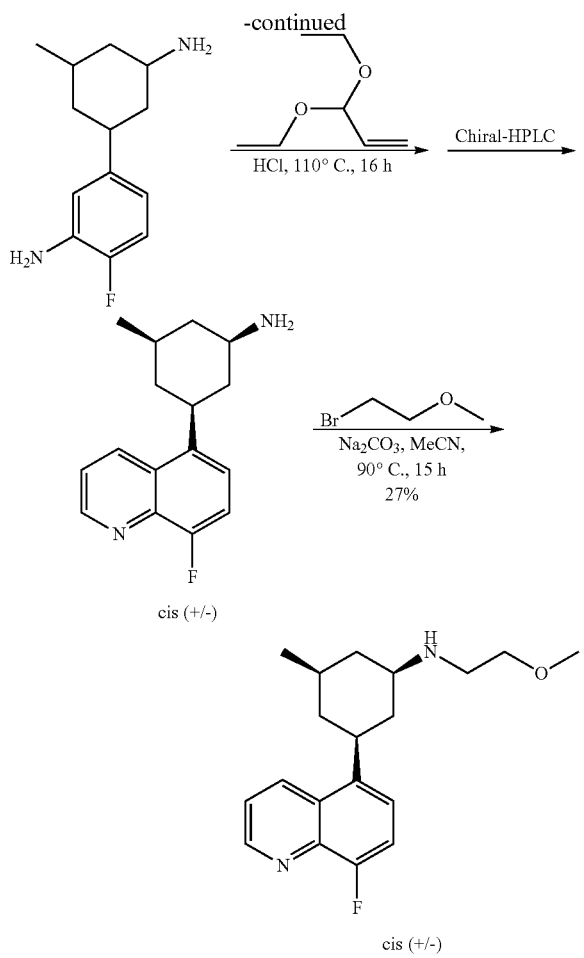

3-(4-fluoro-3-nitrophenyl)-5-methylcyclohex-2-en-1-one

To a solution of 4-bromo-1-fluoro-2-nitrobenzene (4.75 g, 21.59 mmol) in dioxane (150 mL) was added 5-methyl-3-(tetramethyl-1,3,2-dioxaborolan-2-yl)cyclohex-2-en-1-one (5.95 g, 25.20 mmol), Pd(dppf)Cl$_2$·CH$_2$Cl$_2$ (1.26 g, 1.54 mmol) and sodium carbonate solution (6.93 g in 15 mL water, 65.43 mmol) at room temperature. The resulting mixture was stirred for 3 h at 120° C. When the reaction was done, the reaction mixture was concentrated under reduced pressure and the residue was purified by flash chromatography eluting with petroleum ether in EtOAc (0% to 10% gradient) to yield 3-(4-fluoro-3-nitrophenyl)-5-methylcyclohex-2-en-1-one as brown oil (3.20 g, 59%). MS: m/z=250.0 [M+H]$^+$.

N-benzyl-3-(4-fluoro-3-nitrophenyl)-5-methylcyclohex-2-en-1-amine

To a solution of 3-(4-fluoro-3-nitrophenyl)-5-methylcyclohex-2-en-1-one (1.70 g, 6.82 mmol) in dichloromethane (100 mL) was added phenylmethanamine (2.66 g, 24.82 mmol) at room temperature. The resulting solution was stirred for 30 min, and then were added by NaBH(OAc)$_3$ (4.94 g, 23.31 mmol) and AcOH (0.1 mL) at room temperature. The reaction mixture was stirred for 8 at room temperature. When the reaction was done, it was quenched by the addition of water (50 mL). The resulting mixture was extracted with ethyl acetate (150 mL×3). The organic phases were combined, washed with brine and dried over Na$_2$SO$_4$. The solvent was removed under reduced pressure and the residue was purified by flash chromatography eluting with MeOH in DCM (0% to 60% gradient) to yield N-benzyl-3-(4-fluoro-3-nitrophenyl)-5-methylcyclohex-2-en-1-amine as light brown oil (1.20 g, 52%). MS: m/z=341.1 [M+H]$^+$.

5-(3-amino-5-methylcyclohexyl)-2-fluoroaniline

To a solution of N-benzyl-3-(4-fluoro-3-nitrophenyl)-5-methylcyclohex-2-en-1-amine (1.04 g, 3.06 mmol) in methanol (15) was added palladium carbon (26 mg, 0.24 mmol) and acetic acid (10 mg, 0.15 mmol) under nitrogen atmosphere. The reaction tank was vacuumed and flushed with hydrogen. The reaction mixture was hydrogenated for 15 h at 60° C. under 30 atm hydrogen pressures. When the reaction was done, the reaction mixture was filtered through a celite pad and the filtrate was concentrated under reduced pressure. The residue was purified by flash chromatography eluting with MeOH (with 1% ammonia) in DCM (0% to 15% gradient) to yield 5-(3-amino-5-methylcyclohexyl)-2-fluoroaniline as light brown oil (510 mg, 75%). MS: m/z=223.3 [M+H]$^+$.

(cis-1,3,5)-3-(8-fluoroquinolin-5-yl)-5-methylcyclohexan-1-amine

To a solution of 5-(3-amino-5-methylcyclohexyl)-2-fluoroaniline (425 mg, 1.91 mmol) in hydrogen chloride solution (60 mL, IM) was added 3,3-diethoxyprop-1-ene (570 mg, 4.38 mmol) at room temperature. The reaction mixture was stirred for 15 h at 110° C. When the reaction was done, the pH mixture of the reaction mixture was adjusted to 9 with NH$_3$·H$_2$O solution. The resulting mixture was extracted with ethyl acetate (200 mL×3). The organic phases were combined, washed with brine and dried over Na$_2$SO$_4$. The solvent was removed under reduced pressure and the residue was purified by flash chromatography eluting with MeOH in DCM (0% to 10% gradient) to yield 165 mg crude product. The racemic cis-1,3,5 isomers were obtained using the chiral HPLC separation under the following conditions: column, CHIRALPAK IG, 2×25 cm, 5 um; mobile phase, hexane (with 0.2% IPA) in EeOH, 30% isocratic in 15 min; detector, UV 254/220 nm. (cis-1,3,5)-3-(8-fluoroquinolin-5-yl)-5-methylcyclohexan-1-amine was obtained as light yellow oil (50 mg, 10%). MS: m/z=259.1 [M+H]$^+$.

(cis-1,3,5)-3-(8-fluoroquinolin-5-yl)-N-(2-methoxyethyl)-5-methylcyclohexan-1-amine To a solution of (cis-1,3,5)-3-(8-fluoroquinolin-5-yl)-5-methylcyclohexan-1-amine (50 mg, 0.19 mmol) in MeCN (6 mL) was added sodium carbonate (68 mg, 0.65 mmol) and 1-bromo-2-methoxyethane (36 mg, 0.26 mmol) at room temperature. The resulting mixture was stirred for 15 h at 90° C. When the reaction was done, the reaction mixture was filtered to remove insoluable solids and the filtrate was concentrated under reduced pressure. The residue was purified by prep-HPLC under the following conditions: column, XBridge Prep C18 OBD column, 150 mm, 5 um, 13 nm; mobile phase, acetonitrile in water (0.05% NH$_3$·H$_2$O), 38% to 46% gradient in 8 min; detector, UV 254 nm. (cis-1,3,5)-3-(8-fluoroquinolin-5-yl)-N-(2-methoxyethyl)-5-methylcyclohexan-1-amine was obtained as light yellow semi-solid (15 mg, 24%).

Compound 160

HPLC: 98.0% purity, RT=1.34 min. MS: m/z=317.2 [M+H]$^+$. $^1$H NMR (400 MHz, DMSO-d$_6$, ppm) δ 8.96 (dd, J=4.1, 1.5 Hz, 1H), 8.66-8.64 (m, 1H), 7.71-7.62 (m, 1H), 7.59-7.40 (m, 2H), 3.47-3.31 (m, 3H), 3.23 (s, 3H), 2.87-2.60 (m, 3H), 2.07-1.62 (m, 4H), 1.31-1.07 (m, 2H), 0.96 (d, J=6.5 Hz, 3H), 0.86-0.73 (m, 1H).

Example 32: HEK Cell Assay

Into 384 CulturePlates (Corning 3707) was placed 5000 c/w of TLR7/NFKb HEK cells in 30 uL DMEM without Phenil red (gibco #31053) and 10% i.a. FCS and 2 mM L-ZGLutamin. The cells were incubated for 24 h at 37 degrees Celsius, 10% carbon dioxide and 90% relative humidity. 3 uL of controls, standards, and compounds were dispensed to wells, incubated for 30 min then 3 uL of R*48 agonist in 20 mM Hepes was added. After incubation for 5 hours, it was allowed to stand at room temperature for 15 min. 10 uL of Steady-Glo substrate reagent was added and shake assay plate for 5 min at 1500 rpm. The assay plate was allowed to sit for 30 min at room temperature and then read plate on EnVision.

Results are given in the following table.
A: IC$_{50}$<1 uM
B: IC$_{50}$: 1 uM-20 uM
C: IC$_{50}$>20 uM

TABLE 1

| Example | Compound | Potency |
|---|---|---|
| 1 | 1 | A |
| 1 | 2 | A |
| 1 | 19 | A |
| 1 | 20 | C |
| 1 | 21 | C |
| 1 | 22 | A |
| 1 | 23 | A |
| 1 | 24 | C |
| 1 | 25 | B |
| 1 | 26 | C |
| 1 | 27 | C |
| 1 | 28 | B |
| 1 | 29 | A |
| 1 | 30 | A |
| 1 | 31 | B |
| 1 | 32 | B |
| 1 | 33 | B |
| 1 | 34 | B |
| 1 | 35 | A |
| 1 | 36 | C |
| 1 | 37 | C |
| 1 | 38 | C |
| 1 | 39 | B |
| 1 | 107 | C |
| 1 | 108 | B |
| 2 | 3 | A |
| 2 | 4 | A |
| 2 | 11 | B |
| 2 | 12 | C |
| 2 | 13 | C |
| 2 | 14 | C |
| 2 | 15 | C |
| 2 | 16 | C |
| 2 | 17 | C |
| 2 | 18 | A |
| 3 | 5 | C |
| 3 | 6 | C |
| 3 | 78 | A |
| 3 | 79 | A |
| 4 | 7 | C |
| 4 | 8 | C |
| 5 | 9 | C |

TABLE 1-continued

| Example | Compound | Potency |
|---|---|---|
| 5 | 10 | C |
| 6 | 40 | B |
| 6 | 41 | B |
| 7 | 42 | A |
| 7 | 43 | B |
| 7 | 44 | A |
| 7 | 45 | B |
| 7 | 46 | A |
| 7 | 47 | B |
| 8 | 48 | C |
| 9 | 49 | C |
| 10 | 50 | C |
| 10 | 68 | B |
| 10 | 69 | B |
| 10 | 70 | B |
| 10 | 71 | B |
| 10 | 72 | B |
| 10 | 73 | B |
| 10 | 74 | B |
| 10 | 75 | B |
| 10 | 76 | C |
| 10 | 77 | C |
| 11 | 51 | A |
| 11 | 52 | A |
| 12 | 53 | A |
| 12 | 54 | A |
| 12 | 55 | A |
| 12 | 56 | B |
| 13 | 57 | C |
| 13 | 58 | B |
| 13 | 59 | B |
| 14 | 60 | B |
| 14 | 61 | B |
| 14 | 62 | B |
| 14 | 63 | B |
| 14 | 64 | A |
| 14 | 65 | A |
| 15 | 66 | C |
| 15 | 67 | C |
| 16 | 80 | A |
| 16 | 81 | A |
| 16 | 82 | B |
| 16 | 83 | A |
| 16 | 84 | A |
| 16 | 86 | A |
| 16 | 87 | A |
| 16 | 88 | B |
| 16 | 89 | B |
| 16 | 90 | A |
| 17 | 85 | B |
| 17 | 91 | B |
| 17 | 92 | A |
| 17 | 93 | A |
| 17 | 94 | B |
| 17 | 95 | B |
| 17 | 96 | B |
| 17 | 97 | A |
| 17 | 98 | C |
| 17 | 99 | B |
| 17 | 100 | A |
| 17 | 101 | C |
| 17 | 102 | A |
| 17 | 103 | B |
| 17 | 104 | C |
| 17 | 105 | B |
| 18 | 106 | C |
| 19 | 109 | A |
| 19 | 110 | B |
| 19 | 111 | — |
| 19 | 112 | A |
| 19 | 113 | A |
| 19 | 114 | B |
| 19 | 115 | B |
| 20 | 116 | A |
| 20 | 117 | B |
| 21 | 118 | B |
| 21 | 119 | B |
| 22 | 120 | A |

TABLE 1-continued

| Example | Compound | Potency |
|---|---|---|
| 23 | 121 | A |
| 23 | 122 | B |
| 24 | 123 | A |
| 24 | 124 | C |
| 25 | 125 | A |
| 25 | 126 | B |
| 25 | 127 | C |
| 25 | 128 | B |
| 25 | 129 | A |
| 25 | 130 | B |
| 25 | 131 | A |
| 25 | 132 | B |
| 25 | 154 | A |
| 25 | 155 | B |
| 25 | 156 | B |
| 25 | 157 | A |
| 25 | 158 | A |
| 26 | 133 | A |
| 26 | 134 | B |
| 26 | 147 | C |
| 26 | 148 | B |
| 26 | 149 | B |
| 26 | 150 | C |
| 26 | 151 | B |
| 26 | 152 | C |
| 26 | 153 | B |
| 27 | 135 | B |
| 27 | 136 | A |
| 27 | 137 | B |
| 27 | 138 | A |
| 28 | 139 | A |
| 28 | 140 | B |
| 28 | 141 | A |
| 28 | 142 | A |
| 29 | 143 | B |
| 29 | 144 | B |
| 29 | 145 | B |
| 29 | 146 | B |
| 30 | 159 | B |
| 31 | 160 | C |

Example 33. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I-e,

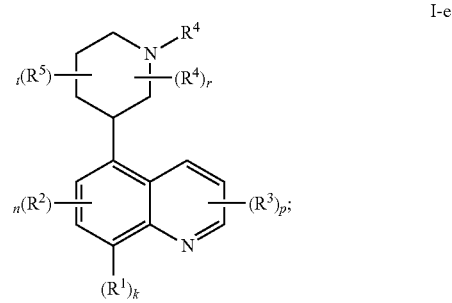

or a pharmaceutically acceptable salt thereof, wherein:
$R^1$ is —$CF_3$ or —CN;
each $R^2$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
each $R^3$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
$R^4$ is $C_{1-6}$ aliphatic, —C(O)R, —C(O)N(R)$_2$, —C(NH)NR$_2$, —NRC(O)R, —N(R)$_2$; or 5-6 membered monocyclic heteroaryl ring having 1-4 heteroatoms independently selected from nitrogen, oxygen, or sulfur; each of which is optionally substituted;
each $R^5$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted, halogen, -haloalkyl, —OR, —SR, —CN, —NO₂, —SO₂R, —SOR, —C(O)R, —CO₂R, —C(O)N(R)₂, —NRC(O)R, —NRC(O)N(R)₂, —NRSO₂R, or —N(R)₂;

each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

k is 1;
n is 0, 1, or 2;
p is 0;
r is 0; and
t is 1 or 2.

2. The compound of claim 1, wherein $R^2$ is —H, —R, halogen, -haloalkyl, —OR, —CN, or —N(R)₂.

3. The compound of claim 1, wherein $R^4$ is

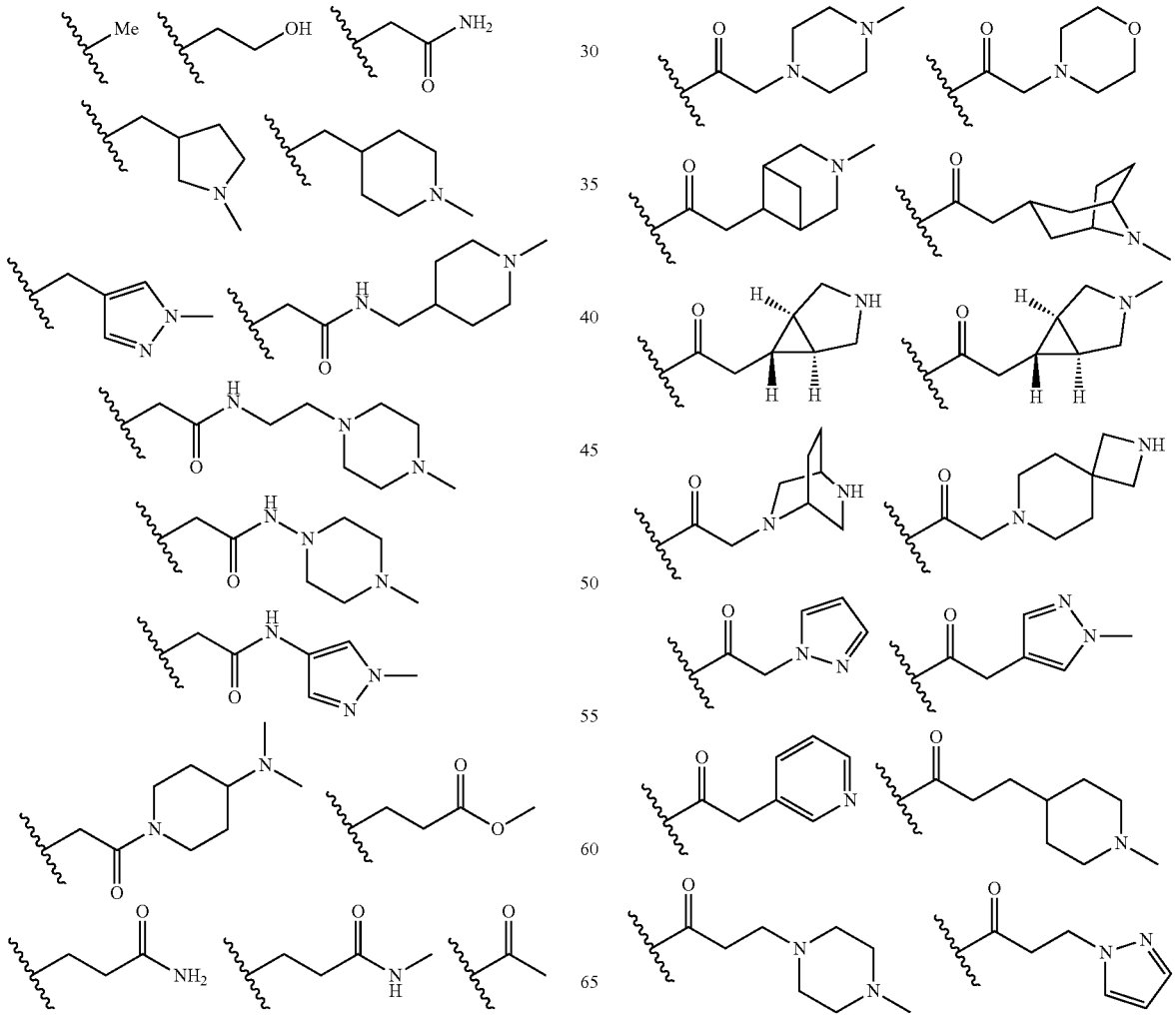

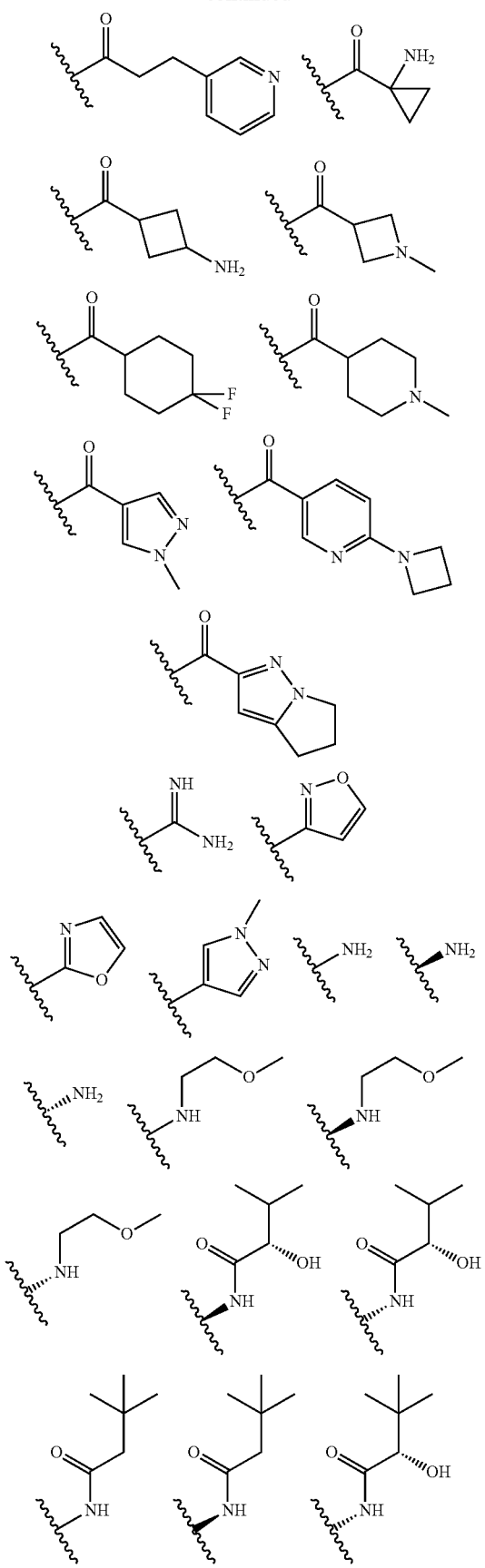

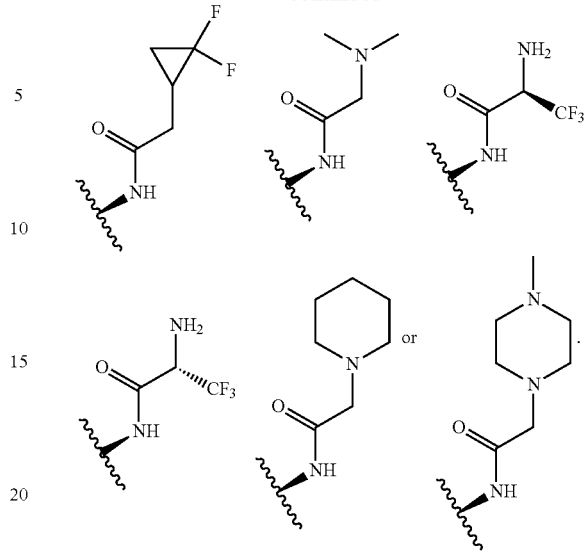

4. The compound of claim 1, wherein each $R^5$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

5. The compound of claim 4, wherein each $R^5$ is independently methyl, ethyl, ethyl, propyl, i-propyl, butyl, s-butyl, t-butyl, straight or branched pentyl, or straight or branched hexyl; each of which is optionally substituted.

6. A compound wherein the compound is selected from the group consisting of compounds shown in the following Table or a pharmaceutically acceptable salt thereof

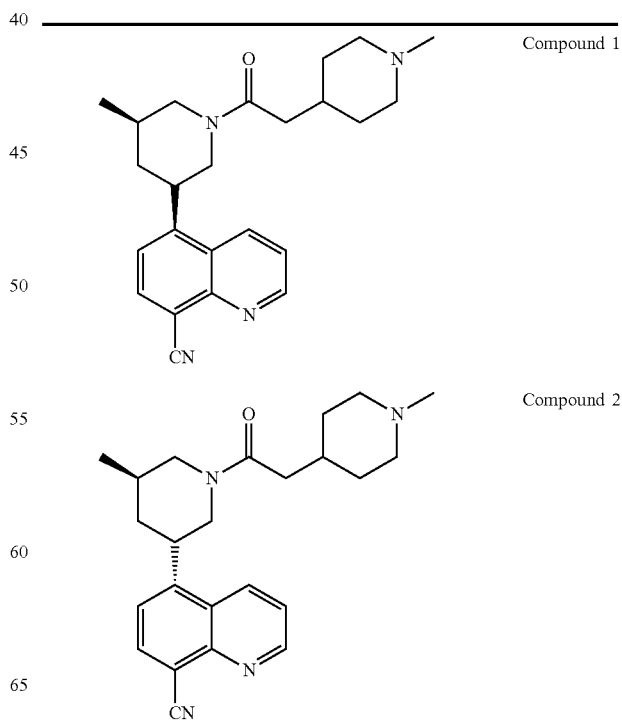

-continued
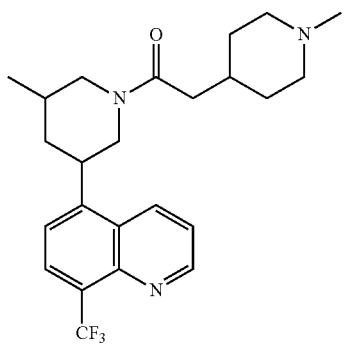
Compound 3
Compound 4
Compound 5
Compound 6
Compound 7
-continued
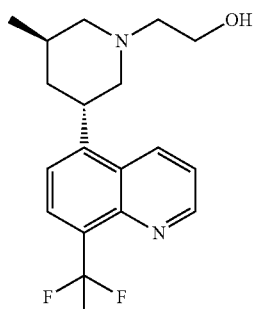
Compound 8
Compound 9
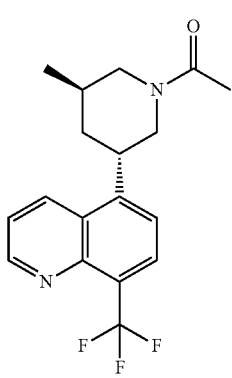 [SMILES: CC(=O)N1C[C@H](C)C[C@@H](c2ccc(C(F)(F)F)c3ncccc23)C1]
Compound 10
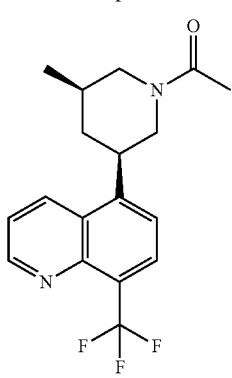
Compound 11
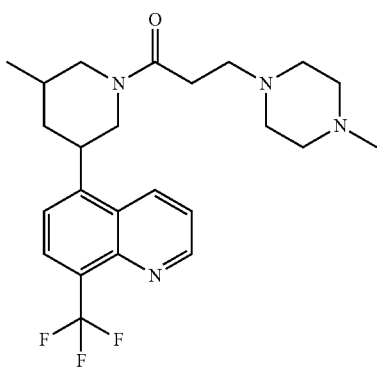

-continued
Compound 12
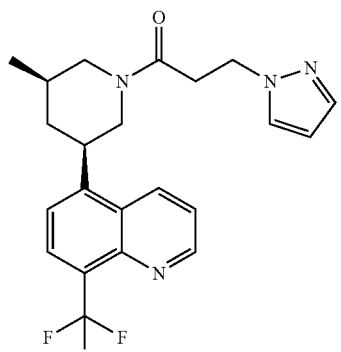
Compound 13
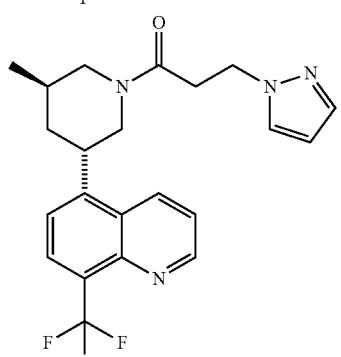
Compound 14
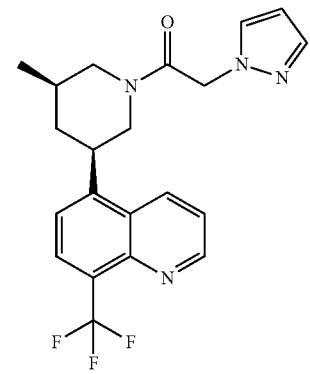 [SMILES: C[C@@H]1C[C@H](c2ccc(C(F)(F)F)c3ncccc23)CN(C(=O)Cn2cccn2)C1]
Compound 15
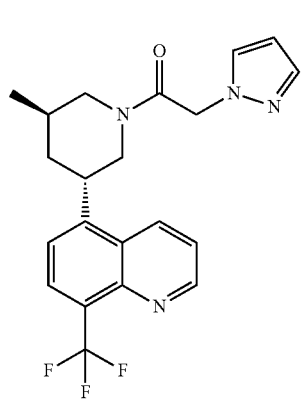 [SMILES: C[C@@H]1C[C@@H](c2ccc(C(F)(F)F)c3ncccc23)CN(C(=O)Cn2cccn2)C1]
-continued
Compound 16
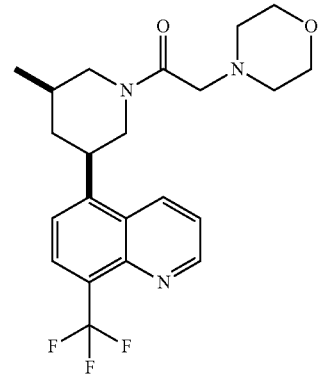
Compound 17
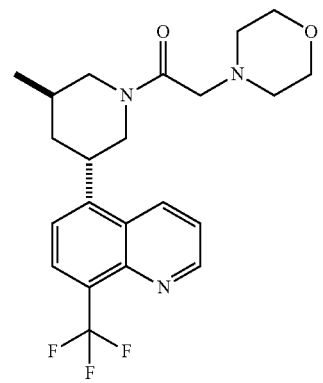
Compound 18
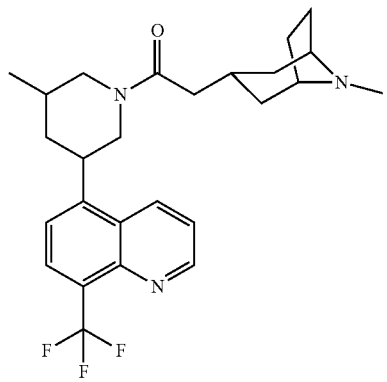
Compound 19
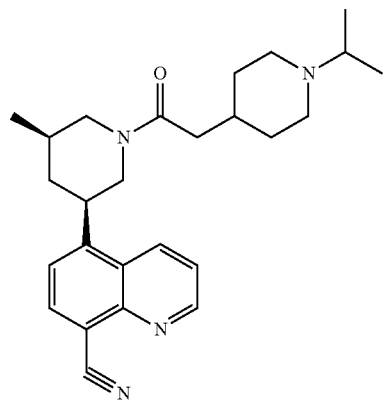 [SMILES: CC(C)N1CCC(CC(=O)N2C[C@H](C)C[C@H](c3ccc(C#N)c4ncccc34)C2)CC1]

US 10,947,214 B2
219
-continued
Compound 20
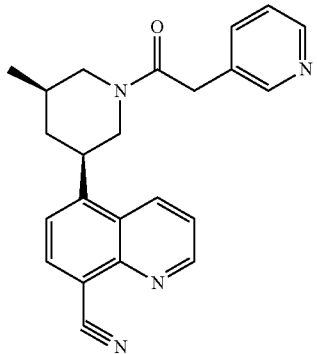 [SMILES: C[C@@H]1C[C@H](c2ccc(C#N)c3ncccc23)CN(C(=O)Cc2cccnc2)C1]
Compound 21
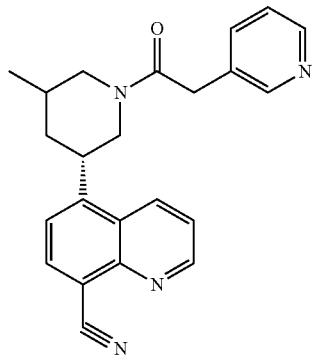 [SMILES: CC1C[C@@H](c2ccc(C#N)c3ncccc23)CN(C(=O)Cc2cccnc2)C1]
Compound 23
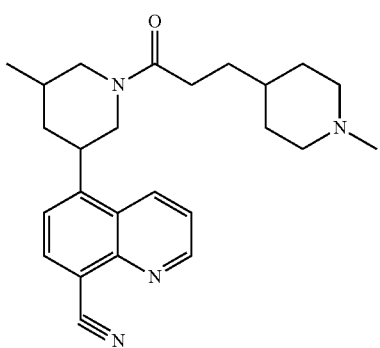
Compound 24
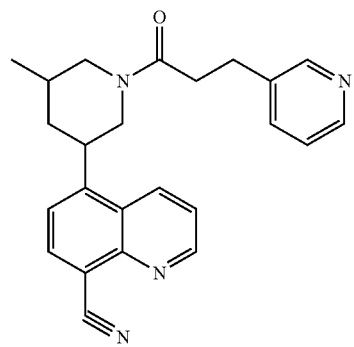
220
-continued
Compound 25
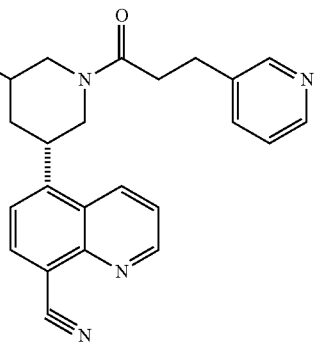
Compound 26
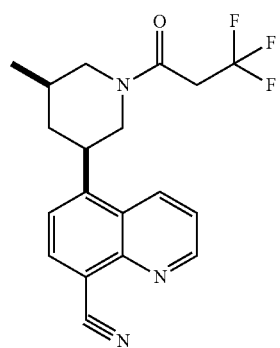
Compound 27
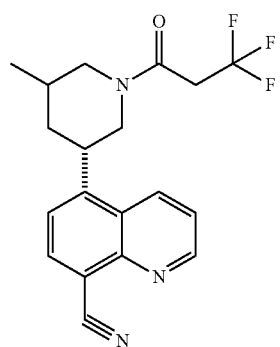
Compound 28
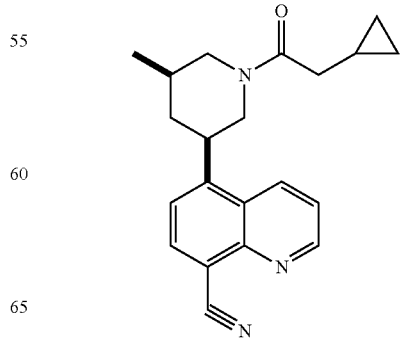

221
-continued
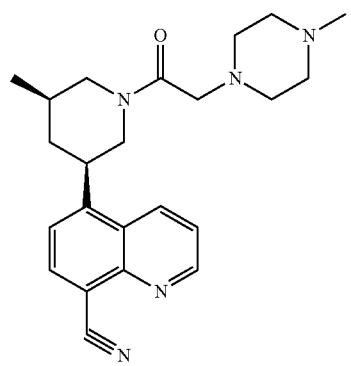
Compound 29
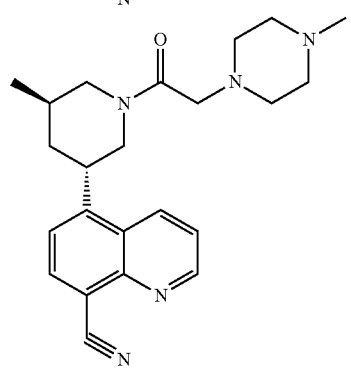
Compound 30
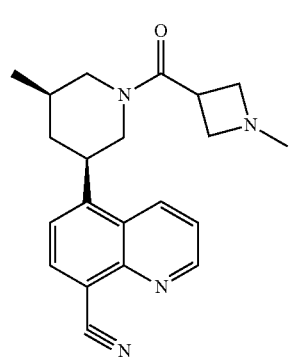
Compound 31
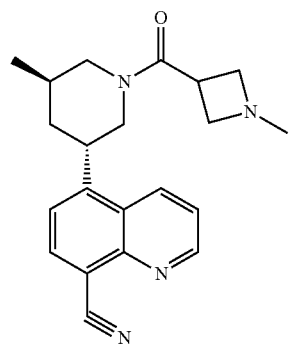
Compound 32
222
-continued
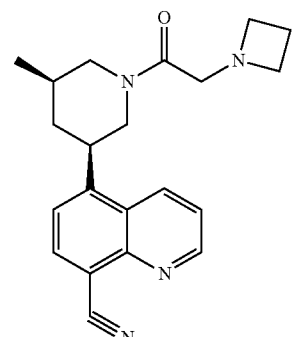
Compound 33
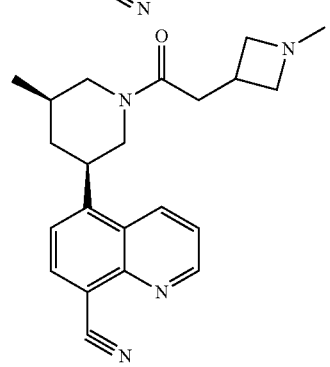
Compound 34
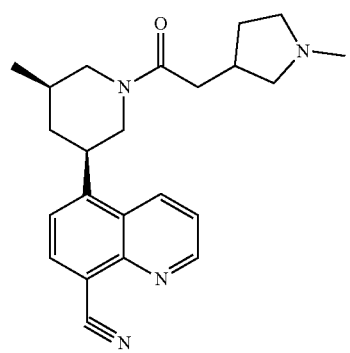
Compound 35
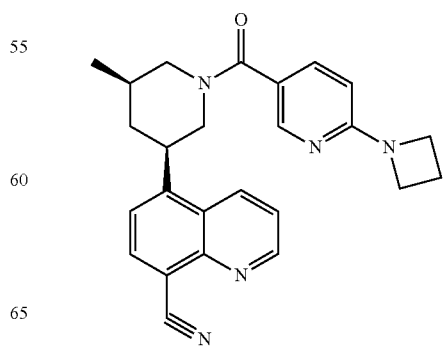
Compound 36

223
-continued
Compound 37
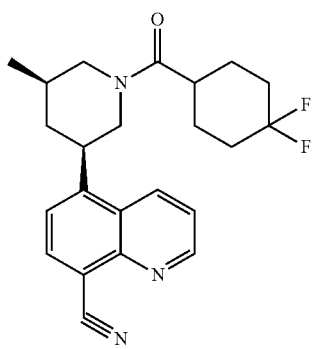 [SMILES: C[C@@H]1C[C@H](c2ccc(C#N)c3ncccc23)CN(C(=O)C2CCC(F)(F)CC2)C1]
Compound 38
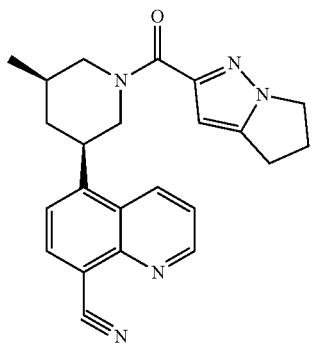 [SMILES: C[C@@H]1C[C@H](c2ccc(C#N)c3ncccc23)CN(C(=O)c2cc3n(n2)CCC3)C1]
Compound 39
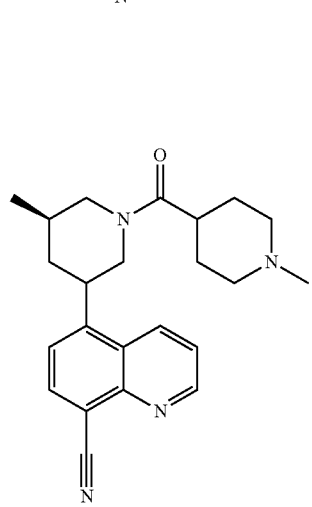
Compound 40
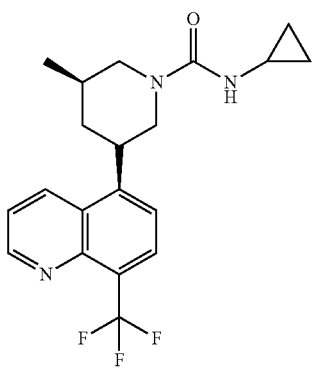
224
-continued
Compound 41
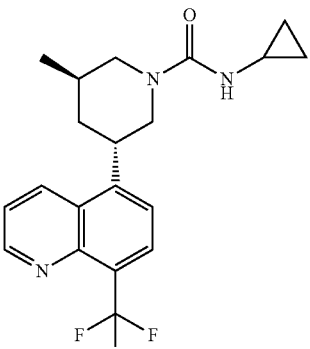
Compound 42
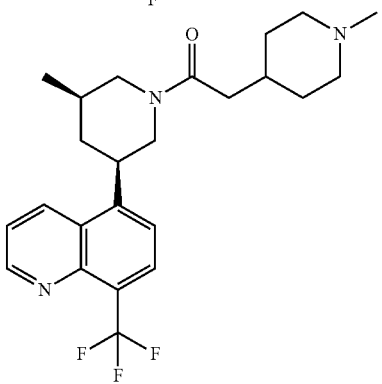
Compound 43
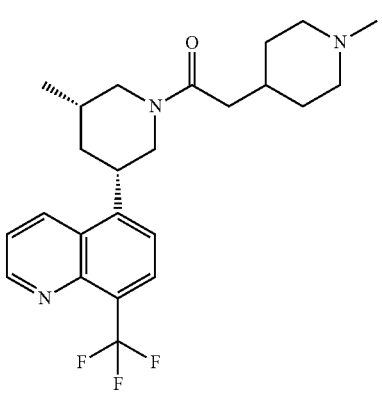 [SMILES: C[C@H]1C[C@@H](c2ccc(C(F)(F)F)c3ncccc23)CN(C(=O)CC2CCN(C)CC2)C1]
Compound 44
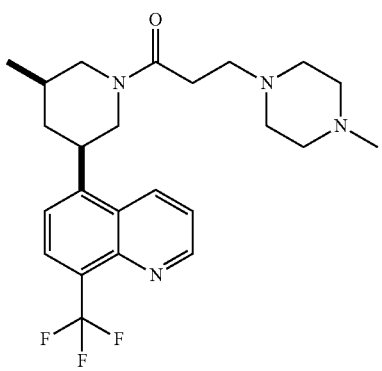

225
-continued
Compound 45
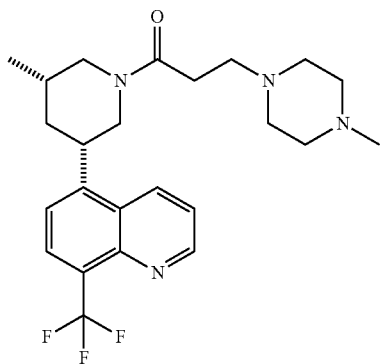
Compound 46
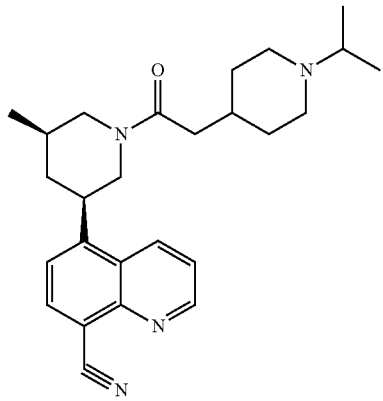 [SMILES: CC(C)N1CCC(CC(=O)N2C[C@H](C)C[C@H](c3ccc(C#N)c4ncccc34)C2)CC1]
Compound 47
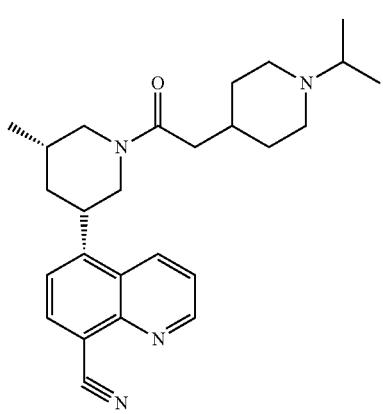
Compound 48
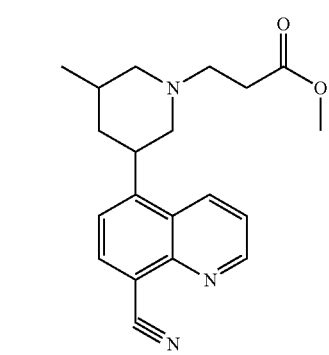
226
-continued
Compound 49
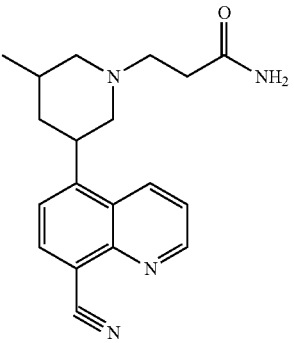 [SMILES: CC1CC(c2ccc(C#N)c3ncccc23)CN(CCC(N)=O)C1]
Compound 50
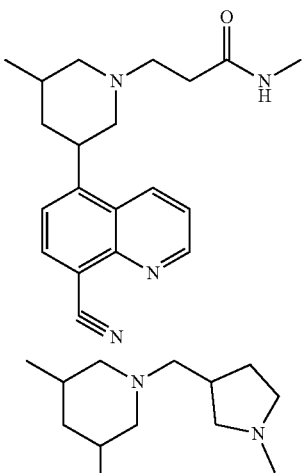
Compound 51
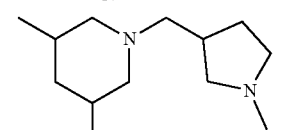
Compound 52
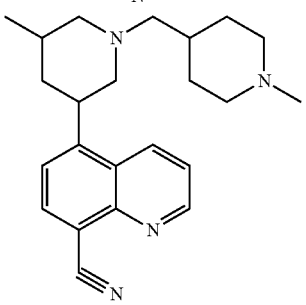
Compound 53
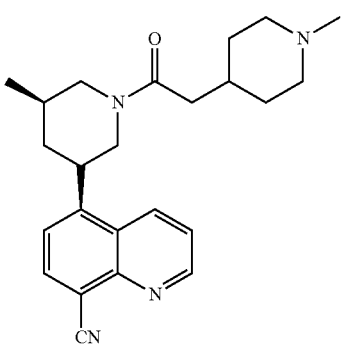

Compound 54
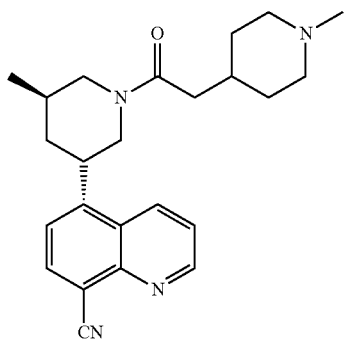
Compound 55
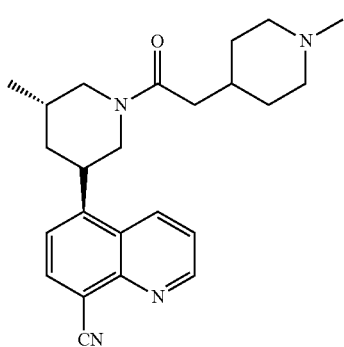
Compound 56
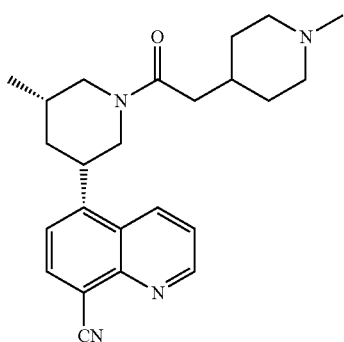
Compound 57
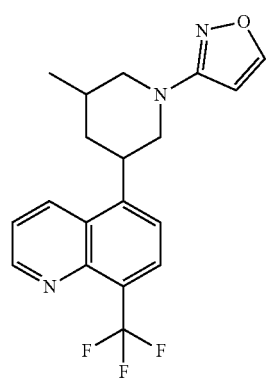 [SMILES: CC1CC(c2ccc(C(F)(F)F)c3ncccc23)CN(c2ccon2)C1]
Compound 58
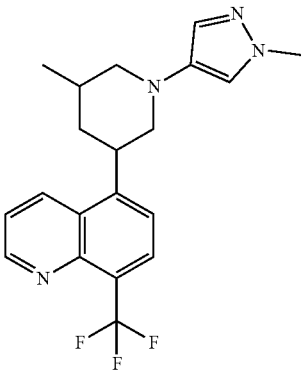 [SMILES: CC1CC(c2ccc(C(F)(F)F)c3ncccc23)CN(c2cnn(C)c2)C1]
Compound 59
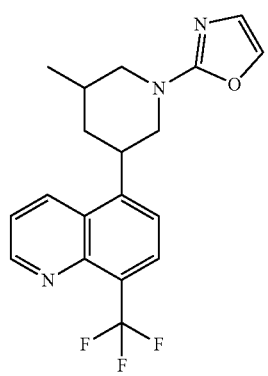 [SMILES: CC1CC(c2ccc(C(F)(F)F)c3ncccc23)CN(c2ncco2)C1]
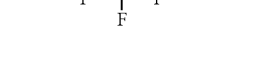
Compound 60
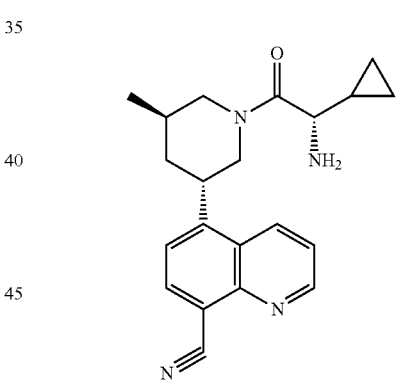
Compound 61
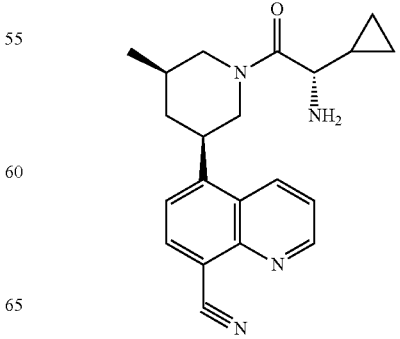

Compound 62
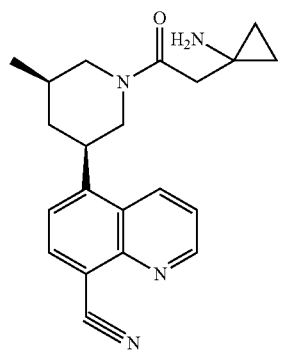
Compound 63
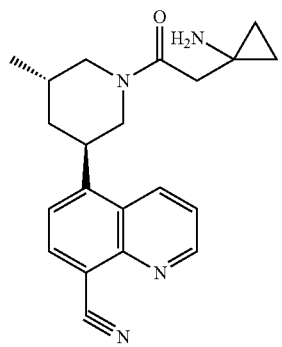 [SMILES: C[C@H]1C[C@H](c2ccc(C#N)c3ncccc23)CN(C(=O)CC2(N)CC2)C1]
Compound 64
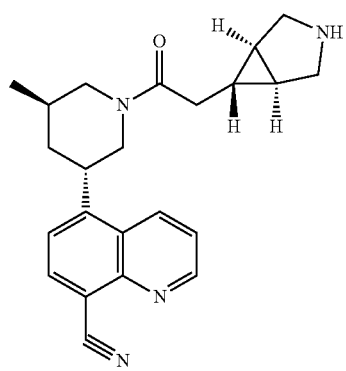
Compound 65
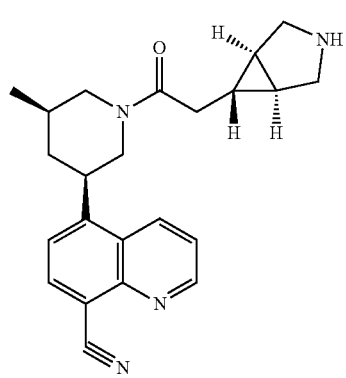 [SMILES: C[C@@H]1C[C@H](c2ccc(C#N)c3ncccc23)CN(C(=O)C[C@H]2[C@@H]3CNC[C@@H]32)C1]
Compound 66
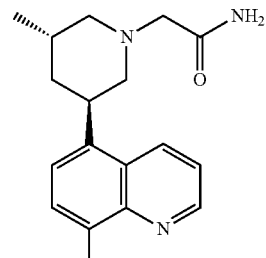
Compound 67
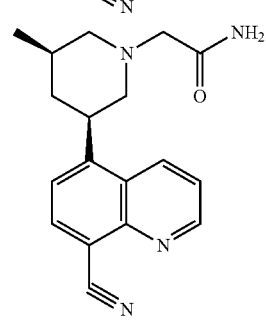
Compound 68
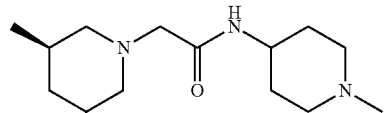
Compound 69
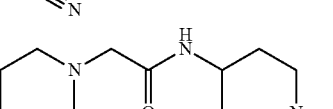
Compound 70
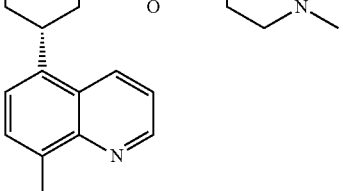

231
-continued
Compound 71
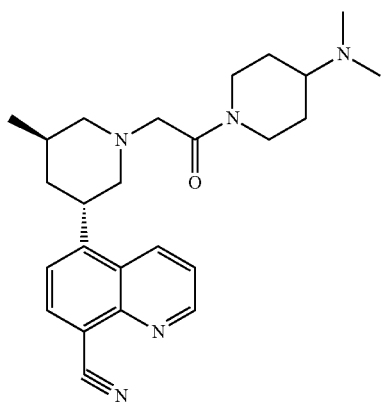
Compound 72
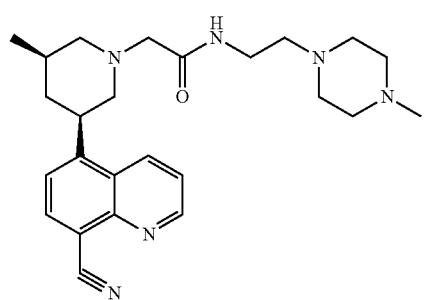
Compound 73
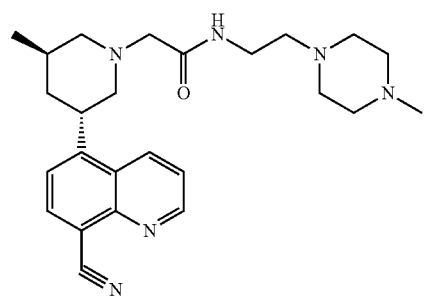
Compound 74
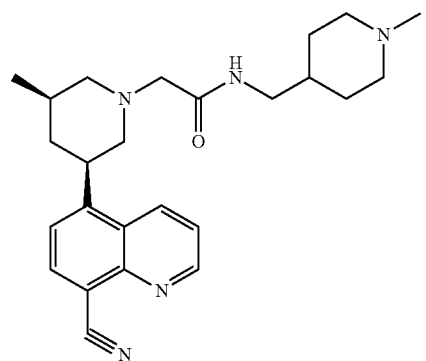
232
-continued
Compound 75
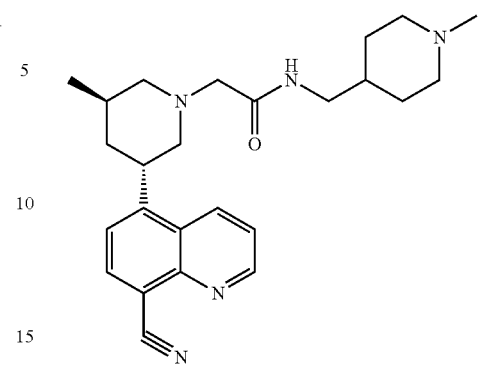
Compound 76
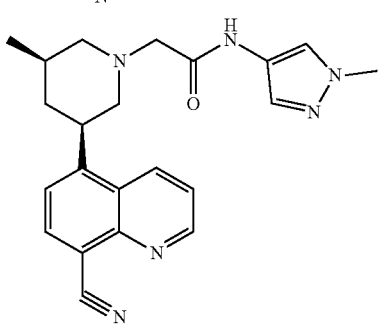
Compound 77
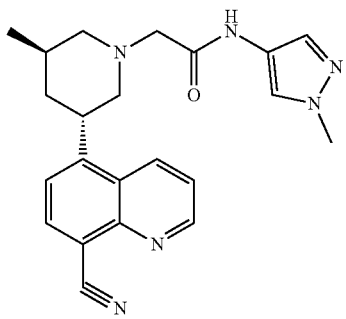 [SMILES: C[C@@H]1C[C@@H](c2ccc(C#N)c3ncccc23)CN(CC(=O)Nc2cnn(C)c2)C1]
Compound 78
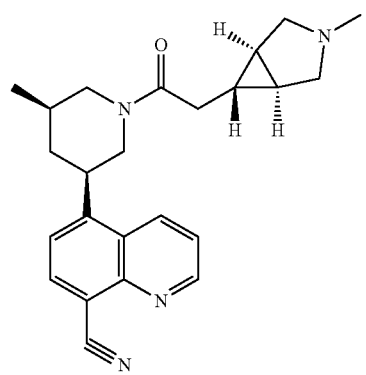

| 233 -continued | 234 -continued |
|---|---|
| 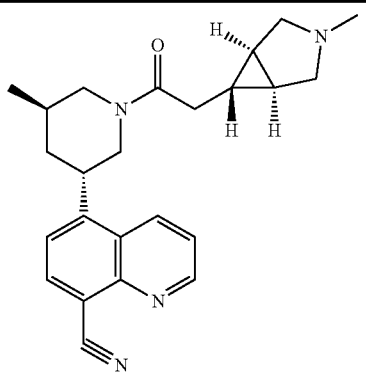 Compound 79 | 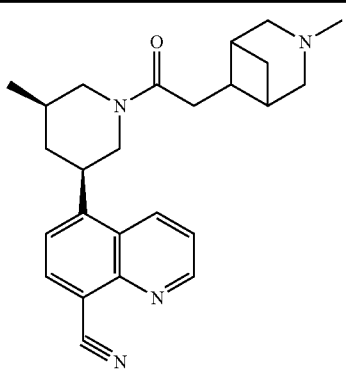 Compound 93 |
| 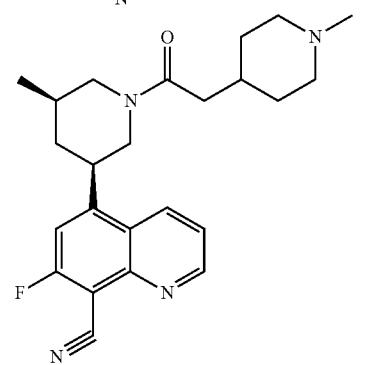 Compound 85 | 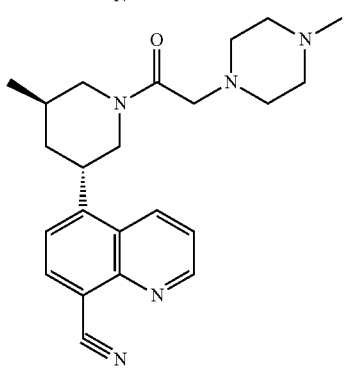 Compound 96 |
|  Compound 91 |  Compound 97 |
| 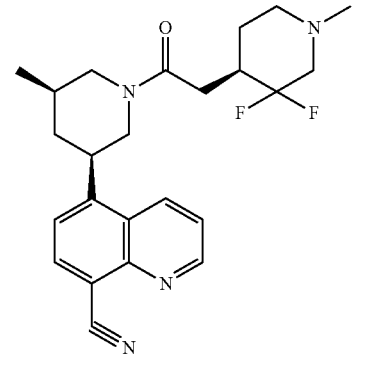 | 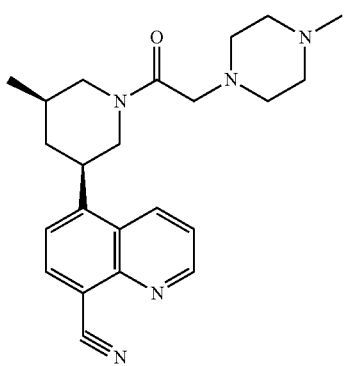 |
| 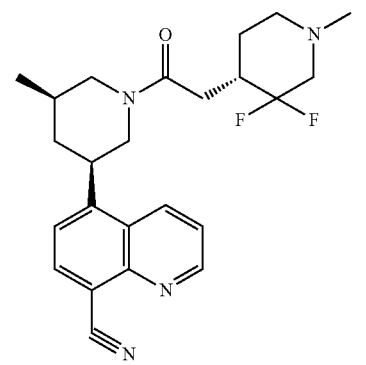 Compound 92 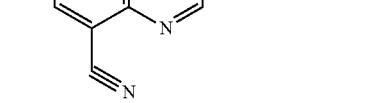 | Compound 98 |

235
-continued
Compound 99
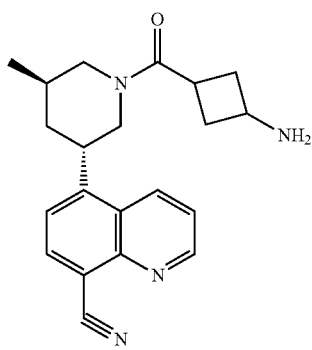 [SMILES: C[C@@H]1C[C@@H](c2ccc(C#N)c3ncccc23)CN(C(=O)C2CC(N)C2)C1]
Compound 100
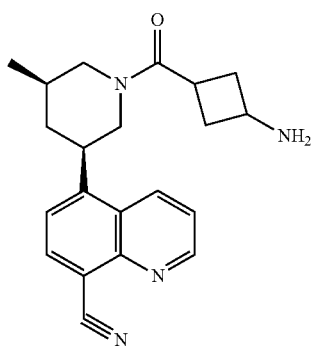 [SMILES: C[C@@H]1C[C@H](c2ccc(C#N)c3ncccc23)CN(C(=O)C2CC(N)C2)C1]
Compound 106
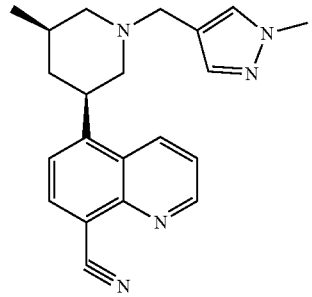
Compound 107
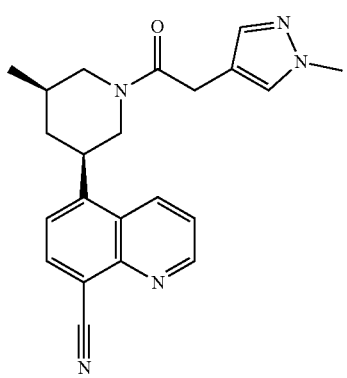
236
-continued
Compound 108
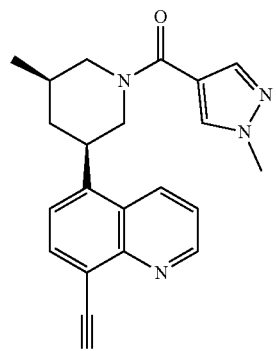
Compound 109
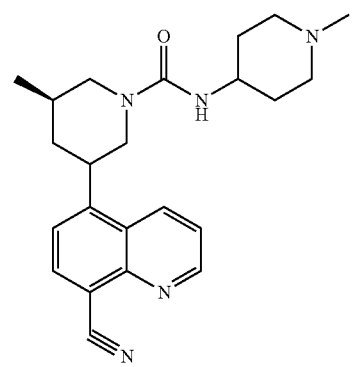
Compound 110
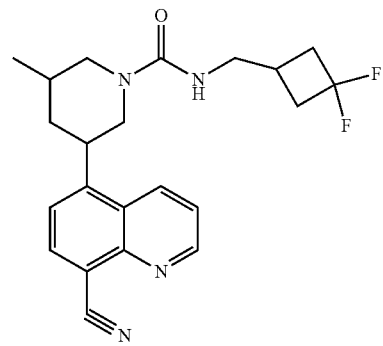 [SMILES: CC1CC(c2ccc(C#N)c3ncccc23)CN(C(=O)NCC2CC(F)(F)C2)C1]
Compound 113
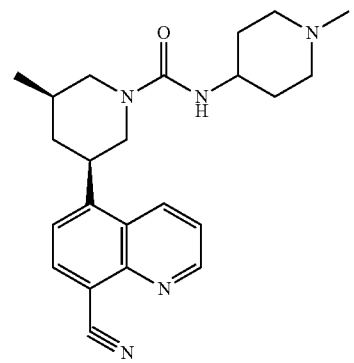

-continued
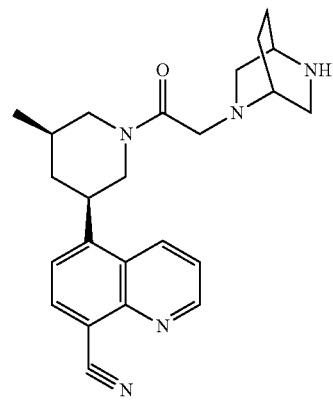 [SMILES: C[C@@H]1C[C@H](c2ccc(C#N)c3ncccc23)CN(C(=O)CN2CC3CCC2CN3)C1]
Compound 116
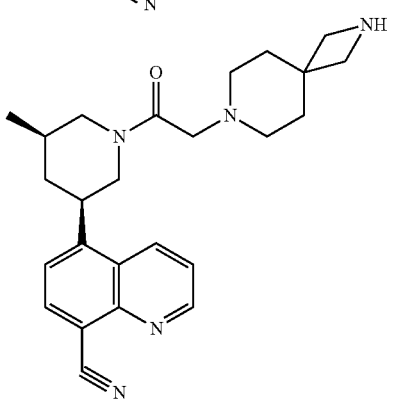
Compound 117
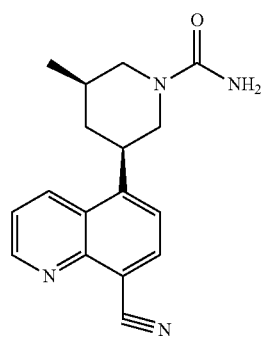 [SMILES: C[C@@H]1C[C@H](c2ccc(C#N)c3ncccc23)CN(C(N)=O)C1]
Compound 118,
-continued
and
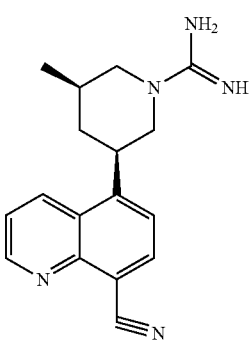 [SMILES: C[C@@H]1C[C@H](c2ccc(C#N)c3ncccc23)CN(C(=N)N)C1]
Compound 119.
7. A pharmaceutical composition, comprising:
a compound of claim 1, and
a pharmaceutically acceptable adjuvant, carrier, or vehicle.
8. The compound of claim 1, wherein each $R^4$ is independently
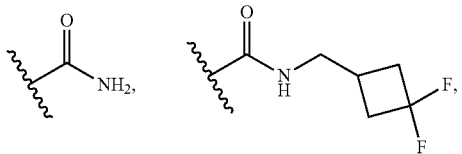
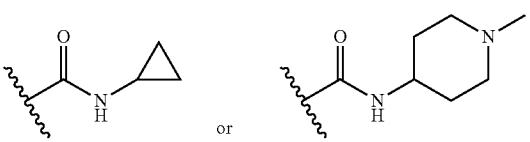
or
* * * * *